US008030471B2

(12) United States Patent
Birkenmeyer et al.

(10) Patent No.: US 8,030,471 B2
(45) Date of Patent: Oct. 4, 2011

(54) ***PLASMODIUM MALARIAE* AND *PLASMODIUM OVALE* GENES AND USES THEREOF**

(75) Inventors: Larry G. Birkenmeyer, Glenview, IL (US); Anthony S. Muerhoff, Kenosha, WI (US); Suresh M. Desai, Libertyville, IL (US); George J. Dawson, Libertyville, IL (US); Bruce J. Dille, Antioch, IL (US)

(73) Assignee: Abbott Laboratories, Abbott Park, IL (US)

( * ) Notice: Subject to any disclaimer, the term of this patent is extended or adjusted under 35 U.S.C. 154(b) by 354 days.

(21) Appl. No.: 12/143,137

(22) Filed: Jun. 20, 2008

(65) Prior Publication Data

US 2009/0226445 A1 Sep. 10, 2009

Related U.S. Application Data

(60) Provisional application No. 61/068,375, filed on Mar. 6, 2008.

(51) Int. Cl.

| | |
|---|---|
| ***C07H 21/04*** | (2006.01) |
| ***C07H 19/00*** | (2006.01) |
| ***A01N 25/26*** | (2006.01) |
| ***A01N 25/28*** | (2006.01) |
| ***A61K 39/015*** | (2006.01) |
| ***A61K 39/00*** | (2006.01) |
| ***A61K 45/00*** | (2006.01) |
| ***A61K 39/40*** | (2006.01) |
| ***A61B 5/055*** | (2006.01) |
| ***C12P 1/00*** | (2006.01) |
| ***C12P 21/06*** | (2006.01) |
| ***G01N 33/53*** | (2006.01) |
| ***C12N 15/09*** | (2006.01) |
| ***C12N 1/10*** | (2006.01) |
| ***C12M 1/34*** | (2006.01) |
| ***C12M 3/00*** | (2006.01) |
| ***C07K 1/00*** | (2006.01) |

(52) U.S. Cl. ... 536/23.7; 536/22.1; 424/418; 424/268.1; 424/178.1; 424/9.34; 424/184.1; 424/134.1; 424/278.1; 424/150.1; 435/41; 435/69.1; 435/7.1; 435/4; 435/69.3; 435/287.2; 435/258.2; 530/350

(58) Field of Classification Search ........................ None
See application file for complete search history.

(56) References Cited

U.S. PATENT DOCUMENTS

| | | | |
|---|---|---|---|
| 4,582,788 | A | 4/1986 | Erlich |
| 4,683,194 | A | 7/1987 | Saiki et al. |
| 4,683,202 | A | 7/1987 | Mullis |
| 5,006,309 | A | 4/1991 | Khalil et al. |
| 5,063,081 | A | 11/1991 | Cozzette et al. |
| 5,089,424 | A | 2/1992 | Khalil et al. |
| 5,107,065 | A | 4/1992 | Shewmaker et al. |
| 5,231,020 | A | 7/1993 | Jorgensen et al. |
| 5,700,671 | A | 12/1997 | Prieto et al. |
| 5,705,330 | A | 1/1998 | Shah et al. |
| 5,750,176 | A | 5/1998 | Prieto et al. |
| 5,912,120 | A | 6/1999 | Goldstein et al. |
| 6,395,472 | B1 | 5/2002 | Leary et al. |
| 2003/0170881 | A1 | 9/2003 | Davis et al. |
| 2004/0018577 | A1 | 1/2004 | Emerson Campbell et al. |
| 2005/0054078 | A1 | 3/2005 | Miller et al. |
| 2006/0160164 | A1 | 7/2006 | Miller et al. |
| 2009/0232797 | A1 * | 9/2009 | Birkenmeyer et al. .... 424/130.1 |

FOREIGN PATENT DOCUMENTS

| | | |
|---|---|---|
| EP | 50424 | 9/1985 |
| EP | 84796 | 5/1990 |
| EP | 201184 | 12/1992 |
| EP | 258017 | 6/1997 |
| WO | WO 02/070542 A2 * | 9/2002 |

OTHER PUBLICATIONS

Lodish et al., Mol. Cell Biol., 3rd ed. Scientific American Books, NY, 1995).*
Kleppe et al. (Tidsskr Nor Laegeforen, Sep. 30, 2001; 121(23):2717-20; Abstract only).*
Hoppner (Horm Re. 2002, 58 Suppl. 3:7-15; Abstract only).*
STIC result 15—sequence alignment; pp. 1-15.*
Altschul et al. Nucleic Acids Research; 25: 3389-3402 (1997).
Cox-Singh et al., Clinical Infectious Diseases; 46: 165-171 (2008).
Doderer et. al., Malaria J.; 6: 19 (2007).
Eck RV & Dayhoff MO, Atlas of Protein Sequence and Structure (1966).
Egan et. al., Infect. Immun.; 68: 1418-1427 (2000).
Elghouzzi et al., VoxSang.; 94: 33-40 (2008).
Escalante and Ayala, PNAS; 91: 11373-11377 (1994).
Faber et al., Infection and Immunity; 75: 5947-5955 (2007).
Fandeur et. al., Parasitology; 120: 11-21 (2000).
Felsenstein J, Evolution; 39: 783-791 (1985).
Girard et. al., Vaccine; 25: 1567-1580 (2007).
Gorbach, Bartlett & Blacklow "InfectiousDiseases", 2nd Edition, TOC, (1992).
Higgins et. al., CABIOS; 5L151-153 (1989).
Ingelbrecht et. al., The Plant Cell; 1: 671-680 (1989).
Jones et. al., Embo J.; 4: 2411-2418 (1985).
Jongwutiwes et al., Emerg. Inf. Dis.; 10: 2211-2213 (2004).
Kitchen et al., Vox Sang.; 87: 150-155 (2004).
Kitchen & Chiodini, Vox Sang; 90: 77-84 (2006).
Kumar et. al., Mol. Med., 1: 325-332 (1995).
Leclerc et. al., Parasitology; 129: 677-684 (2004).Mangold et. al., Journal of Clinical Microbiology; 43: 2435-2440 (2005).
Mertens et. al., Vox Sang; 77: 237-238 (1999).
Mullis et. al., Cold Spring Harbor Symp. Quant. Biol.; 51: 263-273 (1986).
Mungai et. al., N. Engl. J. Med.; 344: 1973-1978 (2001).
Needleman & Wunsch, J. Mol. Biol.; 48: 443 (1970).
Nei M. & Kumar S., Molecular Evolution and Phylogenetics, 128 (2000).

(Continued)

*Primary Examiner* — Vanessa L. Ford
*Assistant Examiner* — Lakia Tongue
(74) *Attorney, Agent, or Firm* — Cheryl L. Becker

(57) ABSTRACT

The subject invention relates to nucleic acid sequences and amino acid sequences encoded thereby, derived from the Merozoite Surface Protein (MSP1) gene of the *Plasmodium* species *P. malariae* and *P. ovale*. Such genes and proteins have many beneficial diagnostic as well as therapeutic uses.

3 Claims, 19 Drawing Sheets

OTHER PUBLICATIONS

Okamuro and Goldberg, Biochemistry of Plants; 15: 1-82 (1989).
Pearson and Lipman, PNAS; 85: 2444 (1988).
Perkins and Schall, J. Parsitol; 88: 972-978 (2002).
Rodrigues et. al., Malaria Journal; 2: 39-46 (2003).
Rosa et. al., Immunology Letters; 92: 259-268 (2004).
Saitou et. al., Molecular Biology and Evolution; 4: 406-425 (1987).
Sambrook et. al., Molecular Cloning A Laboratory Manual ; 2nd edition: 1-30 (1989).
Schwarz R. & Dayoff M.; Matrices for Detecting Distant Relationships: 353-358 (1979).
Seed et. al., Vox Sang.; 88: 98-106 (2005).
Schnieke et. al., Science; 278: 2130-2133 (1997).
She et. al., Journal of Travel Medicine; 14: 105-111 (2007).
Siddiqui et. al., PNAS; 84: 3014-3018 (1987).
Smith and Waterman, Appl. Math.; 2: 482 (1981).
Sneath PHA & Sokal RR, Numerical Taxonomy; TOC (1973).
Srivastava et. al., J Trop Med. Hyg.; 94: 189-194 (1991).
Stowers et. al., Infection and Immunity; 69: 1536-1546 (2001).
Tamura et. al., Molecular Biology and Evolution; 24: 1596-1599 (2007).
Thompson et. al., Nuclear Acids Research; 22: 4673-4680 (1994).
Turner, R. and Foster, G.D., Molecular Biotechnology; 3: 225 (1995).
Vinetz et. al., NEJM: 338(6): 367-371 (2007).
Wild, The Immunassay Handbook, 2nd edition; (2001).
Wyler, D., Plasmodium and Babesia; 287: 2407 (1992).
Zhu et. al., (article in Chinese) Zhingguo Ji Sheng Chong Xue yu Ji Sheng Chong Bing Za Zhi; 24: 70-1 (2006).

* cited by examiner

FIGURE 1

SEQ ID NO:2 (PmMSP1 Gene Sequence)

1
AAAAAAAAATTTTTATTTTACCAATTATAAAATACTCTATATTATCAAGTTTAATTCAAAAATGAAAGCACTTATATTTTTGTTCTCTTTTGTCTTTTTT
TCTATAAATTGTCACTGTGAAACAAATGAAGATTATGAACAACTTATTCAAAAGTTGGGAAAACTGGAGGAACTAGTTGTAGAAGGGTATAACCTATTTC
ACAAAAAAAAAATTTGCCTTAACAGACATTAATAAGGATGGTAATACCAGTACTACTGATGCAAATAATAAAGATGATAGTAAGGTTTCCTCCGTAACAGC
AAAAATAGGAAATTTTGTTAGCAAAGTTCTAAACCTGAATTTGCCAGGTTATGTTCAGTTAACTTTTTCAATTAGGGAATTAATTACAAAGTACAGTGGT
TTGAAATATCTAATTGAAGGATATGAAGAATTCAATGAATTAATGTATGGAATTAATTTTTACTATGATTTATTAAGAGCTAAGTTGAATGATATGCATC
TAAATGGCTACTGTGATATACCTAATCATCTAAAAATTAATGAAAAGGAATTAGAAATGCTTAAAAAAGTCGTATTTGGATATAGAAAACCATTAGAAAA
TATTAAAGACGATATTAACAAAATGGAGAAATTTATCACAACAAATGAAGCAACAGTAAATAATATAAAGGAATTAATTAAGAAGGAATATAATAACATC
GCTGATGAGAATAAAAAATTAGAGGCTCCTAGTGAATCAGGGTCAGATGACGAAGATATAAAGAATTGTAATGAAAAACAGAAAATATACAAATCTCGAT
ATAACATTCTTTTTTACGAAAAGCAGTTGCTAGAGGCACAAAAATTAATAGAAGTTTTAAAGAAGCGTATTCAAACTTTAAAAGAAAATACCGATATAAA
AAAATTGCTCGACGAAATAAAGGAAATTGAAGGGAAACTTCCTACAAGTGGTAGTGAAGCATCTGCCTCTGCAGCAGCTCCTGGTGCTATAAAGGAACCA
GAAAATACTCAAATAAAAGAACGTCAAGAAAAGATTAAAGAAATTGCGAAAAATATAGTATTCAATATGGATGGTCTATTTACAGATGCCTTCGAATTGG
ATTACTATGTAAGAGAAAAAGAAAAAAAATCATTCAACTCGGCAACTACTCAACTAGCTAACGGTAAAGCAGTAAACAGAACACCTCCTGCACCAGTAAT
GTATCCTCATGGAATAATTTATGCTGTATCAGATGATGCTATAAGTAACATACTATCTAAAAGTAGTACACAGTTAACACTTGAAGAATTACAAAATCCT
GACAATAGAAAACAAATTACTATTGACGATCTTAAAGACGAAAACAAAAGAAAAGAATTGATAACTAAAATAAAAAATAAAATTACAGAAGAAGAAGGGA
AATTAAATGCATTAAAAGGAGATGTTGATAGTAAATTAGAGAAATTTAAGAAAATAGAAGGGGAATTTAAACCATTACTTGAAAAATTTTATGATGAAAG
ACTTGATAATAGCATTACAACAGAGAATTTTGAAAAATTTTTAAGTAAAAGAACAGAATATTTAACGGAAAAGAATTTGCTTGAAAGCTCTTCTTACGAA
TTGTCGAAAGCATTGGTAAAGAAATTAAAAAAGCAACTTATGTATTTAGAAGACTATTCATTAAGAAAAGAAGTATTTGATGAAGAGGTAAATCATTTCA
ACTGCTTAGACTTACAATTAAATGCTGATATTCATAAATTAGAAAGTGAAATTAAAAGAAAAGAAAATTTACTTACAGTAGTTGATACCTTAAAATTTTC
AGATGTCGTGGAATTACAAGTACAAAAAGTATTATTAGGTAAAAAAATAGGACAACTAAAAAATGTAGAAGCATTTTTACAAAAAGCAAAATTAAAAGAA
ACGTTTCACATCCCCCAAGCATACGGAACAGGAGAACAATCCGAACCATACTATTTAATTGCACTAAAGAGGGAAATTGATAAATTAAATATTTCTATTC
CAAAAATTGAGGAAATGTTAAAAAATGAGAAAAAACTGGAGGAAGAAAAAATCAAGGCGGCAGCACAAAATGTAAGCGGCCATGTTTCCGGAGCAGATGA
AACATCAAACAGTCATGGATCATCTGGAGGAGGAGGATCAACACAAACAGTAACGACAACACCATCAACTACAACAACAGCAACTACATCATCACAAACA
GTATCAGTAGGAGAAACAGGATCAGCACAAGCACAAGCACAACCACAACCACAACCACAACCACAACCACAAACACAAACACAAACACAAACACAACCAC
AAGCAGCAGGAGCAACGGGAACACCAGGACAATCAGGACAATCAGGACAATCAGGACAATCAGGAGCTGAAGGAACAACAGAAACTACGGGAACAACAGG
ACAGGCAGGAACAACGGGAACACCAGAACAAGCAGCAGCTGCAGGACCACAAGCAGAAACTACGGCAACACCAGGACAAGCAGGAGCTGCAGGAGCTGCA
GGACCACAAGCAGAAACTACGGGAACACCAGGACAAGCGGGAGCTGCAGGACCACAAACAGAGACAGAAGTAGAAGAAACTCAGGAAATTGGAATCGTTG
TTCCGACATTGTCCAAATTGCAATATCTTGAAAAGCTATATGACTTTTTGAAAACTGCTTATGTGTGTCATATCAACATTTTGGTAAATAACTCAACCAT
GAATGAAACGTTACTACAACAATATAAACTGAAGATAGAAGAAGATAAGAAATTATTAGAGAAGTGCGACCAATTAGATTTGTTATTTAATGTTCAGAAT
AACTTACAAGTCATGTATTCAATGTATGACAGTGTGAGCAATGTTCTACAAAATCAGTACAAAGAATTAAACCAAAAGGAAATGATTTATAATATTTATA
AACTGGTGAAGAAGAATGACAAACTTAAAAACTTCTTAAACTTAACTGCAAACAGTGCAGCTGCATCTTCGGCATTACCACCTCCACCATCAGTACCACC
TGCAGTACCACCAGCATCACAACAGCCACAACCTCAAGCAGCATTACCAGCACAACCTCAAGCAGCAGTACCAGCACAATCTCAAGCAACAGTACCAGCA
CAATCTCAAGCAGCAGTACCAGCAACAACTCAATCCTCATCGGTATCAGCACCAACAGGTACAAATGGTGCATCCCCAGCAACTCCTGTAGCTCCAGCTG
GTAGTGAAAATGCGATTCAGTTAAAAGCGAATGACAACGAGGACGATGCAAATGAACTAGATTTCGACATTGACGATATTTATATAAAATACTTAGAACA
AGTGAGCAAATACGACGAGAACTTCAAAAATTTTATAGAGTCCAAAAAAGATATAATAAATAAGATGAGCGAAAGTGAATGGAAAGAATTAGGAGAAGAA
ATCAACACATTGAAACAAGATATACAATCATCATTTGATAATTTTGGAAAATATAAACTTAAATTGGAAAGATTATTAAAAAAGAAAAATAAAATTACAA
GCAGTACTAATCATATTAAAGAATATAGTATTTTAAAAGCACAATTATTAAGGAAAAAAAATATTCTAAATAACCCAAGACATGTACTAGCAGCTTTTGT
AGTATTCTTTAATAAAAAGATAGAAGCAGAAAAGAAAGAAGTTGAAAATGCTTTAAAAAATACTGATATTATGTTGAAATATTATAAGGCAAGAACCAAA
TATTATATTAGTGAAGCATTCCCCTTAAAAACAATAACTGAACAATCACTTCAAAAAGAAATTAACTATTTACATTTAGAAAAATTTAAAGTATATAGTA
GATTAGAAGGACGCATTAAGAAAATGTTGAATTTAGAAAAAGAAAATATTACCTACTTATCTGGTGGATTACATCATGTACTTACAGAATTAAAAGAGAT
CATAAATGATAAAACATACACCGGTTATACACATACTAAAAATAACGAAGAAGTTAACAAAGCGTTAAATGTTTATGAGGAATTGCTTCCAAAGCAAATA
TCCACAGAAGAGCAACCGGATAATGCATTAGCAGATGGAACGGAAAATGCAACAGAAGGTGCAGAAGTGCGTGCAGCAACTGCAGAAAGTTTAGTGCAGG
GAGAAGATGAGTACCCTGAAGAAGTTGATGAGGTGATCGTGTTTCCCATTGTGGGTAAGAAAGAAAAGGAAAATCCATTAGATCAAATAACAAAAGGACA
AGCTGAAACTAAACAAGATGATAATATATTGAAACCAATTACAAATGAGTATGAAGTATTATATATTAAACCATTAGCTGGAGTATATAGAGTTTTAAGA
AAACAAATAGGAGATCAGATAGACGCTTTTAATAGTAATTTGACAAATGCTTTGGATACTCGAAAAAAGAAAAGAACATATTTCTTAGATGTATTAAATT
CTGATTTAATTCAATTTAAACATGCAACTTCCGACAGTTATATTATAAAAGATCCGTATAAACTATTAGATGTTGATAAGAAAGCGAAGCTTATAGGTAG
CTATAAATATATCGTCTCTGCAATAGAAAAGGATATCACTTCAGCTGAGAACGGAGTAGAATATTATGATAAGATGACCAAGTTGTACAAGACTCAGTTA
GAAGCAGTAAAAAGCGCAATTGCTGAAGCACAAAAAGAGGGTGATAAAAAAACTGAAAATGAAAAATATATTCCATTCTTAACGAACATGCAGACATTAT
ATGAAAATTTATTGAATAAAATAAATGGAAACATAATAAATTTAAAAACTTTAATTACAAACTGTAATTTAGAAAAAGATGCAGTAAACATTACTATAAG
TAAATTAACAGAATACAGCAAATTTGATGAAAAAATAGAAATGTTTAAAAACTCTAAAAATGAAAAGGATATAGCAAGTTCTGGAATATTAGACATACTT
AAACAAAAAGGACTTGTTAATAAAAAATGAATCAACTAAGATTATATCAGAATTACTTGGT*GTAGACTCTAATGCATTACTGAATATTAGCGCAAAACATG*
*CATGTACCGAAACAAAATATCCTGAAAATGCAGGATGTTATAGATATGAAGACGGAAAAGAAGTATGGAGATGCTTATTAAATTATAAACTAGTTGATGG*
*AGGATGTGTTGAAGATGAAGAGCCTTCTTGTCAAGTTAACAATGGAGGATGTGCTCCTGAAGCTAACTGTACCAAAGGAGATGACAACAAAATTGTCTGT*
*GCTTGTAACGCACCCTATTCTGAACCTATATTTGAAGGTGTTTTCTGTGGTTCTTCAAGT*TTCCTCGGCTTATCACTATTATTAGCAGCTTTATTAATTA
TGTTTAACTTACTTTAAGAAAAAAAGACAGAAAAGAAGGATACGAATGAACATAAAATGAGAAGGATTAAGACTGAGCAAGAGGAAAAGAGAGAAAATCA
TAGATC 5406

Gray = Start codon
Inverse = Stop codon
Bold = MSP1-p33 encoding sequence
*Italics* = MSP1-p19 encoding sequence

FIGURE 2

SEQ ID NO:1 (PmMSP1 Deduced Amino Acid Sequence)

1
MKALIFLPSFVFFSINCHCETNEDYEQLIQKLGKLEELVVEGYNLFHKKKFALTDINKDGNTSTTDANNKDDSKVSSVTAKIGNFVSKVLNLNLPGYVQL
TFSIRELITKYSGLKYLIEGYEEFNELMYGINFYYDLLRAKLNDMHLNGYCDIPNHLKINEKELEMLKKVVFGYRKPLENIKDDINKMEKFITTNEATVN
NIKELIKKEYNNIADENKKLEAPSESGSDDEDIKNCNEKQKIYKSRYNILFYEKQLLEAQKLIEVLKKRIQTLKENTDIKKLLDEIKEIEGKLPTSGSEA
SASAAAPGAIKEPENTQIKERQEKIKEIAKNIVFNMDGLFTDAFELDYYVREKEKKSFNSATTQLANGKAVNRTPPAPVMYPHGIIYAVSDDAISNILSK
SSTQLTLEELQNPDNRKQITIDDLKDENKRKELITKIKNKITEEEGKLNALKGDVDSKLEKFKKIEGEFKPLLEKFYDERLDNSITTENFEKFLSKRTEY
LTEKNLLESSSYELSKALVKKLKKQLMYLEDYSLRKEVFDEEVNHFNCLDLQLNADIHKLESEIKRKENLLTVVDTLKFSDVVELQVQKVLLGKKIGQLK
NVEAFLQKAKLKETFHIPQAYGTGEQSEPYYLIALKREIDKLNISIPKIEEMLKNEKKLEEEKIKAAAQNVSGHVSGADETSNSHGSSGGGGSTQTVTTT
PSTTTTATTSSQTVSVGETGSAQAQAQPQPQPQPQPQTQTQTQTQPQAAGATGTPGQSGQSGQSGQSGAEGTTETTGTTGQAGTTGTPEQAAAAGPQAET
TATPGQAGAAGAAGPQAETTGTPGQAGAAGPQTETEVEETQEIGIVVPTLSKLQYLEKLYDFLKTAYVCHINILVNNSTMNETLLQQYKLKIEEDKKLLE
KCDQLDLLFNVQNNLQVMYSMYDSVSNVLQNQYKELNQKEMIYNIYKLVKKNDKLKNFLNLTANSAAASSALPPPPSVPPAVPPASQQPQPQAALPAQPQ
AAVPAQSQATVPAQSQAAVPATTQSSSVSAPTGTNGASPATPVAPAGSENAIQLKANDNEDDANELDFDIDDIYIKYLEQVSKYDENFKNFIESKKDIIN
KMSESEWKELGEEINTLKQDIQSSFDNFGKYKLKLERLLKKKNKITSSTNHIKEYSILKAQLLRKKNILNNPRHVLAAFVVFFNKKIEAEKKEVENALKN
TDIMLKYYKARTKYYISEAFPLKTITEQSLQKEINYLHLEKFKVYSRLEGRIKKMLNLEKENITYLSGGLHHVLTELKEIINDKTYTGYTHTKNNEEVNK
ALNVYEELLPKQISTEEQPDNALADGTENATEGAEVRAATAESLVQGEDEYPEEVDEVIVFPIVGKKEKENPLDQITKGQAETKQDDNILKPITNEYEVL
YIKPLAGVYRVLRKQIGDQIDAFNSNLTNALDTRKKKRTYFLDVLNSDLIQFKHATSDSYIIKDPYKLLDVDKKAKLIGSYKYIVSAIEKDITSAENGVE
YYDKMTKLYKTQLEAVKSAIAEAQKEGDKKTENEKYIPFLTNMQTLYENLLNKINGNIINLKTLITNCNLEKDAVNITISKLTEYSKFDEKIEMFKNSKN
EKDIASSGILDILKQKGLVNKNESTKIISELLG*VDSNALLNISAKHACTETKYPENAGCYRYEDGKEVWRCLLNYKLVDGGCVEDEEPSCQVNNGGCAPE*
*ANCTKGDDNKIVCACNAPYSEPIFEGVFCGSSS*FLGLSLLLAALLIMFNLL* 1751

Gray = Signal Peptide
Inverse = Cysteine Residues
Bold = MSP1-p33 Residues
*Italics* = MSP1-p19 Residues

FIGURE 3

SEQ ID NO:4 (PoMSP1 Gene Sequence)

1
AATTCAAAAATGAAGGTGTTCGTATTTGCGCTCTCTTTCATTTTTTTTATTGTGAACTGTCAATGTGAAACGCTCGAAAATTATAAAGAGCTTCTTCATA
AGTTAAATAATTTGGAAGCTCTAGTGGTTGATGGCTACAACTTATTTCACAAAACTCCCTTAACCCTACAAAAGTTAGAAACTGAAGTCACAACTACTGG
AAGAGGTAGTGGTAGCAGTACTACTTCTGTTTCCTCCATTCCAAGTGATGCAAGTAGAGCTGTATCTACCCGTGATTCTAATAGCAACATCAACAACCAA
GTGGTTAGCAAGTTAACAGCGGACATAAGATTCCTTCTATCAAGATTTTTGCAGTTAAATATTCCAGGACATGGAGATTTAATGCATTTCATAAGAGAAA
TTTCGTTAGATACAAACGGACTAAAATATCTAATAGAAGGATATGAAGAATTTAACGAGTTAATGTACATATTGAACTTTTATTATGATCTGTTCAGAGC
TAAACTACATGATATGTGTGCAAATGATTATTGTGAAATACCAGACCATCTTAAAATTAGTGATAAGGAATTGGACATGCTCAAAAAAGTTGTATTAGGA
TACAGAAAACCGTTAGAAAATATAAAAGACGATATTTCAAAAATGGAGACATTCATTCAAAAAAATACTCAAACAGTGGAAAATATAAAGGGCTTAATAG
AGGCAGAAGAAAAAAAAAGGTATGGTGAGGTTGCAGTAAGTGGAAATACAGGAAGTGCAGGAGCTGCCTCAGGAACTAATGCATCTGCAAGTTCAGGCCA
AGAAAATTCTTCTACTGAAAGCGAAACAGAAAAGTATAACAAAGCTAAAGCTTTATATCAATCCATATATAACGCCTTATTTTACAAAAAGCAGTTAACA
GAAGCAGAAAAATTAATCGAAGTTTTAAAAAAGCGTGTGCAAACGTTAAAAGAGCACAAAGAGATAAAAAAATTACTCGAAGAAATCGCGGAAAAGGAAA
GCAAAGTTACCCCACCGAGTAATACCGCTTCACAAACGCAACTGCAGGAAGAAATTAACAAACTTAAAACTCAAATTAAGAACATCGCAAAAACTGTAAA
ATTCGAAATGGAAGGTCTGTTTACTGATCCTGTTGAATTGGATTACTACTTACGAGAAAAGGACAAAAAGGCAAGTAAAGTAGTAGAAACACAAAGTGGT
TCAACAACTCCGCCTAAGCCTACGTATCCCAATGGTCTCATCTACCCTTTGGAAAAAGAAAACATCTCTGAGTTGTTATCAAAAGCCGTGACAGAAACAA
CTTTTGGTGATTTACAAAATGTAGAAATTGGAAAAGCATTAAATAAAGAAATTTTCACGAATGATGATAAGAGAAATGAATTCATAGACAAACTTAAAAA
TAAAATTAAACAACAAGAAGAACTTTTATCTAAACAAAAAGTGGACTATGATGCAAAACTTAAATTGTACGAGGAGCAAAAGAAGAAAGCTATTCCCCTA
TTTGAGCAGTTTCACAATGGAAAACTTGACAACACACTTATTCCTAGTAAATTCGAAGAATTTAAAGTAGAAAGAGACAAGTATATGCAACTCAAGAACG
AGTTAAAAAATTGTCCATACGAAATGACAAAAAACACGGTGGATAAGTTAAATAAACAACTTGCATATTTGAATGACTACTCATTGAGAAAAGAAGTTTT
TAATAAAGAAGTTAAACATTTTACAGGATTAGAGTGGAAACTACAAACTGAAATTGACAAATTAGCAAACGAAATAAAGAAAAATGAAAATATACTTATA
ACAGCATCTACCTTACCATTATCTAATGTAGTAGAATTACAAGTACAAAAGTATTAGTAGCAAAAAAAATTGAACTTTTAAAAAAAGTAGAAAAACTTT
TACACAAAGCACAGTTGAAAGATCACCTTTACGTCCCTCAGGTTTATGGTACACAAGCGAAACCTGAAGCATACTATTTATTTGTCCTGAAAAAGGAAAT
TGACAAACTGGGGGAATTTAAGCCTAAAATAAAGGAGATGTTAGATAAGGAGAAGGCAAACCCCACTCCAGCGACAGCACAGGGAGCCCTTCCAGTTCGA
GGGGTTGATGAAATACTAGTCATGGGAAATCAAAACGAAGCTACAGCAGTAACATCACCATCAACATCAACAGAATCATCCGAGGGAGCAACACAACCAG
CAGCAACAGTACAGCCAGCAGCGCCAGGAGTACAAACGGGAATACCAGTAGCACAGCCAGGAGCATCAGCACCAGGAGTACCAGAAGCACCAGCACCAGA
AGCAACAGCACCAGAAGTACCAGCAATAGAAGCACAAGCACCTGTGCAACCTACGCAAGGACAGGTCCAAGCAGCCACCCAAAATGGCCCAACAATGACA
AAATTACAATATCTCGAGAAGTTATATTACTTTTTGTATACCTCCTATGTATGTCATAAGTACATTTTAGTGACAAACTCTACAATGAACAAAGATTTGT
TGGCAAAATATAATCTTACACCAGAAGAAGAAGAAAAAAAAAAGACAATAAAATGTGATCAGTTAGATTTATTGTTTAACTTACAAAACAATTTACCAGT
CATGTATTCTCTCTTTGATAATATGAGCTCGACTTTGCAAAGCAATTACATTCAATTATATGAAAAGGAAATGCTGTACAATATATACAAGATGAAAAAC
AGTGATAAGGCGATCAAAGAATTTCTAGAGACACAAGGTATAACAGGTACAGCACCAGATGCTACTCCTCTAGTCAATACACAAGCCACTACGCAAGCCG
CTACACAAGTCACTACGCAAGCCGCTACACAAACCGCTACACAAACCGCTACACATGCCTCTACACATGCCTCTACACAAGCCGCTACACAAGGTAATGT
TCCACAAGCCTCTAATGATGAACATACACCTTCAGCAACAACAGTTAATCCGGCAACGACAACACCAGATAAATCTTTGAAAGAAAGCACATCTGAGGGA
ACGTTGATGACACAGGGAAACGCAGATGATGATGTATCTGAGCCTGAAAAAAAGGAAATAGAAGTGGAAGAATTTTACAAGAAGTATTTAGAGGAAGTAG
ATAAGTATGATGACTACTTTAAAGCTTTTCTTTCATCCAAAAAGGATGCTGTAAATAAAATGACAGAAAAAGATTGGAAAGAATTAGAAGAAGAAGTAAA
AACATTAAAGAGTAGGTTAGATATGTCATTAGATCATTATAATAAGTATAAATTAAAATTAGGTAGATTGTTTAAAAAAAATGAAAAAGTTTTAAGTAGT
AAAGAACATATTAAAGAATTGAGTATTTTAAAAGCACAATTGATGAGAAGACAATTTATGCTTAATAACCCAAGACATGTAATACATAACTTTAGAGTTT
TTTTTAATAAAAAAAGAGAAACTGAAAAGAAAGAAGTTGAAAATACACTAAAAAATACAGATGCATTGTTAAAATATTACAAAGCAAGAGTTAAGTACTA
TAATGGAGAAACTTTCCCATTAAAAACAATAAGTGAAGATACATTAGAAAAAGAAAATAATTATCTCAATTTGGAAAAATTTAAGTTATACAGCAGATTG
GAAGGAAAACTAAAACAAAACATAAATTTGGAAAAAGAAAATATCACATACCTATCTAGTGCATTATATCACGTTCTTTCAGAATTAAAGGGGATTATAC
ACAATAAAAAGTACACAGGAAATCCTCATGCTGCAAATATGGTAGAGGTTAACAATGCGTTGAATCTGTACAAAGATTTGCTTCCAAAAGTGGAAACTGT
GGCTTCCACTGGTGCCGCGACGCAGACACAAGGCGGGGAAGGAGCATCAGCAGCAGCAGCACCACCAGCAGCGTTACCAGCAGCACCACCAGCAGCACCA
CCAGCAGCACCACCAGCAGCATCAGCAGCAGCACCTGGAACTGCAAATGGTGAAACAGCAACGGTAGCACACGCAGAAGACTATACGGAAGACGACAATA
ACGTCATTGTACTACCCCTTTTCGGAAAGAAAGGAACACATGCGTTTGACCAAGTGACGCAGGGTGAAGCACAAGACAAGGACGACAATATACTGAATGA
AATCACCAACGAATACGAAGTTGTGTACGTGAAACCGTTAGCTGGTGTATATAAAACGTTGAACAAGCAATTGGAAGCACATGTTACAGCATTTCACAGT
AACGTAACAAACATGTTGGAATCTCGTTTCAAAAAAACAAATTATTTTTTGGAAGTGTTAAACTCTGATTTGACTCAAAACAAACATGCAACTTCTGACA
ATTACGTTATTAGAGATGCGTACAAATTATTAGACTTTGAAAAAAAAAAAAAAATTGTTAAGTAGCTACAAATATATTAAAGATTCTGTTGAGAAAGATGT
AGAAATTGCTACGGATGGAATTGACTATTATGAAAAAATGGCTGCTCTGTATAAGACGTACCTAGAATCGGTTAATGCTCAGGTAGATGCAATAGATAAA
ACTGGGGATGATGCTACTAAGGCAACTAATAAAAAATTTCTTCCCTTTTTGGCTAGTATCAATGCTATGTACGAAACTTTGTTAGAAAAAGTGAACACCT
ACAATTCCCAATTAAAATCAAGTTTAAACAGTTGCCAGTTGGAAAAAATTAGAGTAGGTATTGTTGTGGATAAACTGAATGACTATGTAATGTTTGATGA
AAAATTAGAAGAGTTAAAATCGAGTAAGGAAAAAGATTTGACAAAATTATATAAAGATATAGATACATCTAACATAATAAACAAGTTAAAGAGATCAGGT
TTTGTAGATACAGATGAGTCAAAGAAATTATTATCCGAGTTGTTAGAT*GTAGATTCTGCTCAATTGTTGTCTATGGGATCTAAACATAAATGTATTGATA*
*TAACATATCCAGATAATGCAGGATGTTATAGATTTTCTGATGGACGAGAAGAATGGAGATGTTTGTTAAACTTTAAAAAAGTTGGAGAAACATGTGTACC*
*AAATAACAATCCTACATGTGCAGAAAATAATGGTGGATGTGATCCCACTGCAGATTGTGCAGAATCTGAAAATAATAAAATTACTTGTACATGTACTGGA*
*CAAAATGAATCATTCTTCGAAGGTGTTTTCTGTGGCTCATCAAGT*TTCCTTAGCTTATCTTTCTTATTGGCAGTCTTATTGATCCTATTTAACTTACTT
AAAGGAGAGAGTGAGGGTAAATACAAAAGTTGTTACATTTTTTTTTTTTTTTTTT 5256

Gray = Start codon
Inverse = Stop codon
Bold = MSP1-p33 encoding sequence
*Italics* = MSP1-p19 encoding sequence

FIGURE 4

SEQ ID NO:3 (PoMSP1 Deduced Amino Acid Sequence)

1
MKVFVPALSFIFFIVNCQCETLENYKELLHKLNNLEALVVDGYNLFHKTPLTLQKLETEVTTTGRGSGSSTTSVSSIPSDASRAVSTRDSNSNINNQVVS
KLTADIRFLLSRFLQLNIPGHGDLMHFIREISLDTNGLKYLIEGYEEFNELMYILNFYYDLFRAKLHDMCANDYCEIPDHLKISDKELDMLKKVVLGYRK
PLENIKDDISKMETFIQKNTQTVENIKGLIEAEEKKRYGEVAVSGNTGSAGAASGTNASASSGQENSSTESETEKYNKAKALYQSIYNALFYKKQLTEAE
KLIEVLKKRVQTLKEHKEIKKLLEEIAEKESKVTPPSNTASQTQLQEEINKLKTQIKNIAKTVKFEMEGLFTDPVELDYYLREKDKKASKVVETQSGSTT
PPKPTYPNGLIYPLEKENISELLSKAVTETTFGDLQNVEIGKALNKEIFTNDDKRNEFIDKLKNKIKQQEELLSKQKVDYDAKLKLYEEQKKKAIPLFEQ
FHNGKLDNTLIPSKFEEFKVERDKYMQLKNELKNCPYEMTKNTVDKLNKQLAYLNDYSLRKEVFNKEVKHFTGLEWKLQTEIDKLANEIKKNENILITAS
TLPLSNVVELQVQKVLVAKKIELLKKVEKLLHKAQLKDHLYVPQVYGTQAKPEAYYLFVLKKEIDKLGEFKPKIKEMLDKEKANPTPATAQGALPVRGVD
EILVMGNQNEATAVTSPSTSTESSEGATQPAATVQPAAPGVQTGIPVAQPGASAPGVPEAPAPEATAPEVPAIEAQAPVQPTQGQVQAATQNGPTMTKLQ
YLEKLYYFLYTSYVCHKYILVTNSTMNKDLLAKYNLTPEEEEKKKTIKCDQLDLLFNLQNNLPVMYSLFDNMSSTLQSNYIQLYEKEMLYNIYKMKNSDK
AIKEFLETQGITGTAPDATPLVNTQATTQAATQVTTQAATQTATQTATHASTHASTQAATQGNVPQASNDEHTPSATTVNPATTTPDKSLKESTSEGTLM
TQGNADDDVSEPEKKEIEVEEFYKKYLEEVDKYDDYFKAFLSSKKDAVNKMTEKDWKELEEEVKTLKSRLDMSLDHYNKYKLKLGRLFKKNEKVLSSKEH
IKELSILKAQLMRRQFMLNNPRHVIHNFRVFFNKKRETEKKEVENTLKNTDALLKYYKARVKYYNGETFPLKTISEDTLEKENNYLNLEKFKLYSRLEGK
LKQNINLEKENITYLSSALYHVLSELKGIIHNKKYTGNPHAANMVEVNNALNLYKDLLPKVETVASTGAATQTQGGEGASAAAAPPAALPAAPPAAPPAA
PPAASAAAPGTANGETATVAHAEDYTEDDNNVIVLPLFGKKGTHAFDQVTQGEAQDKDDNILNEITNEYEVVYVKPLAGVYKTLNKQLEAHVTAFHSNVT
NMLESRFKKTNYFLEVLNSDLTQNKHATSDNYVIRDAYKLLDPEKKKKLLSSYKYIKDSVEKDVEIATDGIDYYEKMAALYKTYLESVNAQVDAIDKTGD
DATKATNKKFLPFLASINAMYETLLEKVNTYNSQLKSSLNSCQLEKIRVGIVVDKLNDYVMFDEKLEELKSSKEKDLTKLYKDIDTSNIINKLKRSGFVD
TDESKKLLSELLD*VDSAQLLSMGSKHKCIDITYPDNAGCYRFSDGREEWRCLLNFKKVGETCVPNNNPTCAENNGGCDPTADCAESENNKITCTCTGQNE*
*SFFEGVFCGSSS*FLSLSFLLAVLLILFNLL* 1730

Gray = Signal Peptide
Inverse = Cysteine Residues
Bold = MSP1-p33 Residues
*Italics* = MSP1-p19 Residues

FIGURE 5A

PmMSP1 gene sequence and translation

```
     AAAAAAAAATTTTTATTTTACCAATTATAAAATACTCTATATTATCAAGTTTAATTCAAAAATGAAAGCACTTATATTTTTGTTCTCTTTTGTCTTTTTT
   1 ---------+---------+---------+---------+---------+---------+---------+---------+---------+---------+ 100
                                                                M  K  A  L  I  F  L  F  S  F  V  F  F  -
             As1*                    PmMSP1-F1                 PmMSP1-F2                   PmMSP1-F7
     TCTATAAATTGTCACTGTGAAACAAATGAAGATTATGAACAACTTATTCAAAAGTTGGGAAAACTGGAGGAACTAGTTGTAGAAGGGTATAACCTATTTC
 101 ---------+---------+---------+---------+---------+---------+---------+---------+---------+---------+ 200
     S  I  N  C  H  C  E  T  N  E  D  Y  E  Q  L  I  Q  K  L  G  K  L  E  E  L  V  V  E  G  Y  N  L  F  H -
                                                            PmMSP1-R8               PmMSP1-R7
     ACAAAAAAAAAATTTGCCTTAACAGACATTAATAAGGATGGTAATACCAGTACTACTGATGCAAATAATAAAGATGATAGTAAGGTTTCCTCCGTAACAGC
 201 ---------+---------+---------+---------+---------+---------+---------+---------+---------+---------+ 300
       K  K  K  F  A  L  T  D  I  N  K  D  G  N  T  S  T  T  D  A  N  N  K  D  D  S  K  V  S  S  V  T  A -
                                        PmMSP1-R6                PmMSP1-R1
     AAAAATAGGAAATTTTGTTAGCAAAGTTCTAAACCTGAATTTGCCAGGTTATGTTCAGTTAACTTTTTCAATTAGGGAATTAATTACAAAGTACAGTGGT
 301 ---------+---------+---------+---------+---------+---------+---------+---------+---------+---------+ 400
      K  I  G  N  F  V  S  K  V  L  N  L  N  L  P  G  Y  V  Q  L  T  F  S  I  R  E  L  I  T  K  Y  S  G  -
                                                                      As2*
     TTGAAATATCTAATTGAAGGATATGAAGAATTCAATGAATTAATGTATGGAATTAATTTTTACTATGATTTATTAAGAGCTAAGTTGAATGATATGCATC
 401 ---------+---------+---------+---------+---------+---------+---------+---------+---------+---------+ 500
     L  K  Y  L  I  E  G  Y  E  E  F  N  E  L  M  Y  G  I  N  F  Y  Y  D  L  L  R  A  K  L  N  D  M  H  L -

     TAAATGGCTACTGTGATATACCTAATCATCTAAAAATTAATGAAAAGGAATTAGAAATGCTTAAAAAAGTCGTATTTGGATATAGAAAACCATTAGAAAA
 501 ---------+---------+---------+---------+---------+---------+---------+---------+---------+---------+ 600
       N  G  Y  C  D  I  P  N  H  L  K  I  N  E  K  E  L  E  M  L  K  K  V  V  F  G  Y  R  K  P  L  E  N -

     TATTAAAGACGATATTAACAAAATGGAGAAATTTATCACAACAAATGAAGCAACAGTAAATAATATAAAGGAATTAATTAAGAAGGAATATAATAACATC
 601 ---------+---------+---------+---------+---------+---------+---------+---------+---------+---------+ 700
      I  K  D  D  I  N  K  M  E  K  F  I  T  T  N  E  A  T  V  N  N  I  K  E  L  I  K  K  E  Y  N  N  I  -

     GCTGATGAGAATAAAAAATTAGAGGCTCCTAGTGAATCAGGGTCAGATGACGAAGATATAAAGAATTGTAATGAAAAACAGAAAATATACAAATCTCGAT
 701 ---------+---------+---------+---------+---------+---------+---------+---------+---------+---------+ 800
     A  D  E  N  K  K  L  E  A  P  S  E  S  G  S  D  D  E  D  I  K  N  C  N  E  K  Q  K  I  Y  K  S  R  Y -

     ATAACATTCTTTTTTACGAAAAGCAGTTGCTAGAGGCACAAAAATTAATAGAAGTTTTAAAGAAGCGTATTCAAACTTTAAAAGAAAATACCGATATAAA
 801 ---------+---------+---------+---------+---------+---------+---------+---------+---------+---------+ 900
       N  I  L  F  Y  E  K  Q  L  L  E  A  Q  K  L  I  E  V  L  K  K  R  I  Q  T  L  K  E  N  T  D  I  K -
                                                                                         PmMSP1-F4
     AAAATTGCTCGACGAAATAAAGGAAATTGAAGGGAAACTTCCTACAAGTGGTAGTGAAGCATCTGCCTCTGCAGCAGCTCCTGGTGCTATAAAGGAACCA
 901 ---------+---------+---------+---------+---------+---------+---------+---------+---------+---------+ 1000
      K  L  L  D  E  I  K  E  I  E  G  K  L  P  T  S  G  S  E  A  S  A  S  A  A  A  P  G  A  I  K  E  P  -

     GAAAATACTCAAATAAAAGAACGTCAAGAAAAGATTAAAGAAATTGCGAAAAATATAGTATTCAATATGGATGGTCTATTTACAGATGCCTTCGAATTGG
1001 ---------+---------+---------+---------+---------+---------+---------+---------+---------+---------+ 1100
     E  N  T  Q  I  K  E  R  Q  E  K  I  K  E  I  A  K  N  I  V  F  N  M  D  G  L  F  T  D  A  F  E  L  D -

     ATTACTATGTAAGAGAAAAAGAAAAAAAATCATTCAACTCGGCAACTACTCAACTAGCTAACGGTAAAGCAGTAAACAGAACACCTCCTGCACCAGTAAT
1101 ---------+---------+---------+---------+---------+---------+---------+---------+---------+---------+ 1200
       Y  Y  V  R  E  K  E  K  K  S  F  N  S  A  T  T  Q  L  A  N  G  K  A  V  N  R  T  P  P  A  P  V  M -

     GTATCCTCATGGAATAATTTATGCTGTATCAGATGATGCTATAAGTAACATACTATCTAAAAGTAGTACACAGTTAACACTTGAAGAATTACAAAATCCT
1201 ---------+---------+---------+---------+---------+---------+---------+---------+---------+---------+ 1300
      Y  P  H  G  I  I  Y  A  V  S  D  D  A  I  S  N  I  L  S  K  S  S  T  Q  L  T  L  E  E  L  Q  N  P  -

     GACAATAGAAAACAAATTACTATTGACGATCTTAAAGACGAAAACAAAAGAAAAGAATTGATAACTAAAATAAAAAATAAAATTACAGAAGAAGAAGGGA
1301 ---------+---------+---------+---------+---------+---------+---------+---------+---------+---------+ 1400
     D  N  R  K  Q  I  T  I  D  D  L  K  D  E  N  K  R  K  E  L  I  T  K  I  K  N  K  I  T  E  E  E  G  K -

     AATTAAATGCATTAAAAGGAGATGTTGATAGTAAATTAGAGAAATTTAAGAAAATAGAAGGGGAATTTAAACCATTACTTGAAAAATTTTATGATGAAAG
1401 ---------+---------+---------+---------+---------+---------+---------+---------+---------+---------+ 1500
       L  N  A  L  K  G  D  V  D  S  K  L  E  K  F  K  K  I  E  G  E  F  K  P  L  L  E  K  F  Y  D  E  R -

     ACTTGATAATAGCATTACAACAGAGAATTTTGAAAAATTTTTAAGTAAAAGAACAGAATATTTAACGGAAAAGAATTTGCTTGAAAGCTCTTCTTACGAA
1501 ---------+---------+---------+---------+---------+---------+---------+---------+---------+---------+ 1600
      L  D  N  S  I  T  T  E  N  F  E  K  F  L  S  K  R  T  E  Y  L  T  E  K  N  L  L  E  S  S  S  Y  E  -

     TTGTCGAAAGCATTGGTAAAGAAATTAAAAAAGCAACTTATGTATTTAGAAGACTATTCATTAAGAAAAGAAGTATTTGATGAAGAGGTAAATCATTTCA
1601 ---------+---------+---------+---------+---------+---------+---------+---------+---------+---------+ 1700
     L  S  K  A  L  V  K  K  L  K  K  Q  L  M  Y  L  E  D  Y  S  L  R  K  E  V  F  D  E  E  V  N  H  F  N -

     ACTGCTTAGACTTACAATTAAATGCTGATATTCATAAATTAGAAAGTGAAATTAAAAGAAAAGAAAATTTACTTACAGTAGTTGATACCTTAAAATTTTC
1701 ---------+---------+---------+---------+---------+---------+---------+---------+---------+---------+ 1800
       C  L  D  L  Q  L  N  A  D  I  H  K  L  E  S  E  I  K  R  K  E  N  L  L  T  V  V  D  T  L  K  F  S -
          PmMSP1-F5
     AGATGTCGTGGAATTACAAGTACAAAAAGTATTATTAGGTAAAAAAATAGGACAACTAAAAAAATGTAGAAGCATTTTTACAAAAAGCAAAATTAAAAGAA
1801 ---------+---------+---------+---------+---------+---------+---------+---------+---------+---------+ 1900
      D  V  V  E  L  Q  V  Q  K  V  L  L  G  K  K  I  G  Q  L  K  N  V  E  A  F  L  Q  K  A  K  L  K  E  -
```

FIGURE 5B

```
     ACGTTTCACATCCCCCAAGCATACGGAACAGGAGAACAATCCGAACCATACTATTTAATTGCACTAAAGAGGGAAATTGATAAATTAAATATTTCTATTC
1901 ---------+---------+---------+---------+---------+---------+---------+---------+---------+---------+ 2000
     T  F  H  I  P  Q  A  Y  G  T  G  E  Q  S  E  P  Y  Y  L  I  A  L  K  R  E  I  D  K  L  N  I  S  I  P -

     CAAAAATTGAGGAAATGTTAAAAAATGAGAAAAAACTGGAGGAAGAAAAAATCAAGGCGGCAGCACAAAATGTAAGCGGCCATGTTTCCGGAGCAGATGA
2001 ---------+---------+---------+---------+---------+---------+---------+---------+---------+---------+ 2100
      K  I  E  E  M  L  K  N  E  K  K  L  E  E  E  K  I  K  A  A  A  Q  N  V  S  G  H  V  S  G  A  D  E  -

     AACATCAAACAGTCATGGATCATCTGGAGGAGGAGGATCAACACAAACAGTAACGACAACACCATCAACTACAACAACAGCAACTACATCATCACAAACA
2101 ---------+---------+---------+---------+---------+---------+---------+---------+---------+---------+ 2200
      T  S  N  S  H  G  S  S  G  G  G  G  S  T  Q  T  V  T  T  T  P  S  T  T  T  T  A  T  T  S  S  Q  T  -

     GTATCAGTAGGAGAAACAGGATCAGCACAAGCACAAGCACAACCACAACCACAACCACAACCACAACCACAAACACAAACACAAACACAAACACAACCAC
2201 ---------+---------+---------+---------+---------+---------+---------+---------+---------+---------+ 2300
     V  S  V  G  E  T  G  S  A  Q  A  Q  A  Q  P  Q  P  Q  P  Q  P  Q  P  Q  T  Q  T  Q  T  Q  T  Q  P  Q -

     AAGCAGCAGGAGCAACGGGAACACCAGGACAATCAGGACAATCAGGACAATCAGGACAATCAGGAGCTGAAGGAACAACAGAAACTACGGGAACAACAGG
2301 ---------+---------+---------+---------+---------+---------+---------+---------+---------+---------+ 2400
      A  A  G  A  T  G  T  P  G  Q  S  G  Q  S  G  Q  S  G  Q  S  G  A  E  G  T  T  E  T  T  G  T  T  G  -

     ACAGGCAGGAACAACGGGAACACCAGAACAAGCAGCAGCTGCAGGACCACAAGCAGAAACTACGGCAACACCAGGACAAGCAGGAGCTGCAGGAGCTGCA
2401 ---------+---------+---------+---------+---------+---------+---------+---------+---------+---------+ 2500
      Q  A  G  T  T  G  T  P  E  Q  A  A  A  A  G  P  Q  A  E  T  T  A  T  P  G  Q  A  G  A  A  G  A  A  -

     GGACCACAAGCAGAAACTACGGGAACACCAGGACAAGCGGGAGCTGCAGGACCACAAACAGAGACAGAAGTAGAAGAAACTCAGGAAATTGGAATCGTTG
2501 ---------+---------+---------+---------+---------+---------+---------+---------+---------+---------+ 2600
     G  P  Q  A  E  T  T  G  T  P  G  Q  A  G  A  A  G  P  Q  T  E  T  E  V  E  E  T  Q  E  I  G  I  V  V -

     TTCCGACATTGTCCAAATTGCAATATCTTGAAAAGCTATATGACTTTTTGAAAACTGCTTATGTGTGTCATATCAACATTTTGGTAAATAACTCAACCAT
2601 ---------+---------+---------+---------+---------+---------+---------+---------+---------+---------+ 2700
      P  T  L  S  K  L  Q  Y  L  E  K  L  Y  D  F  L  K  T  A  Y  V  C  H  I  N  I  L  V  N  N  S  T  M  -

     GAATGAAACGTTACTACAACAATATAAACTGAAGATAGAAGAAGATAAGAAATTATTAGAGAAGTGCGACCAATTAGATTTGTTATTTAATGTTCAGAAT
2701 ---------+---------+---------+---------+---------+---------+---------+---------+---------+---------+ 2800
      N  E  T  L  L  Q  Q  Y  K  L  K  I  E  E  D  K  K  L  L  E  K  C  D  Q  L  D  L  L  F  N  V  Q  N  -

     AACTTACAAGTCATGTATTCAATGTATGACAGTGTGAGCAATGTTCTACAAAATCAGTACAAAGAATTAAACCAAAAGGAAATGATTTATAATATTTATA
2801 ---------+---------+---------+---------+---------+---------+---------+---------+---------+---------+ 2900
     N  L  Q  V  M  Y  S  M  Y  D  S  V  S  N  V  L  Q  N  Q  Y  K  E  L  N  Q  K  E  M  I  Y  N  I  Y  K -

     AACTGGTGAAGAAGAATGACAAACTTAAAAACTTCTTAAACTTAACTGCAAACAGTGCAGCTGCATCTTCGGCATTACCACCTCCACCATCAGTACCACC
2901 ---------+---------+---------+---------+---------+---------+---------+---------+---------+---------+ 3000
      L  V  K  K  N  D  K  L  K  N  F  L  N  L  T  A  N  S  A  A  A  S  S  A  L  P  P  P  P  S  V  P  P  -

     TGCAGTACCACCAGCATCACAACAGCCACAACCTCAAGCAGCATTACCAGCACAACCTCAAGCAGCAGTACCAGCACAATCTCAAGCAACAGTACCAGCA
3001 ---------+---------+---------+---------+---------+---------+---------+---------+---------+---------+ 3100
      A  V  P  P  A  S  Q  Q  P  Q  P  Q  A  A  L  P  A  Q  P  Q  A  A  V  P  A  Q  S  Q  A  T  V  P  A  -

     CAATCTCAAGCAGCAGTACCAGCAACAACTCAATCCTCATCGGTATCAGCACCAACAGGTACAAATGGTGCATCCCCAGCAACTCCTGTAGCTCCAGCTG
3101 ---------+---------+---------+---------+---------+---------+---------+---------+---------+---------+ 3200
     Q  S  Q  A  A  V  P  A  T  T  Q  S  S  S  V  S  A  P  T  G  T  N  G  A  S  P  A  T  P  V  A  P  A  G -

     GTAGTGAAAATGCGATTCAGTTAAAAGCGAATGACAACGAGGACGATGCAAATGAACTAGATTTCGACATTGACGATATTTATATAAAATACTTAGAACA
3201 ---------+---------+---------+---------+---------+---------+---------+---------+---------+---------+ 3300
      S  E  N  A  I  Q  L  K  A  N  D  N  E  D  D  A  N  E  L  D  F  D  I  D  D  I  Y  I  K  Y  L  E  Q  -
           PmMSP1-R5
     AGTGAGCAAATACGACGAGAACTTCAAAAATTTTATAGAGTCCAAAAAAGATATAATAAATAAGATGAGCGAAAGTGAATGGAAAGAATTAGGAGAAGAA
3301 ---------+---------+---------+---------+---------+---------+---------+---------+---------+---------+ 3400
      V  S  K  Y  D  E  N  F  K  N  F  I  E  S  K  K  D  I  I  N  K  M  S  E  S  E  W  K  E  L  G  E  E  -

     ATCAACACATTGAAACAAGATATACAATCATCATTTGATAATTTTGGAAAATATAAACTTAAATTGGAAAGATTATTAAAAAAGAAAAATAAAATTACAA
3401 ---------+---------+---------+---------+---------+---------+---------+---------+---------+---------+ 3500
     I  N  T  L  K  Q  D  I  Q  S  S  F  D  N  F  G  K  Y  K  L  K  L  E  R  L  L  K  K  K  N  K  I  T  S -

     GCAGTACTAATCATATTAAAGAATATAGTATTTTAAAAGCACAATTATTAAGGAAAAAAAATATTCTAAATAACCCAAGACATGTACTAGCAGCTTTTGT
3501 ---------+---------+---------+---------+---------+---------+---------+---------+---------+---------+ 3600
      S  T  N  H  I  K  E  Y  S  I  L  K  A  Q  L  L  R  K  K  N  I  L  N  N  P  R  H  V  L  A  A  F  V  -

     AGTATTCTTTAATAAAAAGATAGAAGCAGAAAAGAAAGAAGTTGAAAATGCTTTAAAAAATACTGATATTATGTTGAAATATTATAAGGCAAGAACCAAA
3601 ---------+---------+---------+---------+---------+---------+---------+---------+---------+---------+ 3700
      V  F  F  N  K  K  I  E  A  E  K  K  E  V  E  N  A  L  K  N  T  D  I  M  L  K  Y  Y  K  A  R  T  K  -

     TATTATATTAGTGAAGCATTCCCCTTAAAAACAATAACTGAACAATCACTTCAAAAAGAAATTAACTATTTACATTTAGAAAAATTTAAAGTATATAGTA
3701 ---------+---------+---------+---------+---------+---------+---------+---------+---------+---------+ 3800
     Y  Y  I  S  E  A  F  P  L  K  T  I  T  E  Q  S  L  Q  K  E  I  N  Y  L  H  L  E  K  F  K  V  Y  S  R -

     GATTAGAAGGACGCATTAAGAAAATGTTGAATTTAGAAAAAGAAAATATTACCTACTTATCTGGTGGATTACATCATGTACTTACAGAATTAAAAGAGAT
3801 ---------+---------+---------+---------+---------+---------+---------+---------+---------+---------+ 3900
      L  E  G  R  I  K  K  M  L  N  L  E  K  E  N  I  T  Y  L  S  G  G  L  H  H  V  L  T  E  L  K  E  I  -
```

FIGURE 5C

```
     CATAAATGATAAAACATACACCGGTTATACACATACTAAAAATAACGAAGAAGTTAACAAAGCGTTAAATGTTTATGAGGAATTGCTTCCAAAGCAAATA
3901 ---------+---------+---------+---------+---------+---------+---------+---------+---------+---------+ 4000
      I  N  D  K  T  Y  T  G  Y  T  H  T  K  N  N  E  E  V  N  K  A  L  N  V  Y  E  E  L  L  P  K  Q  I  -

     TCCACAGAAGAGCAACCGGATAATGCATTAGCAGATGGAACGGAAAATGCAACAGAAGGTGCAGAAGTGCGTGCAGCAACTGCAGAAAGTTTAGTGCAGG
4001 ---------+---------+---------+---------+---------+---------+---------+---------+---------+---------+ 4100
     S  T  E  E  Q  P  D  N  A  L  A  D  G  T  E  N  A  T  E  G  A  E  V  R  A  A  T  A  E  S  L  V  Q  G -

     GAGAAGATGAGTACCCTGAAGAAGTTGATGAGGTGATCGTGTTTCCCATTGTGGGTAAGAAAGAAAAGGAAAATCCATTAGATCAAATAACAAAAGGACA
4101 ---------+---------+---------+---------+---------+---------+---------+---------+---------+---------+ 4200
       E  D  E  Y  P  E  E  V  D  E  V  I  V  F  P  I  V  G  K  K  E  K  E  N  P  L  D  Q  I  T  K  G  Q  -
                                                                                      PmMSP1-R4
     AGCTGAAACTAAACAAGATGATAATATATTGAAACCAATTACAAATGAGTATGAAGTATTATATATTAAACCATTAGCTGGAGTATATAGAGTTTTAAGA
4201 ---------+---------+---------+---------+---------+---------+---------+---------+---------+---------+ 4300
      A  E  T  K  Q  D  D  N  I  L  K  P  I  T  N  E  Y  E  V  L  Y  I  K  P  L  A  G  V  Y  R  V  L  R  -

     AAACAAATAGGAGATCAGATAGACGCTTTTAATAGTAATTTGACAAATGCTTTGGATACTCGAAAAAAGAAAAGAACATATTTCTTAGATGTATTAAATT
4301 ---------+---------+---------+---------+---------+---------+---------+---------+---------+---------+ 4400
     K  Q  I  G  D  Q  I  D  A  F  N  S  N  L  T  N  A  L  D  T  R  K  K  K  R  T  Y  F  L  D  V  L  N  S -

     CTGATTTAATTCAATTTAAACATGCAACTTCCGACAGTTATATTATAAAAGATCCGTATAAACTATTAGATGTTGATAAGAAAGCGAAGCTTATAGGTAG
4401 ---------+---------+---------+---------+---------+---------+---------+---------+---------+---------+ 4500
       D  L  I  Q  F  K  H  A  T  S  D  S  Y  I  I  K  D  P  Y  K  L  L  D  V  D  K  K  A  K  L  I  G  S  -

     CTATAAATATATCGTCTCTGCAATAGAAAAGGATATCACTTCAGCTGAGAACGGAGTAGAATATTATGATAAGATGACCAAGTTGTACAAGACTCAGTTA
4501 ---------+---------+---------+---------+---------+---------+---------+---------+---------+---------+ 4600
      Y  K  Y  I  V  S  A  I  E  K  D  I  T  S  A  E  N  G  V  E  Y  Y  D  K  M  T  K  L  Y  K  T  Q  L  -

     GAAGCAGTAAAAAGCGCAATTGCTGAAGCACAAAAAGAGGGTGATAAAAAAACTGAAAATGAAAAATATATTCCATTCTTAACGAACATGCAGACATTAT
4601 ---------+---------+---------+---------+---------+---------+---------+---------+---------+---------+ 4700
     E  A  V  K  S  A  I  A  E  A  Q  K  E  G  D  K  K  T  E  N  E  K  Y  I  P  F  L  T  N  M  Q  T  L  Y -

     ATGAAAATTTATTGAATAAAATAAATGGAAACATAATAAATTTAAAAACTTTAATTACAAACTGTAATTTAGAAAAAGATGCAGTAAACATTACTATAAG
4701 ---------+---------+---------+---------+---------+---------+---------+---------+---------+---------+ 4800
       E  N  L  L  N  K  I  N  G  N  I  I  N  L  K  T  L  I  T  N  C  N  L  E  K  D  A  V  N  I  T  I  S  -

     TAAATTAACAGAATACAGCAAATTTGATGAAAAAATAGAAATGTTTAAAAACTCTAAAAATGAAAAGGATATAGCAAGTTCTGGAATATTAGACATACTT
4801 ---------+---------+---------+---------+---------+---------+---------+---------+---------+---------+ 4900
      K  L  T  E  Y  S  K  F  D  E  K  I  E  M  F  K  N  S  K  N  E  K  D  I  A  S  S  G  I  L  D  I  L  -
                                                                     PmMSP1-F3
     AAACAAAAAGGACTTGTTAATAAAAATGAATCAACTAAGATTATATCAGAATTACTTGGTGTAGACTCTAATGCATTACTGAATATTAGCGCAAAACATG
4901 ---------+---------+---------+---------+---------+---------+---------+---------+---------+---------+ 5000
     K  Q  K  G  L  V  N  K  N  E  S  T  K  I  I  S  E  L  L  G  V  D  S  N  A  L  L  N  I  S  A  K  H  A -
                                                PmMSP1-F6                                     PmMSP1-R3
     CATGTACCGAAACAAAATATCCTGAAAATGCAGGATGTTATAGATATGAAGACGGAAAAGAAGTATGGAGATGCTTATTAAATTATAAACTAGTTGATGG
5001 ---------+---------+---------+---------+---------+---------+---------+---------+---------+---------+ 5100
      C  T  E  T  K  Y  P  E  N  A  G  C  Y  R  Y  E  D  G  K  E  V  W  R  C  L  L  N  Y  K  L  V  D  G  -
                  PmMSP1-R2
     AGGATGTGTTGAAGATGAAGAGCCTTCTTGTCAAGTTAACAATGGAGGATGTGCTCCTGAAGCTAACTGTACCAAAGGAGATGACAACAAAATTGTCTGT
5101 ---------+---------+---------+---------+---------+---------+---------+---------+---------+---------+ 5200
      G  C  V  E  D  E  E  P  S  C  Q  V  N  N  G  G  C  A  P  E  A  N  C  T  K  G  D  D  N  K  I  V  C  -

     GCTTGTAACGCACCCTATTCTGAACCTATATTTGAAGGTGTTTTCTGTGGTTCTTCAAGTTTCCTCGGCTTATCACTATTATTAGCAGCTTTATTAATTA
5201 ---------+---------+---------+---------+---------+---------+---------+---------+---------+---------+ 5300
     A  C  N  A  P  Y  S  E  P  I  F  E  G  V  F  C  G  S  S  S  F  L  G  L  S  L  L  L  A  A  L  L  I  M -
                                PmMSP1-R9
     TGTTTAACTTACTTTAAGAAAAAAAGACAGAAAAGAAGGATACGAATGAACATAAAATGAGAAGGATTAAGACTGAGCAAGAGGAAAAGAGAGAAAATCA
5301 ---------+---------+---------+---------+---------+---------+---------+---------+---------+---------+ 5400
       F  N  L  L  *                                                                                     -

     TAGATC
5401 ------ 5406
         -
```

Gray = Signal Peptide
Inverse = Cysteine Residues
Bold = MSP1-p33
*Italics* = MSP1-p19
Brackets = Primer Sites
* (Degenerate As primer sequences not shown)

FIGURE 6

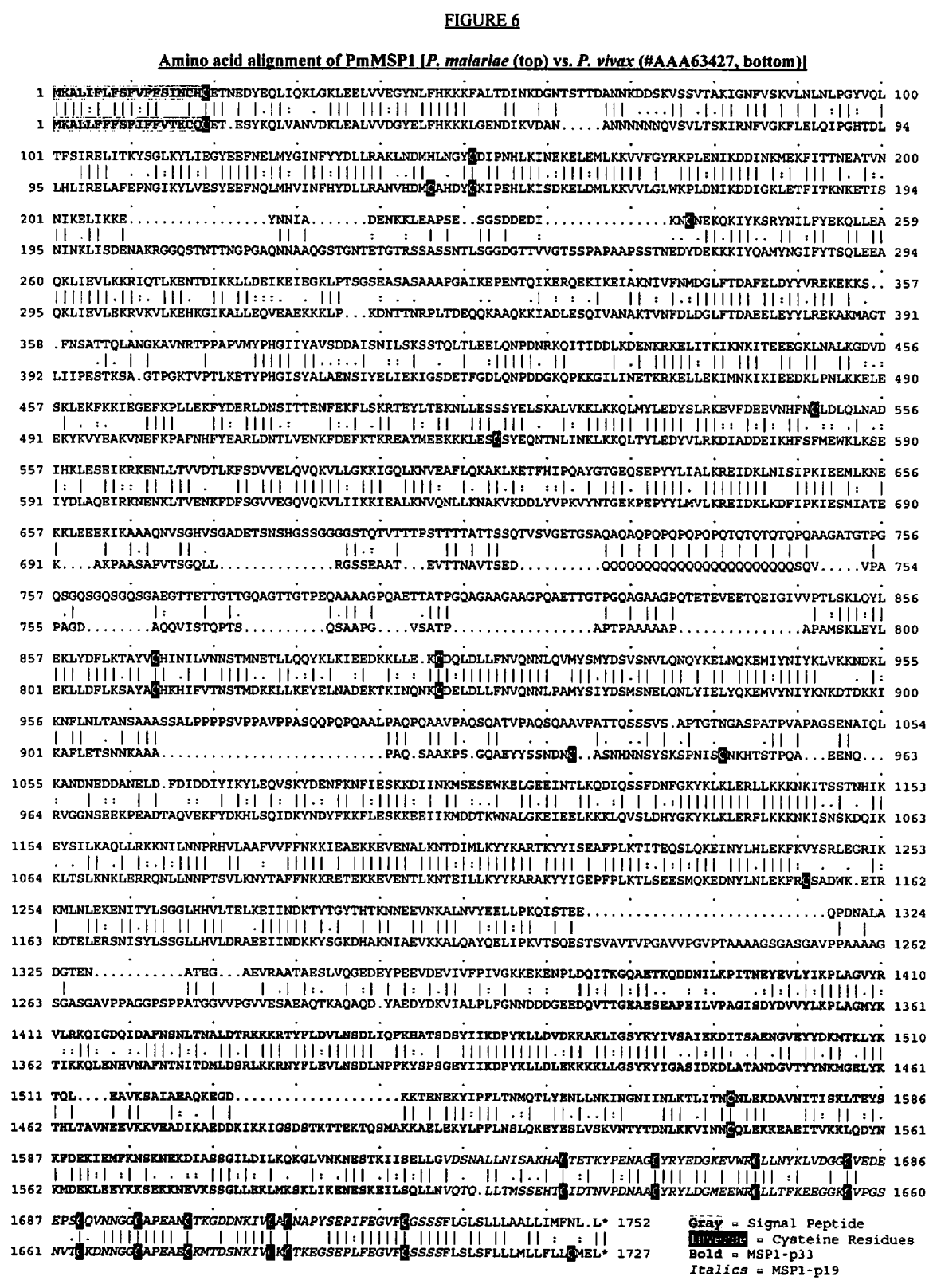

**Amino acid alignment of PmMSP1 [*P. malariae* (top) vs. *P. vivax* (#AAA63427, bottom)]**

```
  1 MKALIFLFSFVPFSINCHETNEDYEQLIQKLGKLEELVVEGYNLFHKKKFALTDINKDGNTSTTDANNKDDSKVSSVTAKIGNFVSKVLNLNLPGYVQL 100
    |||||:| |||:||  | |||  |.||:  . ||| |||:|| |||||   || .||       ||| ....||  .|.|| ||| | ||  ::||:  |
  1 MKALLFFFSPIFFVTKCQQET.ESYKQLVANVDKLEALVVDGYELFHKKKLGENDIKVDAN.....ANNNNNNQVSVLTSKIRNFVGKFLELQIPGHTDL 94

101 TFSIRELITKYSGLKYLIEGYEEFNELMYGINFYYDLLRAKLNDMHLNGYKDIPNHLKINEKELEMLKKVVFGYRKPLENIKDDINKMEKFITTNEATVN 200
    ||||  . .|:|||:| |||||:||  |||:||||||  ..||  . || . || |  ||||.:|||:||||| |  |||:||||||  |:| ||| |. |:.
 95 LHLIRELAFEPNGIKYLVESYEEFNQLMHVINFHYDLLRANVHDMEAHDYGKIPEHLKISDKELDMLKKVVLGLWKPLDNIKDDIGKLETFITKNKETIS 194

201 NIKELIKKE................YNNIA.......DENKKLEAPSE..SGSDDEDI...............KNGNEKQKIYKSRYNILFYEKQLLEA 259
    | .|| |         ||  |       :  : || ||| :        ..||.|||..  ||  :||    || ||
195 NINKLISDENAKRGGQSTNTTNGPGAQNNAAQGSTGNTETGTRSSASSNTLSGGDGTTVVGTSSPAPAAPSSTNEDYDEKKKIYQAMYNGIFYTSQLEEA 294

260 QKLIEVLKKRIQTLKENTDIKKLLDEIKEIEGKLPTSGSEASASAAAPGAIKEPENTQIKERQEKIKEIAKNIVFNMDGLFTDAFELDYYVREKEKKS.. 357
    |||||||.||:. |||. || || ||:::.   |||            :..     .| : : .|   ||:|:||||||||| ||:||.||| | .
295 QKLIEVLEKRVKVLKEHKGIKALLEQVEAEKKKLP...KDNTTNRPLTDEQQKAAQKKIADLESQIVANAKTVNFDLDGLFTDAEELEYYLREKAKMAGT 391

358 .FNSATTQLANGKAVNRTPPAPVMYPHGIIYAVSDDAISNILSKSSTQLTEELQNPDNRKQITIDDLKDENKRKELITKIKNKITEEEGKLNALKGDVD 456
    .|.| |    | ||||||  | |:|    .|.  |  |:| ||||| ||  .|. |  .|  ||||||| ||:|.  ||  ||| || || ||  | :.:
392 LIIPESTKSA.GTPGKTVPTLKETYPHGISYALAENSIYELIEKIGSDETFGDLQNPDDGKQPKKGILINETKRKELLEKIMNKIKIEEDKLPNLKKELE 490

457 SKLEKFKKIEGEFKPLLEKFYDERLDNSITTENFEKFLSKRTEYLTEKNLLESSSYELSKALVKKLKKQLMYLEDYSLRKEVFDEEVNHFNGLDLQLNAD 556
    |  . :.     ||||    ||  ||||:     |:  ||  |  .|| ||:  ||||::||     || :|: ||: .: .|
491 EKYKVYEAKVNEFKPAFNHFYEARLDNTLVENKFDEFKTKREAYMEEKKKLESGSYEQNTNLINKLKKQLTYLEDYVLRKDIADDEIKHFSFMEWKLKSE 590

557 IHKLESEIKRKENLLTVVDTLKFSDVVELQVQKVLLGKKIGQLKNVEAFLQKAKLKETFHIPQAYGTGEQSEPYYLIALKREIDKLNISIPKIEEMLKNE 656
    |:|  | || :: ||  |||  .    || |||||||||: ||| ||||:  |. ||.|.:  ::|. | |||. |||||. ||||||||         |||| |:    |
591 IYDLAQEIRKNENKLTVENKPDFSGVVEGQVQKVLIIKKIEALKNVQNLLKNAKVKDDLYVPKVYNTGEKPEPYYLMVLKREIDKLKDFIPKIESMIATE 690

657 KKLEEEKIKAAAQNVSGHVSGADETSNSHGSSGGGGSTQTVTTTPSTTTTATTSSQTVSVGETGSAQAQAQPQPQPQPQTQTQTQPQAAGATGTPG 756
    |   |  |.|        ||  ||:  |             ||.:  |     ||  |||        |||||||||||  |
691 K....AKPAASAPVTSGQLL..............RGSSEAAT...EVTTNAVTSED..........QQQQQQQQQQQQQQQQQQQQSQV.....VPA 754

757 QSGQSGQSGQSGAEGTTETTGTTGQAGTTGTPEQAAAAGPQAETTATPGQAGAAGAAGPQAETTGTPGQAGAAGPQTETEVEETQEIGIVVPTLSKLQYL 856
    .|     |:     |   |.       |.|| .|||         | |||          |  | |||          |:|||:||
755 PAGD........AQQVISTQPTS..........QSAAPG....VSATP................APTPAAAAAP..............APAMSKLEYL 800

857 EKLYDFLKTAYVEHINILVNNSTMNETLLQQYKLKIEEDKKLLE.KGDQLDLLFNVQNNLQVMYSMYDSVSNVLQNQYKELNQKEMIYNIYKLVKKNDKL 955
    |||  |||||.|| |  || ||.. ||.:|.|  :| |  | :  ||:|||||||||||  |||.|||.|| ||| | || ||||:|||||     .|:
801 EKLLDFLKSAYAEHKHIFVTNSTMDKKLLKEYELNADEKTKINQNKGDELDLLFNVQNNLPAMYSIYDSMSNELQNLYIELYQKEMVYNIYKNKDTDKKI 900

956 KNFLNLTANSAAASSALPPPPSVPPAVPPASQQPQPQAALPAQPQPQAAVPAQSQATVPAQSQAAVPATTQSSSVS.APTGTNGASPATPVAPAGSENAIQL 1054
    | ||  . | |||                          || ||| ||    ||  ||  .||
901 KAPLETSNNKAAA...................PAQ.SAAKPS.GQAEYYSSNDNG.ASNHNNSYSKSPNISGNKHTSTPQA...EENQ... 963

1055 KANDNEDDANELD.FDIDDIYIKYLEQVSKYDENFKNFIESKKDIINKMSESEWKELGEEINTLKQDIQSSFDNFGKYKLKLERLLKKKNKITSSTNHIK 1153
     :    |::   ||    :: ||:| |: || : ||  |:|||| | : ..  ||.||  |  :|||||||||||  |||||||..|  ||
 964 RVGGNSEEKPEADTAQVEKFYDKHLSQIDKYNDYFKKFLESKKEEIIKMDDTKWNALGKEIEELKKKLQVSLDHYGKYKLKLERFLKKKNKISNSKDQIK 1063

1154 EYSILKAQLLRKKNILNNPRHVLAAFVVFFNKKIEAEKKEVENALKNTDIMLKYYKARTKYYISEAFPLKTITEQSLQKEINYLHLEKPFKVYSRLEGRIK 1253
     .. ||  | |:.|:|||| || : ||||| :|||||||||||::|:||||| ||||  |:|:||| |||:|||.  . |:
1064 KLTSLKNKLERRQNLLNNPTSVLKNYTAFFNKKRETEKKEVENTLKNTEILLKYYKARAKYYIGEPFPPLKTLSEESMQKEDNYLNLEKFREGSADWK.EIR 1162

1254 KMLNLEKENITYLSGGLHHVLTELKEIINDKTYTGYTHTKNNEEVNKALNVYEELLPKQISTEE................QPDNALA 1324
      ||: ||.|||  ||   .|||||||| |.|  || | |||  ||:||:||    | |                                        ||
1163 KDTELERSNISYLSSGLLHVLDRAEEIINDKKYSGKDHAKNIAEVKKALQAYQELIPKVTSQESTSVAVTVPGAVVPGVPTAAAAGSGASGAVPPAAAAG 1262

1325 DGTEN...........ATEG...AEVRAATAESLVQGEDEYPEEVDEVIVFPIVGKKEKENPLDQITKGQAETKQDDNILKPITNEYEVLYIKPLAGVYR 1410
          |    ||  .|:.:  .| | |:.|.|| |:  |   :  ||:| |:||..  :   .:|:|.|:|||||.|:
1263 SGASGAVPPAGGPSPPATGGVVPGVVESAEAQTKAQAQD.YAEDYDKVIALPLFGNNDDDGEEDQVTTGEABSBEAPEILVPAGISDYDVVYLKPLAGMYK 1361

1411 VLRKQIGDQIDAPNSNLTNALDTRKEKKRTYPLDVLNSDLIQFKBATSDBYIIKDPYKLLDVDKKAKLIGSYKYIVSAIEKDITSAENGVEYYDKMTKLYK 1510
      ::||: . . :|||.:|: ||..:. ||| |::| :|||:  |  :. ||  ||: ||..:   ||:.|| | |:  | |:|||||: |.| .:
1362 TIKKQLENHVNAFNTNITDMLDSRLKKRNYPLEVLNSDLNPPFKYSPSGEYIIKDPYKLLDLEKKKKLLGSYKYIGASIDKDLATANDGVTYYNKMGELYK 1461

1511 TQL....EAVKSAIAEAQKEGD.................KKTENEKYIPPLTNMQTLYENLLNKINGNIINLKTLITNQNLEKDAVNITISKLTEYS 1586
     |  |   |||   |: ||                       || :|:||:|   ..| |:.. .|     | |||     ||  ||:   || :|.
1462 THLTAVNEEVKKVEADIKAEDDIKKIIGSDSTKTTEKTQSMARKAELEKYLPPLNSLQKEYESLVSKVNTYTDNLKKVINNGQLEKKEAEITVKKLQDYN 1561

1587 KFDEKIEMFKNSKMEKDIASSGILDILKQKGLVNKNESTKIISELLGVDSNALLNISAKHAGTETKYPENAGGYRYEDGKEVVRGLLNYKLVDGGGVEDE 1686
     | |||:| :| :| .  .::  |||:|  |.    .|| .|:|:|  ||  ..|.|:||:    || ::|   :    |:|  |:||| | |||:  :|  |  ||
1562 KMDEKLEEYKKSEKKNEVKSSGLLEKLMKSKLIKENESKEILSQLLNVQTQ.LLTMSSEHTGIDTNVPDNAAGYRYLDGMEEWRGLLTFKEEGGKGVPGS 1660

1687 EPSGQVNNGGGAPEANGTKGDNKIVGAGNAPYSEPIPEGVFGGSSSFLGLSLLLAALLIMFNL.L* 1752            Gray = Signal Peptide
     .|. |||||||  || |||||  |||:|||||| ||||:||||| ||||| ||  ||  | : ||                Inverse = Cysteine Residues
1661 NVTGKDNNGGGAPEAEGKMTDSNKIVKGTKEGSEPLFEGVFGSSSSPLSLSFLLLMLLFLLGMEL* 1727            Bold = MSP1-p33
                                                                                        *Italics* = MSP1-p19
```

FIGURE 7

**Alignment of *P. malariae* (Cameroon 0014) vs. *P. malariae* GenBank sequence AF138881 MSP1 5'-DNA sequence**

```
0014      1    AAATGAAGATTATGAACAACTTATTCAAAAGTTGGGAAAACTGGAGGAACTAGTTGTAGA    60
               ||||||||||||||||||||||| ||||||||||||||||||||||||||||||||||||
AF138881  30   AAATGAAGATTATGAACAACTCATTCAAAAGTTGGGAAAACTGGAGGAACTAGTTGTAGA    89

0014      61   AGGGTATAACCTATTTCACAAAAAAAAATTTGCCTTAACAGACATTAATAAGGATGGTAA   120
               ||||||||||||||||||||||||||||||||||||||||||||||||||||||||||||
AF138881  90   AGGGTATAACCTATTTCACAAAAAAAAATTTGCCTTAACAGACATTAATAAGGATGGTAA   149

0014      121  TACCAGTACTACTGATGCAAATAATAAAGATGATAGTAAGGTTTCCTCCGTAACAGCAAA   180
               ||||||||||||||||||||||||||||||||||||||||||||||||||||||||||||
AF138881  150  TACCAGTACTACTGATGCAAATAATAAAGATGATAGTAAGGTTTCCTCCGTAACAGCAAA   209

0014      181  AATAGGAAATTTTGTTAGCAAAGTTCTAAACCTGAATTTGCCAGGTTATGTTCAGTTAAC   240
               |||||||||||||| |||||||||||||||||||||||||||||||||||||||||||||
AF138881  210  AATAGGAAATTTTGTCAGCAAAGTTCTAAACCTGAATTTGCCAGGTTATGTTCAGTTAAC   269

0014      241  TTTTTCAATTAGGGAATTAATTACAAAGTACAGTGGTTTGAAATATCTAATTGAAGGATA   300
               |||||||||||||||||||||||||||||||||||||||| |||||||||||||||||||
AF138881  270  TTTTTCAATTAGGGAATTAATTACAAAGTACAGTGGTTTGAAAAATCTAATTGAAGGATA   329

0014      301  TGAAGAATTCAATGAATTAATGTATGGAATTAATTTTTACTATGATTTATTAAG        354
               |||||||||||||||||||||||||||||||||||| ||| |||||||||||||||
AF138881  330  TGAAGAATTCAATGAATTAATGTATGGAATTAACTTTCACTATGATTTATTAAGGGCA    383
```

FIGURE 8A

PoMSP1 gene sequence and translation

```
                                                   As1*
     AATTCAAAAAATGAAGGTGTTCGTATTTGCGCTCTCTTTCATTTTTTTATTGTGAACTGTCAATGTGAAACGCTCGAAAATTATAAAGAGCTTCTTCATA
   1 ---------+---------+---------+---------+---------+---------+---------+---------+---------+---------+ 100
                M  K  V  F  V  F  A  L  S  F  I  F  F  I  V  N  C  Q  C  E  T  L  E  N  Y  K  E  L  L  H  K  -

     AGTTAAATAATTTGGAAGCTCTAGTGGTTGATGGCTACAACTTATTTCACAAAACTCCCTTAACCCTACAAAAGTTAGAAACTGAAGTCACAACTACTGG
 101 ---------+---------+---------+---------+---------+---------+---------+---------+---------+---------+ 200
       L  N  N  L  E  A  L  V  V  D  G  Y  N  L  F  H  K  T  P  L  T  L  Q  K  L  E  T  E  V  T  T  T  G  -

                                                                                            PoMSP1-R6
     AAGAGGTAGTGGTAGCAGTACTACTTCTGTTTCCTCCATTCCAAGTGATGCAAGTAGAGCTGTATCTACCCGTGATTCTAATAGCAACATCAACAACCAA
 201 ---------+---------+---------+---------+---------+---------+---------+---------+---------+---------+ 300
       R  G  S  G  S  S  T  T  S  V  S  S  I  P  S  D  A  S  R  A  V  S  T  R  D  S  N  S  N  I  N  N  Q  -
         PoMSP1-F1         PoMSP1-F2
     GTGGTTAGCAAGTTAACAGCGGACATAAGATTCCTTCTATCAAGATTTTTGCAGTTAAATATTCCAGGACATGGAGATTTAATGCATTTCATAAGAGAAA
 301 ---------+---------+---------+---------+---------+---------+---------+---------+---------+---------+ 400
     V  V  S  K  L  T  A  D  I  R  F  L  L  S  R  F  L  Q  L  N  I  P  G  H  G  D  L  M  H  F  I  R  E  I  -
         PoMSP1-R3                                                                          As2*
     TTTCGTTAGATACAAACGGACTAAAATATCTAATAGAAGGATATGAAGAATTTAACGAGTTAATGTACATATTGAACTTTTATTATGATCTGTTCAGAGC
 401 ---------+---------+---------+---------+---------+---------+---------+---------+---------+---------+ 500
       S  L  D  T  N  G  L  K  Y  L  I  E  G  Y  E  E  F  N  E  L  M  Y  I  L  N  F  Y  Y  D  L  F  R  A  -

     TAAACTACATGATATGTGTGCAAATGATTATTGTGAAATACCAGACCATCTTAAAATTAGTGATAAGGAATTGGACATGCTCAAAAAAGTTGTATTAGGA
 501 ---------+---------+---------+---------+---------+---------+---------+---------+---------+---------+ 600
       K  L  H  D  M  C  A  N  D  Y  C  E  I  P  D  H  L  K  I  S  D  K  E  L  D  M  L  K  K  V  V  L  G  -

     TACAGAAAACCGTTAGAAAATATAAAAGACGATATTTCAAAAATGGAGACATTCATTCAAAAAAATACTCAAACAGTGGAAAATATAAAGGGCTTAATAG
 601 ---------+---------+---------+---------+---------+---------+---------+---------+---------+---------+ 700
     Y  R  K  P  L  E  N  I  K  D  D  I  S  K  M  E  T  F  I  Q  K  N  T  Q  T  V  E  N  I  K  G  L  I  E  -

     AGGCAGAAGAAAAAAAAAGGTATGGTGAGGTTGCAGTAAGTGGAAATACAGGAAGTGCAGGAGCTGCCTCAGGAACTAATGCATCTGCAAGTTCAGGCCA
 701 ---------+---------+---------+---------+---------+---------+---------+---------+---------+---------+ 800
       A  E  E  K  K  R  Y  G  E  V  A  V  S  G  N  T  G  S  A  G  A  A  S  G  T  N  A  S  A  S  S  G  Q  -

     AGAAAATTCTTCTACTGAAAGCGAAACAGAAAAGTATAACAAAGCTAAAGCTTTATATCAATCCATATATAACGCCTTATTTTACAAAAAGCAGTTAACA
 801 ---------+---------+---------+---------+---------+---------+---------+---------+---------+---------+ 900
       E  N  S  S  T  E  S  E  T  E  K  Y  N  K  A  K  A  L  Y  Q  S  I  Y  N  A  L  F  Y  K  K  Q  L  T  -

     GAAGCAGAAAAATTAATCGAAGTTTTAAAAAAGCGTGTGCAAACGTTAAAAGAGCACAAAGAGATAAAAAAATTACTCGAAGAAATCGCGGAAAAGGAAA
 901 ---------+---------+---------+---------+---------+---------+---------+---------+---------+---------+ 1000
     E  A  E  K  L  I  E  V  L  K  K  R  V  Q  T  L  K  E  H  K  E  I  K  K  L  L  E  E  I  A  E  K  E  S  -

     GCAAAGTTACCCCACCGAGTAATACCGCTTCACAAACGCAACTGCAGGAAGAAATTAACAAACTTAAAACTCAAATTAAGAACATCGCAAAAACTGTAAA
1001 ---------+---------+---------+---------+---------+---------+---------+---------+---------+---------+ 1100
       K  V  T  P  P  S  N  T  A  S  Q  T  Q  L  Q  E  E  I  N  K  L  K  T  Q  I  K  N  I  A  K  T  V  K  -
                                              PoMSP1-F4
     ATTCGAAATGGAAGGTCTGTTTACTGATCCTGTTGAATTGGATTACTACTTACGAGAAAAGGACAAAAAGGCAAGTAAAGTAGTAGAAACACAAAGTGGT
1101 ---------+---------+---------+---------+---------+---------+---------+---------+---------+---------+ 1200
     F  E  M  E  G  L  F  T  D  P  V  E  L  D  Y  Y  L  R  E  K  D  K  K  A  S  K  V  V  E  T  Q  S  G  -

     TCAACAACTCCGCCTAAGCCTACGTATCCCAATGGTCTCATCTACCCTTTGGAAAAAGAAAACATCTCTGAGTTGTTATCAAAAGCCGTGACAGAAACAA
1201 ---------+---------+---------+---------+---------+---------+---------+---------+---------+---------+ 1300
     S  T  T  P  P  K  P  T  Y  P  N  G  L  I  Y  P  L  E  K  E  N  I  S  E  L  L  S  K  A  V  T  E  T  T  -

     CTTTTGGTGATTTACAAAATGTAGAAATTGGAAAAGCATTAAATAAAGAAATTTTCACGAATGATGATAAGAGAAATGAATTCATAGACAAACTTAAAAA
1301 ---------+---------+---------+---------+---------+---------+---------+---------+---------+---------+ 1400
       F  G  D  L  Q  N  V  E  I  G  K  A  L  N  K  E  I  F  T  N  D  D  K  R  N  E  F  I  D  K  L  K  N  -

     TAAAATTAAACAACAAGAAGAACTTTTATCTAAACAAAAAGTGGACTATGATGCAAAACTTAAATTGTACGAGGAGCAAAAGAAGAAAGCTATTCCCCTA
1401 ---------+---------+---------+---------+---------+---------+---------+---------+---------+---------+ 1500
       K  I  K  Q  Q  E  E  L  L  S  K  Q  K  V  D  Y  D  A  K  L  K  L  Y  E  E  Q  K  K  K  A  I  P  L  -

     TTTGAGCAGTTTCACAATGGAAAACTTGACAACACACTTATTCCTAGTAAATTCGAAGAATTTAAAGTAGAAAGAGACAAGTATATGCAACTCAAGAACG
1501 ---------+---------+---------+---------+---------+---------+---------+---------+---------+---------+ 1600
     F  E  Q  F  H  N  G  K  L  D  N  T  L  I  P  S  K  F  E  E  F  K  V  E  R  D  K  Y  M  Q  L  K  N  E  -

     AGTTAAAAAATTGTCCATACGAAATGACAAAAAACACGGTGGATAAGTTAAATAAACAACTTGCATATTTGAATGACTACTCATTGAGAAAAGAAGTTTT
1601 ---------+---------+---------+---------+---------+---------+---------+---------+---------+---------+ 1700
       L  K  N  C  P  Y  E  M  T  K  N  T  V  D  K  L  N  K  Q  L  A  Y  L  N  D  Y  S  L  R  K  E  V  F  -

     TAATAAAGAAGTTAAACATTTTACAGGATTAGAGTGGAAACTACAAACTGAAATTGACAAATTAGCAAACGAAATAAAGAAAAATGAAAATATACTTATA
1701 ---------+---------+---------+---------+---------+---------+---------+---------+---------+---------+ 1800
       N  K  E  V  K  H  F  T  G  L  E  W  K  L  Q  T  E  I  D  K  L  A  N  E  I  K  K  N  E  N  I  L  I  -

     ACAGCATCTACCTTACCATTATCTAATGTAGTAGAATTACAAGTACAAAAAGTATTAGTAGCAAAAAAAATTGAACTTTTAAAAAAAGTAGAAAAACTTT
1801 ---------+---------+---------+---------+---------+---------+---------+---------+---------+---------+ 1900
     T  A  S  T  L  P  L  S  N  V  V  E  L  Q  V  Q  K  V  L  V  A  K  K  I  E  L  L  K  K  V  E  K  L  L  -
```

FIGURE 8B

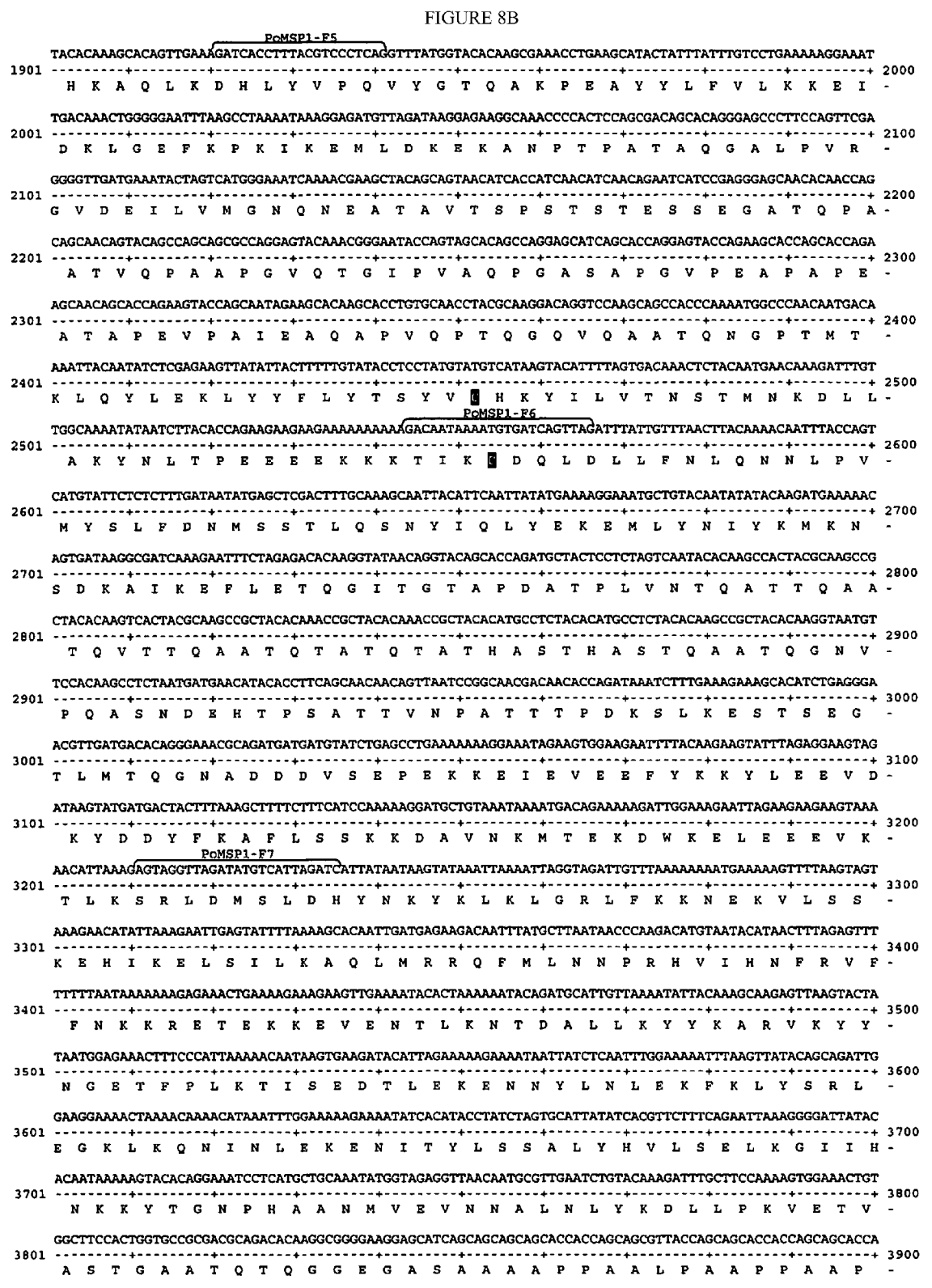

```
                      PoMSP1-F5
     TACACAAAGCACAGTTGAAAGATCACCTTTACGTCCCTCAGGTTTATGGTACACAAGCGAAACCTGAAGCATACTATTTATTTGTCCTGAAAAAGGAAAT
1901 ---------+---------+---------+---------+---------+---------+---------+---------+---------+---------+ 2000
      H  K  A  Q  L  K  D  H  L  Y  V  P  Q  V  Y  G  T  Q  A  K  P  E  A  Y  Y  L  F  V  L  K  K  E  I  -

     TGACAAACTGGGGGAATTTAAGCCTAAAATAAAGGAGATGTTAGATAAGGAGAAGGCAAACCCCACTCCAGCGACAGCACAGGGAGCCCTTCCAGTTCGA
2001 ---------+---------+---------+---------+---------+---------+---------+---------+---------+---------+ 2100
      D  K  L  G  E  F  K  P  K  I  K  E  M  L  D  K  E  K  A  N  P  T  P  A  T  A  Q  G  A  L  P  V  R  -

     GGGGTTGATGAAATACTAGTCATGGGAAATCAAAACGAAGCTACAGCAGTAACATCACCATCAACATCAACAGAATCATCCGAGGGAGCAACACAACCAG
2101 ---------+---------+---------+---------+---------+---------+---------+---------+---------+---------+ 2200
     G  V  D  E  I  L  V  M  G  N  Q  N  E  A  T  A  V  T  S  P  S  T  S  T  E  S  S  E  G  A  T  Q  P  A  -

     CAGCAACAGTACAGCCAGCAGCGCCAGGAGTACAAACGGGAATACCAGTAGCACAGCCAGGAGCATCAGCACCAGGAGTACCAGAAGCACCAGCACCAGA
2201 ---------+---------+---------+---------+---------+---------+---------+---------+---------+---------+ 2300
      A  T  V  Q  P  A  A  P  G  V  Q  T  G  I  P  V  A  Q  P  G  A  S  A  P  G  V  P  E  A  P  A  P  E  -

     AGCAACAGCACCAGAAGTACCAGCAATAGAAGCACAAGCACCTGTGCAACCTACGCAAGGACAGGTCCAAGCAGCCACCCAAAATGGCCCAACAATGACA
2301 ---------+---------+---------+---------+---------+---------+---------+---------+---------+---------+ 2400
      A  T  A  P  E  V  P  A  I  E  A  Q  A  P  V  Q  P  T  Q  G  Q  V  Q  A  A  T  Q  N  G  P  T  M  T  -

     AAATTACAATATCTCGAGAAGTTATATTACTTTTTGTATACCTCCTATGTATGTCATAAGTACATTTTAGTGACAAACTCTACAATGAACAAAGATTTGT
2401 ---------+---------+---------+---------+---------+---------+---------+---------+---------+---------+ 2500
     K  L  Q  Y  L  E  K  L  Y  Y  F  L  Y  T  S  Y  V  C  H  K  Y  I  L  V  T  N  S  T  M  N  K  D  L  L  -
                                                                 PoMSP1-F6
     TGGCAAAATATAATCTTACACCAGAAGAAGAAGAAAAAAAAAAAACAATAAAATGTGATCAGTTAGATTTATTGTTTAACTTACAAAACAATTTACCAGT
2501 ---------+---------+---------+---------+---------+---------+---------+---------+---------+---------+ 2600
      A  K  Y  N  L  T  P  E  E  E  E  K  K  K  T  I  K  C  D  Q  L  D  L  L  F  N  L  Q  N  N  L  P  V  -

     CATGTATTCTCTCTTTGATAATATGAGCTCGACTTTGCAAAGCAATTACATTCAATTATATGAAAAGGAAATGCTGTACAATATATACAAGATGAAAAAC
2601 ---------+---------+---------+---------+---------+---------+---------+---------+---------+---------+ 2700
      M  Y  S  L  F  D  N  M  S  S  T  L  Q  S  N  Y  I  Q  L  Y  E  K  E  M  L  Y  N  I  Y  K  M  K  N  -

     AGTGATAAGGCGATCAAAGAATTTCTAGAGACACAAGGTATAACAGGTACAGCACCAGATGCTACTCCTCTAGTCAATACACAAGCCACTACGCAAGCCG
2701 ---------+---------+---------+---------+---------+---------+---------+---------+---------+---------+ 2800
     S  D  K  A  I  K  E  F  L  E  T  Q  G  I  T  G  T  A  P  D  A  T  P  L  V  N  T  Q  A  T  T  Q  A  A  -

     CTACACAAGTCACTACGCAAGCCGCTACACAAACCGCTACACAAACCGCTACACATGCCTCTACACATGCCTCTACACAAGCCGCTACACAAGGTAATGT
2801 ---------+---------+---------+---------+---------+---------+---------+---------+---------+---------+ 2900
      T  Q  V  T  T  Q  A  A  T  Q  T  A  T  Q  T  A  T  H  A  S  T  H  A  S  T  Q  A  A  T  Q  G  N  V  -

     TCCACAAGCCTCTAATGATGAACATACACCTTCAGCAACAACAGTTAATCCGGCAACGACAACACCAGATAAATCTTTGAAAGAAAGCACATCTGAGGGA
2901 ---------+---------+---------+---------+---------+---------+---------+---------+---------+---------+ 3000
      P  Q  A  S  N  D  E  H  T  P  S  A  T  T  V  N  P  A  T  T  T  P  D  K  S  L  K  E  S  T  S  E  G  -

     ACGTTGATGACACAGGGAAACGCAGATGATGATGTATCTGAGCCTGAAAAAAAGGAAATAGAAGTGGAAGAATTTTACAAGAAGTATTTAGAGGAAGTAG
3001 ---------+---------+---------+---------+---------+---------+---------+---------+---------+---------+ 3100
     T  L  M  T  Q  G  N  A  D  D  D  V  S  E  P  E  K  K  E  I  E  V  E  E  F  Y  K  K  Y  L  E  E  V  D  -

     ATAAGTATGATGACTACTTTAAAGCTTTTCTTTCATCCAAAAAGGATGCTGTAAATAAAATGACAGAAAAAGATTGGAAAGAATTAGAAGAAGAAGTAAA
3101 ---------+---------+---------+---------+---------+---------+---------+---------+---------+---------+ 3200
      K  Y  D  D  Y  F  K  A  F  L  S  S  K  K  D  A  V  N  K  M  T  E  K  D  W  K  E  L  E  E  E  V  K  -
                    PoMSP1-F7
     AACATTAAAGAGTAGGTTAGATATGTCATTAGATCATTATAATAAGTATAAATTAAAATTAGGTAGATTGTTTAAAAAAAATGAAAAAGTTTTAAGTAGT
3201 ---------+---------+---------+---------+---------+---------+---------+---------+---------+---------+ 3300
     T  L  K  S  R  L  D  M  S  L  D  H  Y  N  K  Y  K  L  K  L  G  R  L  F  K  K  N  E  K  V  L  S  S  -

     AAAGAACATATTAAAGAATTGAGTATTTTAAAAGCACAATTGATGAGAAGACAATTTATGCTTAATAACCCAAGACATGTAATACATAACTTTAGAGTTT
3301 ---------+---------+---------+---------+---------+---------+---------+---------+---------+---------+ 3400
     K  E  H  I  K  E  L  S  I  L  K  A  Q  L  M  R  R  Q  F  M  L  N  N  P  R  H  V  I  H  N  F  R  V  F  -

     TTTTTAATAAAAAAAGAGAAACTGAAAAGAAAGAAGTTGAAAATACACTAAAAAATACAGATGCATTGTTAAAATATTACAAAGCAAGAGTTAAGTACTA
3401 ---------+---------+---------+---------+---------+---------+---------+---------+---------+---------+ 3500
      F  N  K  K  R  E  T  E  K  K  E  V  E  N  T  L  K  N  T  D  A  L  L  K  Y  Y  K  A  R  V  K  Y  Y  -

     TAATGGAGAAACTTTCCCATTAAAAACAATAAGTGAAGATACATTAGAAAAAGAAAATAATTATCTCAATTTGGAAAAATTTAAGTTATACAGCAGATTG
3501 ---------+---------+---------+---------+---------+---------+---------+---------+---------+---------+ 3600
      N  G  E  T  F  P  L  K  T  I  S  E  D  T  L  E  K  E  N  N  Y  L  N  L  E  K  F  K  L  Y  S  R  L  -

     GAAGGAAAACTAAAACAAAACATAAATTTGGAAAAAGAAAATATCACATACCTATCTAGTGCATTATATCACGTTCTTTCAGAATTAAAGGGGATTATAC
3601 ---------+---------+---------+---------+---------+---------+---------+---------+---------+---------+ 3700
     E  G  K  L  K  Q  N  I  N  L  E  K  E  N  I  T  Y  L  S  S  A  L  Y  H  V  L  S  E  L  K  G  I  I  H  -

     ACAATAAAAAGTACACAGGAAATCCTCATGCTGCAAATATGGTAGAGGTTAACAATGCGTTGAATCTGTACAAAGATTTGCTTCCAAAAGTGGAAACTGT
3701 ---------+---------+---------+---------+---------+---------+---------+---------+---------+---------+ 3800
      N  K  K  Y  T  G  N  P  H  A  A  N  M  V  E  V  N  N  A  L  N  L  Y  K  D  L  L  P  K  V  E  T  V  -

     GGCTTCCACTGGTGCCGCGACGCAGACACAAGGCGGGGAAGGAGCATCAGCAGCAGCAGCACCACCAGCAGCGTTACCAGCAGCACCACCAGCAGCACCA
3801 ---------+---------+---------+---------+---------+---------+---------+---------+---------+---------+ 3900
     A  S  T  G  A  A  T  Q  T  Q  G  G  E  G  A  S  A  A  A  A  P  P  A  A  L  P  A  A  P  P  A  A  P  -
```

FIGURE 8C

```
     CCAGCAGCACCACCAGCAGCATCAGCAGCAGCACCTGGAACTGCAAATGGTGAAACAGCAACGGTAGCACACGCAGAAGACTATACGGAAGACGACAATA
3901 ---------+---------+---------+---------+---------+---------+---------+---------+---------+---------+ 4000
     P  A  A  P  P  A  A  S  A  A  A  P  G  T  A  N  G  E  T  A  T  V  A  H  A  E  D  Y  T  E  D  D  N  N -

     ACGTCATTGTACTACCCCTTTTCGGAAAGAAAGGAACACATGCGTTTGACCAAGTGACGCAGGGTGAAGCACAAGACAAGGACGACAATATACTGAATGA
4001 ---------+---------+---------+---------+---------+---------+---------+---------+---------+---------+ 4100
      V  I  V  L  P  L  F  G  K  K  G  T  H  A  F  D  Q  V  T  Q  G  E  A  Q  D  K  D  D  N  I  L  N  E -

     AATCACCAACGAATACGAAGTTGTGTACGTGAAACCGTTAGCTGGTGTATATAAAACGTTGAACAAGCAATTGGAAGCACATGTTACAGCATTTCACAGT
4101 ---------+---------+---------+---------+---------+---------+---------+---------+---------+---------+ 4200
     I  T  N  E  Y  E  V  V  Y  V  K  P  L  A  G  V  Y  K  T  L  N  K  Q  L  E  A  H  V  T  A  F  H  S  -
              PoMSP1-R5
     AACGTAACAAACATGTTGGAATCTCGTTTCAAAAAAACAAATTATTTTTTGGAAGTGTTAAACTCTGATTTGACTCAAAACAAACATGCAACTTCTGACA
4201 ---------+---------+---------+---------+---------+---------+---------+---------+---------+---------+ 4300
     N  V  T  N  M  L  E  S  R  F  K  K  T  N  Y  F  L  E  V  L  N  S  D  L  T  Q  N  K  H  A  T  S  D  N -

     ATTACGTTATTAGAGATGCGTACAAATTATTAGACTTTGAAAAAAAAAAAAAATTGTTAAGTAGCTACAAATATATTAAAGATTCTGTTGAGAAAGATGT
4301 ---------+---------+---------+---------+---------+---------+---------+---------+---------+---------+ 4400
      Y  V  I  R  D  A  Y  K  L  L  D  F  E  K  K  K  K  L  L  S  S  Y  K  Y  I  K  D  S  V  E  K  D  V -
                                                     PoMSP1-R4
     AGAAATTGCTACGGATGGAATTGACTATTATGAAAAAATGGCTGCTCTGTATAAGACGTACCTAGAATCGGTTAATGCTCAGGTAGATGCAATAGATAAA
4401 ---------+---------+---------+---------+---------+---------+---------+---------+---------+---------+ 4500
     E  I  A  T  D  G  I  D  Y  Y  E  K  M  A  A  L  Y  K  T  Y  L  E  S  V  N  A  Q  V  D  A  I  D  K  -

     ACTGGGGATGATGCTACTAAGGCAACTAATAAAAAATTTCTTCCCTTTTTGGCTAGTATCAATGCTATGTACGAAACTTTGTTAGAAAAAGTGAACACCT
4501 ---------+---------+---------+---------+---------+---------+---------+---------+---------+---------+ 4600
     T  G  D  D  A  T  K  A  T  N  K  K  F  L  P  F  L  A  S  I  N  A  M  Y  E  T  L  L  E  K  V  N  T  Y -

     ACAATTCCCAATTAAAATCAAGTTTAAACAGTTGCCAGTTGGAAAAAATTAGAGTAGGTATTGTTGTGGATAAACTGAATGACTATGTAATGTTTGATGA
4601 ---------+---------+---------+---------+---------+---------+---------+---------+---------+---------+ 4700
      N  S  Q  L  K  S  S  L  N  S  C  Q  L  E  K  I  R  V  G  I  V  V  D  K  L  N  D  Y  V  M  F  D  E -

     AAAATTAGAAGAGTTAAAATCGAGTAAGGAAAAAGATTTGACAAAATTATATAAAGATATAGATACATCTAACATAATAAACAAGTTAAAGAGATCAGGT
4701 ---------+---------+---------+---------+---------+---------+---------+---------+---------+---------+ 4800
      K  L  E  E  L  K  S  S  K  E  K  D  L  T  K  L  Y  K  D  I  D  T  S  N  I  I  N  K  L  K  R  S  G  -
                                                   PoMSP1-F3
     TTTGTAGATACAGATGAGTCAAAGAAATTATTATCCGAGTTGTTAGATGTAGATTCTGCTCAATTGTTGTCTATGGGATCTAAACATAAATGTATTGATA
4801 ---------+---------+---------+---------+---------+---------+---------+---------+---------+---------+ 4900
     F  V  D  T  D  E  S  K  K  L  L  S  E  L  L  D  V  D  S  A  Q  L  L  S  M  G  S  K  H  K  C  I  D  I -
                                                 PoMSP1-R2                                PoMSP1-R1
     TAACATATCCAGATAATGCAGGATGTTATAGATTTTCTGATGGACGAGAAGAATGGAGATGTTTGTTAAACTTTAAAAAAGTTGGAGAAACATGTGTACC
4901 ---------+---------+---------+---------+---------+---------+---------+---------+---------+---------+ 5000
       T  Y  P  D  N  A  G  C  Y  R  F  S  D  G  R  E  E  W  R  C  L  L  N  F  K  K  V  G  E  T  C  V  P -
                                                       PoMSP1-F8
     AAATAACAATCCTACATGTGCAGAAAATAATGGTGGATGTGATCCCACTGCAGATTGTGCAGAATCTGAAAATAATAAAATTACTTGTACATGTACTGGA
5001 ---------+---------+---------+---------+---------+---------+---------+---------+---------+---------+ 5100
      N  N  N  P  T  C  A  E  N  N  G  G  C  D  P  T  A  D  C  A  E  S  E  N  N  K  I  T  C  T  C  T  G  -

     CAAAATGAATCATTCTTCGAAGGTGTTTTCTGTGGCTCATCAAGTTTCCTTAGCTTATCTTTCTTATTGGCAGTCTTATTGATCCTATTTAACTTACTTT
5101 ---------+---------+---------+---------+---------+---------+---------+---------+---------+---------+ 5200
     Q  N  E  S  F  F  E  G  V  F  C  G  S  S  S  F  L  S  L  S  F  L  L  A  V  L  L  I  L  F  N  L  L  * -

     AAAAGGAGAGAGTGAGGGTAAATACAAAAGTTGTTACATTTTTTTTTTTTTTTTTTT
5201 ---------+---------+---------+---------+---------+------ 5256
                                                              -
```

Gray = Signal Peptide
Inverse = Cysteine Residues
Bold = MSP1-p33
*Italics* = MSP1-p19
Brackets = Primer Sites
* (Degenerate As primer sequences not shown)

FIGURE 9

**Amino acid alignment of PoMSP1 [*P. ovale* (top) vs. *P. vivax* (#AAA63427, bottom)]**

```
   1 MKVFVPALSFIFFIVNCQCETLENYKELLHKLNNLEALVVDGYNLFHKTPLTLQKLETEVTTTGRGSGSSTTSVSSIPSDASRAVSTRDSNSNINNQVVS 100
   1 MKALLPFFSFIFFVTKCQCET.ESYKQLVANVDKLEALVVDGYELFHK.....KKL...........GENDIKV.....DA.......NANNNNNNQ.VS 70

 101 KLTADIRFLLSRFLQLNIPGHGDLMHFIREISLDTNGLKYLIEGYEEFNELMYILNFYYDLFRAKLHDMCANDYCEIPDHLKISDKELDMLKKVVLGYRK 200
  71 VLTSKIRNFVGKFLELQIPGHTDLLHLIRELAFEPNGIKYLVESYEEFNQLMHVINFHYDLLRANVHDMCAHDYCKIPEHLKISDKELDMLKKVVLGLWK 170

 201 PLENIKDDISKMETFIQKNTQTVENIKGLIEAEEKKRYGEV............AVSGNTGS..AGAASGTNASASSGQENSST...........ESETEK 275
 171 PLDNIKDDIGKLETFITKNKETISNINKLISDENAKRGGQSTNTTNGPGAQNNAAQGSTGNTETGTRSSASSNTLSGGDGTTVVGTSSPAPAAPSSTNED 270

 276 YNKAKALYQSIYNALFYKKQLTEAEKLIEVLKKRVQTLKEHKEIKKLLEEIAEKESKVTPPSNTAS.......QTQLQEEINKLKTQIKNIAKTVKPEME 368
 271 YDEKKKIYQAMYNGIFYTSQLEEAQKLIEVLEKRVKVLKEHKGIKALLEQV.EAEKKKLPKDNTTNRPLTDEQQKAAQKKIADLESQIVANAKTVNFDLD 369

 369 GLFTDPVELDYYLREKDKKASKVV...ETQS....GSTTPP.KPTYPNGLIYPLEKENISELLSKAVTETTFGDLQNVEIGKALNKEIFTNDDKRNEFID 460
 370 GLFTDAEELEYYLREKAKMAGTLIIPESTKSAGTPGKTVPTLKETYPHGISYALAENSIYELIEKIGSDETFGDLQNPDDGKQPKKGILINETKRKELLE 469

 461 KLKNKIKQQEELLSKQKVDYDAKLKLYEEQKKKAIPLFEQFHNGKLDNTLIPSKFEEFKVERDKYMQLKNELKNCPYEMTKNTVDKLNKQLAYLNDYSLR 560
 470 KIMNKIKIEEDKLPNLKKELEEKYKVYEAKVNEFKPAFNHFYEARLDNTLVENKFDEFKTKREAYMEEKKKLESCSYEQNTNLINKLKKQLTYLEDYVLR 569

 561 KEVFNKEVKHFTGLEWKLQTEIDKLANEIKKNENILITASTLPLSNVVELQVQKVLVAKKIELLKKVEKLLHKAQLKDHLYVPQVYGTQAKPEAYYLFVL 660
 570 KDIADDEIKHFSFMEWKLKSEIYDLAQEIRKNENKLTVENKFDFSGVVEGQVQKVLIIKKIEALKNVQNLLKNAKVKDDLYVPKVYNTGEKPEPYYLMVL 669

 661 KKEIDKLGEFKPKIKEMLDKEKANPTPATAQGALPVRGVDEILVMGNQNEATAVTSPSTSTE....SSEGATQPAATVQPAAPGVQTGIPVAQPGASAPG 756
 670 KREIDKLKDFIPKIESMIATEKAKPA.ASA....PVTSGQ..LLRGSSEAATEVTTNAVTSEDQQQQQQQQQQQQQQQQQQQQQSQVVPAPAGDAQQV 762

 757 VPEAPAPEATAPEVPAIEAQAPVQPTQGQVQAATQNGPTMTKLQYLEKLYYFLYTSYVCHKYILVTNSTMNKDLLAKYNLTPEEEEKKKTIKCDQLDLLF 856
 763 ISTQPTSQSAAPGVSATPAPTPA........AAAAPAPAMSKLEYLEKLLDFLKSAYACHKHIFVTNSTMDKKLLKEYELNADEKTKINQNKCDELDLLF 854

 857 NLQNNLPVMYSLFDNMSSTLQSNYIQLYEKEMLYNIYKMKNSDKAIKEFLETQGITGTAPDATPLVNTQATTQAATQVTTQAATQTATQTATHASTHAST 956
 855 NVQNNLPAMYSIYDSMSNELQNLYIELYQKEMVYNIYKNKDTDKKIKAFLETSNNKAAAP...........AQSAAKPSGQAEYYSSNDNC..ASNHNNS 941

 957 QAATQGNVPQASNDEHTPSATTVNPATTTPDKSLKESTSEGTLMTQGNADDDVSEPEKKEIEVEEFYKKYLEEVDKYDDYFKAFLSSKKDAVNKMTEKDW 1056
 942 YSKS....PNISCNKH..........TSTP..QAEENQRVG.....GNSEE...KPEADTAQVEKFYDKHLSQIDKYNDYPKKFLESKKEEIIKMDDTKW 1017

1057 KELEEEVKTLKSRLDMSLDHYNKYKLKLGRLFKKNEKVLSSKEHIKELSILKAQLMRRQFMLNNPRHVIHNFRVFFNKKRETEKKEVENTLKNTDALLKY 1156
1018 NALGKEIEELKKKLQVSLDHYGKYKLKLERFLKKKNKISNSKDQIKKLTSLKNKLERRQNLLNNPTSVLKNYTAFFNKKRETEKKEVENTLKNTEILLKY 1117

1157 YKARVKYYNGETPPLKTISEDTLEKENNYLNLEKFKLYSRLEGKLKQNINLEKENITYLSSALYHVLSELKGIIHNKKYTGNPHAANMVEVNNALNLYKD 1256
1118 YKARAKYYIGEPPPLKTLSEESMQKEDNYLNLEKFRCSADWK.EIRKDTELERSNISYLSSGLLHVLDRAEEIINDKKYSGKDHAKNIAEVKKALQAYQE 1216

1257 LLPKVETVAST............GAATQTQGGEGASAAAAPPAAL.PAAPPAAPPA...APPAASAAAPGTA.NGETATVAHAEDYTEDDNNVIVLPLFG 1339
1217 LIPKVTSQESTSVAVTVPGAVVPGVPTAAAAGSGASGAVPPAAAAGSGASGAVPPAGGPSPPATGGVVPGVVESAEAQTKAQAQDYAEDYDKVIALPLFG 1316

1340 KKGTHA.FDQVTQGEAQDKDDNILNEI.TNEYEVVYVKPLAGVYKTLNKQLEAHVTAPHSNVTNMLESRFKKTNYFLEVLNSDLTQNKHATSDNYVIRDA 1437
1317 NNDDDGEEDQVTTGEAESEAPEILVPAGISDYDVVYLKPLAGMYKTIKKQLENHVNAFNTNITDMLDSRLKKRNYFLEVLNSDLNPFKYSPSGEYIIKDP 1416

1438 YKLLDFEKKKKLLSSYKYIKDSVEKDVEIATDGIDYYEKMAALYKTYLESVNAQV...........DAIDKTGDDATKATNK...........KFLPFLA 1515
1417 YKLLDLEKKKKLLGSYKYIGASIDKDLATANDGVTYYNKMGELYKTHLTAVNEEVKKVEADIKAEDDKIKKIGSDSTKTTEKTQSMAKKAELEKYLPFLN 1516

1516 SINAMYETLLEKVNTYNSQLKSSLNSCQLEKIRVGIVVDKLNDYVMFDEKLEELKSSKEKDLTKLYKDIDTSNIINKLKRSGFVDTDESKKLLSELLDVD 1615
1517 SLQKEYESLVSKVNTYTDNLKKVINNCQLEKKEAEITVKKLQDYNKMDEKLEEYKKSEKKN......EVKSSGLLEKLMKSKLIKENESKEILSQLLNVQ 1610

1616 SAQLLSMGSKHKCIDITYPDNAGCYRFSDGREEWRCLLNFKKVGETCVPNNNPTCAENNGGCDPTADCAESENNKITCTCTGQ.NESFFEGVFCGSSSFL 1714
1611 T.QLLTMSSEHTCIDTNVPDNAACYRYLDGMEEWRCLLTFKEEGGKCVPGSNVTCKDNNGGCAPEAECKMTDSNKIVCKCTKEGSEPLFEGVFCSSSSFL 1709

1715 SLSFLLAVLLILFNL.L* 1731
1710 SLSFLLLMLLFLLCMEL* 1727
```

Gray = Signal Peptide
Inverse = Cysteine Residues
Bold = MSP1-p33
*Italics* = MSP1-p19

FIGURE 10

MSP1 Amino Acid Sequence Comparison (% Identity)

| | *P. falciparum* | *P. vivax* | *P. malariae* | *P. ovale* |
|---|---|---|---|---|
| *P. falciparum* | 100.0 | | | |
| *P. vivax* | 42.7 | 100.0 | | |
| *P. malariae* | 43.8 | 50.1 | 100.0 | |
| *P. ovale* | 44.1 | 52.5 | 51.7 | 100.0 |

| Species | Genbank # |
|---|---|
| *P. falciparum* | BAF62278 |
| *P. vivax* | AAA63427 |
| *P. malariae* | (Cameroon 0014) |
| *P. ovale* | (Cameroon 510-10) |

FIGURE 11

**Location of MSP1 and MSP1 Sub-Regions for *P. malariae* and *P. ovale***

| MSP1 Sub-region | (Figure 1) PmMSP1 DNA | (Figure 2) PmMSP1 AA | (Figure 3) PoMSP1 DNA | (Figure 4) PoMSP1 AA |
|---|---|---|---|---|
| p19 | 4961-5260 | 1634-1733 | 4849-5145 | 1614-1712 |
| p33 | 4181-4960 | 1374-1633 | 4048-4848 | 1347-1613 |
| p42 | 4181-5260 | 1374-1733 | 4048-5145 | 1347-1712 |
| MSP1 | 62-5314 | 1-1751 | 10-5199 | 1-1730 |

A Prototype Abbott PRISM® Malaria Assay Format

*PLASMODIUM MALARIAE* AND *PLASMODIUM OVALE* GENES AND USES THEREOF

The subject application claims priority to U.S. Provisional Patent Application No. 61/068,375 filed on Mar. 6, 2008, herein incorporated in its entirety by reference.

BACKGROUND OF THE INVENTION

1. Technical Field

The subject invention relates to nucleic acid sequences and amino acid sequences encoded thereby, derived from the Merozoite Surface Protein (MSP1) gene of the *Plasmodium* species *P. malariae* and *P. ovale*. Such genes and proteins have many beneficial diagnostic as well as therapeutic uses.

2. Background Information

Malaria Transmittance

Malaria is a mosquito-borne disease caused by a parasite. At least four species of malaria parasites can infect humans under natural conditions: *Plasmodium falciparum, P. vivax, P. ovale* and *P. malariae*. The first two species cause the most infections worldwide. In particular, *Plasmodium falciparum* is the agent of severe, potentially fatal malaria, causing an estimated 700,000-2.7 million deaths annually, most of them in young children in Africa. *Plasmodium vivax* and *P. ovale* have dormant liver stage parasites (hypnozoites) which can reactivate (or "relapse") and cause malaria several months or years after the infecting mosquito bite. *Plasmodium malariae* produces long-lasting infections and, if left untreated, can persist asymptomatically in the human host for years, even a lifetime (Gorbach, Bartlett & Blacklow "Infectious Diseases, $2^{nd}$ Edition, Sunders Press, 1992).

More recently, *Plasmodium knowlesi*, whose natural hosts include crab-eating macaques (*Macaca fascicularis*) and pig-tailed macaques, has been shown to infect humans and may be responsible for a significant number of human infections in Malaysia (Cox-Singh et al., Clinical Infectious Diseases 2008; 46:165-71) and has been found in humans in Thailand (Jongwutiwes et al. Emerg. Inf. Dis 2004: 10:2211-2213) and Myanmar (Zhu et al. [article in Chinese], Zhongguo Ji Sheng Chong Xue Yu Ji Sheng Chong Bing Za Zhi 2006; 24:70-1).

In nature, malaria parasites spread by infecting successively two types of hosts: humans and female Anopheles mosquitoes. In humans, the parasites grow and multiply first in the liver cells and then in the red cells of the blood. In the blood, successive broods of parasites grow inside the red cells and destroy them, releasing daughter parasites (merozoites) that continue the cycle by invading other red cells.

The blood stage parasites cause the symptoms of malaria. When certain forms of blood stage parasites ("gametocytes") are picked up by a female Anopheles mosquito during a blood meal, they start another, different cycle of growth and multiplication in the mosquito. After 10-18 days, the parasites are found (as "sporozoitesv") in the mosquito's salivary glands. When the Anopheles mosquito takes a blood meal on another human, the sporozoites are injected with the mosquito's saliva and start another human infection when they parasitize the liver cells. (D. Wyler, "*Plasmodium* and Babesia", Chapter 287, p 2407, in Gorbach, Bartlett & Blacklow "Infectious Diseases, $2^{nd}$ Edition, Sunders Press, 1992; http://www.cdc.gov/malaria/biology/life_cycle.htm)

Malaria Symptoms and Disease

Infection with malaria parasites may result in a wide variety of symptoms, ranging from absent or very mild symptoms to severe disease and even death. Malaria disease can be categorized as uncomplicated or severe (complicated). In general, malaria is a curable disease if diagnosed and treated promptly and correctly. Following the infective bite by the Anopheles mosquito, a period of time (the "incubation period") elapses before the first symptoms appear. The incubation period varies from 7 to 30 days. The shorter periods are observed most frequently with *P. falciparum* and the longer with *P. malariae.*

Although uncomplicated malaria is quite treatable and the symptoms are non-disabling, severe malaria occurs when *P. falciparum* infections are complicated by serious organ failures or abnormalities in the patient's blood or metabolism. The manifestations of severe malaria include, for example cerebral malaria, with abnormal behavior, impairment of consciousness, seizures, coma, or other neurologic abnormalities; severe anemia, hemoglobinuria, pulmonary edema or acute respiratory distress syndrome, abnormalities in blood coagulation and thrombocytopenia, cardiovascular collapse and shock.

Diagnosis

Malaria must be recognized promptly in order to treat the patient in time and to prevent further spread of infection in the community. Malaria should be considered a potential medical emergency and should be treated accordingly. Delay in diagnosis and treatment is a leading cause of death in malaria patients in the United States. Malaria can be suspected based on the patient's symptoms and the physical findings at examination. However, for a definitive diagnosis to be made, laboratory tests must demonstrate presence of the malaria parasites or their components. The diagnostic "gold standard" for malaria depends on the demonstration of parasites on a blood smear examined under a microscope. In *P. falciparum* malaria, additional laboratory findings may include mild anemia, mild decrease in blood platelets (thrombocytopenia), elevation of bilirubin, elevation of aminotransferases, albuminuria, and the presence of abnormal bodies in the urine (urinary "casts").

Detection of *Plasmodium* Antibodies

Antibodies to asexual malaria parasites (i.e. merozoites) appears within days to weeks after invasion of erythrocytes and can persist for months or even years (Vinetz et al., NEJM 2007, 338(6):367-371). Antibody detection for diagnosis of acute malaria is not recommended since presence of antibodies can indicate past or current (recent) infection. Historically, antibody detection used the immunofluorescence assay (IFA) but this assay is not particularly sensitive nor very specific and is labor intensive and requires carefully prepared reagents. Enzyme-linked immunosorbent assays (ELISA) have been developed that use plasmodium-derived antigens (Newmarket Laboratories, UK; Cellabs, Australia) or *P. falciparum* whole organism lysates (DiaMed) to detect immunoglobulins (IgG and/or IgM) in human serum or plasma. These assays are easier to perform, exhibit higher throughput and better sensitivity and specificity than IFA (Srivastava et al. J Trop. Med. Hyg. 1991, 94:189-194; Kitchen et al. Vox Sang. 2004, 87:150-155; Seed et al. Vox Sang. 2005, 88:98-106). Some ELISA assays may be better than others for detection of antibodies directed against each of the four plasmodium species that cause malaria in humans (She et al. J. Trav. Med. 2007, 14:105-111).

Antigens used for capture of antibodies have included vaccine candidates since their ability to elicit antibody response is often determined in animals and human vaccinees and naturally occurring antibodies are measured prior to vaccination. Examples of such antigens include circumsporozoite protein (CSP), apical membrane antigen 1 (AMA-1), merozoite surface protein (MSP) one and two, and, in particular, the 42 KDa and 19 KDa C-terminal fragment of MSP1 (a.k.a. MSP1-42 and MSP1-19) of both *P. vivax* and *P. falciparum* (Kitchen et al. Vox Sang., 2004, 87:150-155; Rodrigues et al. Malaria J. 2003, 2:39-46). Other antigens of interest are MSP-2, -3, -4, -5, -8 -9, glutamate-rich protein, serine repeat antigen (Girard et al. Vaccine, 2007, 25(9):1567-1580).

*Plasmodium falciparum* MSP1 has been extensively studied and was one of the very earliest vaccine candidates. It elicits a protective antibody response against severe malaria and the presence of MSP1 antibodies correlate with protective immunity (Siddiqui et al. PNAS 1987, 84:3014-3018). MSP1 is expressed as a ~200 kDa precursor molecule linked by a glycosyl phosphatidylinositol anchor to the merozoite surface membrane. MSP1 is processed into a complex of polypeptides on the merozoite surface, including N-terminal and central regions of 82, 30, and 38 kDa, as well as the C-terminal region of 42 kDa. At the time of invasion of red blood cells, MSP1-42 is further processed by proteolytic cleavage into a 33-kDa fragment (MSP1-33), which is shed with the rest of the complex, and a C-terminal 19-kDa fragment (MSP1-19). Only the C-terminal MSP1-19 remains anchored on the merozoite surface and is carried into parasitized RBC. In monkeys, immunization with recombinant MSP1-42 and MSP1-19 has been shown to elicit various degrees of protection against *P. falciparum* challenge (Egan et al. Infect. Immun., 2000, 68:1418-1427; Kumar, et al. Mol. Med., 1995, 1:325-332). MSP1-19 proteins from both *P. falciparum* and *P. vivax* have been proposed as vaccine candidates (Roas et al., Immunol Lett. 2004, 92(3):259-68; Stowers et al. Infect. Immun., 2001, 69:1536-1546; Faber et al. Infect. Immun., 2007, 75:5947-5955). The MSP1 genes of *P. ovale* and *P. malariae*, however, the other two major plasmodium parasites causing malaria in humans, have not been available for examination as reagents for vaccination or antibody detection.

Detection of antibodies in donated serum or plasma can be used to identify individual donors who have been exposed to malarial organisms and who may be recently infected and, therefore, potentially parasitemic. All four species of plasmodium that infect humans have been transmitted via blood transfusion, and though the incidence of post-transfusion malaria is low in the United States (Mungai, et. al., N. Engl. J. Med. 344, p. 1973-1978, 2001), the availability of blood donors could be increased by implementation of plasmodium antibody screening assays such that only malaria-organism exposed individuals are deferred from blood donation rather than all donors who have traveled or lived in malaria endemic regions, as is the current practice. Such assays would theoretically detect antibodies against plasmodium species that infect humans and cause malaria (*P. falciparum, P. vivax, P. ovale*, and *P. malariae*). Commercial antibody ELISAs are currently in use (United Kingdom, Australia, France) or are being considered in other countries for the reinstatement of deferred donors (Seed et al. Vox Sang 2005, 88:98-106; Kitchen & Chiodini, Vox Sang(2006) 90:77-84; Elghouzzi et al., Vox Sang., 2008, 94:33-40). In these cases, donors are tested for antibodies to plasmodium derived antigens within several months of deferral.

A commercial assay (Pan Malaria Antibody CELISA) from Cellabs Pty. Ltd. (Brookvale, NSW, Australia) claims detection of antibodies to all four plasmodium species that cause malaria in humans and sensitivity of 94% versus immunofluoresence test (IFAT) (per package insert). Independent evaluation suggests the assay has poor sensitivity for falciparum and non-falciparum malaria antibody detection when compared to IFAT (Mertens et al. Vox Sang. 1999, 77:237-238). Independent evaluation of another assay from DiaMed AG (Switzerland) which utilizes a mixture of extracts of cultured *P. falciparum* and *P. vivax* recombinant protein (circumsporozoite protein), demonstrated poor sensitivity for detection of symptomatic individuals with microscopically confirmed *P. vivax* (18/24) but did detect antibodies in patients infected with *P. ovale* (2/2), or *P. malariae* (2/2) infection (Doderer et al. Malaria J. 2007, 6:19). The malaria antibody assay manufactured by Newmarket Laboratories Ltd (Kentford, UK) claims detection of all four species of plasmodium responsible for human malaria though it contains only *P. falciparum* and *P. vivax* derived recombinant antigens. The package insert indicates sensitivity for *P. ovale* and *P. malariae* antibody detection of only 80% and 67%, respectively. Detection of antibodies among individuals infected with *P. ovale* or *P. malariae* may be due to past infection with either *P. falciparum* or *P. vivax* and hence reactivity is due to detection of persistent antibodies to these agents. Independent evaluation of the assay demonstrated detection of only 9/14 (64%) of patients with acute malaria due to *P. ovale* infection and 85% (15/18) of patients with *P. vivax* malaria (Kitchen et al. Vox Sang. 2004, 87, 150-155). Hence, the claimed ability of these assays to detect human antibodies elicited by infection to *P. falciparum* as well as *P. ovale, P. vivax* and *P. malariae* is certainly questionable. For those assays whose composition of solid phase antigen is known (e.g. Newmarket, DiaMed), the absence of *P. ovale* or *P. malariae* specific antigens suggests that detection of antibodies to these species may be due to antibody cross-reactivity which raises important questions about assay specificity as well as sensitivity—unless reactivity is due to presence of *P. vivax* or *P. falciparum* antibodies from previous infections. Hence, there is presently a significant need for reliable detection of plasmodium antibodies in a low risk population (for example, normal blood donors) which requires an assay with antigen(s) derived from each of the four main plasmodium species All patents and publications referred to herein are hereby incorporated in their entirety by reference.

SUMMARY OF THE INVENTION

The present invention encompasses an isolated nucleic acid sequence or fragment thereof comprising or complementary to a nucleic acid sequence encoding a polypeptide, wherein the amino acid sequence of said polypeptide has at least 70%, preferably at least 80%, and more preferably at least 90% sequence identity to an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2. The present invention also encompasses an isolated protein comprising an amino acid sequence having at least 70%, preferably at least 80%, and more preferably at least 90% sequence identity to the amino acid sequence of SEQ ID NO:47 or SEQ ID NO:48. The invention also includes an isolated nucleic acid molecule comprising a nucleotide sequence having at least 70%, preferably at least 80% identity, and more preferably at least 90% identity to the nucleotide sequence of SEQ ID NO:43 or SEQ ID NO:44. (It should be noted that the present invention encompasses endpoints of the amino acid regions recited herein which may differ by approximately 1-15 amino acids from those recited. Further, the present invention also encompasses those amino acid sequences having differences of 1 to 10 amino acids, either contiguous or non-contiguous from those described herein, which have the same functional properties as the sequences described herein.)

Additionally, the present invention includes an isolated nucleic acid sequence or fragment thereof comprising or complementary to a nucleic acid sequence having at least 70%, preferably at least 80%, and more preferably at least 90% identity to a nucleic acid sequence comprising a nucleotide sequence selected from approximately nucleotides 1-5406 (SEQ ID NO:2) of FIG. 1, approximately nucleotides 62-5317 (i.e., PmMSP1) of SEQ ID NO:2 of FIG. 1, approximately nucleotides 4961-5260 (i.e., PmMSP1-p19) of SEQ ID NO:2 of FIG. 1, approximately nucleotides 4181-4960 (i.e., PmMSP1-p33) of SEQ ID NO:2 of FIG. 1 and approximately nucleotides 4181-5260 (i.e., PmMSP1-p42) of SEQ ID NO:2 of FIG. 1. (It should be noted that the present invention encompasses endpoints of the nucleotide ranges which may differ by approximately 15-100 nucleotides from those recited. Further, the invention also encompasses those nucleotide sequences having from 1 to 30 base differences from those nucleotide sequences described herein provided such sequences have the same functionality as the sequences described. Such differences may be due to degeneracy in the genetic code, point mutations, etc.) The present invention also encompasses an isolated nucleic acid sequence or fragment thereof comprising or complementary to a nucleic acid sequence encoding a polypeptide, wherein the amino acid sequence of the polypeptide has at least 70%, preferably at least 80%, and more preferably at least 90% amino acid identity to an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 of SEQ ID NO:3 (i.e., PoMSP1-p33) of FIG. 4 and approximately amino acids 1347-1712 (i.e., PoMSP1-p42) of SEQ ID NO:3 of FIG. 4.

Additionally, the present invention includes an isolated nucleic acid sequence or fragment thereof comprising or complementary to a nucleic acid sequence having at least 70%, preferably at least 80% and more preferably at least 90% identity to a nucleic acid sequence comprising a nucleotide sequence selected from approximately nucleotides 1-5256 (SEQ ID NO:4) of FIG. 3, approximately nucleotides 10-5202 (i.e., PoMSP1) of SEQ ID NO:4 of FIG. 3, approximately nucleotides 4849-5145 (i.e., PoMSP1-p19) of SEQ ID NO:4 of FIG. 3, approximately nucleotides 4048-4848 (i.e., PoMSP1-p33) of SEQ ID NO:4 of FIG. 3 and approximately nucleotides 4048-5145 (i.e., PoMSP1-p42) of SEQ ID NO:4 of FIG. 3.

Further, the invention includes a method of producing any one or more of the above-described amino acid or protein sequences. This method comprises the steps of (a) isolating a nucleic acid sequence comprising the nucleotide sequence of SEQ ID NO:2 or SEQ ID NO:4 (or any of the nucleotide ranges/regions recited above), (b) constructing a vector comprising the isolated nucleic acid sequence operably linked to a regulatory sequence, and (c) introducing the vector into a host cell for a time and under conditions sufficient for expression of the encoded protein or polypeptide. The host cell may be either a eukaryotic cell or a prokaryotic cell.

The present invention also encompasses a vector comprising a nucleic acid sequence or molecule comprising the nucleotide sequence of SEQ ID NO:2 or SEQ ID NO:4 (or any of the nucleotide ranges/regions described above), operably linked to a regulatory sequence as well as a host cell comprising this vector. Again, the host cell may be either a eukaryotic cell or a prokaryotic cell.

Additionally, the present invention encompasses a method of detecting antibodies to *P. malariae* in a test sample suspected of containing such antibodies. The method comprises the steps of: (a) contacting the test sample with a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, for a time and under conditions sufficient for the formation of antibody/antigen complexes and (b) detecting the presence of antibodies present in the test sample by detecting presence of the antibody/antigen complexes.

Further, the present invention includes another method of detecting antibodies to *P. malariae* in a test sample suspected of containing such antibodies. This method comprises the steps of: (a) contacting the test sample with a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, for a time and under conditions sufficient to allow for the formation of antibody/antigen complexes, (b) adding a conjugate to the resulting antibody/antigen complexes for a time and under conditions sufficient to allow the conjugate to bind to the bound antibody, wherein the conjugate comprises an antibody attached to a signal generating compound capable of generating a detectable signal and (c) detecting the presence of antibodies present in the test sample by detecting presence of the signal generated by the signal generating compound.

Additionally, the present invention includes another method of detecting antibodies to *P. malariae* in a test sample suspected of containing such antibodies. This method comprises the steps of: (a) contacting the test sample with a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, for a time and under conditions sufficient to allow for the formation of antibody/antigen complexes, (b) adding a conjugate to the resulting antibody/antigen complexes for a time and under conditions sufficient to allow the conjugate to bind to the bound antibody, wherein the conjugate comprises a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal and (c) detecting the presence of antibodies present in the test sample by detecting presence of the signal generated by the signal generating compound.

Also, the present invention includes a method of detecting antibodies to *P. ovale* in a test sample. This method comprises the steps of: (a) contacting the test sample suspected of containing the antibodies with a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, for a time and under conditions sufficient for the formation of antibody/antigen complexes and (b) detecting the presence of antibodies present in the test sample by detecting presence of the antibody/antigen complexes.

Moreover, the present invention also encompasses a method of detecting antibodies to *P. ovale* which may be present in a test sample comprising the steps of: (a) contacting the test sample with a *P. ovale* antigen comprising an amino acid sequence comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, for a time and under conditions sufficient to allow for the formation of antibody/antigen complexes, (b) adding a conjugate to the resulting antibody/antigen complexes for a time and under conditions sufficient to allow the conjugate to bind to the bound antibody, wherein the conjugate comprises an antibody attached to a signal generating compound capable of generating a detectable signal and (c) detecting the presence of antibodies present in the test sample by detecting presence of the signal generated by the signal generating compound.

Further, the present invention also encompasses a method of detecting antibodies to *P. ovale* which may be present in a test sample comprising the steps of: (a) contacting the test sample with a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, for a time and under conditions sufficient to allow for the formation of antibody/antigen complexes, (b) adding a conjugate to the resulting antibody/antigen complexes for a time and under conditions sufficient to allow the conjugate to bind to the bound antibody, wherein the conjugate comprises a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4 attached to a signal generating compound capable of generating a detectable signal and (c) detecting the presence of antibodies present in the test sample by detecting presence of the signal generated by the signal generating compound.

Additionally, the present invention includes a method of detecting *P. malariae* antibodies in a test sample suspecting of containing the antibodies comprising the steps of: (a) contacting the test sample with anti-antibody specific for *P. malariae* antibody, wherein said anti-antibody is raised against an antibody raised against a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, for a time and under conditions sufficient to allow for the formation of anti-antibody/*P. malariae* antibody complexes and (b) detecting the presence of *P. malariae* antibodies which may be present in the test sample by detecting the presence of the anti-antibody/*P. malariae* antibody complexes.

Further, the present invention encompasses a method of detecting *P. malariae* antibodies in a test sample suspected of containing the antibodies comprising the steps of: (a) contacting the test sample with anti-antibody specific for the *P. malariae* antibody for a time and under conditions sufficient to allow for formation of anti-antibody/*P. malariae* antibody complexes, (b) adding a conjugate to the resulting anti-antibody/*P. malariae* antibody complexes for a time and under conditions sufficient to allow the conjugate to bind to the bound antibody, wherein the conjugate comprises a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal and (c) detecting the presence of antibodies which may be present in the test sample by detecting presence of the signal generated by the signal generating compound.

Also, the present invention includes a method for detecting antibodies to *P. ovale* in a test sample suspected of containing said antibodies comprising the steps of: (a) contacting the test sample with anti-antibody specific for *P. ovale* antibody wherein said anti-antibody is raised against an antibody raised against a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, for a time and under conditions sufficient to allow for formation of anti-antibody/*P. ovale* antibody complexes and (b) detecting the presence of *P. ovale* antibodies which may be present in the test sample by detecting presence of the anti-antibody/*P. ovale* antibody complexes.

Further, the present invention encompasses a method for detecting antibodies to *P. ovale* in a test sample suspected of containing the antibodies comprising the steps of: (a) contacting the test sample with anti-antibody specific for the *P. ovale* antibody, for a time and under conditions sufficient to allow for formation of anti-antibody/*P. ovale* antibody complexes, (b) adding a conjugate to the resulting anti-antibody/*P. ovale* antibody complexes for a time and under conditions sufficient to allow the conjugate to bind to the bound antibody, wherein the conjugate comprises a *P. ovale* antigen attached to a signal generating compound capable of generating a detectable signal, wherein said antigen comprises an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4 and (c) detecting the presence of antibodies which may be present in said test sample by detecting presence of the signal generated by the signal generating compound.

Moreover, the present invention includes a method for detecting the presence of *P. malariae* antibodies in a test sample suspecting of containing the antibodies comprising the steps of: (a) contacting the test sample with anti-antibody specific for the antibodies for a time and under conditions sufficient to allow for formation of anti-antibody/*P. malariae* antibody complexes, (b) adding *P. malariae* antigen to the resulting anti-antibody/*P. malariae* antibody complexes for a time and under conditions sufficient to allow the antigen to bind to the bound antibody, wherein the antigen comprises an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, (c) adding a conjugate to the resulting anti-antibody/*P. malariae* antibody/antigen complexes, wherein the conjugate comprises a composition comprising a monoclonal or polyclonal antibody attached to a signal generating compound capable of detecting a detectable signal and (d) detecting presence of antibodies which may be present in the test sample by detecting presence of the signal generated by the signal generating compound.

Also, the present invention includes a method of detecting antibodies to *P. ovale* in a test sample suspected of containing the antibodies comprising the steps of: (a) contacting the test sample with anti-antibody for a time and under conditions sufficient to allow for formation of anti-antibody/*P. ovale* antibody complexes, (b) adding *P. ovale* antigen to the resulting anti-antibody/*P. ovale* antibody complexes for a time and under conditions sufficient to allow the antigen to bind to the bound antibody, wherein said anti-antibody is raised against an antibody raised against an antigen comprising an amino acid sequence comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, (c) adding a conjugate to the resulting anti-antibody/*P. ovale* antibody/antigen complexes, wherein the conjugate comprises a composition comprising a monoclonal or polyclonal antibody attached to a signal generating compound capable of detecting a detectable signal and (d) detecting the presence of antibodies which may be present in the test sample by detecting presence of the signal generated by the signal generating compound.

Further, the present invention encompasses a method of detecting antibodies to *P. malariae, P. falciparum, P. vivax* and *P. ovale* in a test sample suspected of containing at least one of these types of antibodies comprising the steps of: (a) contacting the test sample with: 1) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) an antigen of *P. falciparum* and 4) an antigen of *P. vivax*, for a time and under conditions sufficient for the formation of *P. malariae* antibody/antigen complexes, *P. falciparum* antibody/antigen complexes, *P. vivax* antibody/antigen complexes and *P. ovale* antibody/antigen complexes and (b) detecting the presence of antibodies present in the test sample by detecting the presence of complexes. One is able to detect each type of antibody present, if desired, by attaching a different signal-generating compound to each antibody within each compound and then detecting the respective label or labels of choice. Alternatively, if one does not wish to gather information relating to the presence of one or more types of the antibodies, then the method, of course, ensures that all four types of antibodies will be captured by the antigens added to the test sample. In connection with the determination of the suitability of a blood sample donation, one is only concerned whether at least one type of antibody is present in the sample. One is not concerned about the specific type of antibody present.

The present invention also includes a method of detecting antibodies to *P. malariae, P. ovale, P. vivax* and *P. falciparum* in a test sample suspected of containing at least one type of these antibodies comprising the steps of: (a) contacting the test sample with: 1) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) *P. vivax* antigen and 4) a *P. falciparum* antigen, for a time and under conditions sufficient to allow for the formation of *P. malariae* antibody/antigen complexes, *P. ovale* antibody/antigen complexes, *P. vivax* antibody/antigen complexes and *P. falciparum* antibody/antigen complexes, (b) adding four conjugates to the resulting antibody/antigen complexes for a time and under conditions sufficient to allow each conjugate to bind to bound antibody, wherein: 1) a first conjugate comprises an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal, 2) a second conjugate comprises an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, attached to a signal generating compound capable of generating a detectable signal, 3) a third conjugate comprises a *P. vivax* antigen attached to a signal generating signal capable of generating a detectable signal and 4) a fourth conjugate comprises a *P. falciparum* antigen attached to a signal generating compound capable of generating a detectable signal, and (c) detecting the presence of antibody to *P. malariae, P. ovale, P. vivax* and *P. falciparum* which may be present in the test sample by detecting presence of a signal generated by the signal generating compound. (It should be noted that detection of *P. knowlesi* antibodies may also be accomplished in the assays and kits described herein by adding an antigen of *P. knowlesi* or an anti-antibody to a *P. knowlesi* antigen, as is appropriate. Such an antigen may also be included in the vaccine described herein comprising antigens from *P. ovale, P. vivax, P. falciparum* and *P. malariae* (used for active immunization). Further, an antibody to *P. knowlesi* may also be included in the vaccine described herein which includes antibodies against *P. ovale, P. vivax, P. falciparum* and *P. malariae* (used for passive immunization.))

The present invention also includes a method of detecting antibodies to *P. malariae, P. ovale, P. vivax* and *P. falciparum* in a test sample suspected of containing at least one type of these antibodies comprising the steps of: (a) contacting the test sample with: 1) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) *P. vivax* antigen and 4) a *P. falciparum* antigen, for a time and under conditions sufficient to allow for the formation of *P. malariae* antibody/antigen complexes, *P. ovale* antibody/antigen complexes, *P. vivax* antibody/antigen complexes and *P. falciparum* antibody/antigen complexes, (b) adding a conjugate to the resulting antibody/antigen complexes for a time and under conditions sufficient to allow each conjugate to bind to bound antibody, wherein the conjugate comprises an antibody attached to a signal generating compound capable of generating a detectable signal; and (c) detecting the presence of antibody to *P. malariae, P. ovale, P. vivax* and *P. falciparum* antibody which may be present in the test sample by detecting presence of a signal generated by the signal generating compound.

Further, the present invention encompasses a method for detecting the presence of antibodies to *P. malariae, P. ovale, P. vivax* and *P. falciparum* in a test sample suspected of containing at least one type of these antibodies comprising the steps of: (a) contacting the test sample with: 1) anti-antibody specific for *P. malariae* antibody wherein said anti-antibody is raised against an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) anti-antibody specific for *P. ovale* wherein said anti-antibody is raised against an antibody raised against an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) anti-antibody specific for *P. vivax* and 4) anti-antibody/*P. falciparum* antibody complexes and (b) detecting the presence of antibody to *P. malariae, P. ovale, P. vivax* and *P. falciparum* which may be present in the test sample by detecting presence of the complexes. (Again, one does not need to detect the presence of all four types of complexes since the formation of complexes means that there is antibody in the sample against at least one type of species, and the assay covers the detection of all four types of antibodies. However, if one desires to specifically determine if there is antibody to one or more of the specific species in the test sample, this may be accomplished, for example, by labeling each conjugate (if present) with a different signal generating compound and determining whether different signals are generated.) Additionally, the present invention includes a method for detecting the presence of antibodies to *P. malariae, P. ovale, P. vivax* and *P. falciparum* in a test sample suspected of containing one or more of these types of antibodies comprising the steps of: (a) contacting the test sample with anti-antibody to allow for the formation of anti-antibody/antibody complexes, (b) adding a first conjugate, a second conjugate, a third conjugate and a fourth conjugate to resulting anti-antibody/antibody complexes for a time and under conditions sufficient to allow the conjugates to bind to bound antibody, wherein: 1) a first conjugate comprises an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal, 2) a second conjugate comprises an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, attached to a signal generating compound capable of generating a detectable signal, 3) a third conjugate comprises a *P. vivax* antigen attached to a signal generating signal capable of generating a detectable signal and 4) a fourth conjugate comprises a *P. falciparum* antigen attached to a signal generating compound capable of generating a detectable signal and (c) detecting the presence of antibodies to *P. malariae, P. ovale, P. vivax* and *P.*

*falciparum* in the test sample by detecting presence of a signal generated by the signal generating compound.

Moreover, the present invention also encompasses a vaccine comprising: a) at least one antigen selected from the group consisting of: 1) an antigen comprising the amino acid sequence of SEQ ID NO:1 or an epitope thereof, 2) an antigen comprising the amino acid sequence of SEQ ID NO:3 or an epitope thereof, 3) a *P. falciparum* antigen and 4) a *P. vivax* antigen and b) a pharmaceutically acceptable adjuvant.

Additionally, the present invention includes a vaccine comprising: a) an antibody raised against at least one antigen selected from the group consisting of: 1) an antigen comprising the amino acid sequence of SEQ ID NO:1 or an epitope thereof, 2) an antigen comprising the amino acid sequence of SEQ ID NO:3 or an epitope thereof, 3) a *P. falciparum* antigen and 4) a *P. vivax* antigen and b) a pharmaceutically acceptable adjuvant.

The present invention also includes a kit for determining the presence of antibody to *P. malariae* in a test sample comprising: a) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2 and b) a conjugate comprising an antibody attached to a signal-generating compound capable of generating a detectable signal.

Another kit encompassed within the present invention includes a kit for determining the presence of antibody to *P. ovale* in a test sample comprising: a) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4 and b) a conjugate comprising an antibody attached to a signal-generating compound capable of generating a detectable signal.

A further kit of the present invention is a kit for determining the presence of antibody to *P. malariae, P. ovale, P. vivax* and *P. falciparum* in a test sample comprising: a) 1) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) a *P. vivax* antigen and 4) a *P. falciparum* antigen and b) a conjugate comprising an antibody attached to a signal generating compound capable of generating a detectable signal.

Also included within the present invention is a kit for detecting antibodies to *P. malariae* in a test sample comprising: a) an anti-antibody and b) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2.

The present invention also encompasses a kit for detecting antibodies to *P. malariae* in a test sample comprising: a) an anti-antibody and b) a conjugate comprising an antigen of *P. malariae*, wherein the antigen comprises an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2 and wherein the conjugate is attached to a signal-generating compound capable of generating a detectable signal.

Further, the present invention includes a kit for detecting antibodies to *P. ovale* in a test sample comprising: a) an anti-antibody and b) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4.

Additionally, the present invention encompasses a kit for detecting antibodies to *P. ovale* in a test sample comprising: a) an anti-antibody and b) a conjugate comprising an of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, wherein the conjugate is attached to a signal-generating compound capable of generating a detectable signal.

Also, the present invention includes a kit for detecting antibodies to *P. malariae, P. ovale, P. vivax* and *P. falciparum* in a test sample suspected of containing at least one type of these antibodies comprising: a) an anti-antibody and b) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, a *P. vivax* antigen and a *P. falciparum* antigen Moreover, the present invention encompasses a kit for detecting antibodies to *P. malariae, P. ovale, P. vivax* and *P. falciparum* in a test sample suspecting of containing at least one type of such antibodies comprising: a) an anti-antibody and b) a first conjugate comprising an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal, a second conjugate comprising an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, attached to a signal generating compound capable of generating a detectable signal, a third conjugate comprising a *P. vivax* antigen, wherein said conjugate is attached to a signal generating compound capable of generating a detectable signal and a fourth conjugate comprising a *P. falciparum* antigen, wherein said fourth conjugate is attached to a signal generating compound capable of generating a detectable signal.

BRIEF DESCRIPTION OF THE DRAWINGS

FIG. 1 illustrates the *P. malariae* nucleotide sequence (SEQ ID NO:2) of a gene or nucleic acid molecule derived from MSP1.

FIG. 2 illustrates the deduced *P. malariae* amino acid sequence (SEQ ID NO:1) of the protein encoded by SEQ ID NO:2.

FIG. 3 illustrates the *P. ovale* nucleotide sequence (SEQ ID NO:4) of a gene or nucleic acid molecule derived from MSP1.

FIG. 4 illustrates the deduced *P. ovale* amino acid sequence (SEQ ID NO:3) of the protein encoded by SEQ ID NO:4.

FIG. 5 illustrates an alignment of the PmMSP1 gene sequence (SEQ ID NO:2) with the translated amino acid sequence (SEQ ID NO:1) thereof.

FIG. 6 illustrates an amino acid sequence alignment of PmMSP1 (*P. malariae* (top portion) (SEQ ID NO:1) versus *P. vivax* (bottom portion) (SEQ ID NO:5)).

FIG. 7 illustrates the DNA sequence alignment of *P. malariae* (Cameroon Sample 0014)(nucleotides 124-477 of SEQ ID NO:2) versus *P. malariae* (GenBank sequence AF138881 MSP1 5'-DNA sequence)(nucleotides 30-387 of SEQ ID NO:6).

FIG. 8 illustrates an alignment of the *P. ovale* MSP1 gene sequence (SEQ ID NO:4) with the translated amino acid sequence thereof (SEQ ID NO:3).

FIG. 9 illustrates an alignment of the *P. ovale* MSP1 amino acid sequence (top portion) (SEQ ID NO:3) versus *P. vivax* (bottom portion) (SEQ ID NO:5).

FIG. 10 illustrates a MSP1 amino acid sequence comparison (% identity) between *P. falciparum* (Genbank # BAF62278), *P. vivax* (Genbank # AAA63427), *P. malariae* (Cameroon Sample 0014) and *P. ovale* (Cameroon Sample 510-10).

FIG. 11 illustrates the location of MSP1 and MSP1 subregions for *P. malariae* and *P. ovale.*

DETAILED DESCRIPTION OF THE INVENTION

Figure 12:
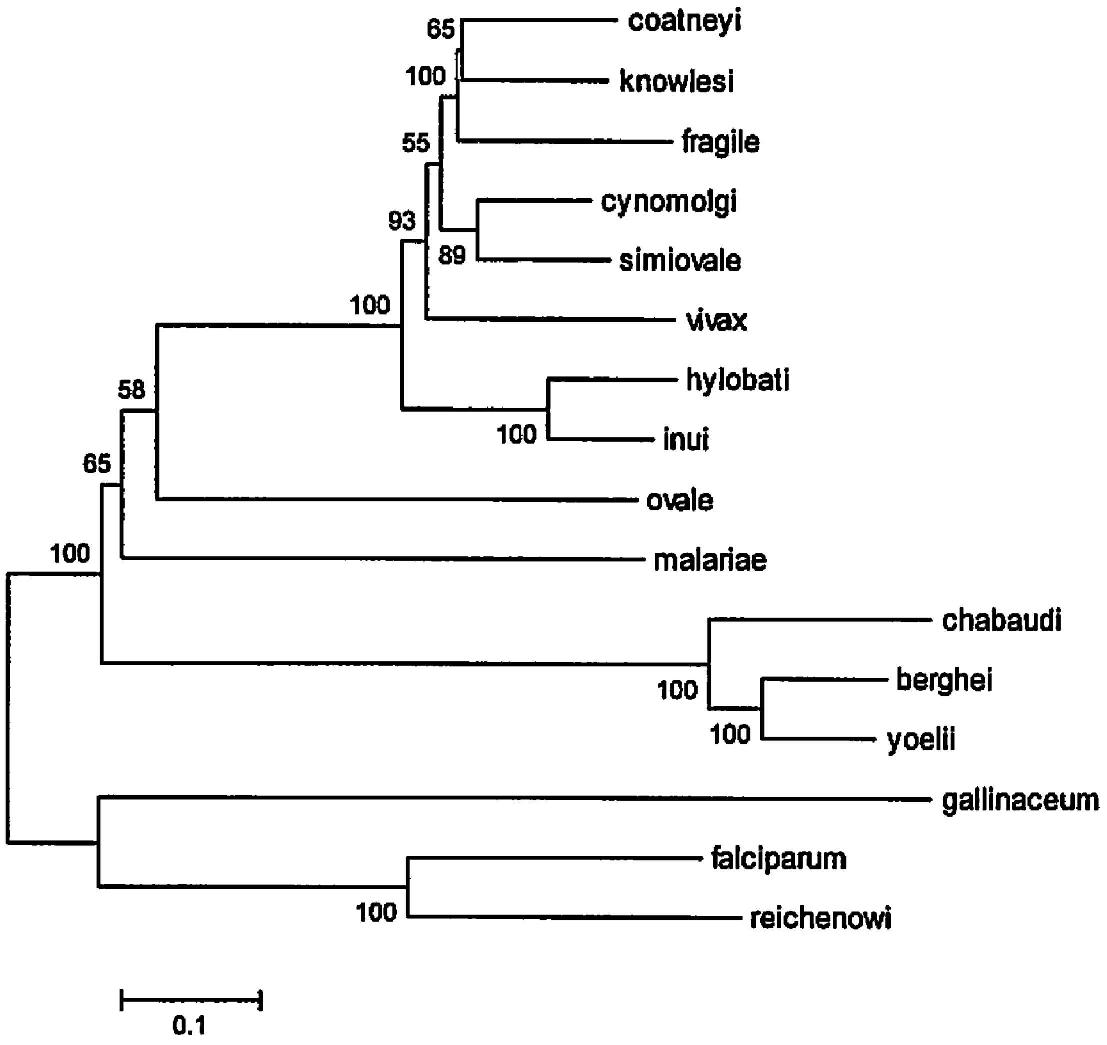
FIG. 12 shows the evolutionary relationships of 16 MSP1 protein sequences inferred using the Neighbor-Joining method (Saitou N & Nei M (1987) *Molecular Biology and Evolution* 4:406-425). The bootstrap consensus tree inferred from 500 replicates (Felsenstein, J. (1985) Evolution 39:783-791) is taken to represent the evolutionary history of the taxa analyzed (Felsenstein, supra). Branches corresponding to partitions reproduced in less than 50% bootstrap replicates are collapsed. The percentage of replicate trees in which the associated taxa clustered together in the bootstrap test (500 replicates) are shown next to the branches (Felsenstein, supra). The tree is drawn to scale, with branch lengths in the same units as those of the evolutionary distances used to infer the phylogenetic tree. The evolutionary distances were computed using the Dayhoff matrix based method (Schwarz R. & Dayhoff M. (1979) Matrices for detecting distant relationships. In Dayhoff M, editor, Atlas of protein sequences, pages 353-58. National Biomedical Research Foundation) and are in the units of the number of amino acid substitutions per site. All positions containing gaps and missing data were eliminated from the dataset (Complete deletion option). There were a total of 1354 positions in the final dataset. Phylogenetic analyses were conducted in MEGA4 (Tamura et al., (2007) *Molecular Biology and Evolution* 24:1596-1599).
Figure 13:
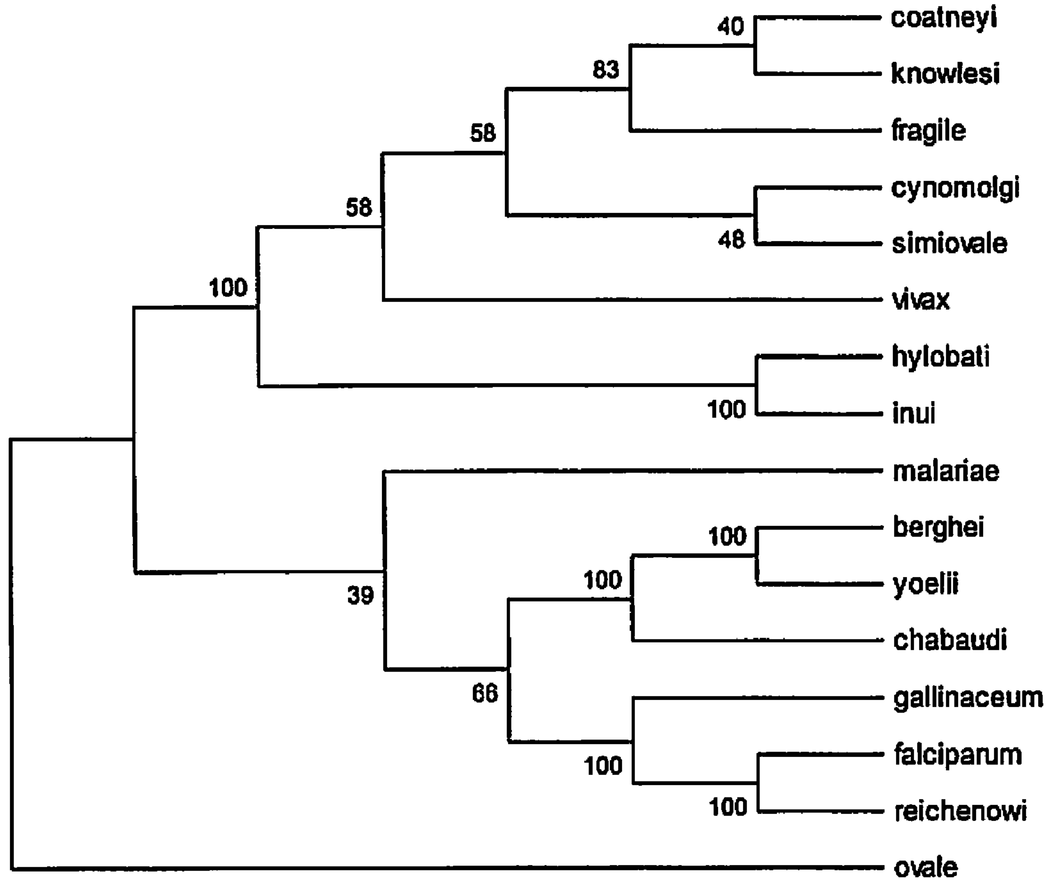
FIG. 13 shows the evolutionary relationships of 16 MSP1 protein sequences inferred using the Maximum Parsimony method (Eck R V & Dayhoff M O (1966) *Atlas of Protein Sequence and Structure*. National Biomedical Research Foundation, Silver Spring, Md.). The bootstrap consensus tree inferred from 500 replicates is taken to represent the evolutionary history of the taxa analyzed (Felsenstein J (1985) *Evolution* 39:783-791.) Branches corresponding to partitions reproduced in less than 50% bootstrap replicates are collapsed. The percentage of replicate trees in which the associated taxa clustered together in the bootstrap test (500 replicates) are shown next to the branches (Felsenstein, supra). The MP tree was obtained using the Close-Neighbor-Interchange algorithm (Nei M & Kumar S (2000) *Molecular Evolution and Phylogenetics*. Oxford University Press, New York, pg. 128) with search level 3 (Felsenstein, supra; Nei M & Kumar S (2000) *Molecular Evolution and Phylogenetics*. Oxford University Press, New York) in which the initial trees were obtained with the random addition of sequences (10 replicates). All positions containing gaps and missing data were eliminated from the dataset (Complete Deletion option). There were a total of 1354 positions in the final dataset, out of which 1001 were parsimony informative. Phylogenetic analyses were conducted in MEGA4 (Tamura et al. (2007) *Molecular Biology and Evolution* 24:1596-1599).
Figure 14:
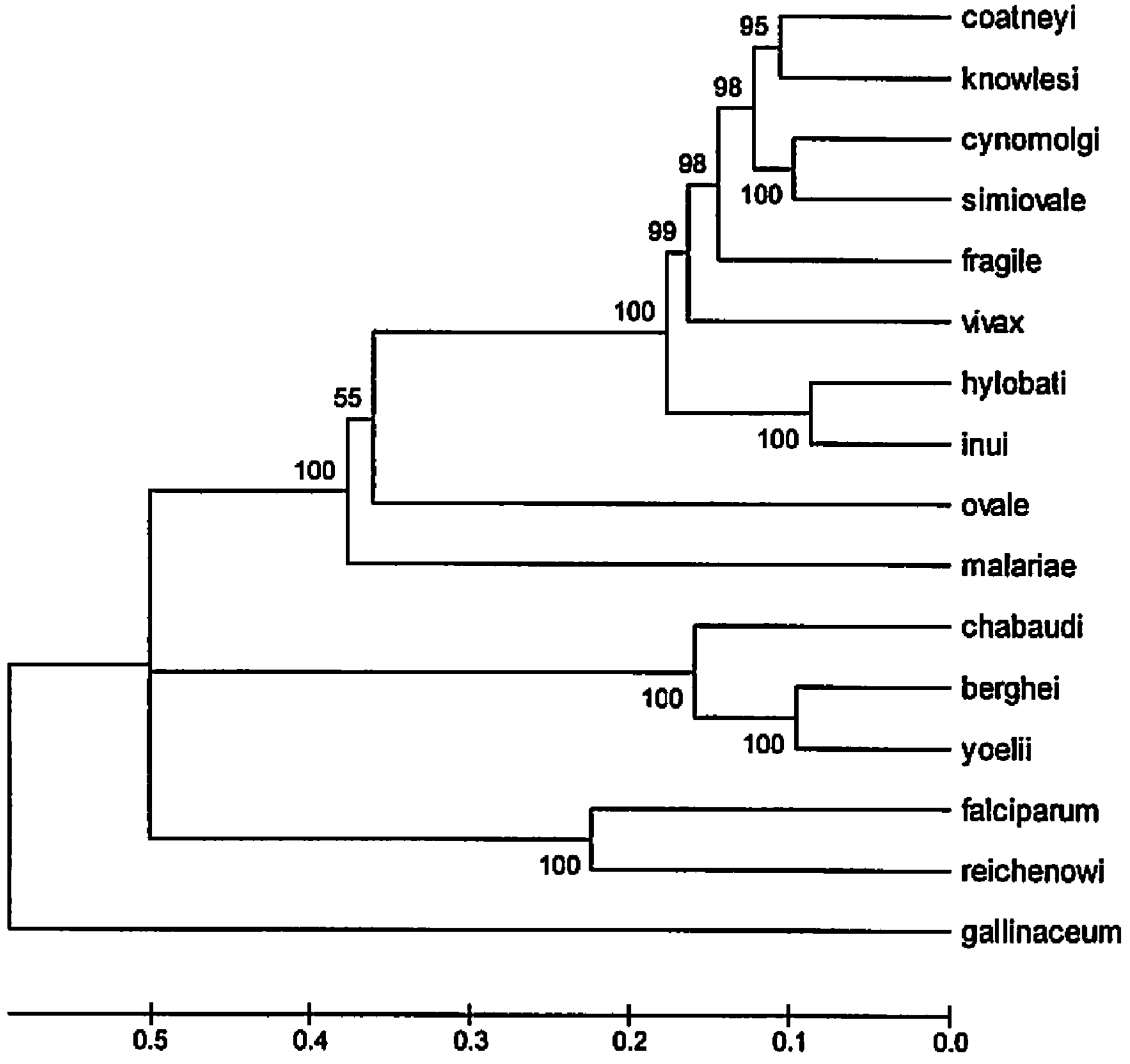
FIG. 14 shows the evolutionary relationships of 16 MSP1 protein sequences inferred using the UPGMA method (Sneath P H A & Sokal R R (1973) *Numerical Taxonomy. Freeman*, San Francisco). The bootstrap consensus tree inferred from 500 replicates (Felsenstein, supra is taken to represent the evolutionary history of the taxa analyzed (Felsenstein, supra). Branches corresponding to partitions reproduced in less than 50% bootstrap replicates are collapsed. The percentage of replicate trees in which the associated taxa clustered together in the bootstrap test (500 replicates) are shown next to the branches (Felsenstein, supra). The tree is drawn to scale, with branch lengths in the same units as those of the evolutionary distances used to infer the phylogenetic tree. The evolutionary distances were computed using the Dayhoff matrix based method (Schwarz R & Dayhoff M (1979) Matrices for detecting distant relationships. In Dayhoff M, editor, Atlas of protein sequences, pages 353-58. National Biomedical Research Foundation) and are in the units of the number of amino acid substitutions per site. All positions containing gaps and missing data were eliminated from the dataset (Complete deletion option). There were a total of 1354 positions in the final dataset. Phylogenetic analyses were conducted in MEGA4 (Tamura et al. (2007) Molecular Biology and Evolution 24:1596-1599).

The subject invention relates to isolated and purified nucleic acid sequences or molecules (and the proteins encoded thereby) never before isolated from *P. malariae* or *P. ovale*. Such nucleic acid sequences and encoded proteins may be utilized for diagnostic as well as therapeutic purposes to be described, in detail, below.

The Nucleic Acid Sequences and Encoded Proteins

The nucleic acid sequence of the isolated gene from *P. malariae* is shown in FIG. 1 (SEQ ID NO:2), and the amino acid sequence of the encoded purified protein encoded by this nucleic acid sequence is shown in FIG. 2 (SEQ ID NO:1). Additionally, the nucleic acid sequence of the isolated gene from *P. ovale* is shown in FIG. 3 (SEQ ID NO:4), and the amino acid sequence of the purified protein encoded by this nucleic acid sequence is shown in FIG. 4 (SEQ ID NO:3).

It should be noted that the present invention also encompasses nucleic acid sequences or molecules comprising nucleotide sequences which are at least about 70% identical to, preferably at least about 80% identical to, and more preferably at least about 90% identical to the nucleotide sequence of SEQ ID NO:2 or SEQ ID NO:4. Complements of these sequences are also encompassed by the present invention. (All integers within the range of 70 to 100 (in terms of percent identity) are also included within the scope of the invention (i.e., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%).

It should be noted that the present invention also encompasses proteins or polypeptides comprising amino acid sequences which are at least about 70% identical to, preferably at least about 80% identical to, and more preferably at least about 90% identical to the amino acid sequence of SEQ ID NO:1 or SEQ ID NO:3. (Again, all integers within the range of 70 to 100 (in terms of percent identity) are also included within the scope of the invention (i.e., 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% and 100%).

Additionally, the present invention encompasses "fragments or peptides" of the full-length polypeptides described herein. Such peptides represent portions of the polypeptide which may, for example, have specific immunogenic or binding properties. The fragment may be, for example, between 3-10 amino acids in length, 10-20 amino acids in length, 20-40 amino acids in length, 40-80 amino acids in length, 80-160 amino acids in length or even longer. Amino acid sequences having at least 70% amino acid identity, preferably at least 80% amino acid identity, and more preferably at least 90% identity to the fragments described herein are also included within the scope of the present invention. (Further, all integers between the range of 70 to 100 percent identity, as recited above, are also considered to fall within the scope of the present invention.)

An "epitope" is an antigenic determinant of a polypeptide. An epitope may comprise at least three amino acids in a spatial conformation which is unique to the epitope. Generally, an epitope consists of at least five such amino acids, and more usually, consists of at least eight to ten amino acids.

The nucleotide or amino acids sequences having the above-described percent identity (or complementary sequences with respect with nucleotide sequences) may be derived from one or more sources other than *P. malariae* and *P. ovale*. For example, the sequences may be derived from other species of malaria and, in particular, *Plasmodium* including but not limited to *P. falciparum* and *P. vivax* as well as from other parasites.

Furthermore, the present invention also encompasses fragments and derivatives of the nucleic acid sequences of the present invention (i.e., SEQ ID NO:2 and SEQ ID NO:4) as well as fragments and portions of the amino acid sequences of the present invention (i.e., SEQ ID NO:1 and SEQ ID NO:3). Corresponding sequences derived from non-*P. malariae* and non-*P. ovale* sources, as described above, and having the above-described complementarity or identity, as appropriate, are also considered to fall within the scope of the present invention. Functional equivalents of the above-sequences (i.e., nucleotide sequences encoding proteins having, for example, the same binding affinities, epitopes, etc. of the encoded proteins) are also encompassed by the present invention.

For purposes of the present invention, "complementarity" is defined as the degree of relatedness between two DNA segments. It is determined by measuring the ability of the sense strand of one DNA segment to hybridize with the antisense strand of the other DNA segment, under appropriate conditions, to form a double helix. In the double helix, wherever adenine appears in one strand, thymine appears in the other strand. Similarly, wherever guanine is found in one strand, cytosine is found in the other. The greater the relatedness between the nucleotide sequences of two DNA segments, the greater the ability to form hybrid duplexes between the strands of two DNA segments.

The term "identity" refers to the relatedness of two sequences on a nucleotide-by-nucleotide basis over a particular comparison window or segment. Thus, identity is defined as the degree of sameness, correspondence or equivalence between the same strands (either sense or antisense) of two DNA segments (or two amino acid sequences). "Percentage of sequence identity" is calculated by comparing two optimally aligned sequences over a particular region, determining the number of positions at which the identical base or amino acid occurs in both sequences in order to yield the number of matched positions, dividing the number of such positions by the total number of positions in the segment being compared and multiplying the result by 100. Optimal alignment of sequences may be conducted by the algorithm of Smith & Waterman, Appl. Math. 2:482 (1981), by the algorithm of Needleman & Wunsch, *J. Mol. Biol.* 48:443 (1970), by the method of Pearson & Lipman, *Proc. Natl. Acad. Sci.* (*USA*) 85:2444 (1988) and by computer programs which implement the relevant algorithms (e.g., Clustal Macaw Pileup (http://cmgm.stanford.edu/biochem218/11Multiple.pdf; Higgins et al., CABIOS. 5L151-153 (1989)), FASTDB (Intelligenetics), BLAST (National Center for Biomedical Information; Altschul et al., Nucleic Acids Research 25:3389-3402 (1997)), PILEUP (Genetics Computer Group, Madison, Wis.) or GAP, BESTFIT, FASTA and TFASTA (Wisconsin Genetics Software Package Release 7.0, Genetics Computer Group, Madison, Wis.). (See U.S. Pat. No. 5,912,120.)

"Identity between two amino acid sequences" is defined as the presence of a series of exactly alike or invariant amino acid residues in both sequences (see above definition for identity between nucleic acid sequences). The definitions of "complementarity" and "identity" are well known to those of ordinary skill in the art.

"Encoded by" refers to a nucleic acid sequence which codes for a polypeptide sequence, wherein the polypeptide sequence or a portion thereof contains an amino acid sequence of at least 3 amino acids, more preferably at least 8 amino acids, and even more preferably at least 15 amino acids from a polypeptide encoded by the nucleic acid sequence.

The present invention also encompasses an isolated nucleic sequence which encodes a protein having functional activity similar to that represented by SEQ ID NO:2 or SEQ ID NO:4, and that is hybridizable, under moderately stringent conditions, to a nucleic acid molecule having a nucleotide sequence comprising or complementary to the nucleotide sequences described above. A nucleic acid molecule is “hybridizable” to another nucleic acid molecule when a single-stranded form of the nucleic acid molecule can anneal to the other nucleic acid molecule under the appropriate conditions of temperature and ionic strength (see Sambrook et al., “Molecular Cloning: A Laboratory Manual, Second Edition (1989), Cold Spring Harbor Laboratory Press, Cold Spring Harbor, N.Y.)). The conditions of temperature and ionic strength determine the “stringency” of the hybridization. “Hybridization” requires that two nucleic acids contain complementary sequences. However, depending on the stringency of the hybridization, mismatches between bases may occur. The appropriate stringency for hybridizing nucleic acids depends on the length of the nucleic acids and the degree of complementation. Such variables are well known in the art. More specifically, the greater the degree of similarity, identity or homology between two nucleotide sequences, the greater the value of Tm for hybrids of nucleic acids having those sequences. For hybrids of greater than 100 nucleotides in length, equations for calculating Tm have been derived (see Sambrook et al., supra (1989)). For hybridization with shorter nucleic acids, the position of mismatches becomes more important, and the length of the oligonucleotide determines its specificity (see Sambrook et al., supra (1989)).

As used herein, an “isolated nucleic acid fragment or sequence” is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. (A “fragment” of a specified polynucleotide refers to a polynucleotide sequence which comprises a contiguous sequence of approximately at least about 6 nucleotides, preferably at least about 8 nucleotides, more preferably at least about 10 nucleotides, and even more preferably at least about 15 nucleotides, and most preferable at least about 25 nucleotides identical or complementary to a region of the specified nucleotide sequence.) Nucleotides (usually found in their 5'-monophosphate form) are referred to by their single letter designation as follows: “A” for adenylate or deoxyadenylate (for RNA or DNA, respectively), “C” for cytidylate or deoxycytidylate, “G” for guanylate or deoxyguanylate, “U” for uridylate, “T” for deoxythymidylate, “R” for purines (A or G), “Y” for pyrimidines (C or T), “K” for G or T, “H” for A or C or T, “I” for inosine, and “N” for any nucleotide.

The terms “fragment or subfragment that is functionally equivalent” and “functionally equivalent fragment or subfragment” are used interchangeably herein. These terms refer to a portion or subsequence of an isolated nucleic acid fragment in which the ability to alter gene expression or produce a certain phenotype is retained whether or not the fragment or subfragment encodes an active enzyme. For example, the fragment or subfragment can be used in the design of chimeric constructs to produce the desired phenotype in a transformed plant. Chimeric constructs can be designed for use in co-suppression or antisense by linking a nucleic acid fragment or subfragment thereof, whether or not it encodes an active protein, in the appropriate orientation relative to a promoter sequence.

The terms “homology”, “homologous”, “substantially similar” and “corresponding substantially” are used interchangeably herein. They refer to nucleic acid fragments wherein changes in one or more nucleotide bases does not affect the ability of the nucleic acid fragment to mediate gene expression or produce a certain phenotype. These terms also refer to modifications of the nucleic acid fragments of the instant invention such as deletion or insertion of one or more nucleotides that do not substantially alter the functional properties of the resulting nucleic acid fragment relative to the initial, unmodified fragment. It is therefore understood, as those skilled in the art will appreciate, that the invention encompasses more than the specific exemplary sequences described herein.

“Gene” refers to a nucleic acid fragment that expresses a specific protein, including regulatory sequences preceding (5' non-coding sequences) and following (3' non-coding sequences) the coding sequence.

“Native gene” refers to a gene as found in nature with its own regulatory sequences. In contrast, “chimeric construct” refers to a combination of nucleic acid fragments that are not normally found together in nature. Accordingly, a chimeric construct may comprise regulatory sequences and coding sequences that are derived from different sources, or regulatory sequences and coding sequences derived from the same source, but arranged in a manner different than that normally found in nature. (The term “isolated” means that the sequence is removed from its natural environment.)

A “foreign” gene refers to a gene not normally found in the host organism, but that is introduced into the host organism by gene transfer. Foreign genes can comprise native genes inserted into a non-native organism, or chimeric constructs. A “transgene” is a gene that has been introduced into the genome by a transformation procedure.

A “probe” or “primer” as used herein is a polynucleotide that is at least 8 nucleotides in length and forms a hybrid structure with a target sequence, due to complementarity of at least one sequence in the probe or primer with a sequence in the target region. The polynucleotide regions of the probe can be composed of DNA and/or RNA and/or synthetic nucleotide analogs. Preferably, the probe does not contain a sequence that is complementary to the sequence or sequences used to prime for a target sequence during the polymerase chain reaction.

“Coding sequence” refers to a DNA sequence that codes for a specific amino acid sequence. “Regulatory sequences” refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include, but are not limited to, promoters, translation leader sequences, introns, and polyadenylation recognition sequences.

“Promoter” (or “regulatory sequence”) refers to a DNA sequence capable of controlling the expression of a coding sequence or functional RNA. The promoter sequence, for example, consists of proximal and more distal upstream elements, the latter elements often referred to as enhancers. Accordingly, an “enhancer” is a DNA sequence that can stimulate promoter activity and may be an innate element of the promoter or a heterologous element inserted to enhance the level or tissue-specificity of a promoter. Regulatory sequences (e.g., a promoter) can also be located within the transcribed portions of genes, and/or downstream of the transcribed sequences. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most host cell types, at most times, are commonly referred to as "constitutive promoters". New promoters of various types useful in plant cells are constantly being discovered; numerous examples may be found in the compilation by Okamuro and Goldberg, (1989) *Biochemistry of Plants* 15:1-82. It is further recognized that since, in most cases, the exact boundaries of regulatory sequences have not been completely defined, DNA fragments of some variation may have identical promoter activity.

An "intron" is an intervening sequence in a gene that does not encode a portion of the protein sequence. Thus, such sequences are transcribed into RNA but are then excised and are not translated. The term is also used for the excised RNA sequences. An "exon" is a portion of the gene sequence that is transcribed and is found in the mature messenger RNA derived from the gene, but is not necessarily a part of the sequence that encodes the final gene product.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671-680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "

Messenger RNA (mRNA)" refers to the RNA that is without introns and that can be translated into protein by the cell. "cDNA" refers to a DNA that is complementary to and synthesized from a mRNA template using the enzyme reverse transcriptase. The cDNA can be single-stranded or converted into the double-stranded form using the Klenow fragment of DNA polymerase I. "Sense" RNA refers to RNA transcript that includes the mRNA and can be translated into protein within a cell or in vitro. "Antisense RNA" refers to an RNA transcript that is complementary to all or part of a target primary transcript or mRNA and that blocks the expression of a target gene (U.S. Pat. No. 5,107,065). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes. The terms "complement" and "reverse complement" are used interchangeably herein with respect to mRNA transcripts, and are meant to define the antisense RNA of the message.

The term "endogenous RNA" refers to any RNA which is encoded by any nucleic acid sequence present in the genome of the host prior to transformation with the recombinant construct of the present invention, whether naturally-occurring or non-naturally occurring, i.e., introduced by recombinant means, mutagenesis, etc.

The term "non-naturally occurring" means artificial, not consistent with what is normally found in nature.

The term "operably linked" refers to the association of nucleic acid sequences on a single nucleic acid fragment so that the function of one is regulated by the other. For example, a promoter is operably linked with a coding sequence when it is capable of regulating the expression of that coding sequence (i.e., that the coding sequence is under the transcriptional control of the promoter). Coding sequences can be operably linked to regulatory sequences in a sense or antisense orientation. In another example, the complementary RNA regions of the invention can be operably linked, either directly or indirectly, 5' to the target mRNA, or 3' to the target mRNA, or within the target mRNA, or a first complementary region is 5' and its complement is 3' to the target mRNA.

The term "expression", as used herein, refers to the production of a functional end-product. Expression of a gene involves transcription of the gene and translation of the mRNA into a precursor or mature protein. "Antisense inhibition" refers to the production of antisense RNA transcripts capable of suppressing the expression of the target protein. "Co-suppression" refers to the production of sense RNA transcripts capable of suppressing the expression of identical or substantially similar foreign or endogenous genes (U.S. Pat. No. 5,231,020).

"Mature" protein refers to a post-translationally processed polypeptide; i.e., one from which any pre- or pro-peptides present in the primary translation product have been removed. "Precursor" protein refers to the primary product of translation of mRNA; i.e., with pre- and pro-peptides still present. Pre- and pro-peptides may be but are not limited to intracellular localization signals.

"Stable transformation" refers to the transfer of a nucleic acid fragment into a genome of a host organism, resulting in genetically stable inheritance. In contrast, "transient transformation" refers to the transfer of a nucleic acid fragment into the nucleus, or DNA-containing organelle, of a host organism resulting in gene expression without integration or stable inheritance. Host organisms containing the transformed nucleic acid fragments are referred to as "transgenic" organisms. The term "transformation" as used herein refers to both stable transformation and transient transformation.

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Sambrook").

The term "recombinant" refers to an artificial combination of two otherwise separated segments of sequence, e.g., by chemical synthesis or by the manipulation of isolated segments of nucleic acids by genetic engineering techniques.

"PCR" or "Polymerase Chain Reaction" is a technique for the synthesis of large quantities of specific DNA segments, consists of a series of repetitive cycles (Perkin Elmer Cetus Instruments, Norwalk, Conn.). Typically, the double stranded DNA is heat denatured, the two primers complementary to the 3' boundaries of the target segment are annealed at low temperature and then extended at an intermediate temperature. One set of these three consecutive steps is referred to as a cycle.

Polymerase chain reaction ("PCR") is a powerful technique used to amplify DNA millions of fold, by repeated replication of a template, in a short period of time. (Mullis et al., *Cold Spring Harbor Symp. Quant. Biol.* 51:263-273 (1986); Erlich et al., European Patent Application No. 50,424; European Patent Application No. 84,796; European Patent Application No. 258,017, European Patent Application No. 237,362; European Patent Application No. 201,184, U.S. Pat. Nos. 4,683,202; 4,582,788; and 4,683,194). The process utilizes sets of specific in vitro synthesized oligonucleotides to prime DNA synthesis. The design of the primers is dependent upon the sequences of DNA that are to be analyzed. The technique is carried out through many cycles (usually 20-50) of melting the template at high temperature, allowing the primers to anneal to complementary sequences within the template and then replicating the template with DNA polymerase.

The products of PCR reactions are analyzed by separation in agarose gels followed by ethidium bromide staining and visualization with UV transillumination. Alternatively, radioactive dNTPs can be added to the PCR in order to incorporate label into the products. In this case the products of PCR are visualized by exposure of the gel to x-ray film. The added advantage of radiolabeling PCR products is that the levels of individual amplification products can be quantitated.

The terms "recombinant construct", "expression construct" and "recombinant expression construct" are used interchangeably herein. These terms refer to a functional unit of genetic material that can be inserted into the genome of a cell using standard methodology well known to one skilled in the art. Such a construct may be itself or may be used in conjunction with a vector. If a vector is used, then the choice of vector is dependent upon the method that will be used to transform host plants, as is well known to those skilled in the art. For example, a plasmid can be used. The skilled artisan is well aware of the genetic elements that must be present on the vector in order to successfully transform, select and propagate host cells comprising any of the isolated nucleic acid fragments of the invention. The skilled artisan will also recognize that different independent transformation events will result in different levels and patterns of expression (Jones et al., (1985) *EMBO J.* 4:2411-2418; De Almeida et al., (1989) *Mol. Gen. Genetics* 218:78-86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

Production of the Proteins

Once the gene encoding the protein of interest has been isolated, it may then be introduced into either a prokaryotic or eukaryotic host cell, through the use of a vector or construct, in order for the host cell to express the protein of interest. The vector, for example, a bacteriophage, cosmid or plasmid, may comprise the nucleic acid sequence encoding the enzyme, as well as any regulatory sequence (e.g., promoter) that is functional in the host cell and is able to elicit expression of the protein encoded by the nucleic acid sequence. The regulatory sequence (e.g., promoter) is in operable association with, or operably linked to, the nucleotide sequence. (A regulatory sequence (e.g., promoter) is said to be "operably linked" with a coding sequence if the regulatory sequence affects transcription or expression of the coding sequence.) Suitable promoters include, for example, those from genes encoding alcohol dehydrogenase, glyceraldehyde-3-phosphate dehydrogenase, phosphoglucoisomerase, phosphoglycerate kinase, acid phosphatase, T7, TPI, lactase, metallothionein, cytomegalovirus immediate early, whey acidic protein, glucoamylase, promoters activated in the presence of galactose, for example, GAL1 and GAL10, as well as any other promoters involved in prokaryotic and eukaryotic expression systems. Additionally, nucleic acid sequences that encode other proteins may also be included within the vector as well as other non-promoter regulatory sequences such as, for example, a polyadenylation signal (e.g., the poly-A signal of SV-40T-antigen, ovalalbumin or bovine growth hormone). The choice of sequences present in the construct is dependent upon the desired expression products as well as the nature of the host cell.

As noted above, once the vector has been constructed, it may then be introduced into the host cell of choice by methods known to those of ordinary skill in the art including, for example, transfection, transformation and electroporation (see *Molecular Cloning: A Laboratory Manual,* $2^{nd}$ ed., Vol. 1-3, ed. Sambrook et al., Cold Spring Harbor Laboratory Press (1989)). The host cell is then cultured under suitable conditions permitting expression of the desired protein that is then recovered and purified.

Examples of suitable prokaryotic host cells include, for example, bacteria such as *Escherichia coli, Bacillus subtilis*, Actinomycetes such as *Streptomyces coelicolor, Streptomyces lividans*, as well as cyanobacteria such as *Spirulina* spp. (i.e., blue-green algae). Examples of suitable eukaryotic host cells include, for example, mammalian cells, plant cells, yeast cells such as *Saccharomyces* spp., *Lipomyces* spp., *Candida* spp. such as *Yarrowia* (*Candida*) spp., *Kluyveromyces* spp., *Pichia* spp., *Trichoderma* spp. or *Hansenula* spp., or fungal cells such as filamentous fungal cells, for example, *Aspergillus, Neurospora* and *Penicillium*. Preferably, *Saccharomyces cerevisiae* (baker's yeast) cells are utilized.

Expression in a host cell can be accomplished in a transient or stable fashion. Transient expression can occur from introduced constructs which contain expression signals functional in the host cell, but which constructs do not replicate and rarely integrate in the host cell, or where the host cell is not proliferating. Transient expression also can be accomplished by inducing the activity of a regulatable promoter operably linked to the gene of interest, although such inducible systems frequently exhibit a low basal level of expression. Stable expression can be achieved by introduction of a construct that can integrate into the host genome or that autonomously replicates in the host cell. Stable expression of the gene of interest can be selected for through the use of a selectable marker located on or transfected with the expression construct, followed by selection for cells expressing the marker. When stable expression results from integration, the site of the construct's integration can occur randomly within the host genome or can be targeted through the use of constructs containing regions of homology with the host genome sufficient to target recombination with the host locus. Where constructs are targeted to an endogenous locus, all or some of the transcriptional and translational regulatory regions can be provided by the endogenous locus.

A transgenic mammal may also be used in order to express the protein of interest encoded by one or both of the above-described nucleic acid sequences. More specifically, once the above-described construct is created, it may be inserted into the pronucleus of an embryo. The embryo may then be implanted into a recipient female. Alternatively, a nuclear transfer method could also be utilized (Schnieke et al., *Science* (1997) 278:2130-2133). Gestation and birth are then permitted to occur (see, e.g., U.S. Pat. Nos. 5,750,176 and 5,700,671), and milk, tissue or other fluid samples from the offspring should then contain the protein of interest. The mammal utilized as the host may be selected from the group consisting of, for example, a mouse, a rat, a rabbit, a pig, a goat, a sheep, a horse and a cow. However, any mammal may be used provided it has the ability to incorporate DNA encoding the protein of interest into its genome.

In view of the above, the present invention also encompasses a method of producing one or more of the proteins described above comprising the steps of: 1) isolating the desired nucleic acid sequence(s) of the gene encoding the protein(s) (i.e., SEQ ID NO:2 and/or SEQ ID NO:4; 2) constructing a vector comprising said nucleic acid sequence(s); and 3) introducing said vector into a host cell for a time and conditions sufficient for the production of the protein(s).

Uses of the Genes and Proteins Encoded Thereby

As noted above, the isolated nucleic acid sequences (or genes) and the corresponding proteins (or purified polypeptides) encoded thereby have many beneficial uses. The difficulties of existing assays for the detection of antibodies to all four species of *Plasmodium* have been described, in detail, above. Thus, there was a significant need to discover antigens in connection with all four species that could be used in immunoassays that could accurately detect the presence of such antibodies in positive serum or plasma, thereby eliminating the problem of false negatives tests. The present invention provides such needed immunoassays and, in particular, sole antigens or combinations of antigens which accurately detect the presence of antibodies to all four species of *Plasmodium* in human sera.

Furthermore, the present invention also includes a polyclonal or monoclonal antibody raised against the above-described proteins. Such an antibody may be used, for example, in an immunoassay, a vaccine (for passive immunization), a kit, or for research purposes.

The uses noted above are described, in detail, as follows:

Immunoassays

There are two basic types of assays, competitive and non-competitive (e.g., immunometric and sandwich, respectively). In both assays, antibody or antigen reagents are covalently or non-covalently attached to the solid phase. (See *The Immunoassay Handbook*, $2^{nd}$ Edition, edited by David Wild, Nature Publishing Group, London 2001). Linking agents for covalent attachment are known and may be part of the solid phase or derivatized to it prior to coating. Examples of solid phases used in immunoassays are porous and non-porous materials, latex particles, magnetic particles, microparticles, strips, beads, membranes, microtiter wells and plastic tubes. The choice of solid phase material and method of labeling the antigen or antibody reagent are determined based upon desired assay format performance characteristics. For some immunoassays, no label is required. For example, if the antigen is on a detectable particle such as a red blood cell, reactivity can be established based upon agglutination. Alternatively, an antigen-antibody reaction may result in a visible change (e.g., radial immunodiffusion). In most cases, one of the antibody or antigen reagents used in an immunoassay is attached to a signal generating compound or "label". This signal generating compound or "label" is in itself detectable or may be reacted with one or more additional compounds to generate a detectable product (see also U.S. Pat. No. 6,395,472 B1). Examples of such signal generating compounds include chromogens, radioisotopes (e.g., 125I, 131I, 32P, 3H, 35S, and 14C), fluorescent compounds (e.g., fluorescein, rhodamine), chemiluminescent compounds, particles (visible or fluorescent), nucleic acids, complexing agents, or catalysts such as enzymes (e.g., alkaline phosphatase, acid phosphatase, horseradish peroxidase, beta-galactosidase, and ribonuclease). In the case of enzyme use, addition of chromo-, fluoro-, or lumo-genic substrate results in generation of a detectable signal. Other detection systems such as time-resolved fluorescence, internal-reflection fluorescence, amplification (e.g., polymerase chain reaction) and Raman spectroscopy are also useful.

There are two general formats commonly used to monitor specific antibody titer and type in humans: (1) antigen is presented on a solid phase, as described above, the human biological fluid containing the specific antibodies is allowed to react with the antigen, and then antibody bound to antigen is detected with an anti-human antibody coupled to a signal generating compound and (2) an anti-human antibody is bound to the solid phase, the human biological fluid containing specific antibodies is allowed to react with the bound antibody, and then antigen attached to a signal generating compound is added to detect specific antibody present in the fluid sample. In both formats, the anti-human antibody reagent may recognize all antibody classes, or alternatively, be specific for a particular class or subclass of antibody, depending upon the intended purpose of the assay. These assays formats as well as other known formats are intended to be within the scope of the present invention and are well known to those of ordinary skill in the art.

Of course, any of the exemplary formats herein and any assay or kit according to the invention can be adapted or optimized for use in automated and semi-automated systems (including those in which there is a solid phase comprising a microparticle), as described, e.g., in U.S. Pat. Nos. 5,089,424 and 5,006,309, and as, e.g., commercially marketed by Abbott Laboratories (Abbott Park, Ill.) including but not limited to Abbott's ARCHITECT®, AxSYM, IMX, PRISM, and Quantum II platforms, as well as other platforms.

Additionally, the assays and kits of the present invention optionally can be adapted or optimized for point of care assay systems, including Abbott's Point of Care (i-STAT™) electrochemical immunoassay system. Immunosensors and methods of manufacturing and operating them in single-use test devices are described, for example in U.S. Pat. No. 5,063,081 and published U.S. Patent Application Nos. 20030170881, 20040018577, 20050054078, and 20060160164 (incorporated by reference herein for their teachings regarding same).

In view of the above, the present invention includes a method of detecting antibodies to *P. malariae* in a test sample comprising the steps of: (a) contacting the test sample suspected of containing the antibodies with a *P. malariae* protein or antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2; and (b) detecting the presence of antibodies present in the test sample. More specifically, the present invention includes a method of detecting antibodies to *P. malariae* in a test sample comprising the steps of: (a) contacting the test sample suspected of containing the antibodies with a *P. malariae* protein or antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, for a time and under conditions sufficient to allow the formation of antibody/antigen complexes; (b) adding a conjugate to the resulting antibody/antigen complexes for a time and under conditions sufficient to allow the conjugate to bind to the bound antibody, the conjugate comprising an antibody attached to a signal generating compound capable of generating a detectable signal; (c) detecting the presence of the antibody which may be present in the test sample by detecting the signal generated by the signal generating compound. A control or calibrator may also be used which binds to the antigen.

Additionally, the present invention encompasses a method of detecting antibodies to *P. ovale* which may be present in a test sample comprising the steps of (a) contacting the test sample suspected of containing the antibodies with a *P. ovale* protein or antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4; and (b) detecting the presence of antibodies present in the test sample. More specifically, the present invention includes a method of detecting antibodies to *P. ovale* in a test sample comprising the steps of: (a) contacting the test sample suspected of containing the *P. ovale* antibodies with a *P. ovale* protein or antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, for a time and under conditions sufficient to allow the formation of antibody/antigen complexes; (b) adding a conjugate to the resulting antibody/antigen complexes for a time and under conditions sufficient to allow the conjugate to bind to the bound antibody, the conjugate comprising an antibody attached to a signal generating compound capable of generating a detectable signal; (c) detecting the presence of the antibody which may be present in the test sample by detecting the signal generated by the signal generating compound. Again, a control or calibrator may also be used which binds to the antigen.

The present invention further includes a different method for detecting the presence of antibodies which may be present in a test sample. This method comprises the steps of: (a) contacting the test sample suspected of containing antibodies to *P. malariae* with anti-antibody, for a time and under conditions sufficient to allow for formation of anti-antibody/*P. malariae* antibody complexes and (b) detecting the presence of *P. malariae* antibody which may be present in the test sample. (Such anti-antibodies are commercially available and may be created, for example, by immunizing a mammal with purified mu-chain of the antibody.) More specifically, this method may comprise the steps of: (a) contacting the test sample suspected of containing antibodies to *P. malariae* with anti-antibody for a time and under conditions sufficient to allow the formation of anti-antibody/*P. malariae* antibody complexes; (b) adding a conjugate to the resulting anti-antibody/*P. malariae* antibody complexes for a time and under conditions sufficient to allow the conjugate to bind to the bound antibody, the conjugate comprising a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal; and (c) detecting the presence of the antibodies which may be present in the test sample by detecting the signal generated by the signal generating compound. A control or calibrator may be used which comprises antibody to the anti-antibody.

Additionally, the present invention includes a method for detecting antibodies to *P. ovale* in a test sample comprising the steps of: (a) contacting the test sample suspected of containing antibodies to *P. ovale* with anti-antibody specific for *P. ovale* antibody, for a time and under conditions sufficient to allow for formation of anti-antibody/*P. ovale* antibody complexes and (b) detecting the presence of *P. ovale* antibody which may be present in the test sample. More specifically, this method may comprise the steps of: (a) contacting the test sample suspected of containing the antibodies to *P. ovale* with anti-antibody for a time and under conditions sufficient to allow the formation of anti-antibody/*P. ovale* antibody complexes; (b) adding a conjugate to the resulting anti-antibody/*P. ovale* antibody complexes for a time and under conditions sufficient to allow the conjugate to bind to the bound antibody, the conjugate comprising a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, attached to a signal generating compound capable of generating a detectable signal; and (c) detecting the presence of the antibodies which may be present in the test sample by detecting the signal generated by the signal generating compound. Again, a control or calibrator may be used which comprises antibody to the anti-antibody.

The present invention also encompasses a third method for detecting the presence of *P. malariae* antibodies in a test sample. This method comprises the steps of: (a) contacting the test sample suspected of containing the antibodies with anti-antibody, for a time and under conditions sufficient to allow the formation of anti-antibody/*P. malariae* antibody complexes; (b) adding *P. malariae* antigen to the resulting anti-antibody/*P. malariae* antibody complexes for a time and under conditions sufficient to allow the antigen to bind to the bound antibody, the antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2; and (c) adding a conjugate to the resulting anti-antibody/*P. malariae* antibody/antigen complexes, the conjugate comprising a composition comprising monoclonal or polyclonal antibody attached to a signal generating compound capable of detecting a detectable signal; and (d) detecting the presence of the antibodies which may be present in the test sample by detecting the signal generated by the signal generating compound. Again, a control or calibrator may be used which comprises antibody to the anti-antibody.

In a similar manner, the present invention also includes a third method for detecting antibodies to *P. ovale* in a test sample. This method comprises the steps of: (a) contacting the test sample suspected of containing the antibodies with anti-antibody, for a time and under conditions sufficient to allow the formation of anti-antibody/*P. ovale* antibody complexes; (b) adding *P. ovale* antigen to the resulting anti-antibody/*P. ovale* antibody complexes for a time and under conditions sufficient to allow the antigen to bind to the bound antibody, the antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4; and (c) adding a conjugate to the resulting anti-antibody/*P. ovale* antibody/antigen complexes, the conjugate comprising a composition comprising a monoclonal or polyclonal antibody attached to a signal generating compound capable of detecting a detectable signal; and (d) detecting the presence of the antibodies which may be present in the test sample by detecting the signal generated by the signal generating compound. Again, a control or calibrator may be used which comprises antibody to the anti-antibody.

In addition to the above-described assays in which one is detecting the presence of antibodies against one species of *Plasmodium* (e.g., *P. malariae* or *P. ovale*), one may also carry out assays that detect antibodies in a test sample against two or more species of *Plasmodium*. For example, one may wish to carry out an assay in which one can detect all four known species of *Plasmodium* (as well as *P. knowlesi*), thereby eliminating the risk of false negative results obtained with existing assays. Thus, the present invention includes a method of detecting antibodies to *P. malariae, P. falciparum, P. vivax* and *P. ovale* in a test sample comprising the steps of: (a) contacting the test sample suspected of containing at least one of these four types of antibodies with: 1) an antigen of *P. malariae* comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) an antigen of *P. ovale* comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) an antigen of *P. falciparum* and 4) an antigen of *P. vivax;* and (b) detecting the presence of antibodies, to one or more of said antigens, present in the test sample, by detecting presence of complexes, for example. More specifically, the present invention includes a method of detecting antibodies to *P. malariae, P. ovale, P. vivax* and *P. falciparum* in a test sample comprising the steps of: (a) contacting the test sample suspected of containing at least one of these four types of antibodies with a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, a *P. ovale* antigen comprising selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, a *P. vivax* antigen and a *P. falciparum* antigen for a time and under conditions sufficient to allow the formation of antibody/antigen complexes; (b) adding a conjugate to the resulting antibody/antigen complexes for a time and under conditions sufficient to allow each conjugate to bind to the bound antibody wherein said conjugate comprises an antibody attached to a signal generating compound capable of generating a detectable signal; and (c) detecting the presence of antibody which may be present in the test sample by detecting the signal generated by the signal generating compound. A control or calibrator may also be used which binds to the antigens. (The presence of the complexes indicates that at least one of the four types of antibodies is present in the test sample. In particular, the assay has the ability to detect the presence of all four types of antibodies in a sample thereby rendering the sample positive and preventing false negatives. One may not wish to know precisely which one or more of the antibody types is present (as when screening a suitable blood sample for donation purposes); however, as is described herein, such a determination is possible if desired.)

It should be noted that any previously described *P. falciparum, P. vivax, P. malariae* and *P. ovale* antigen or antigens may be utilized in combination with any one or more of the antigens of the present invention (e.g., Merozoite Surface Protein, Circumsporozoite Surface Protein Exported Protein 1, Apical Membrane Antigen, Cystoadherence-Linked Asexual Gene, Histidine-rich protein 2, FeSOD, pLDH and Erythrocyte binding antigen) with respect to the kits, vaccines and assays described herein.

Additionally, the present invention further includes a different method for detecting the presence of the four types of *Plasmodium* antibodies which may be present in a test sample. This method comprises the steps of: (a) contacting the test sample with: 1) anti-antibody for a time and under conditions sufficient to allow for formation of anti-antibody/*P. malariae* antibody complexes, anti-antibody/*P. ovale* antibody complexes, anti-antibody/*P. vivax* antibody complexes and 4) anti-antibody/*P. falciparum* antibody complexes and (b) detecting the presence of *P. malariae* antibody, *P. ovale* antibody, *P. vivax* antibody and *P. falciparum* antibody which may be present in the test sample. (Anti-antibodies to *P. vivax* and *P. falciparum* are commercially available and may be created, for example, by immunizing a mammal with purified mu-chain of the antibody.) More specifically, this method may comprise the steps of: (a) contacting the test sample with anti-antibody, for a time and conditions sufficient to allow the formation of anti-antibody/*P. malariae* antibody complexes, anti-antibody/*P. ovale* antibody complexes, anti-antibody/*P. vivax* antibody complexes and anti-antibody/*P. falciparum* antibody complexes; (b) adding a first conjugate, a second conjugate, a third conjugate and a fourth conjugate to resulting anti-antibody/antibody complexes for a time and under conditions sufficient to allow the conjugates to bind to bound antibody, the first conjugate comprising a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a signal generating compound capable of generating a detectable signal, the second conjugate comprising a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, attached to a signal generating compound capable of generating a detectable signal, the third conjugate comprising a *P. vivax* antigen attached to a signal generating compound capable of generating a detectable signal and the fourth conjugate comprising a *P. falciparum* antigen attached to a signal generating compound capable of generating a detectable signal; and (c) detecting the presence of antibody which may be present in the test sample by detecting a signal generated by the signal generating compounds. Control or calibrators may be used which comprise antibody to the anti-antibodies.

Vaccines

The present invention also includes a vaccine comprising one or more of the antigens described herein. Such a vaccine is used for active immunization of a mammal, for example, a human who will be exposed to one or more *Plasmodium* antigens (for example, due to travel within a region in which malaria is prevalent). For example, the vaccine may contain at least one antigen selected from the group consisting of: 1) a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) a *P. vivax* antigen, and 4) a *P. falciparum* antigen. The vaccine may also comprise a pharmaceutically acceptable adjuvant (e.g., Freund's adjuvant or Phosphate Buffered Saline). Preferably, all four antigens are present within the vaccine or administered composition.

Alternatively, if passive immunization is desired, one may administer one or more antibodies to the following antigens (as a vaccination): 1) a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) a *P. vivax* antigen and 4)a *P. falciparum* antigen. Again, preferably all four types of antibodies are present within the vaccine in order to provide the most protection to the mammal in question.

Diagnostic Kits

Diagnostic kits are also included within the scope of the present invention. More specifically, the present invention includes kits for determining the presence of antibodies to *P. malariae* in a test sample. In particular, the present invention includes a kit for determining the presence of antibody to *P. malariae* in a test sample. The kit comprises: a) a *P. malariae* antigen comprising the amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2 and b) a conjugate comprising an antibody attached to a signal-generating compound capable of generating a detectable signal. The kit may also contain a control or calibrator which comprises a reagent which binds to the antigen.

The present invention also includes a kit for determining the presence of antibody to *P. ovale* in a test sample. The kit comprises: a) a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4 and b) a conjugate comprising an antibody attached to a signal-generating compound capable of generating a detectable signal.

Additionally, the present invention includes a kit for determining the presence of antibody to *P. malariae, P. ovale, P. vivax* and *P. falciparum*. This kit comprises: a) 1) a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, 2) a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, 3) a *P. vivax* antigen and 4) a *P. falciparum* antigen and b) a conjugate comprising an antibody attached to a first signal generating compound capable of generating a detectable signal.

The present invention also includes another type of kit for detecting antibodies to *P. malariae* in a test sample. The kit may comprise a) an anti-antibody and b) a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2. A control or calibrator comprising a reagent which binds to the *P. malariae* antigen may also be included. More specifically, the kit may comprise a) an anti-antibody and b) a conjugate comprising a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, the conjugate being attached to a signal-generating compound capable of generating a detectable signal. Again, the kit may also comprise a control or calibrator comprising a reagent which binds to the *P. malariae* antigen.

The present invention also includes another type of kit for detecting antibodies to *P. ovale* in a test sample. The kit may comprise a) an anti-antibody specific for *P. ovale* antibody and b) a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4. A control or calibrator comprising a reagent which binds to the *P. ovale* antigen may also be included. More specifically, the kit may comprise a) an anti-antibody specific for *P. ovale* antibody and b) a conjugate comprising a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, the conjugate being attached to a signal-generating compound capable of generating a detectable signal. Again, the kit may also comprise a control or calibrator comprising a reagent which binds to the *P. ovale* antigen.

The present invention also includes another type of kit for detecting antibodies to *P. malariae, P. ovale, P. vivax* and *P. falciparum* in a test sample. The kit may comprise: a) an anti-antibody and b) a *P. malariae* antigen comprising an amino acid sequence comprising selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4, a *P. vivax* antigen and a *P. falciparum* antigen. A control or calibrator comprising a reagent which binds to the *P. ovale* antigen may also be included. More specifically, the kit may comprise a) an anti-antibody and b) a first conjugate comprising a *P. malariae* antigen comprising an amino acid sequence selected from the group consisting of approximately amino acids 1-1751 (i.e., PmMSP1) (SEQ ID NO:1) of FIG. 2, approximately amino acids 1634-1733 (i.e., PmMSP1-p19) of SEQ ID NO:1 of FIG. 2, approximately amino acids 1374-1633 (i.e., PmMSP1-p33) of SEQ ID NO:1 of FIG. 2 and approximately amino acids 1374-1733 (i.e., PmMSP1-p42) of SEQ ID NO:1 of FIG. 2, attached to a first signal generating compound capable of generating a detectable signal, a second conjugate comprising a *P. ovale* antigen comprising an amino acid sequence selected from the group consisting of approximately amino acids 1-1730 (i.e., PoMSP1) (SEQ ID NO:3) of FIG. 4, approximately amino acids 1614-1712 (i.e., PoMSP1-p19) of SEQ ID NO:3 of FIG. 4, approximately amino acids 1347-1613 (i.e., PoMSP1-p33) of SEQ ID NO:3 of FIG. 4 and approximately amino acids 1347-1712 (i.e., PoMSP1-p42) of SEQ ID NO:3 of FIG. 4 attached to a second signal generating compound capable of generating a detectable signal, a third conjugate comprising a *P. falciparum* antigen attached to a third signal generating compound and a fourth conjugate comprising a *P. vivax* antigen attached to a forth signal-generating compound capable of generating a detectable signal. Again, the kit may also comprise one or more controls or calibrators comprising one or more reagents which bind to the *Plasmodium* antigen(s).

The present invention may be illustrated by the use of the following non-limiting examples:

EXAMPLES

Example 1

Identification of Clinical Samples Infected With *P. malariae* and *P. ovate*

DNA was extracted from 82 whole blood samples (200 µl each) obtained from a malaria endemic region (Cameroon) using the QIAamp DNA Blood Mini Kit (Qiagen, Valencia, Calif.) according to the package insert. Subsequently, the method of Mangold et. al. (J. Clin. Micro., 43, p. 2435-2440, 2005, described below) was used to screen for the presence of *Plasmodium* DNA, and when detected, to make a species determination.

PCR was performed on each of the extracted Cameroon samples using a pair of primers designed to amplify a short portion of the 18S rRNA gene from any of the four human-infective *Plasmodium* species (*P. falciparum, P. vivax, P. malariae* and *P. ovale*). The PCR's were performed in a final volume of 25 µl containing 1×SYBR Green I Master (Roche, Indianapolis, Ind.), 0.5 µM each of the two primers PL1473F18 (SEQ ID No: 7) and PL1679R18 (SEQ ID No: 8) and DNA extracted from the equivalent of 1 µl of whole blood. Thermal cycling conditions for amplification were as follows: 1 cycle (95° C. for 9 minutes), 40 cycles (94° C. for 20 seconds, 50° C. for 30 seconds, 72° C. for 30 seconds) and 1 cycle (72° C. for 5 minutes). For comparison, four control PCR's were performed, each containing $10^5$ plasmid copies of the cloned 18S rRNA gene (available from the American Type Culture Collection, Manassas, Va.) from one of the four human-infective *Plasmodium* species.

A portion (5 µl) of each reaction was electrophoresed on a 1.0% agarose TAE ethidium bromide gel to screen for the presence of the 18S rDNA amplicon. Of the 82 samples tested, 30 were selected for further analysis based on the presence of an amplicon of the predicted size (~200 base pairs). A melting curve analysis was performed on the remainder (20 µl) of the 30 selected PCR's as described (Mangold et. al., J. Clin. Micro., 43, p. 2435-2440, 2005) and the Tm for each amplicon was compared to those of the of the four control amplicons, each of which has a characteristic Tm. Based on these results, three potential *P. malariae* infected samples, and four potential *P. ovale* infected samples were identified. The three *P. malariae* (#0014, #609-39, #240-16) and two of the *P. ovale* containing samples (#684-22, #1045-36) appeared to be co-infected with *P. falciparum*, whereas the other two *P. ovale* samples (#283-4, #510-10) appear to be single infections. All the other samples appeared to be singly infected with *P. falciparum*.

More 18S rDNA amplicons were generated as described above, and the amplicons subsequently purified using the Gene Clean Spin Kit (MP Biochemcials, Solon, Ohio) according to the package insert. Sequence of the 18S rDNA amplicons was determined for the two *P. ovale*-only samples (#283-4, #510-10), and for one of the *P. malariae*/*P. falciparum* co-infected samples (#0014). Blast analysis vs. Genbank demonstrated 100% homology of the putative *P. ovale* amplicons with *P. ovale* rDNA sequences in the database, confirming the presence of *P. ovale* DNA in these two samples. Sequence from the 0014 co-infected sample was highly homologous to *P. falciparum*. However, from the sequencing chromatograms, it was clear that a second underlying sequence was also present. This was not the case for the two *P. ovale* sequences, which had no indication of the presence of a secondary sequence. Confirmation of the presence of *P. malariae* DNA in the 0014 co-infected sample is described in Example 2.

Example 2

Amplification and Sequencing of the *P. malariae* MSP1 Gene

5'- Region of PmMSP1

This section describes the approach used to obtain sequence from near the 5'-end of the *P. malariae* MSP1 gene. A short stretch of sequence located near the 5'-end of the *P. malariae* MSP1 gene has been published (Fandeur et. al., Parasitology, 120, p. 11-21, 2000) and can be found in the Genbank database (Accession # AF138881). Degenerate primers As1 (SEQ ID No:9) and As2 (SEQ ID No:10) designed to amplify an approximately 387 base pair region of the 5'-end of the MSP1 gene from multiple *Plasmodium* species have been described, along with a nested *P. malariae*-specific primer pair, PmMSP1-F1 (SEQ ID No:11) and PmMSP1-R1 (SEQ ID No:12) (Fandeur et. al., Parasitology, 120, p. 11-21, 2000). The sequences of primers As1 (SEQ ID NO:9) and PmMSP1-F1 (SEQ ID NO:11) used here are slightly different than those reported by Fandeur et. al.

Nested PCR amplification using the degenerate and *P. malariae*-specific primers was performed on the three extracted samples previously identified as possibly containing *P. malariae* DNA (#0014, #609-39, #240-16, see Example 1) as follows. The first round PCR's were performed in a final volume of 20 μl containing 1×SYBR Green I Master (Roche, Indianapolis, Ind.), 1.0 μM each of the two primers As1 (SEQ ID NO:9) and As2 (SEQ ID NO:10) and DNA extracted from the equivalent of 1 μl of whole blood (see Example 1). Thermal cycling conditions for amplification were as follows: 1 cycle (95° C. for 5 minutes), 3 cycles (94° C. for 30 seconds, 45° C. for 30 seconds, 72° C. for 1 minute), 35 cycles (94° C. for 10 seconds, 54° C. for 1.5 minutes, 72° C. for 2 minutes) and 1 cycle (72° C. for 3 minutes). Based on MSP1 sequences in Genbank, the predicted amplicon size generated by the As primers ranges from 326 base pairs to 536 base pairs depending on the *Plasmodium* species.

The second round PCR's were performed in a final volume of 20 μl containing 1×SYBR Green I Master (Roche, Indianapolis, Ind.), 1.0 μM each of the two primers PmMSP1-F1 (SEQ ID NO:11) and PmMSP1-R1 (SEQ ID NO:12) and 1 μl of the first round PCR (see above). Thermal cycling conditions for amplification were as follows: 1 cycle (95° C. for 5 minutes), 20 cycles (94° C. for 1 minute, 55° C. for 1.5 minutes, 72° C. for 2 minutes) and 1 cycle (72° C. for 3 minutes). Based on MSP1 sequences in Genbank for *P. malariae*, or the highly related species *P. brasilianum*, the predicted amplicon size generated by the PmMSP1 primers is either 237 base pairs or 261 base pairs depending on the presence or absence of a 24 base pair insert sequence.

A portion (5 μl) of each first round and each second round PCR was electrophoresed on a 1.0% agarose TAE ethidium bromide gel to screen for the presence of amplicons. One of the *P. malariae* samples (#0014) resulted in an amplicon of the predicted size after the first round of PCR. After the second round of PCR, all three *P. malaria* samples contained an amplicon of the correct size. The amplicons from the remaining volume (14 μl) of the three second round PCR's were electrophoresed and then excised from an agarose gel, and the DNA was extracted from the agarose using the QIAEX II Agarose Gel Extraction Kit (Qiagen, Valencia, Calif.) according to the package insert.

DNA sequences of the three gel-purified amplicons were obtained, using PmMSP1-F1 (SEQ ID NO:11) and PmMSP1-R1 (SEQ ID NO:12) as primers, and compared to sequences in the Genbank database by blast analysis. All three were highly homologous (>98%) to *P. malariae* and *P. brasilianum* DNA sequences located at the 5'-end of the MSP1 gene, confirming the presence of *P. malariae* DNA in these three samples.

3'-Region of PmMSP1

This section describes the approach used to obtain sequence from near the 3'-end of the *P. malariae* MSP1 gene. Nucleotide sequences near the 3'-end of the MSP1 open reading frame were collected from the Genbank database for all available *Plasmodium* species (14 species total). *P. malariae* sequence is not available from this region. The sequences were aligned and degenerate reverse primers, targeting the most conserved region, were designed. These primers, MSP1-R1 (SEQ ID NO:13) and MSP1-R2 (SEQ ID NO:14) were used in conjunction with the *P. malariae*-specific forward primers PmMSP1-F1 (SEQ ID NO:11) and PmMSP1-F2 (SEQ ID NO:15) to PCR amplify the near full-length *P. malariae* MSP1 gene.

The PCR's were performed in a final volume of 20 μl containing 1×LA PCR Buffer II ($Mg^{2+}$ plus), 0.4 mM each dNTP, 1 unit LA Taq HS per PCR (Takara, Otsu, Shiga, Japan), DNA extracted from the equivalent of 1 μl of whole blood (see Example 1) from the *P. malariae* infected sample #0014 and 1.0 μM each of the forward primer [PmMSP1-F1 (SEQ ID NO:11) or PmMSP1-F2 (SEQ ID NO:15)] and the reverse primer [MSP1-R1 (SEQ ID NO:13) or MSP1-R2 (SEQ ID NO:14)]. PCR's containing all four possible combinations of forward and reverse primers were performed. Thermal cycling conditions for amplification were as follows: 1 cycle (94° C. for 1 minute), 3 cycles (94° C. for 30 seconds, 45° C. for 1 minute, 72° C. for 5 minutes), 35 cycles (94° C. for 30 seconds, 54° C. for 1.5 minutes, 72° C. for 5 minutes) and 1 cycle (72° C. for 5 minutes). Based on MSP1 sequences in Genbank, the predicted amplicon size is about 5000 base pairs.

A portion (5 μl) of each PCR was electrophoresed on a 0.8% agarose TAE ethidium bromide gel to screen for the presence of amplicons. Two of the primer combinations (i.e.

PmMSP1-F1/MSP1-R2 and PmMSP1-F2/MSP1-R2) generated a minor amplicon of the predicted size. The 5000 base pair amplicon from the remaining volume (14 μl) of the PmMSP1-F1/MSP1-R2 PCR was electrophoresed and then excised from an agarose gel, and the DNA was extracted from the agarose using the QIAEX II Agarose Gel Extraction Kit (Qiagen, Valencia, Calif.) according to the package insert.

Sequence from one end of the purified 5000 base pair amplicon was obtained using MSP1-R2 (SEQ ID NO:14) as a primer. The sequence contained a single long open reading frame, and the deduced amino acid sequence was compared to those in the Genbank database by BLAST analysis. Highly significant matches were obtained to amino acid sequences from the C-terminal region of MSP1 from multiple *Plasmodium* species, none of which exhibited more than 50% identity to the deduced amino acid sequence of sample #0014. This indicates it was derived from a *Plasmodium* species for which this region of the MSP1 sequence had not been previously determined.

3'-terminus of PmMSP1

Remaining sequence at the 3'-end of the PmMSP1 gene, extending through the stop codon, was obtained by performing a PCR walking experiment. DNA extracted from the *P. malariae* infected sample #0014 (26 μl equivalents of whole blood) was digested in a 30 μl reaction for 1 hr. at 37° C. in the presence of 50 units of the restriction enzyme DpnII and 1×DpnII Buffer (New England Biolabs, Beverly, Mass.). The digestion products were purified using the QBiogene Geneclean Spin Kit (MP Biochemcials, Solon, Ohio) according to the package insert.

All of the DpnII digested DNA was added to a ligation reaction mix (30 μl) containing 1×T4 DNA Ligase Buffer (New England Biolabs, Beverly, Mass.) and 15 μM each of adaptor oligonucleotides S-Bam24 (SEQ ID NO:16) and S-Bam12 (SEQ ID NO:17). The ligation reaction mix was heated to 50° C. and then cooled to 10° C. over a one hour period to anneal the S-Bam24/12 adaptor to the DpnII cut ends and then placed on ice. T4 DNA Ligase (400 units/μl) (New England Biolabs, Beverly, Mass.) was added to the annealed ligation mix and the reaction incubated overnight at 16° C. The ligation products were purified using the QBiogene Geneclean Spin Kit (MP Biochemcials, Solon, Ohio) according to the package insert, and subsequently heat denatured.

The walking PCR was performed in a final volume of 20 μl containing 1×SYBR Green I Master (Roche, Indianapolis, Ind.), 0.2 μM each of the two primers S-Bam24 (SEQ ID NO:16) and PmMSP1-F3 (SEQ ID NO:18) and 1 μl denatured DNA extracted from of the ligation reaction described above. Thermal cycling conditions for amplification were as follows: 1 cycle (95° C. for 4.5 minutes), 40 cycles (94 ° C. for 30 seconds, 55° C. for 30 seconds, 72° C. for 1 minute) and 1 cycle (72° C. for 4 minutes).

The walking PCR (20 ml) was electrophoresed on a 1.0% agarose TAE ethidium bromide gel to screen for the presence of amplicons. A 500 bp amplicon was excised from the agarose gel, and the DNA was extracted from the agarose using the QBiogene Geneclean Kit (MP Biochemcials, Solon, Ohio) according to the package insert, and subsequently heat denatured.

The walking PCR was performed in a final volume of 20 μl containing 1×SYBR Green I Master (Roche, Indianapolis, Ind.), 0.2 μM each of the two primers S-Bam24 (SEQ ID NO:16) and PmMSP1-F3 (SEQ ID NO:18) and 1 μl denatured DNA extracted from of the ligation reaction described above. Thermal cycling conditions for amplification were as follows: 1 cycle (95° C. for 4.5 minutes), 40 cycles (94° C. for 30 seconds, 55° C. for 30 seconds, 72° C. for 1 minute) and 1 cycle (72° C. for 4 minutes)

The walking PCR (20 μl) was electrophoresed on a 1.0% agarose TAE ethidium bromide gel to screen for the presence of amplicons. A 500 bp amplicon was excised from the agarose gel, and the DNA was extracted from the agarose using the QBiogene Geneclean Kit (MP Biochemcials, Solon, Ohio) according to the package insert.

Sequence from the purified 500 base pair amplicon was obtained using S-Bam24 (SEQ ID NO:16) and PmMSP1-F3 (SEQ ID NO:18) as primers. The sequence overlapped with that from the previously determined 3'-region of PmMSP1 (described above), and contained an open reading frame that ended with a stop codon. The deduced amino acid sequence was compared to those in the Genbank database by BLAST analysis. Highly significant matches were obtained to amino acid sequences from the C-terminus of MSP1 from multiple *Plasmodium* species, indicating that the complete PmMSP1 C-terminal sequence had been obtained.

5'-terminus of PmMSP1

Remaining sequence at the 5'-end of the PmMSP1 gene, extending through the start codon, was obtained by performing an inverse PCR walking experiment. DNA extracted from the equivalent of 20 μl of whole blood (see Example 1) from the *P. malariae* infected sample #0014 was digested in a 100 μl reaction for 1 hr. at 37° C. in the presence of 20 units of the restriction enzyme ApoI and 1×ApoI Buffer (New England Biolabs, Beverly, Mass.). The digestion products were purified using the QIAquick PCR Purification Kit (Qiagen, Valencia, Calif.) according to the package insert.

All of the purified ApoI digested DNA was added to a self-ligation reaction mix (500 μl) containing 1×T4 DNA Ligase Buffer and 2000 units T4 DNA Ligase (New England Biolabs, Beverly, Mass.). The ligation reaction mix was incubated overnight at 14° C., and the ligation products were purified using the QIAquick PCR Purification Kit (Qiagen, Valencia, Calif.) according to the package insert.

The inverse PCR was performed in a final volume of 20 μl containing 1×SYBR Green I Master (Roche, Indianapolis, Ind.), 0.5 μM each of the two primers PmMSP1-F7 (SEQ ID NO:19) and PmMSP1-R8 (SEQ ID NO:20) and 2 μl (~7%) of the purified self-ligation reaction described above. Thermal cycling conditions for amplification were as follows: 1 cycle (95° C. for 4.5 minutes), 40 cycles (94° C. for 30 seconds, 55° C. for 30 seconds, 72° C. for 1 minute) and 1 cycle (72° C. for 4 minutes)

The inverse PCR (15 μl) was electrophoresed on a 0.8% agarose TAE ethidium bromide gel to screen for the presence of amplicons. A 250 bp amplicon was excised from the agarose gel, and the DNA was extracted from the agarose using the QBiogene Geneclean Kit (MP Biochemcials, Solon, Ohio) according to the package insert.

Sequence from the purified 250 base pair amplicon was obtained using PmMSP1-F7 (SEQ ID NO:19) and PmMSP1-R8 (SEQ ID NO:20) as primers. The sequence overlapped with that from the previously determined 5'-end region of PmMSP1 (described above), and contained an open reading frame that began with a start codon. The deduced amino acid sequence was compared to those in the Genbank database by blast analysis. Highly significant matches were obtained to amino acid sequences from the N-terminus of MSP1 from multiple *Plasmodium* species, indicating that the complete PmMSP1 N-terminal sequence had been determined.

Full-Length PmMSP1

This section describes the approach used to obtain the remaining sequence of the *P. malariae* MSP1 gene. Based on sequences obtained from the 3'-end of the PmMSP1 gene (see above), two new *P. malariae*-specific reverse primers were designed. These primers, PmMSP1-R2 (SEQ ID NO:21) and PmMSP1-R3 (SEQ ID NO:22) were used in conjunction with the *P. malariae*-specific forward primers PmMSP1-F1 (SEQ ID NO:11) and PmMSP1-F2 (SEQ ID NO:15) to perform a nested PCR amplification specific for the near full-length *P. malariae* MSP1 gene.

The first round PCR's were performed in a final volume of 20 μl containing 1×LA PCR Buffer II (Mg plus), 0.4 mM each dNTP, 1 unit LA Taq HS per PCR (Takara, Otsu, Shiga, Japan), DNA extracted from the equivalent of 1 μl of whole blood (see Example 1) from the *P. malariae* infected sample #0014 and 0.5 μM each of the forward primer [PmMSP1-F1 (SEQ ID NO:11) or PmMSP1-F2 (SEQ ID NO:15)] and the reverse primer [PmMSP1-R2 (SEQ ID NO:21) or PmMSP1-R3 (SEQ ID NO:22)]. PCR's containing all four possible combinations of forward and reverse primers were performed. Thermal cycling conditions for amplification were as follows: 1 cycle (94° C. for 1 minute), 35 cycles (94° C. for 30 seconds, 55° C. for 30 seconds, 72° C. for 5 minutes) and 1 cycle (72° C. for 5 minutes).

The second round PCR's were performed as described for the first round except that only fully-nested or hemi-nested primer combinations were used, and that the template was 1 μl of the first round PCR.

A portion (5 μl) of all first and second round PCR's was electrophoresed on a 0.8% agarose TAE ethidium bromide gel to screen for the presence of amplicons. No amplicons were observed after the first round of PCR. However, all except one of the second round PCR's generated single band amplicons of the predicted size. The 5000 base pair amplicons from the remaining volume (15 μl) of the second round PCR's were purified using the QIAquick PCR Purification Kit (Qiagen, Valencia, Calif.) according to the package insert.

The purified 5000 base pair PCR's served as template for several rounds of sequencing using *P. malariae*-specific forward and reverse sequencing primers targeting the unknown central portion of the PmMSP1 gene. After each round of sequencing, additional *P. malariae*-specific primers were designed from the newly acquired sequence to use in the next round. This process was continued until sequence was obtained across the remainder of the PmMSP1 gene. The resulting sequence was combined with sequences from the 5' and 3'-terminii (described above) to generate the complete PmMSP1 gene. Additional *P. malariae*-specific primers used for sequencing are PmMSP1-F3 (SEQ ID NO:18), PmMSP1-F4 (SEQ ID NO:23), PmMSP1-F5 (SEQ ID NO:24), PmMSP1-R4 (SEQ ID NO:25) and PmMSP1-R5 (SEQ ID NO:26).

Example 3

Amplification and sequencing of the *P. ovale* MSP1 Gene

5'-region of PoMSP1 (sample 510-10)

This section describes the approach used to obtain sequence from near the 5'-end of the *P. ovale* MSP1 gene. Degenerate primers As1 (SEQ ID NO:9) and As2 (SEQ ID NO:10) designed to amplify an approximately 387 base pair region of the 5'-end of the MSP1 gene from multiple *Plasmodium* species were described in Example 2.

A first round of amplification using the degenerate As primers was performed on two of the extracted samples (#283-4 and #510-10) previously identified as containing *P. ovale* DNA (see Example 1) as follows. PCR's were performed in a final volume of 20 μl containing 1×SYBR Green I Master (Roche, Indianapolis, Ind.), 1.0 μM each of the two primers As1 (SEQ ID NO:9) and As2 (SEQ ID NO:10) and DNA extracted from the equivalent of 1 μl of whole blood (see Example 1). Thermal cycling conditions for amplification were as follows: 1 cycle (95° C. for 5 minutes), 3 cycles (94° C. for 30 seconds, 45° C. for 30 seconds, 72° C. for 1 minute), 35 cycles (94° C. for 10 seconds, 54° C. for 1.5 minutes, 72° C. for 2 minutes) and 1 cycle (72° C. for 3 minutes). Based on MSP1 sequences in Genbank, the predicted amplicon size generated by the As primers ranges from 326 base pairs to 536 base pairs depending on the *Plasmodium* species.

A portion (5 μl) of each PCR was electrophoresed on a 1.0% agarose TAE ethidium bromide gel to screen for the presence of amplicons. Both of the *P. ovale* PCR's generated a very faint amplicon (~420 bp) within the predicted size range. This amplicon was gel purified for the 510-10 sample and re-amplified as described above except that thermal cycling conditions for amplification were as follows: 1 cycle (95° C. for 5 minutes), 20 cycles (94° C. for 1 minute, 55° C. for 1.5 minutes, 72° C. for 2 minutes) and 1 cycle (72° C. for 3 minutes). The re-amplified PCR product was purified using the QIAquick PCR Purification Kit (Qiagen, Valencia, Calif.) according to the package insert.

DNA sequence of the re-amplified amplicon was obtained using As1 (SEQ ID NO:9) and As2 (SEQ ID NO:10) as primers. The sequence contained a single long open reading frame, and the deduced amino acid sequence was compared to those in the Genbank database by BLAST analysis. Highly significant matches were obtained to amino acid sequences from the N-terminal region of MSP1 from multiple *Plasmodium* species, none of which exhibited more than 45% identity to the deduced amino acid sequence. This indicates it was derived from a *Plasmodium* species for which this region of the MSP1 sequence had not been previously determined.

3'-End PoMSP1

This section describes the approach used to obtain sequence from near the 3'-end of the *P. ovale* MSP1 gene. A pair of *P. ovale*-specific primers were designed based on the 5'-PoMSP1 sequence obtained above. The *P. ovale*-specific forward primers PoMSP1-F1 (SEQ ID NO:27) and PoMSP1-F2 (SEQ ID NO:28) were used in conjunction with the degenerate reverse primers MSP1-R1 (SEQ ID NO:13) and MSP1-R2 (SEQ ID NO:14) from the 3'-end of the MSP1 gene (described in Example 2) to perform nested amplification of the near full-length *P. ovale* MSP1 gene. Based on MSP1 sequences in Genbank, the predicted amplicon size is about 5000 base pairs.

The first round PCR's were performed in a final volume of 20 μl containing 1×LA PCR Buffer II (Mg plus), 0.4 mM each dNTP, 1 unit LA Taq HS per PCR (Takara, Otsu, Shiga, Japan), DNA extracted from the equivalent of 1 μl of whole blood (see Example 1) from the *P. ovale* infected sample #510-10 and 1.0 μM each of the forward primer [PoMSP1-F1 (SEQ ID NO:27) or PoMSP1-F2 (SEQ ID NO:28)] and the reverse primer [MSP1-R1 (SEQ ID NO:13) or MSP1-R2 (SEQ ID NO:14)]. PCR's containing all four possible combinations of forward and reverse primers were performed. Thermal cycling conditions for amplification were as follows: 1 cycle (94° C. for 1 minute), 3 cycles (94° C. for 30 seconds, 45° C. for 1 minute, 72° C. for 5 minutes), 35 cycles (94° C. for 30 seconds, 50° C. for 1.5 minutes, 72° C. for 5 minutes) and 1 cycle (72° C. for 5 minutes).

The second round PCR's were performed as described for the first round except that only fully-nested or hemi-nested primer combinations were used, and that the template was 0.2 μl of the first round PCR.

A portion (5 μl) of all first and second round PCR's was electrophoresed on a 0.8% agarose TAE ethidium bromide gel to screen for the presence of amplicons. None of the first round PCR's resulted in amplicons of the predicted size. However, one of the second round PCR's did generate a minor amplicon of about 5000 base pairs. This product resulted from a fully nested second round PCR using the PoMSP1-F2 (SEQ ID NO:28) and the MSP1-R2 (SEQ ID NO:14) primers to amplify the first round PCR performed with the PoMSP1-F1 (SEQ ID NO:27) and the MSP1-R1 (SEQ ID NO:13) primers. The 5000 base pair amplicon from the remaining volume (15 μl) of the fully nested PCR was electrophoresed and then excised from an agarose gel, and the DNA was extracted from the agarose using the QIAEX II Agarose Gel Extraction Kit (Qiagen, Valencia, Calif.) according to the package insert.

Sequence from the 3'-end of the purified 5000 base pair amplicon was obtained using MSP1-R2 (SEQ ID NO:14) as a primer. The sequence contained a single long open reading frame, and the deduced amino acid sequence was compared to those in the Genbank database by blast analysis. Highly significant matches were obtained to amino acid sequences from the C-terminal region of MSP1 from multiple *Plasmodium* species, none of which exhibited more than 51% identity to the deduced amino acid sequence. This indicates it was derived from a *Plasmodium* species for which this region of the MSP1 sequence had not been previously determined.

5'-terminus of PoMSP1 (Sample 510-10)

Remaining sequence at the 5'-end of the PoMSP1 gene, extending through the start codon, was obtained by performing an inverse PCR walking experiment. DNA extracted from the equivalent of 20 μl of whole blood (see Example 1) from the *P. ovale* infected sample #510-10 was digested in a 100 μl reaction for 1 hr. at 37° C. in the presence of 20 units of the restriction enzyme ApoI and 1×ApoI Buffer (New England Biolabs, Beverly, Mass.). The digestion products were purified using the QIAquick PCR Purification Kit (Qiagen, Valencia, Calif.) according to the package insert.

All of the purified ApoI digested DNA was added to a self-ligation reaction mix (500 μl) containing 1×T4 DNA Ligase Buffer and 2000 units T4 DNA Ligase (New England Biolabs, Beverly, Mass.). The ligation reaction mix was incubated overnight at 14° C., and the ligation products were purified using the QIAquick PCR Purification Kit (Qiagen, Valencia, Calif.) according to the package insert.

A pair of *P. ovale*-specific forward primers [PoMSP1-F1 (SEQ ID NO:27) and PoMSP1-F2 (SEQ ID NO:28)] were used in conjunction with the *P. ovale*-specific reverse primers [PoMSP1-R3 (SEQ ID NO:29) and PoMSP1-R6 (SEQ ID NO:30)] to perform nested inverse PCR at the 5'-end of the *P. ovale* MSP1 gene.

The first round of inverse PCR was performed in a final volume of 20 μl containing 1×SYBR Green I Master (Roche, Indianapolis, Ind.), 0.5 μM each of the forward primer [PoMSP1-F1 (SEQ ID NO:27)] and the reverse primer [PoMSP1-R3 (SEQ ID NO:29)] and 2 μl (~7%) of the purified self-ligation reaction described above. Thermal cycling conditions for amplification were as follows: 1 cycle (95° C. for 4.5 minutes), 40 cycles (94° C. for 30 seconds, 55° C. for 30 seconds, 72° C. for 1 minute) and 1 cycle (72° C. for 4 minutes).

The second round PCR (35 cycles) was performed as described for the first round except that a fully-nested primer combination was used [PoMSP1-F2 (SEQ ID NO:28) and PoMSP1-R6 (SEQ ID NO:30)], and that the template was 1.0 μl of the first round PCR.

A portion (15 μl) of the second round inverse PCR was electrophoresed on a 1.0% agarose TAE ethidium bromide gel to screen for the presence of amplicons. A 250 bp amplicon was excised from the agarose gel, and the DNA was extracted from the agarose using the QBiogene Geneclean Kit (MP Biochemcials, Solon, Ohio) according to the package insert.

Sequence from the purified 250 base pair amplicon was obtained using PoMSP1-F2 (SEQ ID NO:28) and PoMSP1-R6 (SEQ ID NO:30) as primers. The sequence overlapped with that from the previously determined 5'-end region of PoMSP1 (described above), and contained an open reading frame that began with a start codon. The deduced amino acid sequence was compared to those in the Genbank database by blast analysis. Highly significant matches were obtained to amino acid sequences from the N-terminus of MSP1 from multiple *Plasmodium* species, indicating that the complete PoMSP1 N-terminal sequence had been determined.

3'-terminus of PoMSP1 (Sample 510-10)

Remaining sequence at the 3'-end of the PoMSP1 gene, extending through the start codon, was obtained by performing an inverse PCR walking experiment. Digestion, ligation and purification of the template was performed as described for the PoMSP1 5'-terminus inverse PCR experiment (see above).

A *P. ovale*-specific forward primer [PoMSP1-F8 (SEQ ID NO:31)] was used in conjunction with the *P. ovale*-specific reverse primers [PoMSP1-R1 (SEQ ID NO:32) and PoMSP1-R2 (SEQ ID NO:33)] to perform hemi-nested inverse PCR at the 3'-end of the *P. ovale* MSP1 gene.

The first round of inverse PCR was performed in a final volume of 20 μl containing 1×LA PCR Buffer II ($Mg^{2+}$ plus), 0.4 mM each dNTP, 1 unit LA Taq HS (Takara, Otsu, Shiga, Japan), 0.5 μM each of the forward primer [PoMSP1-F8 (SEQ ID NO:31)] and the reverse primer [PoMSP1-R1 (SEQ ID NO:32)] and 2 μl (~7%) of the purified self-ligation reaction described above. Thermal cycling conditions for amplification were as follows: 1 cycle (95° C. for 1.0 minutes), 40 cycles (94° C. for 30 seconds, 55° C. for 30 seconds, 72° C. for 5 minute) and 1 cycle (72° C. for 5 minutes).

The second round PCR (35 cycles) was performed as described for the first round except that a hemi-nested primer combination was used [PoMSP1-F8 (SEQ ID NO:31) and PoMSP1-R2 (SEQ ID NO:33)], and that the template was 1.0 μl of the first round PCR.

A portion (15 μl) of the second round inverse PCR was electrophoresed on a 1.0% agarose TAE ethidium bromide gel to screen for the presence of amplicons. A 800 base pair amplicon was excised from the agarose gel, and the DNA was extracted from the agarose using the QBiogene Geneclean Kit (MP Biochemcials, Solon, Ohio) according to the package insert.

The purified 800 base pair product was cloned into the pGEM-T Easy vector (Promega, Madison, Wis.) according to the package insert, and transformants containing the cloned amplicon were obtained in XL10-Gold Untracompetent cells (Stratagene, La Jolla, Calif.) according to the package insert.

Sequence from the cloned 800 base pair amplicon was obtained using vector primers pGEM T7 and pGEM SP6 (Promega, Wis.). The sequence overlapped with that from the previously determined 3'-end region of PoMSP1 (described above), and contained an open reading frame that ended with a stop codon. The deduced amino acid sequence was compared to those in the Genbank database by blast analysis. Highly significant matches were obtained to amino acid sequences from the C-terminus of MSP1 from multiple *Plas-*

*modium* species, indicating that the complete PoMSP1 C-terminal sequence had been determined.

Full-Length PoMSP1 (Sample 510-10)

This section describes the approach used to obtain the remaining sequence of the *P. ovale* MSP1 gene. Based on sequences obtained from the 3'-end of the PoMSP1 gene (see above), two new *P. ovale*-specific reverse primers were designed. These primers, PoMSP1-R1 (SEQ ID NO:32) and PoMSP1-R2 (SEQ ID NO:33) were used in conjunction with the *P. ovale*-specific forward primers PoMSP1-F1 (SEQ ID NO:27) and PoMSP1-F2 (SEQ ID NO:28) to perform a PCR amplification specific for the near full-length PoMSP1 gene.

The PCR's were performed in a final volume of 20 µl containing 1×LA PCR Buffer II ($Mg^{2+}$ plus), 0.4 mM each dNTP, 1 unit LA Taq HS per PCR (Takara, Otsu, Shiga, Japan), DNA extracted from the equivalent of 1 µl of whole blood (see Example 1) from the *P. ovale* infected sample #510-10 and 0.5 µM each of the forward primer [PoMSP1-F1 (SEQ ID NO:27) or PoMSP1-F2 (SEQ ID NO:28)] and the reverse primer [PoMSP1-R1 (SEQ ID NO:32) or PoMSP1-R2 (SEQ ID NO:33)]. PCR's containing all four possible combinations of forward and reverse primers were performed. Thermal cycling conditions for amplification were as follows: 1 cycle (94° C. for 1 minute), 35 cycles (94° C. for 30 seconds, 55° C. for 30 seconds, 72° C. for 5 minutes) and 1 cycle (72° C. for 5 minutes).

A portion (15 µl) of all PCR's was electrophoresed on a 1.0% agarose TAE ethidium bromide gel to screen for the presence of amplicons. All PCR's generated single band amplicons of the predicted size. The 5000 base pair amplicons were then excised from the agarose gel, and the DNA was extracted from the agarose using the QIAEX II Agarose Gel Extraction Kit (Qiagen, Valencia, Calif.) according to the package insert.

The gel purified 5000 base pair amplicons served as template for several rounds of sequencing using *P. ovale*-specific forward and reverse sequencing primers targeting the unknown central portion of the PoMSP1 gene. After each round of sequencing, additional *P. ovale*-specific primers were designed from the newly acquired sequence to use in the next round. This process was continued until sequence was obtained across the remainder of the PoMSP1 gene. The resulting sequence was combined with sequences from the 5' and 3'-terminii (described above) to generate the complete PoMSP1 gene. Additional *P. ovale*-specific primers used for sequencing are PoMSP1-F3 (SEQ ID NO:34), PoMSP1-F4 (SEQ ID NO:35), PoMSP1-F5 (SEQ ID NO:36), PoMSP1-F6 (SEQ ID NO:37), PoMSP1-F7 (SEQ ID NO:38), PoMSP1-R4 (SEQ ID NO:39) and PoMSP1-R5 (SEQ ID NO:40).

Example 4

Design, Cloning and Expression of the MSP1p19 Gene

MSP1-p19 Gene Design

This section describes the design of synthetic MSP1-p19 genes, encoding the C-terminal p19 portion of the MSP1 protein, from *P. falciparum, P. vivax, P. malariae* and *P. ovale*, which are optimized for expression in *E. coli*. Gene Designer software from DNA 2.0, Inc. (Menlo Park, Calif.) was used to design the gene sequences discussed below. The encoded p19 proteins for *P. falciparum* and *P. vivax* constructs are identical to Genbank accession numbers P19598 and AAN86211 respectively, while the encoded p19 proteins for *P. malariae* and *P. ovale* constructs are derived from the deduced sequences presented in this patent. Nucleotide sequences for the optimized *P. falciparum, P. vivax, P. malariae* and *P. ovale* MSP1-p19 genes are presented in SEQ ID NO's: 41, 42, 43 and 44 respectively, and the encoded amino acid sequences for the *P. falciparum, P. vivax, P. malariae* and *P. ovale* MSP1-p19 proteins are presented in SEQ ID NO's: 45, 46, 47 and 48, respectively. Each gene contains a 5'-EcoRI site followed by a start codon, the body of the gene encoding the p19 amino acid sequence, a sequence encoding a 6-histidine tag, a stop codon and a BamHI site. The restriction enzyme sites were used for cloning into expression vectors and the 6-histidine tag was included to facilitate subsequent purification of the expressed protein. The C-terminal nine amino acid residues encoded at the end of the MSP1-p19 portion of the *P. malariae* and *P. ovale* constructs, prior to the 6-histidine tag, were designed to match the consensus sequence derived from alignment of this highly conserved segment of MSP1-p19 from 14 other *Plasmodium* species. The *P. malariae* and *P. ovale* proteins encoded by the designed sequences (SEQ ID NOs: 47 and 48, respectively) within this nine amino acid stretch differ at a single position vs. the deduced sequences from the native *P. malariae* and *P. ovale* genes (SEQ ID NOs: 1 and 3, respectively), both of which encode Gly (native) instead of Ser (designed) immediately following the last Cys residue.

Preparation of Synthetic MSP1-p19 Genes from *P. falciparum* and *P. vivax*

Oligonucleotides encoding adjacent portions of the MSP1-p19 protein from either *P. falciparum* or *P. vivax*, and containing complementary overlapping ends, were assembled and the resulting assembled products further modified in a two step PCR process. In the first PCR modification step, the 5'-cloning site (EcoRI) and a sequence coding a portion of the C-terminal histidine tag were introduced at the 5' and 3'-ends respectively of the assembled genes. In the second PCR modification step, the remainder of the histidine tag encoding sequence was incorporated followed by a stop codon and the 3'-cloning site (BamHI).

The assembly reactions (25 µl) contained 1×Amplitaq Gold Buffer, 2 mM $MgCl_2$, 1.25 units Amplitaq Gold DNA polymerase (Roche, Branchburg, N.J.), 0.25 mM each dNTP (New England Biolabs, Beverly, Mass.) and 0.4 µM of each of the four oligonucleotides (Oligos Etc., Inc., Wilsonville, Oreg.) used to form the gene for *P. falciparum* [MSP1 (SEQ ID NO:49), MSP2 (SEQ ID NO:50), MSP3 (SEQ ID NO:51) and MSP4 (SEQ ID NO:52)] or for *P. vivax* [MSP5 (SEQ ID NO:53), MSP6 (SEQ ID NO:54), MSP7 (SEQ ID NO:55) and MSP8 (SEQ ID NO:56)]. Thermal cycling conditions for assembly were as follows: 1 cycle (95° C. for 9 minutes), 10 cycles (94° C. for 20 seconds, 50° C. for 30 seconds, 72° C. for 30 seconds) and 1 cycle (72° C. for 5 minutes).

The first PCR modification mix (50 µl) contained 1×Amplitaq Gold Buffer, 2 mM $MgCl_2$, 5 units Amplitaq Gold DNA polymerase (Branchburg, N.J.), 0.25 mM each dNTP (New England Biolabs, Beverly, Mass.), 5 µl (20%) of the assembly reaction (see above) and 0.5 µM of each PCR primer (Oligos Etc., Inc., Wilsonville, Oreg.) [*P. falciparum*=fMSP1-F1 (SEQ ID NO:57) and fMSP1-R1 (SEQ ID NO:58)] or [*P. vivax*=vMSP1-F1 (SEQ ID NO:59) and vMSP1-R1 (SEQ ID NO:60)]. Thermal cycling conditions were as follows: 1 cycle (95° C. for 9 minutes), 35 cycles (94° C. for 20 seconds, 50° C. for 30 seconds, 72° C. for 30 seconds) and 1 cycle (72° C. for 5 minutes). The PCR's (50 µl) were electrophoresed on a 1.0% agarose gel, and the amplicons were extracted from the agarose using the QIAEX II Agarose Gel Extraction Kit (Qiagen, Valencia, Calif.) according to the package insert.

The second PCR modification mix (25 μl) contained 1×LA Taq PCR Buffer, 2.5 mM $MgCl_2$, 0.2 mM each dNTP, 1.7 units LA Taq DNA polymerase per PCR (Takara, Otsu, Shiga, Japan), 1.0 μl (5%) of the purified amplicon from the first PCR and 0.5 μM of each PCR primer (Oligos Etc., Inc., Wilsonville, Oreg.) [*P. falciparum*=fMSP1-F1 (SEQ ID NO:57) and pL-His (SEQ ID NO:61)] or [*P. vivax*=vMSP1-F1 (SEQ ID NO:59) and pL-His (SEQ ID NO:61)]. Thermal cycling conditions were as follows: 1 cycle (94° C. for 2 minutes), 5 cycles (94° C. for 30 seconds, 43° C. for 30 seconds, 72° C. for 2 minutes), 35 cycles (94° C. for 30 seconds, 65° C. for 30 seconds, 72° C. for 2 minutes) and 1 cycle (72° C. for 10 minutes). The PCR's were electrophoresed on a 1.0% agarose gel, and the amplicons were extracted from the agarose using the QIAEX II Agarose Gel Extraction Kit (Qiagen, Valencia, Calif.) according to the package insert. Each purified amplicon was digested in a 100 μl reaction for 45 minutes at 37° C. in the presence of 20 units of the restriction enzyme EcoRI, 20 units of the restriction enzyme BamHI and 1×EcoRI Buffer (New England Biolabs, Beverly, Mass.). The digestion products were purified using the QIAquick PCR Purification Kit (Qiagen, Valencia, Calif.) according to the package insert.

Preparation of synthetic MSP1-p19 Genes from *P. malariae* and *P. ovale*

*E. coli* cells containing plasmid clones of the *P. malariae* and *P. ovale* synthetic MPS1-p19 genes [GenScript Corp. (Piscataway, N.J.)] were grown, and the plasmids purified using the Wizard Plus SV Minipreps DNA Purification Kit (Promega, Madison, Wis.) according to the package insert. Each plasmid was digested in a 200 μl reaction for 1 hr. at 37° C. in the presence of 100 units of the restriction enzyme EcoRI, 100 units of the restriction enzyme BamHI and 1×EcoRI Buffer (New England Biolabs, Beverly, Mass.). The digests were electrophoresed on a 0.8% agarose TAE ethidium bromide gel to separate the insert from the vector. The approximately 350 base pair inserts were then excised from the agarose gel, and the DNA was extracted from the agarose using the QIAEX II Agarose Gel Extraction Kit (Qiagen, Valencia, Calif.) according to the package insert.

Preparation of the CKS-fusion Expression Vector for Cloning

*E. coli* cells containing the CKS-fusion expression vector pJO200 (Abbott Laboratories, Abbott Park, Ill.) was grown, and the plasmid purified using the Wizard Plus SV Minipreps DNA Purification Kit (Promega, Madison, Wis.) according to the package insert. The plasmid (10 μg) was digested in a 1500 μl reaction for 2.5 hrs. at 37° C. in the presence of 200 units of the restriction enzyme EcoRI, 200 units of the restriction enzyme BamHI and 1×EcoRI Buffer (New England Biolabs, Beverly, Mass.). The digests were electrophoresed on a 1.0% agarose TAE ethidium bromide gel to separate the insert from the vector. Linearized vector was then excised from the agarose gel, and the DNA was extracted from the agarose using the QIAEX II Agarose Gel Extraction Kit (Qiagen, Valencia, Calif.) according to the package insert.

Cloning of the MSP1-p19 Inserts into the Expression Vector

A portion (2 μl) of each of the four purified EcoRI/BamHI digested MSP1-p19 inserts (see above) were added to separate ligation reactions (10 μl) containing EcoRI/BamHI digested expression vector pJO200 (~0.6 μg, see above), 1×T4 DNA Ligase Buffer and 400 units T4 DNA Ligase (New England Biolabs, Beverly, Mass.). The ligation reactions were incubated overnight at either 4° C. or 16° C. then transformed into *E. coli* XL1-Blue competent cells (Stratagene, La Jolla, Calif.) according to the package insert. Plasmids were purified from the XL1-Blue clones as described above and transformed into competent cells of the protease deficient *E. coli* strain BL21 (Novagen, Madison, Wis.) according to the package insert.

Expression and Purification of MSP1-p19 Recombinant Proteins

BL21 cells containing each of the four MSP1-p19 expression plasmids (see above) were grown in separate 100 ml cultures at 37° C. until an OD595 of approximately 0.5 was reached, at which time IPTG was added to a final concentration of 1 mM to induce expression. After 3 hours of induction at 37° C., the cells were harvested by centrifugation and the pelleted cells were lysed with BugBuster Extraction Reagent (Novagen, Madison, Wis.) according to the package insert. The expressed MSP1-p19 present in the soluble fraction of each lysate, was purified using a His·Bind Purification Kit (Novagen, Madison, Wis.) according to the package insert. The purified recombinant proteins were dialyzed into 0.01 M phosphate buffer, pH 7.4 containing 0.15 M NaCl (PBS) prior to quantitation.

Example 5

Phylogenetic Analysis of MSP1 Sequences

Related organisms generally have a high degree of agreement in the molecular structure of DNA, RNA and proteins, while the molecules of organisms distantly related usually show a pattern of dissimilarity. Molecular phylogeny uses sequence data to build a "relationship tree" that shows the probable evolution of various organisms based upon the degree of dissimilarity between sequences. Evolutionary relationships among plasmodium species have been examined using sequences of genes that encode proteins (e.g. cytochrome b or circumsporozoite protein) or RNA molecules (i.e. small subunit ribosomal RNA, a.k.a. ssRNA or 18S RNA). Some of these genes (cytochrome b and ssRNA) are house-keeping genes that are highly conserved not only within the phylum Apicomplexa, wherein the genus *Plasmodium* is classified, but also in multicellular organisms. Such genes accumulate mutations slowly and thus ancient relationships have not been obscured by random mutation events, as can occur in genes that are less essential or are under intense immune selection pressure. The cytochrome b and ssRNA gene sequences from *P. ovale* and *P. malariae* have been used to examine their evolutionary relationship to primate, rodent and avian plasmodium species (Perkins and Schall, 2002, J. Parsitol. 88:972-978; Escalante AND Ayala, 1995, PNAS 91:11373-11377; Leclerc et al., 2004, Parasitology 129:677-684). Based on these published analyses, while their evolutionary origins are still a matter of debate, *P. ovale* and *P. malariae* have been shown to be unique *Plasmodium* parasites of humans.

The MSP1 protein sequences of *P. ovale* and *P. malariae* were compared with all available orthologous genes from other primate, human and bird plasmodium parasites to determine their degree of relatedness. Full-length MSP1 amino acid sequences for *P. malariae* (SEQ ID NO:1) and *P. ovale* (SEQ ID NO:3) were aligned with 14 other full-length MSP1 protein sequences available in GenBank (see Table 1). Alignments were produced using CLUSTALW software (Thompson et al., 1994, Nucl. Acids Res. 22:4673-4680). Phylogenetic trees were produced using MEGA4 software (Tamura et al., 2007, Mol. Biol Evol. 24:1596-1599) under three different evolutionary models.

The models are in basic agreement in that all rodent and primate (monkey) sequences form subgroups with significant bootstrap support (i.e. >70%). *P. ovale* and *P. malariae* are not subsumed by any of the rodent or primate sequence groups, nor are they grouped together by any of the models. The *P. ovale* and *P. malariae* MSP1 sequences occupy branches at the center of the tree indicating that they are sufficiently divergent from all other sequences (and each other) as to occupy individual branches on the tree.

TABLE 1

MSP1 sequences of plasmodium species from GenBank

| Species | Host | Accession No. |
|---|---|---|
| *P. berghei* | Rodent | AAF13063.1 |
| *P. chabaudi* | Rodent (*Thamnonys rutilans*) | AAA29499.1 |
| *P. coatneyi* | Primate (*Macaca fascicularis*) | BAF74048.1 |
| *P. cynomolgi* | Primate | BAF74063.1 |
| *P. falciparum* | Human | BAF62278.1 |
| *P. fragile* | Primate (*Macaca sinica*) | BAF74049.1 |
| *P. gallinaceum* | Bird (*Gallus gallus*) | CAH10838.1 |
| *P. hylobati* | Primate (gibbon) | BAF74050.1 |
| *P. inui* | Primate (*Cynopithecus niger*) | BAF74051.1 |
| *P. knowlesi* | Primate (*Macaca fascicularis*) | BAF74052.1 |
| *P. reichenowi* | Chimpanzee (*Pan troglodytes*) | CAH10285.1 |
| *P. simiovale* | Primate (*Macaca sinica*) | BAF74053.1 |
| *P. vivax* | Human | AAA63427.1 |
| *P. yoelii* | Rodent (*Thamnonys rutilans*) | EAA17822.1 |

Example 6

Preparation of Microparticles

Microparticles were coated with recombinant antigens cloned from the MSP1 regions of *Plasmodium.*

Microparticles for Antibody Assay:

The following recombinant proteins were used to coat the microparticles for antibody assay.

A. Preparation of Recombinant Proteins:

See Example 4 above.

i. *P. ovale* MSP1-19.

ii. *P. malariae* MSP1-19.

iii. *P. falciparum* MSP1-19.

iv. *P. vivax* MSP1-19.

A1. Preparation of R-antigen Coated Microparticles i. Preparation of Single Antigen Coated Particles Microparticles coated with one of the recombinant MSP1-19 proteins were prepared in the following manner. Briefly, a 250 µl aliquot of microparticles (4% weight/volume, 3.2 micron diameter (Interfacial Dynamics Corp., Portland, Oreg.) was mixed with 1.25 ml of a coating buffer (2-(N-Morpholino)ethanesulfonic acid (MES) buffer, pH 6.0) and pelleted in a microfuge for 2 minutes at 14,000×g. The particles were resuspended in 0.5 ml of the MES coating buffer, and 100 µg of one of the recombinant proteins was added. (In this example, *P. ovale* MSP1-19 solution: 350 µl for a final concentration of 0.12 mg/ml; *P. malariae* MSP1-19 solution: 200 µl for a final concentration of 0.14 mg/ml; *P. vivax* MSP1-19 solution: 15.3 µl for a final concentration of 0.19 mg/ml; or *P. falciparum* MSP1-19 solution: 10 µl for a final concentration of 0.20 mg/ml.) The microparticle/protein solution was mixed and tumbled for 16 hours at room temperature. The microparticles were pelleted at 14,000×g for 2 minutes, and the solution was removed. The particles were resuspended in 1 ml phosphate buffered saline (pH 7.2) (PBS) and repelleted. The particles were washed with PBS twice more, then resuspended in 1 ml Microparticle Diluent (phosphate buffered saline (pH 6.5) with 11.5% sucrose). The microparticle concentration was determined by absorbance at 700 nm compared to a standard curve prepared from known concentrations of microparticles. The microparticle solution was diluted to a final concentration of 0.05% in Microparticle Diluent.

ii. Preparation of Mixed Antigen Coated Particles

Microparticles coated with a mixture of the recombinant MSP1-19 proteins were prepared in the following manner. Briefly, a 250 µl aliquot of microparticles (4% weight/volume, 3.2 micron diameter (Interfacial Dynamics Corp., Portland, Oreg.) was mixed with 1.25 ml of a coating buffer (MES buffer, pH 6.0) and pelleted in a microfuge for 2 minutes at 14,000×g. The particles were resuspended in 0.5 ml of the MES coating buffer and 25 µg of each of the recombinant proteins was added (*P. ovale* MSP1-19 solution: 87.5 µl; *P. malariae* MSP1-19 solution: 50 µl; *P. vivax* MSP1-19 solution: 3.8 up; *P. falciparum* MSP1-19 solution: 2.5 µl). The microparticle/protein solution was mixed and tumbled for 16 hours at room temperature. The microparticles were pelleted at 14,000×g for 2 minutes and the solution was removed. The particles were resuspended in 1 ml PBS (pH 7.2) and repelleted. The particles were washed with PBS twice more, then resuspended in 1 ml Microparticle Diluent (phosphate buffered saline (pH 6.5) with 11.5% sucrose). The microparticle concentration was determined by absorbance at 700 nm compared to a standard curve prepared from known concentrations of microparticles. The microparticle solution was diluted to a final concentration of 0.05% in Microparticle Diluent.

iii. Blending of Single Antigen Coated Particles

Single antigen coated microparticles were resuspended to a concentration of 0.1% in Microparticle Diluent. An equal volume of each of the four solutions of particles was mixed together to form the blend of single antigen coated particles with a final particle concentration of 0.1%.

Example 7

Preparation of Acridinium-Labeled Conjugates

A. Conjugate for Antibody Assay:

For the antibody assay, mouse anti-human IgG directly labeled with acridinium can be prepared as follows:

(i) Acridinium Labeled Mouse Anti-Human IgG:

53.6 µl of conjugation buffer (CB) containing sodium phosphate, NaCl, 3-(3-chlolamidopropyl)-dimethylammonio-1-propane-sulfonate (CHAPS, Sigma Chemical Company, Saint Louis, Mo.), pH 8.0 and 7.2 µl of N-hydroxysuccinimide ester of 10-(3-sulfopropyl)-N-tosyl-N-(2-carboxyethyl)-9-acridinium carboxamide (4 mg/ml in dimethyl formamide) was added to 131 µl of Mouse anti-Human IgG (4.59 mg/ml) and 601 µl of PBS at room temperature. The reaction mixture was mixed with a rotator for 20 minutes at room temperature. The reaction was quenched by loading the reaction mixture onto the HPLC. This was applied to a 300×7.8 mm Bio-Sil SEC-250 gel filtration column (Bio-Rad, Richmond, Calif.) which had been equilibrated with buffer containing CHAPS, NaCl and sodium phosphate, pH 6.3. The column was eluted at 1.0 ml/min with the same buffer using a Beckman 421A controller equipped with a model 114M pump. Fractions of 1 ml were collected and the absorbance determined at 280 nm and 370 nm with a Beckman DU-7 spectrophotometer. The extent of acridinium incorporation was calculated as described in U.S. Pat. No. 5,705,330. The acridinium to IgG ratio (mole/mole) obtained was approximately 2.5. The conjugate was stored at 4 degrees C.

Example 8

PRISM Anti-*Plasmodium* Antibody Assay

The PRISM antibody assay is described in U.S. Pat. No. 5,705,330, incorporated herein by reference, and the PRISM antigen and antibody assays are described in Shah and Stewart, The Immunoassay Handbook, second edition, edited by David Wild, p 297-303 (2001), also incorporated herein by reference.

Figure 15:
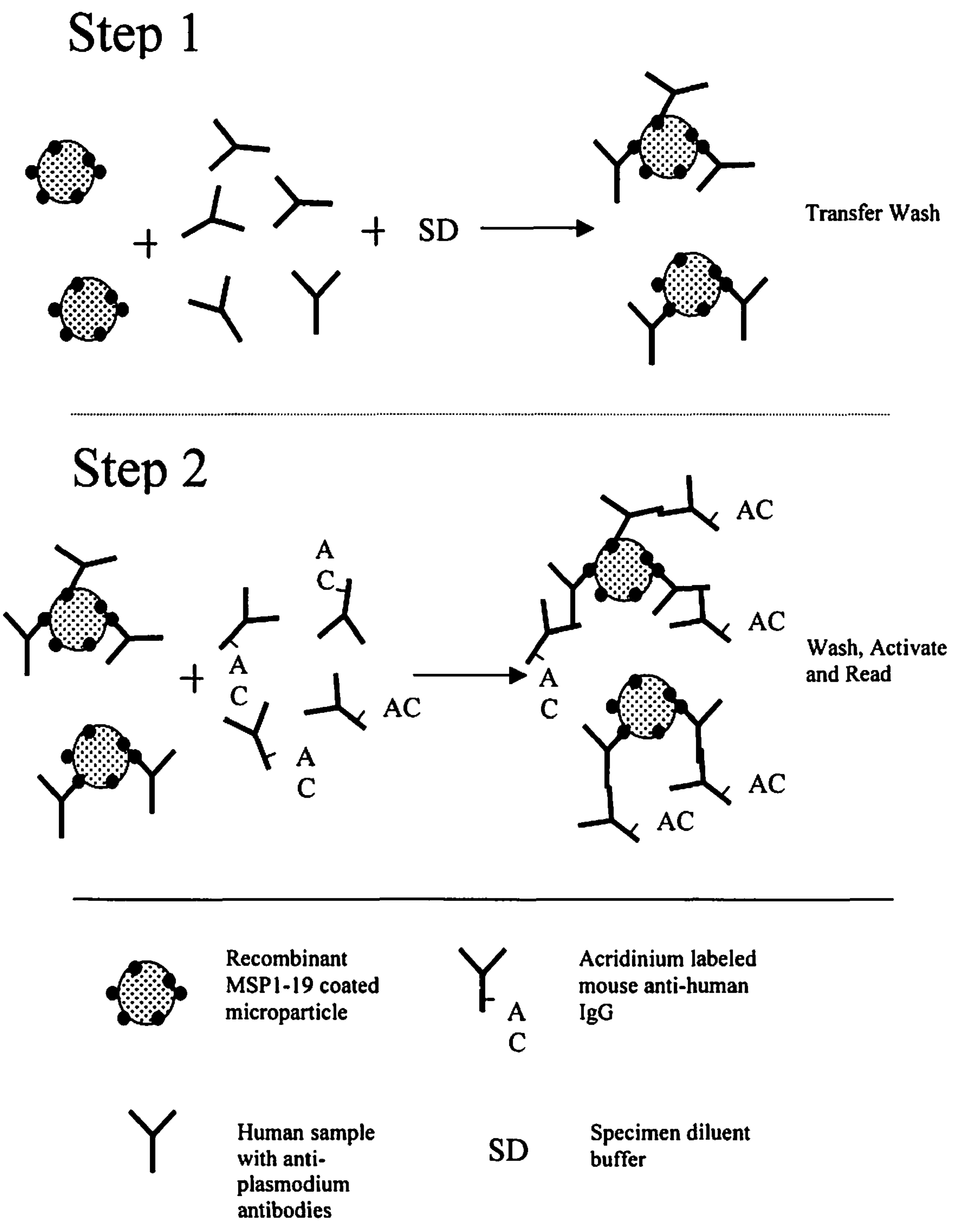
FIG. 15 illustrates a prototype Abbott PRISM® (Abbott Laboratories, Abbott Park, Ill.) malaria assay format.

With respect to the present invention, the following procedures were utilized:

Individual *Plasmodium* species Antibody Assay:

The assay format is provided in FIG. 15. Generally, at station 1, 50 μl of control or sample, 50 μl of specimen diluent buffer (SDB, borate buffer, pH 7.5 containing Tween 20, triton X-100, urea, bovine serum albumin, newborn calf serum, NaCl, *E. coli* lysate and azide), and 50 μl of individual recombinant antigen coated microparticles [(prepared as described in Example (6) (A1) (i) above] were dispensed into each incubation well and assay timing was started. These were mixed by mutual diffusion of each into the other without external agitation or shaking to form a reaction mixture. At station 4, the reaction mixture was transferred to a detection well that contained a fibrous matrix and washed twice with 300 μl of transfer wash (TW, containing borate buffer, pH 7.0, with NaCl, Tween-20, Glycerol, urea, and Proclin 300). After 18 minutes of incubation at 37 degrees C., 50 μl of acridinium labeled mouse anti-human antibody was dispensed into the matrix of the detection well at station 5. The well was incubated for 23 minutes at 37 degrees C., and the fibrous matrix containing the reaction mixture was washed three times with 100 μl of Final Wash (FW), containing tris buffer, pH 9.0, with LiCl, lithium dodecyl sulfate, polyethylene glycol 1500 and Proclin 300 at station 8. At station 9, a chemiluminescence (CL) signal was generated by addition of an alkaline hydrogen peroxide solution, and the photons were measured by a photo multiplier tube. The amount of light emitted is proportional to the amount of antibody in the sample. The presence or absence of antibody in the sample is determined by comparing the number of photons collected from the sample to a negative (S/N) value. The results are expressed as S/N (signal to negative) in Table 2 below. Samples which have an S/N greater than 5.0 are considered to be reactive for the antigen. The results are compared to results obtained from a commercially available enzyme-linked immunoassay.

Four species *Plasmodium* Antibody Assay:

The assay format is provided in FIG. 15. Generally, at station 1, 50 μl of control or sample, 50 μl of SDB, and 50 μl of mixed recombinant antigen coated microparticles [prepared as described in Example (6) (A1) (ii) above] or 50 μl of blended individual recombinant antigen coated microparticles [prepared as described in Example (6) (A1) (iii) above] were dispensed into each incubation well, and assay timing was started. These were mixed by mutual diffusion of each into the other without external agitation or shaking to form a reaction mixture. At station 4, the reaction mixture was transferred to a detection well, which contained a fibrous matrix and washed twice with 300 μl of TW. After 18 minutes of incubation at 37 degrees C., 50 μl of acridinium labeled mouse anti-human antibody was dispensed into the matrix of the detection well at station 5. The well was incubated for 23 minutes at 37 degrees C., and the fibrous matrix containing the reaction mixture was washed three times with 100 μl of FW at station 8. At station 9, a chemiluminescence (CL) signal was generated by addition of an alkaline hydrogen peroxide solution, and the photons were measured by a photo multiplier tube. The amount of light emitted is proportional to the amount of antibody in the sample. The presence or absence of antibody in the sample is determined by comparing the number of photons collected from the sample to a negative (S/N) value. The results are expressed as S/N in Table XII below. Samples which have an S/N greater than 5.0 are considered to be reactive for the antigen. The results are compared to results obtained from a commercially available enzyme-linked immunoassay (Newmarket Labs., Kentford, UK).

TABLE 2

Detection of *P. ovale* and *P. malariae* samples with PoMSP1-19 and PmMSP1-19

| Sample ID | Species determined by blood smear | Microparticle PoMSP1-19 | Microparticle PmMSP1-19 | Commercial ELISA test results |
|---|---|---|---|---|
| 01 | *P. ovale* | 29.63 | 1.49 | positive |
| 19 | *P. ovale* | 40.25 | 15.12 | positive |
| 20 | *P. ovale* | 2.28 | 1.73 | negative |
| 21 | *P. ovale* | 84.90 | 31.82 | positive |
| 23 | *P. ovale* | 80.73 | 11.57 | positive |
| 24 | *P. ovale* | 32.92 | 3.85 | positive |
| 25 | *P. ovale* | 44.06 | 0.97 | negative |
| 26 | *P. ovale* | 31.31 | 3.78 | negative |
| 2 | *P. malariae* | 1.29 | 8.88 | negative |
| 15 | *P. malariae* | 0.99 | 20.25 | negative |

TABLE 3

Detection of *P. falciparum* and *P. vivax* samples with PfMSP1-19 and PvMSP1-19

| Sample ID | Species determined by blood smear | Microparticle PvMSP1-19 | Microparticle PfMSP1-19 | Commercial ELISA test results |
|---|---|---|---|---|
| 1 | *P. vivax* | 7.40 | 1.63 | Positive |
| 2 | *P. vivax* | 89.38 | 1.39 | Positive |
| 5 | *P. vivax* | 97.07 | 1.13 | Positive |
| 9 | *P. vivax* | 90.17 | 1.17 | Positive |
| 10 | *P. vivax* | 5.47 | 1.38 | Positive |
| 11 | *P. vivax* | 105.07 | 60.22 | Positive |
| 12 | *P. vivax* | 28.84 | 3.31 | Positive |
| 14 | *P. vivax* | 75.24 | 54.86 | Positive |
| 6 | *P. falciparum* | 1.23 | 133.29 | Positive |
| 17 | *P. falciparum* | 35.34 | 7.36 | Positive |
| 18 | *P. falciparum* | 38.41 | 3.92 | Positive |
| 16 | *P. falciparum* | 23.13 | 65.58 | Positive |

TABLE 4

Multispecies detection using mixed recombinant coating or blended individual coating microparticles

| Sample ID | Species determined by blood smear | Microparticle Mixed Recombinant Coating | Microparticle Blended Individual Coating | Commercial ELISA test results |
|---|---|---|---|---|
| 01 | *P. ovale* | 15.57 | 20.41 | positive |
| 19 | *P. ovale* | 99.31 | 63.90 | positive |
| 20 | *P. ovale* | 2.03 | 1.83 | negative |
| 21 | *P. ovale* | 78.71 | 58.97 | positive |
| 23 | *P. ovale* | 62.03 | 49.27 | positive |
| 24 | *P. ovale* | 33.74 | 34.29 | positive |
| 25 | *P. ovale* | 16.94 | 21.19 | negative |
| 26 | *P. ovale* | 27.44 | 23.95 | negative |
| 1 | *P. vivax* | 2.54 | 3.49 | positive |

TABLE 4-continued

Multispecies detection using mixed recombinant coating or blended individual coating microparticles

| | | Microparticle | | |
|---|---|---|---|---|
| Sample ID | Species determined by blood smear | Mixed Recombinant Coating | Blended Individual Coating | Commercial ELISA test results |
| 2 | *P. vivax* | 59.88 | 47.38 | positive |
| 5 | *P. vivax* | 65.85 | 44.38 | positive |
| 9 | *P. vivax* | 73.14 | 45.25 | positive |
| 10 | *P. vivax* | 2.32 | 2.43 | positive |
| 11 | *P. vivax* | 81.37 | 65.27 | positive |
| 12 | *P. vivax* | 18.35 | 19.27 | positive |
| 14 | *P. vivax* | 78.32 | 52.69 | positive |
| 6 | *P. falciparum* | 87.76 | 54.63 | positive |
| 17 | *P. falciparum* | 31.40 | 25.33 | positive |
| 18 | *P. falciparum* | 37.35 | 23.50 | positive |
| 16 | *P. falciparum* | 42.98 | 27.04 | positive |
| 2 | *P. malariae* | 3.38 | 5.70 | negative |
| 15 | *P. malariae* | 11.41 | 10.04 | negative |

Samples 25, 26, 2, and 15 were reactive in both the mixed antigen coating and blended individual coating assays, but were negative in the commercial ELISA, demonstrating an improved detection using recombinant antigens representing all four species of *Plasmodium.*

Example 9

Detection of IgG Antibodies Using *P. ovate* and *P. malariae* MSP1-19 Recombinant Antigens Detection of antibodies in serum or plasma directed against the MSP1-19 protein of *P. ovale* and *P. malariae* was performed using an enzyme immunoassay (EIA). The CKS-MSP1-19 recombinant antigens described in Example 4 were coated onto a solid phase support, and antibodies present in the test samples that bound to the recombinant proteins were detected using a goat anti-human antibody horseradish peroxidase conjugate.

Coating of Polystyrene Beads:

One quarter-inch polystyrene beads were used as the solid phase for the peptide EIAs. Prior to coating, beads were washed with 15% 1-propanol (in water) at room temperature for 20 minutes without agitation. Propanol was removed, and the beads were rinsed twice with deionized water. The washed beads were then added to a vial containing recombinant antigen diluted to 0.25-5 microgram per mL in 0.1 M sodium phosphate, pH 7.0 (0.233 ml per bead). Beads were incubated at 40° C. for 2 hours with gentle mixing. Beads were then washed three times with PBS and then incubated in PBS containing 0.1% Triton X-100 at 40° C. for 1 hour with gentle mixing. They were again washed three times in PBS and then incubated at 40° C. in 5% BSA in PBS for 1 hour with gentle mixing. Beads were washed four times with PBS and then incubated at room temperature in PBS containing 5% sucrose without mixing for 20 minutes. Sucrose buffer was removed and beads air-dried. Coated beads were stored desiccated at 4° C.

Immunoassay Method:

Serum and plasma were tested for their immunoreactivity to CKS-MSP1-19 coated polystyrene beads. Specimens were diluted 1:16 in diluent buffer (Tris-phosphate buffer pH 7.8 comprising 20% goat serum, 10% calf serum, 0.2% Triton X-100 and sodium azide), and 0.010 ml was added to a well of a plastic test tray and then combined with an additional 0.20 mL of the same diluent buffer for a final sample dilution of 1:336. The recombinant protein coated bead was added to the diluted sample and incubated at 37° C. for 90 min with mixing. Beads were then washed with 11-14 mL of deionized water followed by the addition of 0.2 ml of peroxidase-labeled goat anti-human IgG (0.02 microgram per mL). Beads were incubated at 37° C. for 30 min with mixing. Beads were washed with 11-14 mL deionized water and then transferred into plastic tubes to which 0.3 ml of OPD (0.3% O-phenylenediamine-2-HCl in citrate buffer containing 0.02% $H_2O_2$) substrate was added and incubated in the dark at room temperature for 30 min without mixing. Reactions were quenched by the addition of 1 ml of 1N $H_2SO_4$ and the optical density (OD) at 492 nm determined. The OD is directly proportional to the amount of antibody bound to the bead. Signal to negative (S/N) ratios are calculated for each test sample by dividing the test sample OD by the mean negative control OD. Specimens with S/N values greater-than or equal-to 5.00 (provisional cutoff value) were assumed to be immunoreactive.

*Plasmodium* Infected Individuals:

Human serum samples from individuals infected with *P. ovale, P. malariae, P. falciparum* or *P. vivax* were obtained from Marianna Wilson, Chief, Reference Immunodiagnostic Laboratory, Center for Disease Control and Prevention, Atlanta, Ga., USA. Immunofluorescent antibody titers for each human infective plasmodium species for each sample was provided, as was the plasmodium species identification determined by blood smear (see Table 5, below). All samples were collected prior to 1990 and are considered "anonymized residual human specimens" since original records regarding the identity of the donor/patient no longer exist.

TABLE 5

| | | CDC IFA Results | | | |
|---|---|---|---|---|---|
| Sample | Species | *P. vivax* | *P. falciparum* | *P. malariae* | *P. ovale* |
| Pv-1 | *P. vivax* | 1024 | 64 | <4 | 16 |
| Pv-2 | *P. vivax* | >4096 | 64 | 16 | 64 |
| Pv-5 | *P. vivax* | >4096 | 64 | 16 | 256 |
| Pv-9 | *P. vivax* | 1024 | 64 | 64 | 256 |
| Pv-10 | *P. vivax* | >4096 | 64 | 16 | 64 |
| Pv-11 | *P. vivax* | 1024 | 64 | 4 | 256 |
| Pv-12 | *P. vivax* | >4096 | 64 | 16 | 16 |
| Pv-14 | *P. vivax* | 1024 | 256 | 4 | 16 |
| Pf-6 | *P. falciparum* | 64 | 1024 | 16 | 64 |
| Pf-16 | *P. falciparum* | 64 | 256 | 64 | 64 |
| Pf-17 | *P. falciparum* | 256 | 256 | 64 | 256 |
| Pf-18 | *P. falciparum* | 256 | 1024 | 64 | 64 |
| Pm-2 | *P. malariae* | 16 | 64 | >4096 | 64 |
| Pm-15 | *P. malariae* | 64 | >4096 | >4096 | 64 |
| Po-1 | *P. ovale* | <4 | 256 | 16 | 1024 |
| Po-19 | *P. ovale* | 256 | 64 | 64 | 1024 |
| Po-20 | *P. ovale* | <4 | 16 | <4 | 256 |
| Po-21 | *P. ovale* | 256 | 64 | 64 | 1024 |
| Po-23 | *P. ovale* | <4 | 256 | 64 | 1024 |
| Po-24 | *P. ovale* | 4 | 64 | 4 | 64 |
| Po-25 | *P. ovale* | <4 | 16 | 4 | 256 |
| Po-26 | *P. ovale* | 64 | 64 | 64 | 256 |

Po and Pm MSP1-19 Antibody EIA:

The presence of IgG antibodies against Po-MSP1-19 and Pm-MSP1-19 was determined using the procedure described above in those individuals shown to be infected with *P. malariae* or *P. ovale* by IFA and/or blood smear. The S/N ratios obtained are shown in Table 6, below. Specimens were also tested for the presence of anti-*Plasmodium* antibodies using a commercially available ELISA test (NewMarket Labs., Kentford, UK).

TABLE 6

| Sample | Species determined by blood smear | Antigen coated bead P. malariae CKS-MSP1-19 | P. ovale CKS-MSP1-19 | Commercial ELISA test results |
|---|---|---|---|---|
| Pm-2 | *P. malariae* | 67.42 | 0.90 | Negative |
| Pm-15 | *P. malariae* | 7.96 | 0.55 | Negative |
| Po-1 | *P. ovale* | 4.31 | 100.00 | Positive |
| Po-19 | *P. ovale* | 6.34 | 43.70 | Positive |
| Po-20 | *P. ovale* | 0.51 | 11.50 | Negative |
| Po-21 | *P. ovale* | 24.84 | 100.00 | Positive |
| Po-23 | *P. ovale* | 5.33 | 100.00 | Positive |
| Po-24 | *P. ovale* | 1.25 | 47.80 | Positive |
| Po-25 | *P. ovale* | 0.78 | 44.30 | Negative |
| Po-26 | *P. ovale* | 2.16 | 69.25 | Negative |

These data demonstrate that individuals with confirmed *P. ovale* or *P. malariae* infections possess detectable species-specific MSP1-19 IgG antibodies. In addition, samples that test negative in the commercial ELISA are antibody positive in at least one of the bead EIAs. The apparent cross-species immunoreactivity observed corresponds in some cases to the immunofluorescent antibody assay results, i.e. many individuals have antibodies against more than one *Plasmodium* species.

Example 10

Detection of *P. ovale* and *P. malariae* MSP1-19 IgG Antibodies in Gene Cloning Source Samples Human serum samples from West African blood donors were tested for the presence of *P. ovale* and *P. malariae* MSP1-19 antibodies using the assay described in Example 9. West Africa is endemic for malaria including *P. falciparum, P. malariae, P. ovale*, and to a lesser extent, *P. vivax*. Whole blood samples were also available from the same donors for DNA extraction and subsequent testing using a PCR assay for the detection of ribosomal DNA gene sequences (see Example 1) which allowed identification of the plasmodium species present at the time the donation was obtained. DNA extracted from the blood of Donor 0014 was used as the cloning source for *P. malariae* MSP1 gene. DNA extracted from the blood of Donor 510-10 was used as the cloning source for the *P. ovale* MSP1 gene. The MSP1-P19 fragments of these genes were cloned and expressed as CKS fusions in *E. coli* (Example 4), coated onto beads and used for antibody detection as described in Example 9.

The results shown in Table 7 below (S/N values) demonstrate that IgG antibodies against *P. malariae* MSPL-19 are present in serum from Donor 0014, the cloning source for the *P. malariae* MSP1 gene. Similarly, IgG antibodies against *P. ovale* MSP1 are present in the serum from Donor 510-10, the cloning source for the *P. ovale* MSP1 gene. Serum from two additional blood donors shown to be actively infected with *P. malariae* also exhibit IgG immunoreactivity to the type-homologous antigen. Serum from two of three other blood donors shown to be infected with *P. ovale* exhibit immunoreactivity to the type-homologous antigen.

These data indicate that serum from individuals with demonstrated *P. malariae* parasitemia harbor antibodies directed against the *P. malariae* MSP1-19 antigen. Similarly, serum from individuals with demonstrated *P. ovale* parasitemia harbor antibodies against the *P. ovale* MSP1-19 antigen.

TABLE 7

| Sample ID | Species identified by rDNA PCR | P. malariae MSP1-19 Bead EIA, S/N | P. ovale MSP1-19 Bead EIA, S/N |
|---|---|---|---|
| 0014 | Pm, Pf | 55.94 | 3.82 |
| 609-39 | Pm, Pf | 55.94 | 4.79 |
| 240-16 | Pm, Pf | 46.13 | 6.07 |
| 510-10 | Po | 55.94 | 87.91 |
| 283-4 | Po | 24.98 | 76.18 |
| 1045-36 | Po, Pf | 27.50 | 3.30 |
| 684-22 | Po, Pf | 55.94 | 35.96 |

Example 11

Detection of *P. falciparum* and *P. vivax* MSP1-19 IgG Antibodies

Detection of *P. vivax*, and *P. falciparum* MSP1-19 antibodies was performed using individual EIAs.

Recombinant MSP1-19 CKS fusion antigens from each plasmodium species (see Example 4) were coated onto polystyrene beads as described in Example 9. IgG antibodies were measured in the serum of individuals shown to be infected with *P. vivax* or *P. falciparum* using the indirect EIA method described in Example 9. Signal to negative (S/N) ratios are shown in Table 8. Specimens were also tested for the presence of anti-plasmodium antibodies using a commercially available ELISA test (NewMarket Labs., Kentford, UK).

TABLE 8

| Sample | Species determined by Blood Smear | Antigen coated bead P. falciparum CKS-MSP1-19 | P. vivax CKS-MSP1-19 | Commercial ELISA test results |
|---|---|---|---|---|
| Pv-1 | *P. vivax* | 1.27 | 62.12 | Positive |
| Pv-2 | *P. vivax* | 1.34 | 67.42 | Positive |
| Pv-5 | *P. vivax* | 1.34 | 67.42 | Positive |
| Pv-9 | *P. vivax* | 0.61 | 67.42 | Positive |
| Pv-10 | *P. vivax* | 1.70 | 49.52 | Positive |
| Pv-11 | *P. vivax* | 10.63 | 67.42 | Positive |
| Pv-12 | *P. vivax* | 0.54 | 40.96 | Positive |
| Pv-14 | *P. vivax* | 11.39 | 67.42 | Positive |
| Pf-6 | *P. falciparum* | 72.29 | 0.98 | Positive |
| Pf-16 | *P. falciparum* | 7.81 | 2.93 | Positive |
| Pf-17 | *P. falciparum* | 1.77 | 14.63 | Positive |
| Pf-18 | *P. falciparum* | 1.01 | 8.19 | Positive |

These results demonstrate the ability of the MSP1-19 fusion proteins to detect antibodies in individuals infected with type-homologous plasmodium species. Apparent cross-species immunoreactivity observed corresponds in some cases to the immunofluorescent antibody assay results, i.e., many individuals have antibodies against more than one species of plasmodium.

Example 12

Multispecies EIA

Detection of IgG antibodies against *P. ovale, P. malariae, P. vivax* or *P. falciparum*, using a single assay, was accomplished by simultaneous coating of polystyrene beads with purified CKS-MSP1-19 recombinant antigens from each of the four species. Beads were coated simultaneously with recombinant antigens (see Example 4 for cloning & expression pf Pf/Pv and Po/Pm MSP1-19 rAgs, respectively) at 0.5 microgram per mL as described in Example 9, except that the coating buffer used 50 mM MES pH 6.3. Immunoreactivity of human sera from individuals with diagnosed plasmodium infections representing each of the four species was determined using the EIA method described in Example 9. S/N ratios are shown Table 9. Specimens were also tested for the presence of anti-plasmodium antibodies using a commercially available ELISA test (NewMarket Labs, Kentford, UK).

TABLE 9

| Sample | Species determined by blood smear | Pf/Pv/Po/Pm MSP1-19 co-coated bead | Commercial ELISA test results |
|---|---|---|---|
| Pv-1 | *P. vivax* | 58.35 | Positive |
| Pv-2 | *P. vivax* | 65.93 | Positive |
| Pv-5 | *P. vivax* | 65.93 | Positive |
| Pv-9 | *P. vivax* | 65.93 | Positive |
| Pv-10 | *P. vivax* | 47.27 | Positive |
| Pv-11 | *P. vivax* | 65.93 | Positive |
| Pv-12 | *P. vivax* | 37.62 | Positive |
| Pv-14 | *P. vivax* | 65.93 | Positive |
| Pf-6 | *P. falciparum* | 65.93 | Positive |
| Pf-16 | *P. falciparum* | 8.51 | Positive |
| Pf-17 | *P. falciparum* | 20.27 | Positive |

TABLE 9-continued

| Sample | Species determined by blood smear | Pf/Pv/Po/Pm MSP1-19 co-coated bead | Commercial ELISA test results |
|---|---|---|---|
| Pf-18 | *P. falciparum* | 12.76 | Positive |
| Pm-2 | *P. malariae* | 65.93 | Negative |
| Pm-15 | *P. malariae* | 5.11 | Negative |
| Po-1 | *P. ovale* | 65.93 | Positive |
| Po-19 | *P. ovale* | 65.93 | Positive |
| Po-20 | *P. ovale* | 2.64 | Negative |
| Po-21 | *P. ovale* | 65.93 | Positive |
| Po-23 | *P. ovale* | 65.93 | Positive |
| Po-24 | *P. ovale* | 55.35 | Positive |
| Po-25 | *P. ovale* | 23.47 | Negative |
| Po-26 | *P. ovale* | 32.37 | Negative |

These data demonstrate the ability of *P. ovale, P. malariae, P. vivax* and *P. falciparum* CKS-MSP1-19 antigens to be coated simultaneously onto a solid support and retain their ability to detect IgG antibodies in serum from individuals infected with one of the four plasmodium species. Four of the five specimens that are negative in the commercial assay are positive in the four-species MSP1-19 bead assay.

What is claimed is:

1. An isolated nucleic molecule comprising a nucleotide sequence encoding a polypeptide, wherein the amino acid sequence of said polypeptide has at least 90% identity to the amino acid sequence selected from the group consisting of SEQ ID NO: 1, amino acids 1634-1733 of SEQ ID NO: 1, amino acids 1374-1633 of SEQ ID NO: 1 and amino acids 1374-1733 of SEQ ID NO: 1.

2. The isolated nucleic acid molecule of claim 1, wherein said molecule is isolated from *Plasmodium malariae*.

3. An isolated nucleic acid molecule comprising a nucleotide sequence having at least 90% identity to a nucleic acid sequence comprising the nucleotide sequence selected from the group consisting of SEQ ID NO: 2, nucleotides 62-5317 of SEQ ID NO: 2, nucleotides 4961-5260 of SEQ ID NO: 2, nucleotides 4181-4960 of SEQ ID NO: 2 and nucleotides 4181-5260 of SEQ ID NO: 2.

* * * * *

UNITED STATES PATENT AND TRADEMARK OFFICE

CERTIFICATE OF CORRECTION

PATENT NO. : 8,030,471 B2
APPLICATION NO. : 12/143137
DATED : October 4, 2011
INVENTOR(S) : Birkenmeyer et al.

It is certified that error appears in the above-identified patent and that said Letters Patent is hereby corrected as shown below:

In the Claims:

Column 125, line 16, claim 1: "An isolated nucleic molecule" to read as
--An isolated nucleic acid molecule--

Signed and Sealed this
Eighteenth Day of June, 2013

Teresa Stanek Rea
*Acting Director of the United States Patent and Trademark Office*

SEQUENCE LISTING

```
<160> NUMBER OF SEQ ID NOS: 61

<210> SEQ ID NO 1
<211> LENGTH: 1751
<212> TYPE: PRT
<213> ORGANISM: Plasmodium malariae

<400> SEQUENCE: 1

Met Lys Ala Leu Ile Phe Leu Phe Ser Phe Val Phe Phe Ser Ile Asn
1               5                   10                  15

Cys His Cys Glu Thr Asn Glu Asp Tyr Glu Gln Leu Ile Gln Lys Leu
            20                  25                  30

Gly Lys Leu Glu Glu Leu Val Val Glu Gly Tyr Asn Leu Phe His Lys
        35                  40                  45

Lys Lys Phe Ala Leu Thr Asp Ile Asn Lys Asp Gly Asn Thr Ser Thr
    50                  55                  60

Thr Asp Ala Asn Asn Lys Asp Asp Ser Lys Val Ser Ser Val Thr Ala
65                  70                  75                  80

Lys Ile Gly Asn Phe Val Ser Lys Val Leu Asn Leu Asn Leu Pro Gly
                85                  90                  95

Tyr Val Gln Leu Thr Phe Ser Ile Arg Glu Leu Ile Thr Lys Tyr Ser
            100                 105                 110

Gly Leu Lys Tyr Leu Ile Glu Gly Tyr Glu Glu Phe Asn Glu Leu Met
        115                 120                 125

Tyr Gly Ile Asn Phe Tyr Tyr Asp Leu Leu Arg Ala Lys Leu Asn Asp
    130                 135                 140

Met His Leu Asn Gly Tyr Cys Asp Ile Pro Asn His Leu Lys Ile Asn
145                 150                 155                 160

Glu Lys Glu Leu Glu Met Leu Lys Lys Val Val Phe Gly Tyr Arg Lys
                165                 170                 175

Pro Leu Glu Asn Ile Lys Asp Asp Ile Asn Lys Met Glu Lys Phe Ile
            180                 185                 190

Thr Thr Asn Glu Ala Thr Val Asn Asn Ile Lys Glu Leu Ile Lys Lys
        195                 200                 205
```

```
Glu Tyr Asn Asn Ile Ala Asp Glu Asn Lys Lys Leu Glu Ala Pro Ser
    210                 215                 220

Glu Ser Gly Ser Asp Asp Glu Asp Ile Lys Asn Cys Asn Glu Lys Gln
225                 230                 235                 240

Lys Ile Tyr Lys Ser Arg Tyr Asn Ile Leu Phe Tyr Glu Lys Gln Leu
                245                 250                 255

Leu Glu Ala Gln Lys Leu Ile Glu Val Leu Lys Lys Arg Ile Gln Thr
            260                 265                 270

Leu Lys Glu Asn Thr Asp Ile Lys Lys Leu Leu Asp Glu Ile Lys Glu
        275                 280                 285

Ile Glu Gly Lys Leu Pro Thr Ser Gly Ser Glu Ala Ser Ala Ser Ala
    290                 295                 300

Ala Ala Pro Gly Ala Ile Lys Glu Pro Glu Asn Thr Gln Ile Lys Glu
305                 310                 315                 320

Arg Gln Glu Lys Ile Lys Glu Ile Ala Lys Asn Ile Val Phe Asn Met
                325                 330                 335

Asp Gly Leu Phe Thr Asp Ala Phe Glu Leu Asp Tyr Tyr Val Arg Glu
            340                 345                 350

Lys Glu Lys Lys Ser Phe Asn Ser Ala Thr Thr Gln Leu Ala Asn Gly
        355                 360                 365

Lys Ala Val Asn Arg Thr Pro Pro Ala Pro Val Met Tyr Pro His Gly
    370                 375                 380

Ile Ile Tyr Ala Val Ser Asp Asp Ala Ile Ser Asn Ile Leu Ser Lys
385                 390                 395                 400

Ser Ser Thr Gln Leu Thr Leu Glu Glu Leu Gln Asn Pro Asp Asn Arg
                405                 410                 415

Lys Gln Ile Thr Ile Asp Asp Leu Lys Asp Glu Asn Lys Arg Lys Glu
            420                 425                 430

Leu Ile Thr Lys Ile Lys Asn Lys Ile Thr Glu Glu Glu Gly Lys Leu
        435                 440                 445

Asn Ala Leu Lys Gly Asp Val Asp Ser Lys Leu Glu Lys Phe Lys Lys
    450                 455                 460

Ile Glu Gly Glu Phe Lys Pro Leu Leu Glu Lys Phe Tyr Asp Glu Arg
465                 470                 475                 480

Leu Asp Asn Ser Ile Thr Thr Glu Asn Phe Glu Lys Phe Leu Ser Lys
                485                 490                 495

Arg Thr Glu Tyr Leu Thr Glu Lys Asn Leu Leu Glu Ser Ser Ser Tyr
            500                 505                 510

Glu Leu Ser Lys Ala Leu Val Lys Lys Leu Lys Lys Gln Leu Met Tyr
        515                 520                 525

Leu Glu Asp Tyr Ser Leu Arg Lys Glu Val Phe Asp Glu Glu Val Asn
    530                 535                 540

His Phe Asn Cys Leu Asp Leu Gln Leu Asn Ala Asp Ile His Lys Leu
545                 550                 555                 560

Glu Ser Glu Ile Lys Arg Lys Glu Asn Leu Leu Thr Val Val Asp Thr
                565                 570                 575

Leu Lys Phe Ser Asp Val Val Glu Leu Gln Val Gln Lys Val Leu Leu
            580                 585                 590

Gly Lys Lys Ile Gly Gln Leu Lys Asn Val Glu Ala Phe Leu Gln Lys
        595                 600                 605

Ala Lys Leu Lys Glu Thr Phe His Ile Pro Gln Ala Tyr Gly Thr Gly
    610                 615                 620

Glu Gln Ser Glu Pro Tyr Tyr Leu Ile Ala Leu Lys Arg Glu Ile Asp
625                 630                 635                 640
```

```
Lys Leu Asn Ile Ser Ile Pro Lys Ile Glu Glu Met Leu Lys Asn Glu
                645                 650                 655

Lys Lys Leu Glu Glu Glu Lys Ile Lys Ala Ala Ala Gln Asn Val Ser
            660                 665                 670

Gly His Val Ser Gly Ala Asp Glu Thr Ser Asn Ser His Gly Ser Ser
        675                 680                 685

Gly Gly Gly Gly Ser Thr Gln Thr Val Thr Thr Thr Pro Ser Thr Thr
    690                 695                 700

Thr Thr Ala Thr Thr Ser Ser Gln Thr Val Ser Val Gly Glu Thr Gly
705                 710                 715                 720

Ser Ala Gln Ala Gln Ala Gln Pro Gln Pro Gln Pro Gln Pro Gln Pro
                725                 730                 735

Gln Thr Gln Thr Gln Thr Gln Thr Gln Pro Gln Ala Ala Gly Ala Thr
            740                 745                 750

Gly Thr Pro Gly Gln Ser Gly Gln Ser Gly Gln Ser Gly Gln Ser Gly
        755                 760                 765

Ala Glu Gly Thr Thr Glu Thr Thr Gly Thr Thr Gly Gln Ala Gly Thr
    770                 775                 780

Thr Gly Thr Pro Glu Gln Ala Ala Ala Ala Gly Pro Gln Ala Glu Thr
785                 790                 795                 800

Thr Ala Thr Pro Gly Gln Ala Gly Ala Ala Gly Ala Ala Gly Pro Gln
                805                 810                 815

Ala Glu Thr Thr Gly Thr Pro Gly Gln Ala Gly Ala Ala Gly Pro Gln
            820                 825                 830

Thr Glu Thr Glu Val Glu Glu Thr Gln Glu Ile Gly Ile Val Val Pro
        835                 840                 845

Thr Leu Ser Lys Leu Gln Tyr Leu Glu Lys Leu Tyr Asp Phe Leu Lys
    850                 855                 860

Thr Ala Tyr Val Cys His Ile Asn Ile Leu Val Asn Asn Ser Thr Met
865                 870                 875                 880

Asn Glu Thr Leu Leu Gln Gln Tyr Lys Leu Lys Ile Glu Glu Asp Lys
                885                 890                 895

Lys Leu Leu Glu Lys Cys Asp Gln Leu Asp Leu Leu Phe Asn Val Gln
            900                 905                 910

Asn Asn Leu Gln Val Met Tyr Ser Met Tyr Asp Ser Val Ser Asn Val
        915                 920                 925

Leu Gln Asn Gln Tyr Lys Glu Leu Asn Gln Lys Glu Met Ile Tyr Asn
    930                 935                 940

Ile Tyr Lys Leu Val Lys Lys Asn Asp Lys Leu Lys Asn Phe Leu Asn
945                 950                 955                 960

Leu Thr Ala Asn Ser Ala Ala Ala Ser Ser Ala Leu Pro Pro Pro Pro
                965                 970                 975

Ser Val Pro Pro Ala Val Pro Pro Ala Ser Gln Gln Pro Gln Pro Gln
            980                 985                 990

Ala Ala Leu Pro Ala Gln Pro Gln  Ala Ala Val Pro Ala  Gln Ser Gln
        995                 1000                1005

Ala Thr  Val Pro Ala Gln Ser  Gln Ala Ala Val Pro  Ala Thr Thr
    1010                1015                1020

Gln Ser  Ser Ser Val Ser Ala  Pro Thr Gly Thr Asn  Gly Ala Ser
    1025                1030                1035

Pro Ala  Thr Pro Val Ala Pro  Ala Gly Ser Glu Asn  Ala Ile Gln
    1040                1045                1050

Leu Lys  Ala Asn Asp Asn Glu  Asp Asp Ala Asn Glu  Leu Asp Phe
```

-continued

```
    1055                1060                1065

Asp Ile  Asp Asp Ile Tyr Ile  Lys Tyr Leu Glu Gln  Val Ser Lys
    1070                1075                1080

Tyr Asp  Glu Asn Phe Lys Asn  Phe Ile Glu Ser Lys  Lys Asp Ile
    1085                1090                1095

Ile Asn  Lys Met Ser Glu Ser  Glu Trp Lys Glu Leu  Gly Glu Glu
    1100                1105                1110

Ile Asn  Thr Leu Lys Gln Asp  Ile Gln Ser Ser Phe  Asp Asn Phe
    1115                1120                1125

Gly Lys  Tyr Lys Leu Lys Leu  Glu Arg Leu Leu Lys  Lys Lys Asn
    1130                1135                1140

Lys Ile  Thr Ser Ser Thr Asn  His Ile Lys Glu Tyr  Ser Ile Leu
    1145                1150                1155

Lys Ala  Gln Leu Leu Arg Lys  Lys Asn Ile Leu Asn  Asn Pro Arg
    1160                1165                1170

His Val  Leu Ala Ala Phe Val  Val Phe Phe Asn Lys  Lys Ile Glu
    1175                1180                1185

Ala Glu  Lys Lys Glu Val Glu  Asn Ala Leu Lys Asn  Thr Asp Ile
    1190                1195                1200

Met Leu  Lys Tyr Tyr Lys Ala  Arg Thr Lys Tyr Tyr  Ile Ser Glu
    1205                1210                1215

Ala Phe  Pro Leu Lys Thr Ile  Thr Glu Gln Ser Leu  Gln Lys Glu
    1220                1225                1230

Ile Asn  Tyr Leu His Leu Glu  Lys Phe Lys Val Tyr  Ser Arg Leu
    1235                1240                1245

Glu Gly  Arg Ile Lys Lys Met  Leu Asn Leu Glu Lys  Glu Asn Ile
    1250                1255                1260

Thr Tyr  Leu Ser Gly Gly Leu  His His Val Leu Thr  Glu Leu Lys
    1265                1270                1275

Glu Ile  Ile Asn Asp Lys Thr  Tyr Thr Gly Tyr Thr  His Thr Lys
    1280                1285                1290

Asn Asn  Glu Glu Val Asn Lys  Ala Leu Asn Val Tyr  Glu Glu Leu
    1295                1300                1305

Leu Pro  Lys Gln Ile Ser Thr  Glu Glu Gln Pro Asp  Asn Ala Leu
    1310                1315                1320

Ala Asp  Gly Thr Glu Asn Ala  Thr Glu Gly Ala Glu  Val Arg Ala
    1325                1330                1335

Ala Thr  Ala Glu Ser Leu Val  Gln Gly Glu Asp Glu  Tyr Pro Glu
    1340                1345                1350

Glu Val  Asp Glu Val Ile Val  Phe Pro Ile Val Gly  Lys Lys Glu
    1355                1360                1365

Lys Glu  Asn Pro Leu Asp Gln  Ile Thr Lys Gly Gln  Ala Glu Thr
    1370                1375                1380

Lys Gln  Asp Asp Asn Ile Leu  Lys Pro Ile Thr Asn  Glu Tyr Glu
    1385                1390                1395

Val Leu  Tyr Ile Lys Pro Leu  Ala Gly Val Tyr Arg  Val Leu Arg
    1400                1405                1410

Lys Gln  Ile Gly Asp Gln Ile  Asp Ala Phe Asn Ser  Asn Leu Thr
    1415                1420                1425

Asn Ala  Leu Asp Thr Arg Lys  Lys Lys Arg Thr Tyr  Phe Leu Asp
    1430                1435                1440

Val Leu  Asn Ser Asp Leu Ile  Gln Phe Lys His Ala  Thr Ser Asp
    1445                1450                1455
```

```
Ser Tyr  Ile Ile Lys Asp Pro  Tyr Lys Leu Leu Asp  Val Asp Lys
    1460                 1465                 1470

Lys Ala  Lys Leu Ile Gly Ser  Tyr Lys Tyr Ile Val  Ser Ala Ile
    1475                 1480                 1485

Glu Lys  Asp Ile Thr Ser Ala  Glu Asn Gly Val Glu  Tyr Tyr Asp
    1490                 1495                 1500

Lys Met  Thr Lys Leu Tyr Lys  Thr Gln Leu Glu Ala  Val Lys Ser
    1505                 1510                 1515

Ala Ile  Ala Glu Ala Gln Lys  Glu Gly Asp Lys Lys  Thr Glu Asn
    1520                 1525                 1530

Glu Lys  Tyr Ile Pro Phe Leu  Thr Asn Met Gln Thr  Leu Tyr Glu
    1535                 1540                 1545

Asn Leu  Leu Asn Lys Ile Asn  Gly Asn Ile Ile Asn  Leu Lys Thr
    1550                 1555                 1560

Leu Ile  Thr Asn Cys Asn Leu  Glu Lys Asp Ala Val  Asn Ile Thr
    1565                 1570                 1575

Ile Ser  Lys Leu Thr Glu Tyr  Ser Lys Phe Asp Glu  Lys Ile Glu
    1580                 1585                 1590

Met Phe  Lys Asn Ser Lys Asn  Glu Lys Asp Ile Ala  Ser Ser Gly
    1595                 1600                 1605

Ile Leu  Asp Ile Leu Lys Gln  Lys Gly Leu Val Asn  Lys Asn Glu
    1610                 1615                 1620

Ser Thr  Lys Ile Ile Ser Glu  Leu Leu Gly Val Asp  Ser Asn Ala
    1625                 1630                 1635

Leu Leu  Asn Ile Ser Ala Lys  His Ala Cys Thr Glu  Thr Lys Tyr
    1640                 1645                 1650

Pro Glu  Asn Ala Gly Cys Tyr  Arg Tyr Glu Asp Gly  Lys Glu Val
    1655                 1660                 1665

Trp Arg  Cys Leu Leu Asn Tyr  Lys Leu Val Asp Gly  Gly Cys Val
    1670                 1675                 1680

Glu Asp  Glu Glu Pro Ser Cys  Gln Val Asn Asn Gly  Gly Cys Ala
    1685                 1690                 1695

Pro Glu  Ala Asn Cys Thr Lys  Gly Asp Asp Asn Lys  Ile Val Cys
    1700                 1705                 1710

Ala Cys  Asn Ala Pro Tyr Ser  Glu Pro Ile Phe Glu  Gly Val Phe
    1715                 1720                 1725

Cys Gly  Ser Ser Ser Phe Leu  Gly Leu Ser Leu Leu  Leu Ala Ala
    1730                 1735                 1740

Leu Leu  Ile Met Phe Asn Leu  Leu
    1745                 1750


<210> SEQ ID NO 2
<211> LENGTH: 5406
<212> TYPE: DNA
<213> ORGANISM: Plasmodium malariae
<220> FEATURE:
<221> NAME/KEY: CDS
<222> LOCATION: (62)..(5314)

<400> SEQUENCE: 2

aaaaaaaaat ttttatttta ccaattataa aatactctat attatcaagt ttaattcaaa      60

a atg aaa gca ctt ata ttt ttg ttc tct ttt gtc ttt ttt tct ata aat     109
  Met Lys Ala Leu Ile Phe Leu Phe Ser Phe Val Phe Phe Ser Ile Asn
  1               5                   10                  15

tgt cac tgt gaa aca aat gaa gat tat gaa caa ctt att caa aag ttg      157
Cys His Cys Glu Thr Asn Glu Asp Tyr Glu Gln Leu Ile Gln Lys Leu
            20                  25                  30
```

-continued

```
gga aaa ctg gag gaa cta gtt gta gaa ggg tat aac cta ttt cac aaa      205
Gly Lys Leu Glu Glu Leu Val Val Glu Gly Tyr Asn Leu Phe His Lys
        35                  40                  45

aaa aaa ttt gcc tta aca gac att aat aag gat ggt aat acc agt act      253
Lys Lys Phe Ala Leu Thr Asp Ile Asn Lys Asp Gly Asn Thr Ser Thr
    50                  55                  60

act gat gca aat aat aaa gat gat agt aag gtt tcc tcc gta aca gca      301
Thr Asp Ala Asn Asn Lys Asp Asp Ser Lys Val Ser Ser Val Thr Ala
65                  70                  75                  80

aaa ata gga aat ttt gtt agc aaa gtt cta aac ctg aat ttg cca ggt      349
Lys Ile Gly Asn Phe Val Ser Lys Val Leu Asn Leu Asn Leu Pro Gly
                85                  90                  95

tat gtt cag tta act ttt tca att agg gaa tta att aca aag tac agt      397
Tyr Val Gln Leu Thr Phe Ser Ile Arg Glu Leu Ile Thr Lys Tyr Ser
            100                 105                 110

ggt ttg aaa tat cta att gaa gga tat gaa gaa ttc aat gaa tta atg      445
Gly Leu Lys Tyr Leu Ile Glu Gly Tyr Glu Glu Phe Asn Glu Leu Met
        115                 120                 125

tat gga att aat ttt tac tat gat tta tta aga gct aag ttg aat gat      493
Tyr Gly Ile Asn Phe Tyr Tyr Asp Leu Leu Arg Ala Lys Leu Asn Asp
    130                 135                 140

atg cat cta aat ggc tac tgt gat ata cct aat cat cta aaa att aat      541
Met His Leu Asn Gly Tyr Cys Asp Ile Pro Asn His Leu Lys Ile Asn
145                 150                 155                 160

gaa aag gaa tta gaa atg ctt aaa aaa gtc gta ttt gga tat aga aaa      589
Glu Lys Glu Leu Glu Met Leu Lys Lys Val Val Phe Gly Tyr Arg Lys
                165                 170                 175

cca tta gaa aat att aaa gac gat att aac aaa atg gag aaa ttt atc      637
Pro Leu Glu Asn Ile Lys Asp Asp Ile Asn Lys Met Glu Lys Phe Ile
            180                 185                 190

aca aca aat gaa gca aca gta aat aat ata aag gaa tta att aag aag      685
Thr Thr Asn Glu Ala Thr Val Asn Asn Ile Lys Glu Leu Ile Lys Lys
        195                 200                 205

gaa tat aat aac atc gct gat gag aat aaa aaa tta gag gct cct agt      733
Glu Tyr Asn Asn Ile Ala Asp Glu Asn Lys Lys Leu Glu Ala Pro Ser
    210                 215                 220

gaa tca ggg tca gat gac gaa gat ata aag aat tgt aat gaa aaa cag      781
Glu Ser Gly Ser Asp Asp Glu Asp Ile Lys Asn Cys Asn Glu Lys Gln
225                 230                 235                 240

aaa ata tac aaa tct cga tat aac att ctt ttt tac gaa aag cag ttg      829
Lys Ile Tyr Lys Ser Arg Tyr Asn Ile Leu Phe Tyr Glu Lys Gln Leu
                245                 250                 255

cta gag gca caa aaa tta ata gaa gtt tta aag aag cgt att caa act      877
Leu Glu Ala Gln Lys Leu Ile Glu Val Leu Lys Lys Arg Ile Gln Thr
            260                 265                 270

tta aaa gaa aat acc gat ata aaa aaa ttg ctc gac gaa ata aag gaa      925
Leu Lys Glu Asn Thr Asp Ile Lys Lys Leu Leu Asp Glu Ile Lys Glu
        275                 280                 285

att gaa ggg aaa ctt cct aca agt ggt agt gaa gca tct gcc tct gca      973
Ile Glu Gly Lys Leu Pro Thr Ser Gly Ser Glu Ala Ser Ala Ser Ala
    290                 295                 300

gca gct cct ggt gct ata aag gaa cca gaa aat act caa ata aaa gaa     1021
Ala Ala Pro Gly Ala Ile Lys Glu Pro Glu Asn Thr Gln Ile Lys Glu
305                 310                 315                 320

cgt caa gaa aag att aaa gaa att gcg aaa aat ata gta ttc aat atg     1069
Arg Gln Glu Lys Ile Lys Glu Ile Ala Lys Asn Ile Val Phe Asn Met
                325                 330                 335

gat ggt cta ttt aca gat gcc ttc gaa ttg gat tac tat gta aga gaa     1117
Asp Gly Leu Phe Thr Asp Ala Phe Glu Leu Asp Tyr Tyr Val Arg Glu
            340                 345                 350
```

-continued

```
aaa gaa aaa aaa tca ttc aac tcg gca act act caa cta gct aac ggt      1165
Lys Glu Lys Lys Ser Phe Asn Ser Ala Thr Thr Gln Leu Ala Asn Gly
        355                 360                 365

aaa gca gta aac aga aca cct cct gca cca gta atg tat cct cat gga      1213
Lys Ala Val Asn Arg Thr Pro Pro Ala Pro Val Met Tyr Pro His Gly
    370                 375                 380

ata att tat gct gta tca gat gat gct ata agt aac ata cta tct aaa      1261
Ile Ile Tyr Ala Val Ser Asp Asp Ala Ile Ser Asn Ile Leu Ser Lys
385                 390                 395                 400

agt agt aca cag tta aca ctt gaa gaa tta caa aat cct gac aat aga      1309
Ser Ser Thr Gln Leu Thr Leu Glu Glu Leu Gln Asn Pro Asp Asn Arg
                405                 410                 415

aaa caa att act att gac gat ctt aaa gac gaa aac aaa aga aaa gaa      1357
Lys Gln Ile Thr Ile Asp Asp Leu Lys Asp Glu Asn Lys Arg Lys Glu
            420                 425                 430

ttg ata act aaa ata aaa aat aaa att aca gaa gaa gaa ggg aaa tta      1405
Leu Ile Thr Lys Ile Lys Asn Lys Ile Thr Glu Glu Glu Gly Lys Leu
        435                 440                 445

aat gca tta aaa gga gat gtt gat agt aaa tta gag aaa ttt aag aaa      1453
Asn Ala Leu Lys Gly Asp Val Asp Ser Lys Leu Glu Lys Phe Lys Lys
    450                 455                 460

ata gaa ggg gaa ttt aaa cca tta ctt gaa aaa ttt tat gat gaa aga      1501
Ile Glu Gly Glu Phe Lys Pro Leu Leu Glu Lys Phe Tyr Asp Glu Arg
465                 470                 475                 480

ctt gat aat agc att aca aca gag aat ttt gaa aaa ttt tta agt aaa      1549
Leu Asp Asn Ser Ile Thr Thr Glu Asn Phe Glu Lys Phe Leu Ser Lys
                485                 490                 495

aga aca gaa tat tta acg gaa aag aat ttg ctt gaa agc tct tct tac      1597
Arg Thr Glu Tyr Leu Thr Glu Lys Asn Leu Leu Glu Ser Ser Ser Tyr
            500                 505                 510

gaa ttg tcg aaa gca ttg gta aag aaa tta aaa aag caa ctt atg tat      1645
Glu Leu Ser Lys Ala Leu Val Lys Lys Leu Lys Lys Gln Leu Met Tyr
        515                 520                 525

tta gaa gac tat tca tta aga aaa gaa gta ttt gat gaa gag gta aat      1693
Leu Glu Asp Tyr Ser Leu Arg Lys Glu Val Phe Asp Glu Glu Val Asn
    530                 535                 540

cat ttc aac tgc tta gac tta caa tta aat gct gat att cat aaa tta      1741
His Phe Asn Cys Leu Asp Leu Gln Leu Asn Ala Asp Ile His Lys Leu
545                 550                 555                 560

gaa agt gaa att aaa aga aaa gaa aat tta ctt aca gta gtt gat acc      1789
Glu Ser Glu Ile Lys Arg Lys Glu Asn Leu Leu Thr Val Val Asp Thr
                565                 570                 575

tta aaa ttt tca gat gtc gtg gaa tta caa gta caa aaa gta tta tta      1837
Leu Lys Phe Ser Asp Val Val Glu Leu Gln Val Gln Lys Val Leu Leu
            580                 585                 590

ggt aaa aaa ata gga caa cta aaa aat gta gaa gca ttt tta caa aaa      1885
Gly Lys Lys Ile Gly Gln Leu Lys Asn Val Glu Ala Phe Leu Gln Lys
        595                 600                 605

gca aaa tta aaa gaa acg ttt cac atc ccc caa gca tac gga aca gga      1933
Ala Lys Leu Lys Glu Thr Phe His Ile Pro Gln Ala Tyr Gly Thr Gly
    610                 615                 620

gaa caa tcc gaa cca tac tat tta att gca cta aag agg gaa att gat      1981
Glu Gln Ser Glu Pro Tyr Tyr Leu Ile Ala Leu Lys Arg Glu Ile Asp
625                 630                 635                 640

aaa tta aat att tct att cca aaa att gag gaa atg tta aaa aat gag      2029
Lys Leu Asn Ile Ser Ile Pro Lys Ile Glu Glu Met Leu Lys Asn Glu
                645                 650                 655

aaa aaa ctg gag gaa gaa aaa atc aag gcg gca gca caa aat gta agc      2077
Lys Lys Leu Glu Glu Glu Lys Ile Lys Ala Ala Ala Gln Asn Val Ser
            660                 665                 670
```

```
ggc cat gtt tcc gga gca gat gaa aca tca aac agt cat gga tca tct      2125
Gly His Val Ser Gly Ala Asp Glu Thr Ser Asn Ser His Gly Ser Ser
        675                 680                 685

gga gga gga gga tca aca caa aca gta acg aca aca cca tca act aca      2173
Gly Gly Gly Gly Ser Thr Gln Thr Val Thr Thr Thr Pro Ser Thr Thr
    690                 695                 700

aca aca gca act aca tca tca caa aca gta tca gta gga gaa aca gga      2221
Thr Thr Ala Thr Thr Ser Ser Gln Thr Val Ser Val Gly Glu Thr Gly
705                 710                 715                 720

tca gca caa gca caa gca caa cca caa cca caa cca caa cca caa cca      2269
Ser Ala Gln Ala Gln Ala Gln Pro Gln Pro Gln Pro Gln Pro Gln Pro
                725                 730                 735

caa aca caa aca caa aca caa aca caa cca caa gca gca gga gca acg      2317
Gln Thr Gln Thr Gln Thr Gln Thr Gln Pro Gln Ala Ala Gly Ala Thr
            740                 745                 750

gga aca cca gga caa tca gga caa tca gga caa tca gga caa tca gga      2365
Gly Thr Pro Gly Gln Ser Gly Gln Ser Gly Gln Ser Gly Gln Ser Gly
        755                 760                 765

gct gaa gga aca aca gaa act acg gga aca aca gga cag gca gga aca      2413
Ala Glu Gly Thr Thr Glu Thr Thr Gly Thr Thr Gly Gln Ala Gly Thr
    770                 775                 780

acg gga aca cca gaa caa gca gca gct gca gga cca caa gca gaa act      2461
Thr Gly Thr Pro Glu Gln Ala Ala Ala Ala Gly Pro Gln Ala Glu Thr
785                 790                 795                 800

acg gca aca cca gga caa gca gga gct gca gga gct gca gga cca caa      2509
Thr Ala Thr Pro Gly Gln Ala Gly Ala Ala Gly Ala Ala Gly Pro Gln
                805                 810                 815

gca gaa act acg gga aca cca gga caa gcg gga gct gca gga cca caa      2557
Ala Glu Thr Thr Gly Thr Pro Gly Gln Ala Gly Ala Ala Gly Pro Gln
            820                 825                 830

aca gag aca gaa gta gaa gaa act cag gaa att gga atc gtt gtt ccg      2605
Thr Glu Thr Glu Val Glu Glu Thr Gln Glu Ile Gly Ile Val Val Pro
        835                 840                 845

aca ttg tcc aaa ttg caa tat ctt gaa aag cta tat gac ttt ttg aaa      2653
Thr Leu Ser Lys Leu Gln Tyr Leu Glu Lys Leu Tyr Asp Phe Leu Lys
    850                 855                 860

act gct tat gtg tgt cat atc aac att ttg gta aat aac tca acc atg      2701
Thr Ala Tyr Val Cys His Ile Asn Ile Leu Val Asn Asn Ser Thr Met
865                 870                 875                 880

aat gaa acg tta cta caa caa tat aaa ctg aag ata gaa gaa gat aag      2749
Asn Glu Thr Leu Leu Gln Gln Tyr Lys Leu Lys Ile Glu Glu Asp Lys
                885                 890                 895

aaa tta tta gag aag tgc gac caa tta gat ttg tta ttt aat gtt cag      2797
Lys Leu Leu Glu Lys Cys Asp Gln Leu Asp Leu Leu Phe Asn Val Gln
            900                 905                 910

aat aac tta caa gtc atg tat tca atg tat gac agt gtg agc aat gtt      2845
Asn Asn Leu Gln Val Met Tyr Ser Met Tyr Asp Ser Val Ser Asn Val
        915                 920                 925

cta caa aat cag tac aaa gaa tta aac caa aag gaa atg att tat aat      2893
Leu Gln Asn Gln Tyr Lys Glu Leu Asn Gln Lys Glu Met Ile Tyr Asn
    930                 935                 940

att tat aaa ctg gtg aag aag aat gac aaa ctt aaa aac ttc tta aac      2941
Ile Tyr Lys Leu Val Lys Lys Asn Asp Lys Leu Lys Asn Phe Leu Asn
945                 950                 955                 960

tta act gca aac agt gca gct gca tct tcg gca tta cca cct cca cca      2989
Leu Thr Ala Asn Ser Ala Ala Ala Ser Ser Ala Leu Pro Pro Pro Pro
                965                 970                 975

tca gta cca cct gca gta cca cca gca tca caa cag cca caa cct caa      3037
Ser Val Pro Pro Ala Val Pro Pro Ala Ser Gln Gln Pro Gln Pro Gln
            980                 985                 990
```

```
gca gca tta cca gca caa cct caa  gca gca gta cca gca  caa tct caa    3085
Ala Ala Leu Pro Ala Gln Pro Gln  Ala Ala Val Pro Ala  Gln Ser Gln
        995                 1000                1005

gca aca  gta cca gca caa tct  caa gca gca gta cca  gca aca act      3130
Ala Thr  Val Pro Ala Gln Ser  Gln Ala Ala Val Pro  Ala Thr Thr
    1010                 1015                 1020

caa tcc  tca tcg gta tca gca  cca aca ggt aca aat  ggt gca tcc      3175
Gln Ser  Ser Ser Val Ser Ala  Pro Thr Gly Thr Asn  Gly Ala Ser
    1025                 1030                 1035

cca gca  act cct gta gct cca  gct ggt agt gaa aat  gcg att cag      3220
Pro Ala  Thr Pro Val Ala Pro  Ala Gly Ser Glu Asn  Ala Ile Gln
    1040                 1045                 1050

tta aaa  gcg aat gac aac gag  gac gat gca aat gaa  cta gat ttc      3265
Leu Lys  Ala Asn Asp Asn Glu  Asp Asp Ala Asn Glu  Leu Asp Phe
    1055                 1060                 1065

gac att  gac gat att tat ata  aaa tac tta gaa caa  gtg agc aaa      3310
Asp Ile  Asp Asp Ile Tyr Ile  Lys Tyr Leu Glu Gln  Val Ser Lys
    1070                 1075                 1080

tac gac  gag aac ttc aaa aat  ttt ata gag tcc aaa  aaa gat ata      3355
Tyr Asp  Glu Asn Phe Lys Asn  Phe Ile Glu Ser Lys  Lys Asp Ile
    1085                 1090                 1095

ata aat  aag atg agc gaa agt  gaa tgg aaa gaa tta  gga gaa gaa      3400
Ile Asn  Lys Met Ser Glu Ser  Glu Trp Lys Glu Leu  Gly Glu Glu
    1100                 1105                 1110

atc aac  aca ttg aaa caa gat  ata caa tca tca ttt  gat aat ttt      3445
Ile Asn  Thr Leu Lys Gln Asp  Ile Gln Ser Ser Phe  Asp Asn Phe
    1115                 1120                 1125

gga aaa  tat aaa ctt aaa ttg  gaa aga tta tta aaa  aag aaa aat      3490
Gly Lys  Tyr Lys Leu Lys Leu  Glu Arg Leu Leu Lys  Lys Lys Asn
    1130                 1135                 1140

aaa att  aca agc agt act aat  cat att aaa gaa tat  agt att tta      3535
Lys Ile  Thr Ser Ser Thr Asn  His Ile Lys Glu Tyr  Ser Ile Leu
    1145                 1150                 1155

aaa gca  caa tta tta agg aaa  aaa aat att cta aat  aac cca aga      3580
Lys Ala  Gln Leu Leu Arg Lys  Lys Asn Ile Leu Asn  Asn Pro Arg
    1160                 1165                 1170

cat gta  cta gca gct ttt gta  gta ttc ttt aat aaa  aag ata gaa      3625
His Val  Leu Ala Ala Phe Val  Val Phe Phe Asn Lys  Lys Ile Glu
    1175                 1180                 1185

gca gaa  aag aaa gaa gtt gaa  aat gct tta aaa aat  act gat att      3670
Ala Glu  Lys Lys Glu Val Glu  Asn Ala Leu Lys Asn  Thr Asp Ile
    1190                 1195                 1200

atg ttg  aaa tat tat aag gca  aga acc aaa tat tat  att agt gaa      3715
Met Leu  Lys Tyr Tyr Lys Ala  Arg Thr Lys Tyr Tyr  Ile Ser Glu
    1205                 1210                 1215

gca ttc  ccc tta aaa aca ata  act gaa caa tca ctt  caa aaa gaa      3760
Ala Phe  Pro Leu Lys Thr Ile  Thr Glu Gln Ser Leu  Gln Lys Glu
    1220                 1225                 1230

att aac  tat tta cat tta gaa  aaa ttt aaa gta tat  agt aga tta      3805
Ile Asn  Tyr Leu His Leu Glu  Lys Phe Lys Val Tyr  Ser Arg Leu
    1235                 1240                 1245

gaa gga  cgc att aag aaa atg  ttg aat tta gaa aaa  gaa aat att      3850
Glu Gly  Arg Ile Lys Lys Met  Leu Asn Leu Glu Lys  Glu Asn Ile
    1250                 1255                 1260

acc tac  tta tct ggt gga tta  cat cat gta ctt aca  gaa tta aaa      3895
Thr Tyr  Leu Ser Gly Gly Leu  His His Val Leu Thr  Glu Leu Lys
    1265                 1270                 1275

gag atc  ata aat gat aaa aca  tac acc ggt tat aca  cat act aaa      3940
Glu Ile  Ile Asn Asp Lys Thr  Tyr Thr Gly Tyr Thr  His Thr Lys
    1280                 1285                 1290
```

```
aat aac  gaa gaa gtt aac aaa  gcg tta aat gtt tat  gag gaa ttg      3985
Asn Asn  Glu Glu Val Asn Lys  Ala Leu Asn Val Tyr  Glu Glu Leu
    1295                 1300                 1305

ctt cca  aag caa ata tcc aca  gaa gag caa ccg gat  aat gca tta      4030
Leu Pro  Lys Gln Ile Ser Thr  Glu Glu Gln Pro Asp  Asn Ala Leu
    1310                 1315                 1320

gca gat  gga acg gaa aat gca  aca gaa ggt gca gaa  gtg cgt gca      4075
Ala Asp  Gly Thr Glu Asn Ala  Thr Glu Gly Ala Glu  Val Arg Ala
    1325                 1330                 1335

gca act  gca gaa agt tta gtg  cag gga gaa gat gag  tac cct gaa      4120
Ala Thr  Ala Glu Ser Leu Val  Gln Gly Glu Asp Glu  Tyr Pro Glu
    1340                 1345                 1350

gaa gtt  gat gag gtg atc gtg  ttt ccc att gtg ggt  aag aaa gaa      4165
Glu Val  Asp Glu Val Ile Val  Phe Pro Ile Val Gly  Lys Lys Glu
    1355                 1360                 1365

aag gaa  aat cca tta gat caa  ata aca aaa gga caa  gct gaa act      4210
Lys Glu  Asn Pro Leu Asp Gln  Ile Thr Lys Gly Gln  Ala Glu Thr
    1370                 1375                 1380

aaa caa  gat gat aat ata ttg  aaa cca att aca aat  gag tat gaa      4255
Lys Gln  Asp Asp Asn Ile Leu  Lys Pro Ile Thr Asn  Glu Tyr Glu
    1385                 1390                 1395

gta tta  tat att aaa cca tta  gct gga gta tat aga  gtt tta aga      4300
Val Leu  Tyr Ile Lys Pro Leu  Ala Gly Val Tyr Arg  Val Leu Arg
    1400                 1405                 1410

aaa caa  ata gga gat cag ata  gac gct ttt aat agt  aat ttg aca      4345
Lys Gln  Ile Gly Asp Gln Ile  Asp Ala Phe Asn Ser  Asn Leu Thr
    1415                 1420                 1425

aat gct  ttg gat act cga aaa  aag aaa aga aca tat  ttc tta gat      4390
Asn Ala  Leu Asp Thr Arg Lys  Lys Lys Arg Thr Tyr  Phe Leu Asp
    1430                 1435                 1440

gta tta  aat tct gat tta att  caa ttt aaa cat gca  act tcc gac      4435
Val Leu  Asn Ser Asp Leu Ile  Gln Phe Lys His Ala  Thr Ser Asp
    1445                 1450                 1455

agt tat  att ata aaa gat ccg  tat aaa cta tta gat  gtt gat aag      4480
Ser Tyr  Ile Ile Lys Asp Pro  Tyr Lys Leu Leu Asp  Val Asp Lys
    1460                 1465                 1470

aaa gcg  aag ctt ata ggt agc  tat aaa tat atc gtc  tct gca ata      4525
Lys Ala  Lys Leu Ile Gly Ser  Tyr Lys Tyr Ile Val  Ser Ala Ile
    1475                 1480                 1485

gaa aag  gat atc act tca gct  gag aac gga gta gaa  tat tat gat      4570
Glu Lys  Asp Ile Thr Ser Ala  Glu Asn Gly Val Glu  Tyr Tyr Asp
    1490                 1495                 1500

aag atg  acc aag ttg tac aag  act cag tta gaa gca  gta aaa agc      4615
Lys Met  Thr Lys Leu Tyr Lys  Thr Gln Leu Glu Ala  Val Lys Ser
    1505                 1510                 1515

gca att  gct gaa gca caa aaa  gag ggt gat aaa aaa  act gaa aat      4660
Ala Ile  Ala Glu Ala Gln Lys  Glu Gly Asp Lys Lys  Thr Glu Asn
    1520                 1525                 1530

gaa aaa  tat att cca ttc tta  acg aac atg cag aca  tta tat gaa      4705
Glu Lys  Tyr Ile Pro Phe Leu  Thr Asn Met Gln Thr  Leu Tyr Glu
    1535                 1540                 1545

aat tta  ttg aat aaa ata aat  gga aac ata ata aat  tta aaa act      4750
Asn Leu  Leu Asn Lys Ile Asn  Gly Asn Ile Ile Asn  Leu Lys Thr
    1550                 1555                 1560

tta att  aca aac tgt aat tta  gaa aaa gat gca gta  aac att act      4795
Leu Ile  Thr Asn Cys Asn Leu  Glu Lys Asp Ala Val  Asn Ile Thr
    1565                 1570                 1575

ata agt  aaa tta aca gaa tac  agc aaa ttt gat gaa  aaa ata gaa      4840
Ile Ser  Lys Leu Thr Glu Tyr  Ser Lys Phe Asp Glu  Lys Ile Glu
    1580                 1585                 1590
```

```
atg ttt  aaa aac tct aaa aat  gaa aag gat ata gca  agt tct gga      4885
Met Phe  Lys Asn Ser Lys Asn  Glu Lys Asp Ile Ala  Ser Ser Gly
    1595                 1600                 1605

ata tta  gac ata ctt aaa caa  aaa gga ctt gtt aat  aaa aat gaa      4930
Ile Leu  Asp Ile Leu Lys Gln  Lys Gly Leu Val Asn  Lys Asn Glu
    1610                 1615                 1620

tca act  aag att ata tca gaa  tta ctt ggt gta gac  tct aat gca      4975
Ser Thr  Lys Ile Ile Ser Glu  Leu Leu Gly Val Asp  Ser Asn Ala
    1625                 1630                 1635

tta ctg  aat att agc gca aaa  cat gca tgt acc gaa  aca aaa tat      5020
Leu Leu  Asn Ile Ser Ala Lys  His Ala Cys Thr Glu  Thr Lys Tyr
    1640                 1645                 1650

cct gaa  aat gca gga tgt tat  aga tat gaa gac gga  aaa gaa gta      5065
Pro Glu  Asn Ala Gly Cys Tyr  Arg Tyr Glu Asp Gly  Lys Glu Val
    1655                 1660                 1665

tgg aga  tgc tta tta aat tat  aaa cta gtt gat gga  gga tgt gtt      5110
Trp Arg  Cys Leu Leu Asn Tyr  Lys Leu Val Asp Gly  Gly Cys Val
    1670                 1675                 1680

gaa gat  gaa gag cct tct tgt  caa gtt aac aat gga  gga tgt gct      5155
Glu Asp  Glu Glu Pro Ser Cys  Gln Val Asn Asn Gly  Gly Cys Ala
    1685                 1690                 1695

cct gaa  gct aac tgt acc aaa  gga gat gac aac aaa  att gtc tgt      5200
Pro Glu  Ala Asn Cys Thr Lys  Gly Asp Asp Asn Lys  Ile Val Cys
    1700                 1705                 1710

gct tgt  aac gca ccc tat tct  gaa cct ata ttt gaa  ggt gtt ttc      5245
Ala Cys  Asn Ala Pro Tyr Ser  Glu Pro Ile Phe Glu  Gly Val Phe
    1715                 1720                 1725

tgt ggt  tct tca agt ttc ctc  ggc tta tca cta tta  tta gca gct      5290
Cys Gly  Ser Ser Ser Phe Leu  Gly Leu Ser Leu Leu  Leu Ala Ala
    1730                 1735                 1740

tta tta  att atg ttt aac tta  ctt taagaaaaaa agacagaaaa            5334
Leu Leu  Ile Met Phe Asn Leu  Leu
    1745                 1750

gaaggatacg aatgaacata aaatgagaag gattaagact gagcaagagg aaaagagaga   5394

aaatcataga tc                                                       5406


<210> SEQ ID NO 3
<211> LENGTH: 1730
<212> TYPE: PRT
<213> ORGANISM: Plasmodium ovale

<400> SEQUENCE: 3

Met Lys Val Phe Val Phe Ala Leu Ser Phe Ile Phe Phe Ile Val Asn
1               5                   10                  15

Cys Gln Cys Glu Thr Leu Glu Asn Tyr Lys Glu Leu Leu His Lys Leu
            20                  25                  30

Asn Asn Leu Glu Ala Leu Val Val Asp Gly Tyr Asn Leu Phe His Lys
        35                  40                  45

Thr Pro Leu Thr Leu Gln Lys Leu Glu Thr Glu Val Thr Thr Thr Gly
    50                  55                  60

Arg Gly Ser Gly Ser Ser Thr Thr Ser Val Ser Ser Ile Pro Ser Asp
65                  70                  75                  80

Ala Ser Arg Ala Val Ser Thr Arg Asp Ser Asn Ser Asn Ile Asn Asn
                85                  90                  95

Gln Val Val Ser Lys Leu Thr Ala Asp Ile Arg Phe Leu Leu Ser Arg
            100                 105                 110

Phe Leu Gln Leu Asn Ile Pro Gly His Gly Asp Leu Met His Phe Ile
        115                 120                 125
```

-continued

```
Arg Glu Ile Ser Leu Asp Thr Asn Gly Leu Lys Tyr Leu Ile Glu Gly
    130                 135                 140

Tyr Glu Glu Phe Asn Glu Leu Met Tyr Ile Leu Asn Phe Tyr Tyr Asp
145                 150                 155                 160

Leu Phe Arg Ala Lys Leu His Asp Met Cys Ala Asn Asp Tyr Cys Glu
                165                 170                 175

Ile Pro Asp His Leu Lys Ile Ser Asp Lys Glu Leu Asp Met Leu Lys
            180                 185                 190

Lys Val Val Leu Gly Tyr Arg Lys Pro Leu Glu Asn Ile Lys Asp Asp
        195                 200                 205

Ile Ser Lys Met Glu Thr Phe Ile Gln Lys Asn Thr Gln Thr Val Glu
    210                 215                 220

Asn Ile Lys Gly Leu Ile Glu Ala Glu Glu Lys Lys Arg Tyr Gly Glu
225                 230                 235                 240

Val Ala Val Ser Gly Asn Thr Gly Ser Ala Gly Ala Ala Ser Gly Thr
                245                 250                 255

Asn Ala Ser Ala Ser Ser Gly Gln Glu Asn Ser Ser Thr Glu Ser Glu
            260                 265                 270

Thr Glu Lys Tyr Asn Lys Ala Lys Ala Leu Tyr Gln Ser Ile Tyr Asn
        275                 280                 285

Ala Leu Phe Tyr Lys Lys Gln Leu Thr Glu Ala Glu Lys Leu Ile Glu
    290                 295                 300

Val Leu Lys Lys Arg Val Gln Thr Leu Lys Glu His Lys Glu Ile Lys
305                 310                 315                 320

Lys Leu Leu Glu Glu Ile Ala Glu Lys Glu Ser Lys Val Thr Pro Pro
                325                 330                 335

Ser Asn Thr Ala Ser Gln Thr Gln Leu Gln Glu Glu Ile Asn Lys Leu
            340                 345                 350

Lys Thr Gln Ile Lys Asn Ile Ala Lys Thr Val Lys Phe Glu Met Glu
        355                 360                 365

Gly Leu Phe Thr Asp Pro Val Glu Leu Asp Tyr Tyr Leu Arg Glu Lys
    370                 375                 380

Asp Lys Lys Ala Ser Lys Val Val Glu Thr Gln Ser Gly Ser Thr Thr
385                 390                 395                 400

Pro Pro Lys Pro Thr Tyr Pro Asn Gly Leu Ile Tyr Pro Leu Glu Lys
                405                 410                 415

Glu Asn Ile Ser Glu Leu Leu Ser Lys Ala Val Thr Glu Thr Thr Phe
            420                 425                 430

Gly Asp Leu Gln Asn Val Glu Ile Gly Lys Ala Leu Asn Lys Glu Ile
        435                 440                 445

Phe Thr Asn Asp Asp Lys Arg Asn Glu Phe Ile Asp Lys Leu Lys Asn
    450                 455                 460

Lys Ile Lys Gln Gln Glu Glu Leu Leu Ser Lys Gln Lys Val Asp Tyr
465                 470                 475                 480

Asp Ala Lys Leu Lys Leu Tyr Glu Glu Gln Lys Lys Lys Ala Ile Pro
                485                 490                 495

Leu Phe Glu Gln Phe His Asn Gly Lys Leu Asp Asn Thr Leu Ile Pro
            500                 505                 510

Ser Lys Phe Glu Glu Phe Lys Val Glu Arg Asp Lys Tyr Met Gln Leu
        515                 520                 525

Lys Asn Glu Leu Lys Asn Cys Pro Tyr Glu Met Thr Lys Asn Thr Val
    530                 535                 540

Asp Lys Leu Asn Lys Gln Leu Ala Tyr Leu Asn Asp Tyr Ser Leu Arg
```

-continued

```
545                 550                 555                 560

Lys Glu Val Phe Asn Lys Glu Val Lys His Phe Thr Gly Leu Glu Trp
                565                 570                 575

Lys Leu Gln Thr Glu Ile Asp Lys Leu Ala Asn Glu Ile Lys Lys Asn
            580                 585                 590

Glu Asn Ile Leu Ile Thr Ala Ser Thr Leu Pro Leu Ser Asn Val Val
        595                 600                 605

Glu Leu Gln Val Gln Lys Val Leu Val Ala Lys Lys Ile Glu Leu Leu
    610                 615                 620

Lys Lys Val Glu Lys Leu Leu His Lys Ala Gln Leu Lys Asp His Leu
625                 630                 635                 640

Tyr Val Pro Gln Val Tyr Gly Thr Gln Ala Lys Pro Glu Ala Tyr Tyr
                645                 650                 655

Leu Phe Val Leu Lys Lys Glu Ile Asp Lys Leu Gly Glu Phe Met Pro
            660                 665                 670

Lys Ile Lys Glu Met Leu Asp Lys Glu Lys Ala Asn Pro Thr Pro Ala
        675                 680                 685

Thr Ala Gln Gly Ala Leu Pro Val Arg Gly Val Asp Glu Ile Leu Val
    690                 695                 700

Met Gly Asn Gln Asn Glu Ala Thr Ala Val Thr Ser Pro Ser Thr Ser
705                 710                 715                 720

Thr Glu Ser Ser Glu Gly Ala Thr Gln Pro Ala Ala Thr Val Gln Pro
                725                 730                 735

Ala Ala Pro Gly Val Gln Thr Gly Ile Pro Val Ala Gln Pro Gly Ala
            740                 745                 750

Ser Ala Pro Gly Val Pro Glu Ala Pro Ala Pro Glu Ala Thr Ala Pro
        755                 760                 765

Glu Val Pro Ala Ile Glu Ala Gln Ala Pro Val Gln Pro Thr Gln Gly
    770                 775                 780

Gln Val Gln Ala Ala Thr Gln Asn Gly Pro Thr Met Thr Lys Leu Gln
785                 790                 795                 800

Tyr Leu Glu Lys Leu Tyr Tyr Phe Leu Tyr Thr Ser Tyr Val Cys His
                805                 810                 815

Lys Tyr Ile Leu Val Thr Asn Ser Thr Met Asn Lys Asp Leu Leu Ala
            820                 825                 830

Lys Tyr Asn Leu Thr Pro Glu Glu Glu Glu Lys Lys Lys Thr Ile Lys
        835                 840                 845

Cys Asp Gln Leu Asp Leu Leu Phe Asn Leu Gln Asn Asn Leu Pro Val
    850                 855                 860

Met Tyr Ser Leu Phe Asp Asn Met Ser Ser Thr Leu Gln Ser Asn Tyr
865                 870                 875                 880

Ile Gln Leu Tyr Glu Lys Glu Met Leu Tyr Asn Ile Tyr Lys Met Lys
                885                 890                 895

Asn Ser Asp Lys Ala Ile Lys Glu Phe Leu Glu Thr Gln Gly Ile Thr
            900                 905                 910

Gly Thr Ala Pro Asp Ala Thr Pro Leu Val Asn Thr Gln Ala Thr Thr
        915                 920                 925

Gln Ala Ala Thr Gln Val Thr Thr Gln Ala Ala Thr Gln Thr Ala Thr
    930                 935                 940

Gln Thr Ala Thr His Ala Ser Thr His Ala Ser Thr Gln Ala Ala Thr
945                 950                 955                 960

Gln Gly Asn Val Pro Gln Ala Ser Asn Asp Glu His Thr Pro Ser Ala
                965                 970                 975
```

-continued

```
Thr Thr Val Asn Pro Ala Thr Thr Thr Pro Asp Lys Ser Leu Lys Glu
            980                 985                 990

Ser Thr Ser Glu Gly Thr Leu Met  Thr Gln Gly Asn Ala  Asp Asp Asp
        995                 1000                 1005

Val Ser  Glu Pro Glu Lys Lys  Glu Ile Glu Val Glu  Glu Phe Tyr
    1010                 1015                 1020

Lys Lys  Tyr Leu Glu Glu Val  Asp Lys Tyr Asp Asp  Tyr Phe Lys
    1025                 1030                 1035

Ala Phe  Leu Ser Ser Lys Lys  Asp Ala Val Asn Lys  Met Thr Glu
    1040                 1045                 1050

Lys Asp  Trp Lys Glu Leu Glu  Glu Glu Val Lys Thr  Leu Lys Ser
    1055                 1060                 1065

Arg Leu  Asp Met Ser Leu Asp  His Tyr Asn Lys Tyr  Lys Leu Lys
    1070                 1075                 1080

Leu Gly  Arg Leu Phe Lys Lys  Asn Glu Lys Val Leu  Ser Ser Lys
    1085                 1090                 1095

Glu His  Ile Lys Glu Leu Ser  Ile Leu Lys Ala Gln  Leu Met Arg
    1100                 1105                 1110

Arg Gln  Phe Met Leu Asn Asn  Pro Arg His Val Ile  His Asn Phe
    1115                 1120                 1125

Arg Val  Phe Phe Asn Lys Lys  Arg Glu Thr Glu Lys  Lys Glu Val
    1130                 1135                 1140

Glu Asn  Thr Leu Lys Asn Thr  Asp Ala Leu Leu Lys  Tyr Tyr Lys
    1145                 1150                 1155

Ala Arg  Val Lys Tyr Tyr Asn  Gly Glu Thr Phe Pro  Leu Lys Thr
    1160                 1165                 1170

Ile Ser  Glu Asp Thr Leu Glu  Lys Glu Asn Asn Tyr  Leu Asn Leu
    1175                 1180                 1185

Glu Lys  Phe Lys Leu Tyr Ser  Arg Leu Glu Gly Lys  Leu Lys Gln
    1190                 1195                 1200

Asn Ile  Asn Leu Glu Lys Glu  Asn Ile Thr Tyr Leu  Ser Ser Ala
    1205                 1210                 1215

Leu Tyr  His Val Leu Ser Glu  Leu Lys Gly Ile Ile  His Asn Lys
    1220                 1225                 1230

Lys Tyr  Thr Gly Asn Pro His  Ala Ala Asn Met Val  Glu Val Asn
    1235                 1240                 1245

Asn Ala  Leu Asn Leu Tyr Lys  Asp Leu Leu Pro Lys  Val Glu Thr
    1250                 1255                 1260

Val Ala  Ser Thr Gly Ala Ala  Thr Gln Thr Gln Gly  Gly Glu Gly
    1265                 1270                 1275

Ala Ser  Ala Ala Ala Ala Pro  Pro Ala Ala Leu Pro  Ala Ala Pro
    1280                 1285                 1290

Pro Ala  Ala Pro Pro Ala Ala  Pro Pro Ala Ala Ser  Ala Ala Ala
    1295                 1300                 1305

Pro Gly  Thr Ala Asn Gly Glu  Thr Ala Thr Val Ala  His Ala Glu
    1310                 1315                 1320

Asp Tyr  Thr Glu Asp Asp Asn  Asn Val Ile Val Leu  Pro Leu Phe
    1325                 1330                 1335

Gly Lys  Lys Gly Thr His Ala  Phe Asp Gln Val Thr  Gln Gly Glu
    1340                 1345                 1350

Ala Gln  Asp Lys Asp Asp Asn  Ile Leu Asn Glu Ile  Thr Asn Glu
    1355                 1360                 1365

Tyr Glu  Val Val Tyr Val Lys  Pro Leu Ala Gly Val  Tyr Lys Thr
    1370                 1375                 1380
```

```
Leu Lys  Lys Gln Leu Glu Ala  His Val Thr Ala Phe  His Ser Asn
    1385                 1390                 1395

Val Thr  Asn Met Leu Glu Ser  Arg Leu Lys Lys Arg  Asn Tyr Phe
    1400                 1405                 1410

Leu Glu  Val Leu Asn Ser Asp  Leu Thr Gln Tyr Lys  His Ala Thr
    1415                 1420                 1425

Ser Asp  Asn Tyr Val Ile Arg  Asp Ala Tyr Lys Leu  Leu Asp Phe
    1430                 1435                 1440

Glu Lys  Lys Lys Lys Leu Leu  Ser Ser Tyr Lys Tyr  Ile Lys Asp
    1445                 1450                 1455

Ser Val  Glu Lys Asp Val Glu  Ile Ala Thr Asp Gly  Ile Asp Tyr
    1460                 1465                 1470

Tyr Glu  Lys Met Ala Ala Leu  Tyr Lys Thr Tyr Leu  Glu Ser Val
    1475                 1480                 1485

Asn Ala  Gln Val Asp Ala Ile  Asp Lys Thr Gly Asp  Asp Ala Thr
    1490                 1495                 1500

Lys Ala  Thr Asn Lys Lys Phe  Leu Pro Phe Leu Ala  Ser Ile Asn
    1505                 1510                 1515

Ala Met  Tyr Glu Thr Leu Leu  Glu Lys Val Asn Thr  Tyr Asn Ser
    1520                 1525                 1530

Gln Leu  Lys Ser Ser Leu Asn  Ser Cys Gln Leu Glu  Lys Ile Arg
    1535                 1540                 1545

Val Gly  Ile Val Val Asp Lys  Leu Asn Asp Tyr Val  Met Phe Asp
    1550                 1555                 1560

Glu Lys  Leu Glu Glu Leu Lys  Ser Ser Lys Glu Lys  Asp Leu Thr
    1565                 1570                 1575

Lys Leu  Tyr Lys Asp Ile Asp  Thr Ser Asn Ile Ile  Asn Lys Leu
    1580                 1585                 1590

Lys Arg  Ser Gly Phe Val Asp  Thr Asp Glu Ser Lys  Lys Leu Leu
    1595                 1600                 1605

Ser Glu  Leu Leu Asp Val Asp  Ser Ala Gln Leu Leu  Ser Met Gly
    1610                 1615                 1620

Ser Lys  His Lys Cys Ile Asp  Ile Thr Tyr Pro Asp  Asn Ala Gly
    1625                 1630                 1635

Cys Tyr  Arg Phe Ser Asp Gly  Arg Glu Glu Trp Arg  Cys Leu Leu
    1640                 1645                 1650

Asn Phe  Lys Lys Val Gly Glu  Thr Cys Val Pro Asn  Asn Asn Pro
    1655                 1660                 1665

Thr Cys  Ala Glu Asn Asn Gly  Gly Cys Asp Pro Thr  Ala Asp Cys
    1670                 1675                 1680

Ala Glu  Ser Glu Asn Asn Lys  Ile Thr Cys Thr Cys  Thr Gly Gln
    1685                 1690                 1695

Asn Glu  Ser Phe Phe Glu Gly  Val Phe Cys Gly Ser  Ser Ser Phe
    1700                 1705                 1710

Leu Ser  Leu Ser Phe Leu Leu  Ala Val Leu Leu Ile  Leu Phe Asn
    1715                 1720                 1725

Leu Leu
    1730
```

<210> SEQ ID NO 4
<211> LENGTH: 5256
<212> TYPE: DNA
<213> ORGANISM: Plasmodium ovale
<220> FEATURE:
<221> NAME/KEY: CDS

<222> LOCATION: (10)..(5199)

<400> SEQUENCE: 4 aattcaaaa atg aag gtg ttc gta ttt gcg ctc tct ttc att ttt ttt att 51
Met Lys Val Phe Val Phe Ala Leu Ser Phe Ile Phe Phe Ile
1 5 10 gtg aac tgt caa tgt gaa acg ctc gaa aat tat aaa gag ctt ctt cat 99
Val Asn Cys Gln Cys Glu Thr Leu Glu Asn Tyr Lys Glu Leu Leu His
15 20 25 30 aag tta aat aat ttg gaa gct cta gtg gtt gat ggc tac aac tta ttt 147
Lys Leu Asn Asn Leu Glu Ala Leu Val Val Asp Gly Tyr Asn Leu Phe
35 40 45 cac aaa act ccc tta acc cta caa aag tta gaa act gaa gtc aca act 195
His Lys Thr Pro Leu Thr Leu Gln Lys Leu Glu Thr Glu Val Thr Thr
50 55 60 act gga aga ggt agt ggt agc agt act act tct gtt tcc tcc att cca 243
Thr Gly Arg Gly Ser Gly Ser Ser Thr Thr Ser Val Ser Ser Ile Pro
65 70 75 agt gat gca agt aga gct gta tct acc cgt gat tct aat agc aac atc 291
Ser Asp Ala Ser Arg Ala Val Ser Thr Arg Asp Ser Asn Ser Asn Ile
80 85 90 aac aac caa gtg gtt agc aag tta aca gcg gac ata aga ttc ctt cta 339
Asn Asn Gln Val Val Ser Lys Leu Thr Ala Asp Ile Arg Phe Leu Leu
95 100 105 110 tca aga ttt ttg cag tta aat att cca gga cat gga gat tta atg cat 387
Ser Arg Phe Leu Gln Leu Asn Ile Pro Gly His Gly Asp Leu Met His
115 120 125 ttc ata aga gaa att tcg tta gat aca aac gga cta aaa tat cta ata 435
Phe Ile Arg Glu Ile Ser Leu Asp Thr Asn Gly Leu Lys Tyr Leu Ile
130 135 140 gaa gga tat gaa gaa ttt aac gag tta atg tac ata ttg aac ttt tat 483
Glu Gly Tyr Glu Glu Phe Asn Glu Leu Met Tyr Ile Leu Asn Phe Tyr
145 150 155 tat gat ctg ttc aga gct aaa cta cat gat atg tgt gca aat gat tat 531
Tyr Asp Leu Phe Arg Ala Lys Leu His Asp Met Cys Ala Asn Asp Tyr
160 165 170 tgt gaa ata cca gac cat ctt aaa att agt gat aag gaa ttg gac atg 579
Cys Glu Ile Pro Asp His Leu Lys Ile Ser Asp Lys Glu Leu Asp Met
175 180 185 190 ctc aaa aaa gtt gta tta gga tac aga aaa ccg tta gaa aat ata aaa 627
Leu Lys Lys Val Val Leu Gly Tyr Arg Lys Pro Leu Glu Asn Ile Lys
195 200 205 gac gat att tca aaa atg gag aca ttc att caa aaa aat act caa aca 675
Asp Asp Ile Ser Lys Met Glu Thr Phe Ile Gln Lys Asn Thr Gln Thr
210 215 220 gtg gaa aat ata aag ggc tta ata gag gca gaa gaa aaa aaa agg tat 723
Val Glu Asn Ile Lys Gly Leu Ile Glu Ala Glu Glu Lys Lys Arg Tyr
225 230 235 ggt gag gtt gca gta agt gga aat aca gga agt gca gga gct gcc tca 771
Gly Glu Val Ala Val Ser Gly Asn Thr Gly Ser Ala Gly Ala Ala Ser
240 245 250 gga act aat gca tct gca agt tca ggc caa gaa aat tct tct act gaa 819
Gly Thr Asn Ala Ser Ala Ser Ser Gly Gln Glu Asn Ser Ser Thr Glu
255 260 265 270 agc gaa aca gaa aag tat aac aaa gct aaa gct tta tat caa tcc ata 867
Ser Glu Thr Glu Lys Tyr Asn Lys Ala Lys Ala Leu Tyr Gln Ser Ile
275 280 285 tat aac gcc tta ttt tac aaa aag cag tta aca gaa gca gaa aaa tta 915
Tyr Asn Ala Leu Phe Tyr Lys Lys Gln Leu Thr Glu Ala Glu Lys Leu
290 295 300

-continued

```
atc gaa gtt tta aaa aag cgt gtg caa acg tta aaa gag cac aaa gag      963
Ile Glu Val Leu Lys Lys Arg Val Gln Thr Leu Lys Glu His Lys Glu
        305                 310                 315

ata aaa aaa tta ctc gaa gaa atc gcg gaa aag gaa agc aaa gtt acc     1011
Ile Lys Lys Leu Leu Glu Glu Ile Ala Glu Lys Glu Ser Lys Val Thr
    320                 325                 330

cca ccg agt aat acc gct tca caa acg caa ctg cag gaa gaa att aac     1059
Pro Pro Ser Asn Thr Ala Ser Gln Thr Gln Leu Gln Glu Glu Ile Asn
335                 340                 345                 350

aaa ctt aaa act caa att aag aac atc gca aaa act gta aaa ttc gaa     1107
Lys Leu Lys Thr Gln Ile Lys Asn Ile Ala Lys Thr Val Lys Phe Glu
            355                 360                 365

atg gaa ggt ctg ttt act gat cct gtt gaa ttg gat tac tac tta cga     1155
Met Glu Gly Leu Phe Thr Asp Pro Val Glu Leu Asp Tyr Tyr Leu Arg
            370                 375                 380

gaa aag gac aaa aag gca agt aaa gta gta gaa aca caa agt ggt tca     1203
Glu Lys Asp Lys Lys Ala Ser Lys Val Val Glu Thr Gln Ser Gly Ser
        385                 390                 395

aca act ccg cct aag cct acg tat ccc aat ggt ctc atc tac cct ttg     1251
Thr Thr Pro Pro Lys Pro Thr Tyr Pro Asn Gly Leu Ile Tyr Pro Leu
    400                 405                 410

gaa aaa gaa aac atc tct gag ttg tta tca aaa gcc gtg aca gaa aca     1299
Glu Lys Glu Asn Ile Ser Glu Leu Leu Ser Lys Ala Val Thr Glu Thr
415                 420                 425                 430

act ttt ggt gat tta caa aat gta gaa att gga aaa gca tta aat aaa     1347
Thr Phe Gly Asp Leu Gln Asn Val Glu Ile Gly Lys Ala Leu Asn Lys
            435                 440                 445

gaa att ttc acg aat gat gat aag aga aat gaa ttc ata gac aaa ctt     1395
Glu Ile Phe Thr Asn Asp Asp Lys Arg Asn Glu Phe Ile Asp Lys Leu
            450                 455                 460

aaa aat aaa att aaa caa caa gaa gaa ctt tta tct aaa caa aaa gtg     1443
Lys Asn Lys Ile Lys Gln Gln Glu Glu Leu Leu Ser Lys Gln Lys Val
        465                 470                 475

gac tat gat gca aaa ctt aaa ttg tac gag gag caa aag aag aaa gct     1491
Asp Tyr Asp Ala Lys Leu Lys Leu Tyr Glu Glu Gln Lys Lys Lys Ala
    480                 485                 490

att ccc cta ttt gag cag ttt cac aat gga aaa ctt gac aac aca ctt     1539
Ile Pro Leu Phe Glu Gln Phe His Asn Gly Lys Leu Asp Asn Thr Leu
495                 500                 505                 510

att cct agt aaa ttc gaa gaa ttt aaa gta gaa aga gac aag tat atg     1587
Ile Pro Ser Lys Phe Glu Glu Phe Lys Val Glu Arg Asp Lys Tyr Met
            515                 520                 525

caa ctc aag aac gag tta aaa aat tgt cca tac gaa atg aca aaa aac     1635
Gln Leu Lys Asn Glu Leu Lys Asn Cys Pro Tyr Glu Met Thr Lys Asn
            530                 535                 540

acg gtg gat aag tta aat aaa caa ctt gca tat ttg aat gac tac tca     1683
Thr Val Asp Lys Leu Asn Lys Gln Leu Ala Tyr Leu Asn Asp Tyr Ser
        545                 550                 555

ttg aga aaa gaa gtt ttt aat aaa gaa gtt aaa cat ttt aca gga tta     1731
Leu Arg Lys Glu Val Phe Asn Lys Glu Val Lys His Phe Thr Gly Leu
    560                 565                 570

gag tgg aaa cta caa act gaa att gac aaa tta gca aac gaa ata aag     1779
Glu Trp Lys Leu Gln Thr Glu Ile Asp Lys Leu Ala Asn Glu Ile Lys
575                 580                 585                 590

aaa aat gaa aat ata ctt ata aca gca tct acc tta cca tta tct aat     1827
Lys Asn Glu Asn Ile Leu Ile Thr Ala Ser Thr Leu Pro Leu Ser Asn
            595                 600                 605

gta gta gaa tta caa gta caa aaa gta tta gta gca aaa aaa att gaa     1875
Val Val Glu Leu Gln Val Gln Lys Val Leu Val Ala Lys Lys Ile Glu
            610                 615                 620
```

-continued

```
ctt tta aaa aaa gta gaa aaa ctt tta cac aaa gca cag ttg aaa gat      1923
Leu Leu Lys Lys Val Glu Lys Leu Leu His Lys Ala Gln Leu Lys Asp
        625                 630                 635

cac ctt tac gtc cct cag gtt tat ggt aca caa gcg aaa cct gaa gca      1971
His Leu Tyr Val Pro Gln Val Tyr Gly Thr Gln Ala Lys Pro Glu Ala
    640                 645                 650

tac tat tta ttt gtc ctg aaa aag gaa att gac aaa ctg ggg gaa ttt      2019
Tyr Tyr Leu Phe Val Leu Lys Lys Glu Ile Asp Lys Leu Gly Glu Phe
655                 660                 665                 670

atg cct aaa ata aag gag atg tta gat aag gag aag gca aac ccc act      2067
Met Pro Lys Ile Lys Glu Met Leu Asp Lys Glu Lys Ala Asn Pro Thr
                675                 680                 685

cca gcg aca gca cag gga gcc ctt cca gtt cga ggg gtt gat gaa ata      2115
Pro Ala Thr Ala Gln Gly Ala Leu Pro Val Arg Gly Val Asp Glu Ile
            690                 695                 700

cta gtc atg gga aat caa aac gaa gct aca gca gta aca tca cca tca      2163
Leu Val Met Gly Asn Gln Asn Glu Ala Thr Ala Val Thr Ser Pro Ser
        705                 710                 715

aca tca aca gaa tca tcc gag gga gca aca caa cca gca gca aca gta      2211
Thr Ser Thr Glu Ser Ser Glu Gly Ala Thr Gln Pro Ala Ala Thr Val
    720                 725                 730

cag cca gca gcg cca gga gta caa acg gga ata cca gta gca cag cca      2259
Gln Pro Ala Ala Pro Gly Val Gln Thr Gly Ile Pro Val Ala Gln Pro
735                 740                 745                 750

gga gca tca gca cca gga gta cca gaa gca cca gca cca gaa gca aca      2307
Gly Ala Ser Ala Pro Gly Val Pro Glu Ala Pro Ala Pro Glu Ala Thr
                755                 760                 765

gca cca gaa gta cca gca ata gaa gca caa gca cct gtg caa cct acg      2355
Ala Pro Glu Val Pro Ala Ile Glu Ala Gln Ala Pro Val Gln Pro Thr
            770                 775                 780

caa gga cag gtc caa gca gcc acc caa aat ggc cca aca atg aca aaa      2403
Gln Gly Gln Val Gln Ala Ala Thr Gln Asn Gly Pro Thr Met Thr Lys
        785                 790                 795

tta caa tat ctc gag aag tta tat tac ttt ttg tat acc tcc tat gta      2451
Leu Gln Tyr Leu Glu Lys Leu Tyr Tyr Phe Leu Tyr Thr Ser Tyr Val
    800                 805                 810

tgt cat aag tac att tta gtg aca aac tct aca atg aac aaa gat ttg      2499
Cys His Lys Tyr Ile Leu Val Thr Asn Ser Thr Met Asn Lys Asp Leu
815                 820                 825                 830

ttg gca aaa tat aat ctt aca cca gaa gaa gaa gaa aaa aaa aag aca      2547
Leu Ala Lys Tyr Asn Leu Thr Pro Glu Glu Glu Glu Lys Lys Lys Thr
                835                 840                 845

ata aaa tgt gat cag tta gat tta ttg ttt aac tta caa aac aat tta      2595
Ile Lys Cys Asp Gln Leu Asp Leu Leu Phe Asn Leu Gln Asn Asn Leu
            850                 855                 860

cca gtc atg tat tct ctc ttt gat aat atg agc tcg act ttg caa agc      2643
Pro Val Met Tyr Ser Leu Phe Asp Asn Met Ser Ser Thr Leu Gln Ser
        865                 870                 875

aat tac att caa tta tat gaa aag gaa atg ctg tac aat ata tac aag      2691
Asn Tyr Ile Gln Leu Tyr Glu Lys Glu Met Leu Tyr Asn Ile Tyr Lys
    880                 885                 890

atg aaa aac agt gat aag gcg atc aaa gaa ttt cta gag aca caa ggt      2739
Met Lys Asn Ser Asp Lys Ala Ile Lys Glu Phe Leu Glu Thr Gln Gly
895                 900                 905                 910

ata aca ggt aca gca cca gat gct act cct cta gtc aat aca caa gcc      2787
Ile Thr Gly Thr Ala Pro Asp Ala Thr Pro Leu Val Asn Thr Gln Ala
                915                 920                 925

act acg caa gcc gct aca caa gtc act acg caa gcc gct aca caa acc      2835
Thr Thr Gln Ala Ala Thr Gln Val Thr Thr Gln Ala Ala Thr Gln Thr
            930                 935                 940
```

-continued

```
gct aca caa acc gct aca cat gcc tct aca cat gcc tct aca caa gcc      2883
Ala Thr Gln Thr Ala Thr His Ala Ser Thr His Ala Ser Thr Gln Ala
        945                 950                 955

gct aca caa ggt aat gtt cca caa gcc tct aat gat gaa cat aca cct      2931
Ala Thr Gln Gly Asn Val Pro Gln Ala Ser Asn Asp Glu His Thr Pro
    960                 965                 970

tca gca aca aca gtt aat ccg gca acg aca aca cca gat aaa tct ttg      2979
Ser Ala Thr Thr Val Asn Pro Ala Thr Thr Thr Pro Asp Lys Ser Leu
975                 980                 985                 990

aaa gaa agc aca tct gag gga acg ttg atg  aca cag gga aac gca  gat    3027
Lys Glu Ser Thr Ser Glu Gly Thr Leu Met  Thr Gln Gly Asn Ala  Asp
                995                 1000                1005

gat gat gta tct  gag cct gaa aaa aag  gaa ata gaa gtg gaa  gaa      3072
Asp Asp Val Ser  Glu Pro Glu Lys Lys  Glu Ile Glu Val Glu  Glu
            1010                 1015                 1020

ttt tac aag aag  tat tta gag gaa gta  gat aag tat gat gac  tac      3117
Phe Tyr Lys Lys  Tyr Leu Glu Glu Val  Asp Lys Tyr Asp Asp  Tyr
            1025                 1030                 1035

ttt aaa gct ttt  ctt tca tcc aaa aag  gat gct gta aat aaa  atg      3162
Phe Lys Ala Phe  Leu Ser Ser Lys Lys  Asp Ala Val Asn Lys  Met
            1040                 1045                 1050

aca gaa aaa gat  tgg aaa gaa tta gaa  gaa gaa gta aaa aca  tta      3207
Thr Glu Lys Asp  Trp Lys Glu Leu Glu  Glu Glu Val Lys Thr  Leu
            1055                 1060                 1065

aag agt agg tta  gat atg tca tta gat  cat tat aat aag tat  aaa      3252
Lys Ser Arg Leu  Asp Met Ser Leu Asp  His Tyr Asn Lys Tyr  Lys
            1070                 1075                 1080

tta aaa tta ggt  aga ttg ttt aaa aaa  aat gaa aaa gtt tta  agt      3297
Leu Lys Leu Gly  Arg Leu Phe Lys Lys  Asn Glu Lys Val Leu  Ser
            1085                 1090                 1095

agt aaa gaa cat  att aaa gaa ttg agt  att tta aaa gca caa  ttg      3342
Ser Lys Glu His  Ile Lys Glu Leu Ser  Ile Leu Lys Ala Gln  Leu
            1100                 1105                 1110

atg aga aga caa  ttt atg ctt aat aac  cca aga cat gta ata  cat      3387
Met Arg Arg Gln  Phe Met Leu Asn Asn  Pro Arg His Val Ile  His
            1115                 1120                 1125

aac ttt aga gtt  ttt ttt aat aaa aaa  aga gaa act gaa aag  aaa      3432
Asn Phe Arg Val  Phe Phe Asn Lys Lys  Arg Glu Thr Glu Lys  Lys
            1130                 1135                 1140

gaa gtt gaa aat  aca cta aaa aat aca  gat gca ttg tta aaa  tat      3477
Glu Val Glu Asn  Thr Leu Lys Asn Thr  Asp Ala Leu Leu Lys  Tyr
            1145                 1150                 1155

tac aaa gca aga  gtt aag tac tat aat  gga gaa act ttc cca  tta      3522
Tyr Lys Ala Arg  Val Lys Tyr Tyr Asn  Gly Glu Thr Phe Pro  Leu
            1160                 1165                 1170

aaa aca ata agt  gaa gat aca tta gaa  aaa gaa aat aat tat  ctc      3567
Lys Thr Ile Ser  Glu Asp Thr Leu Glu  Lys Glu Asn Asn Tyr  Leu
            1175                 1180                 1185

aat ttg gaa aaa  ttt aag tta tac agc  aga ttg gaa gga aaa  cta      3612
Asn Leu Glu Lys  Phe Lys Leu Tyr Ser  Arg Leu Glu Gly Lys  Leu
            1190                 1195                 1200

aaa caa aac ata  aat ttg gaa aaa gaa  aat atc aca tac cta  tct      3657
Lys Gln Asn Ile  Asn Leu Glu Lys Glu  Asn Ile Thr Tyr Leu  Ser
            1205                 1210                 1215

agt gca tta tat  cac gtt ctt tca gaa  tta aag ggg att ata  cac      3702
Ser Ala Leu Tyr  His Val Leu Ser Glu  Leu Lys Gly Ile Ile  His
            1220                 1225                 1230

aat aaa aag tac  aca gga aat cct cat  gct gca aat atg gta  gag      3747
Asn Lys Lys Tyr  Thr Gly Asn Pro His  Ala Ala Asn Met Val  Glu
            1235                 1240                 1245
```

-continued

```
gtt aac aat gcg  ttg aat ctg tac aaa  gat ttg ctt cca aaa  gtg       3792
Val Asn Asn Ala  Leu Asn Leu Tyr Lys  Asp Leu Leu Pro Lys  Val
            1250                 1255                 1260

gaa act gtg gct  tcc act ggt gcc gcg  acg cag aca caa ggc  ggg       3837
Glu Thr Val Ala  Ser Thr Gly Ala Ala  Thr Gln Thr Gln Gly  Gly
            1265                 1270                 1275

gaa gga gca tca  gca gca gca gca cca  cca gca gcg tta cca  gca       3882
Glu Gly Ala Ser  Ala Ala Ala Ala Pro  Pro Ala Ala Leu Pro  Ala
            1280                 1285                 1290

gca cca cca gca  gca cca cca gca gca  cca cca gca gca tca  gca       3927
Ala Pro Pro Ala  Ala Pro Pro Ala Ala  Pro Pro Ala Ala Ser  Ala
            1295                 1300                 1305

gca gca cct gga  act gca aat ggt gaa  aca gca acg gta gca  cac       3972
Ala Ala Pro Gly  Thr Ala Asn Gly Glu  Thr Ala Thr Val Ala  His
            1310                 1315                 1320

gca gaa gac tat  acg gaa gac gac aat  aac gtc att gta cta  ccc       4017
Ala Glu Asp Tyr  Thr Glu Asp Asp Asn  Asn Val Ile Val Leu  Pro
            1325                 1330                 1335

ctt ttc gga aag  aaa gga aca cat gcg  ttt gac caa gtg acg  cag       4062
Leu Phe Gly Lys  Lys Gly Thr His Ala  Phe Asp Gln Val Thr  Gln
            1340                 1345                 1350

ggt gaa gca caa  gac aag gac gac aat  ata ctg aat gaa atc  acc       4107
Gly Glu Ala Gln  Asp Lys Asp Asp Asn  Ile Leu Asn Glu Ile  Thr
            1355                 1360                 1365

aac gaa tac gaa  gtt gtg tac gtg aaa  ccg tta gct ggt gta  tat       4152
Asn Glu Tyr Glu  Val Val Tyr Val Lys  Pro Leu Ala Gly Val  Tyr
            1370                 1375                 1380

aaa acg ttg aag  aag caa ttg gaa gca  cat gtt aca gca ttt  cac       4197
Lys Thr Leu Lys  Lys Gln Leu Glu Ala  His Val Thr Ala Phe  His
            1385                 1390                 1395

agt aac gta aca  aac atg ttg gaa tct  cgt ttg aaa aaa aga  aat       4242
Ser Asn Val Thr  Asn Met Leu Glu Ser  Arg Leu Lys Lys Arg  Asn
            1400                 1405                 1410

tat ttt ttg gaa  gtg tta aac tct gat  ttg act caa tac aaa  cat       4287
Tyr Phe Leu Glu  Val Leu Asn Ser Asp  Leu Thr Gln Tyr Lys  His
            1415                 1420                 1425

gca act tct gac  aat tac gtt att aga  gat gcg tac aaa tta  tta       4332
Ala Thr Ser Asp  Asn Tyr Val Ile Arg  Asp Ala Tyr Lys Leu  Leu
            1430                 1435                 1440

gac ttt gaa aaa  aaa aaa aaa ttg tta  agt agc tac aaa tat  att       4377
Asp Phe Glu Lys  Lys Lys Lys Leu Leu  Ser Ser Tyr Lys Tyr  Ile
            1445                 1450                 1455

aaa gat tct gtt  gag aaa gat gta gaa  att gct acg gat gga  att       4422
Lys Asp Ser Val  Glu Lys Asp Val Glu  Ile Ala Thr Asp Gly  Ile
            1460                 1465                 1470

gac tat tat gaa  aaa atg gct gct ctg  tat aag acg tac cta  gaa       4467
Asp Tyr Tyr Glu  Lys Met Ala Ala Leu  Tyr Lys Thr Tyr Leu  Glu
            1475                 1480                 1485

tcg gtt aat gct  cag gta gat gca ata  gat aaa act ggg gat  gat       4512
Ser Val Asn Ala  Gln Val Asp Ala Ile  Asp Lys Thr Gly Asp  Asp
            1490                 1495                 1500

gct act aag gca  act aat aaa aaa ttt  ctt ccc ttt ttg gct  agt       4557
Ala Thr Lys Ala  Thr Asn Lys Lys Phe  Leu Pro Phe Leu Ala  Ser
            1505                 1510                 1515

atc aat gct atg  tac gaa act ttg tta  gaa aaa gtg aac acc  tac       4602
Ile Asn Ala Met  Tyr Glu Thr Leu Leu  Glu Lys Val Asn Thr  Tyr
            1520                 1525                 1530

aat tcc caa tta  aaa tca agt tta aac  agt tgc cag ttg gaa  aaa       4647
Asn Ser Gln Leu  Lys Ser Ser Leu Asn  Ser Cys Gln Leu Glu  Lys
            1535                 1540                 1545
```

```
att aga gta ggt  att gtt gtg gat aaa  ctg aat gac tat gta  atg      4692
Ile Arg Val Gly  Ile Val Val Asp Lys  Leu Asn Asp Tyr Val  Met
            1550                 1555                 1560

ttt gat gaa aaa  tta gaa gag tta aaa  tcg agt aag gaa aaa  gat      4737
Phe Asp Glu Lys  Leu Glu Glu Leu Lys  Ser Ser Lys Glu Lys  Asp
            1565                 1570                 1575

ttg aca aaa tta  tat aaa gat ata gat  aca tct aac ata ata  aac      4782
Leu Thr Lys Leu  Tyr Lys Asp Ile Asp  Thr Ser Asn Ile Ile  Asn
            1580                 1585                 1590

aag tta aag aga  tca ggt ttt gta gat  aca gat gag tca aag  aaa      4827
Lys Leu Lys Arg  Ser Gly Phe Val Asp  Thr Asp Glu Ser Lys  Lys
            1595                 1600                 1605

tta tta tcc gag  ttg tta gat gta gat  tct gct caa ttg ttg  tct      4872
Leu Leu Ser Glu  Leu Leu Asp Val Asp  Ser Ala Gln Leu Leu  Ser
            1610                 1615                 1620

atg gga tct aaa  cat aaa tgt att gat  ata aca tat cca gat  aat      4917
Met Gly Ser Lys  His Lys Cys Ile Asp  Ile Thr Tyr Pro Asp  Asn
            1625                 1630                 1635

gca gga tgt tat  aga ttt tct gat gga  cga gaa gaa tgg aga  tgt      4962
Ala Gly Cys Tyr  Arg Phe Ser Asp Gly  Arg Glu Glu Trp Arg  Cys
            1640                 1645                 1650

ttg tta aac ttt  aaa aaa gtt gga gaa  aca tgt gta cca aat  aac      5007
Leu Leu Asn Phe  Lys Lys Val Gly Glu  Thr Cys Val Pro Asn  Asn
            1655                 1660                 1665

aat cct aca tgt  gca gaa aat aat ggt  gga tgt gat ccc act  gca      5052
Asn Pro Thr Cys  Ala Glu Asn Asn Gly  Gly Cys Asp Pro Thr  Ala
            1670                 1675                 1680

gat tgt gca gaa  tct gaa aat aat aaa  att act tgt aca tgt  act      5097
Asp Cys Ala Glu  Ser Glu Asn Asn Lys  Ile Thr Cys Thr Cys  Thr
            1685                 1690                 1695

gga caa aat gaa  tca ttc ttc gaa ggt  gtt ttc tgt ggc tca  tca      5142
Gly Gln Asn Glu  Ser Phe Phe Glu Gly  Val Phe Cys Gly Ser  Ser
            1700                 1705                 1710

agt ttc ctt agc  tta tct ttc tta ttg  gca gtc tta ttg atc  cta      5187
Ser Phe Leu Ser  Leu Ser Phe Leu Leu  Ala Val Leu Leu Ile  Leu
            1715                 1720                 1725

ttt aac tta ctt  taaaaggaga gagtgagggt aaatacaaaa gttgttacat        5239
Phe Asn Leu Leu
            1730

ttttttttt tttttt                                                    5256


<210> SEQ ID NO 5
<211> LENGTH: 1726
<212> TYPE: PRT
<213> ORGANISM: Plasmodium vivax

<400> SEQUENCE: 5

Met Lys Ala Leu Leu Phe Phe Phe Ser Phe Ile Phe Phe Val Thr Lys
1               5                   10                  15

Cys Gln Cys Glu Thr Glu Ser Tyr Lys Gln Leu Val Ala Asn Val Asp
            20                  25                  30

Lys Leu Glu Ala Leu Val Val Asp Gly Tyr Glu Leu Phe His Lys Lys
        35                  40                  45

Lys Leu Gly Glu Asn Asp Ile Lys Val Asp Ala Asn Ala Asn Asn Asn
    50                  55                  60

Asn Asn Asn Gln Val Ser Val Leu Thr Ser Lys Ile Arg Asn Phe Val
65                  70                  75                  80

Gly Lys Phe Leu Glu Leu Gln Ile Pro Gly His Thr Asp Leu Leu His
                85                  90                  95
```

```
Leu Ile Arg Glu Leu Ala Phe Glu Pro Asn Gly Ile Lys Tyr Leu Val
            100                 105                 110

Glu Ser Tyr Glu Glu Phe Asn Gln Leu Met His Val Ile Asn Phe His
        115                 120                 125

Tyr Asp Leu Leu Arg Ala Asn Val His Asp Met Cys Ala His Asp Tyr
    130                 135                 140

Cys Lys Ile Pro Glu His Leu Lys Ile Ser Asp Lys Glu Leu Asp Met
145                 150                 155                 160

Leu Lys Lys Val Val Leu Gly Leu Trp Lys Pro Leu Asp Asn Ile Lys
                165                 170                 175

Asp Asp Ile Gly Lys Leu Glu Thr Phe Ile Thr Lys Asn Lys Glu Thr
            180                 185                 190

Ile Ser Asn Ile Asn Lys Leu Ile Ser Asp Glu Asn Ala Lys Arg Gly
        195                 200                 205

Gly Gln Ser Thr Asn Thr Thr Asn Gly Pro Gly Ala Gln Asn Asn Ala
    210                 215                 220

Ala Gln Gly Ser Thr Gly Asn Thr Glu Thr Gly Thr Arg Ser Ser Ala
225                 230                 235                 240

Ser Ser Asn Thr Leu Ser Gly Gly Asp Gly Thr Thr Val Val Gly Thr
                245                 250                 255

Ser Ser Pro Ala Pro Ala Ala Pro Ser Ser Thr Asn Glu Asp Tyr Asp
            260                 265                 270

Glu Lys Lys Lys Ile Tyr Gln Ala Met Tyr Asn Gly Ile Phe Tyr Thr
        275                 280                 285

Ser Gln Leu Glu Glu Ala Gln Lys Leu Ile Glu Val Leu Glu Lys Arg
    290                 295                 300

Val Lys Val Leu Lys Glu His Lys Gly Ile Lys Ala Leu Leu Glu Gln
305                 310                 315                 320

Val Glu Ala Glu Lys Lys Lys Leu Pro Lys Asp Asn Thr Thr Asn Arg
                325                 330                 335

Pro Leu Thr Asp Glu Gln Gln Lys Ala Ala Gln Lys Lys Ile Ala Asp
            340                 345                 350

Leu Glu Ser Gln Ile Val Ala Asn Ala Lys Thr Val Asn Phe Asp Leu
        355                 360                 365

Asp Gly Leu Phe Thr Asp Ala Glu Glu Leu Glu Tyr Tyr Leu Arg Glu
    370                 375                 380

Lys Ala Lys Met Ala Gly Thr Leu Ile Ile Pro Glu Ser Thr Lys Ser
385                 390                 395                 400

Ala Gly Thr Pro Gly Lys Thr Val Pro Thr Leu Lys Glu Thr Tyr Pro
                405                 410                 415

His Gly Ile Ser Tyr Ala Leu Ala Glu Asn Ser Ile Tyr Glu Leu Ile
            420                 425                 430

Glu Lys Ile Gly Ser Asp Glu Thr Phe Gly Asp Leu Gln Asn Pro Asp
        435                 440                 445

Asp Gly Lys Gln Pro Lys Lys Gly Ile Leu Ile Asn Glu Thr Lys Arg
    450                 455                 460

Lys Glu Leu Leu Glu Lys Ile Met Asn Lys Ile Lys Ile Glu Glu Asp
465                 470                 475                 480

Lys Leu Pro Asn Leu Lys Lys Glu Leu Glu Glu Lys Tyr Lys Val Tyr
                485                 490                 495

Glu Ala Lys Val Asn Glu Phe Lys Pro Ala Phe Asn His Phe Tyr Glu
            500                 505                 510

Ala Arg Leu Asp Asn Thr Leu Val Glu Asn Lys Phe Asp Glu Phe Lys
        515                 520                 525
```

```
Thr Lys Arg Glu Ala Tyr Met Glu Glu Lys Lys Lys Leu Glu Ser Cys
    530                 535                 540

Ser Tyr Glu Gln Asn Thr Asn Leu Ile Asn Lys Leu Lys Lys Gln Leu
545                 550                 555                 560

Thr Tyr Leu Glu Asp Tyr Val Leu Arg Lys Asp Ile Ala Asp Asp Glu
                565                 570                 575

Ile Lys His Phe Ser Phe Met Glu Trp Lys Leu Lys Ser Glu Ile Tyr
            580                 585                 590

Asp Leu Ala Gln Glu Ile Arg Lys Asn Glu Asn Lys Leu Thr Val Glu
        595                 600                 605

Asn Lys Phe Asp Phe Ser Gly Val Val Glu Gly Gln Val Gln Lys Val
    610                 615                 620

Leu Ile Ile Lys Lys Ile Glu Ala Leu Lys Asn Val Gln Asn Leu Leu
625                 630                 635                 640

Lys Asn Ala Lys Val Lys Asp Asp Leu Tyr Val Pro Lys Val Tyr Asn
                645                 650                 655

Thr Gly Glu Lys Pro Glu Pro Tyr Tyr Leu Met Val Leu Lys Arg Glu
            660                 665                 670

Ile Asp Lys Leu Lys Asp Phe Ile Pro Lys Ile Glu Ser Met Ile Ala
        675                 680                 685

Thr Glu Lys Ala Lys Pro Ala Ala Ser Ala Pro Val Thr Ser Gly Gln
    690                 695                 700

Leu Leu Arg Gly Ser Ser Glu Ala Ala Thr Glu Val Thr Thr Asn Ala
705                 710                 715                 720

Val Thr Ser Glu Asp Gln Gln Gln Gln Gln Gln Gln Gln Gln Gln Gln
                725                 730                 735

Gln Gln Gln Gln Gln Gln Gln Gln Gln Gln Gln Gln Ser Gln Val Val
            740                 745                 750

Pro Ala Pro Ala Gly Asp Ala Gln Gln Val Ile Ser Thr Gln Pro Thr
        755                 760                 765

Ser Gln Ser Ala Ala Pro Gly Val Ser Ala Thr Pro Ala Pro Thr Pro
    770                 775                 780

Ala Ala Ala Ala Ala Pro Ala Pro Ala Met Ser Lys Leu Glu Tyr Leu
785                 790                 795                 800

Glu Lys Leu Leu Asp Phe Leu Lys Ser Ala Tyr Ala Cys His Lys His
                805                 810                 815

Ile Phe Val Thr Asn Ser Thr Met Asp Lys Lys Leu Leu Lys Glu Tyr
            820                 825                 830

Glu Leu Asn Ala Asp Glu Lys Thr Lys Ile Asn Gln Asn Lys Cys Asp
        835                 840                 845

Glu Leu Asp Leu Leu Phe Asn Val Gln Asn Asn Leu Pro Ala Met Tyr
    850                 855                 860

Ser Ile Tyr Asp Ser Met Ser Asn Glu Leu Gln Asn Leu Tyr Ile Glu
865                 870                 875                 880

Leu Tyr Gln Lys Glu Met Val Tyr Asn Ile Tyr Lys Asn Lys Asp Thr
                885                 890                 895

Asp Lys Lys Ile Lys Ala Phe Leu Glu Thr Ser Asn Asn Lys Ala Ala
            900                 905                 910

Ala Pro Ala Gln Ser Ala Ala Lys Pro Ser Gly Gln Ala Glu Tyr Tyr
        915                 920                 925

Ser Ser Asn Asp Asn Cys Ala Ser Asn His Asn Asn Ser Tyr Ser Lys
    930                 935                 940

Ser Pro Asn Ile Ser Cys Asn Lys His Thr Ser Thr Pro Gln Ala Glu
```

-continued

```
945                 950                 955                 960

Glu Asn Gln Arg Val Gly Gly Asn Ser Glu Glu Lys Pro Glu Ala Asp
                965                 970                 975

Thr Ala Gln Val Glu Lys Phe Tyr Asp Lys His Leu Ser Gln Ile Asp
            980                 985                 990

Lys Tyr Asn Asp Tyr Phe Lys Lys  Phe Leu Glu Ser Lys  Lys Glu Glu
        995                 1000                1005

Ile Ile  Lys Met Asp Asp Thr  Lys Trp Asn Ala Leu  Gly Lys Glu
    1010                1015                1020

Ile Glu  Glu Leu Lys Lys Lys  Leu Gln Val Ser Leu  Asp His Tyr
    1025                1030                1035

Gly Lys  Tyr Lys Leu Lys Leu  Glu Arg Phe Leu Lys  Lys Lys Asn
    1040                1045                1050

Lys Ile  Ser Asn Ser Lys Asp  Gln Ile Lys Lys Leu  Thr Ser Leu
    1055                1060                1065

Lys Asn  Lys Leu Glu Arg Arg  Gln Asn Leu Leu Asn  Asn Pro Thr
    1070                1075                1080

Ser Val  Leu Lys Asn Tyr Thr  Ala Phe Phe Asn Lys  Lys Arg Glu
    1085                1090                1095

Thr Glu  Lys Lys Glu Val Glu  Asn Thr Leu Lys Asn  Thr Glu Ile
    1100                1105                1110

Leu Leu  Lys Tyr Tyr Lys Ala  Arg Ala Lys Tyr Tyr  Ile Gly Glu
    1115                1120                1125

Pro Phe  Pro Leu Lys Thr Leu  Ser Glu Glu Ser Met  Gln Lys Glu
    1130                1135                1140

Asp Asn  Tyr Leu Asn Leu Glu  Lys Phe Arg Cys Ser  Ala Asp Trp
    1145                1150                1155

Lys Glu  Ile Arg Lys Asp Thr  Glu Leu Glu Arg Ser  Asn Ile Ser
    1160                1165                1170

Tyr Leu  Ser Ser Gly Leu Leu  His Val Leu Asp Arg  Ala Glu Glu
    1175                1180                1185

Ile Ile  Asn Asp Lys Lys Tyr  Ser Gly Lys Asp His  Ala Lys Asn
    1190                1195                1200

Ile Ala  Glu Val Lys Lys Ala  Leu Gln Ala Tyr Gln  Glu Leu Ile
    1205                1210                1215

Pro Lys  Val Thr Ser Gln Glu  Ser Thr Ser Val Ala  Val Thr Val
    1220                1225                1230

Pro Gly  Ala Val Val Pro Gly  Val Pro Thr Ala Ala  Ala Ala Gly
    1235                1240                1245

Ser Gly  Ala Ser Gly Ala Val  Pro Pro Ala Ala Ala  Ala Gly Ser
    1250                1255                1260

Gly Ala  Ser Gly Ala Val Pro  Pro Ala Gly Gly Pro  Ser Pro Pro
    1265                1270                1275

Ala Thr  Gly Gly Val Val Pro  Gly Val Val Glu Ser  Ala Glu Ala
    1280                1285                1290

Gln Thr  Lys Ala Gln Ala Gln  Asp Tyr Ala Glu Asp  Tyr Asp Lys
    1295                1300                1305

Val Ile  Ala Leu Pro Leu Phe  Gly Asn Asn Asp Asp  Asp Gly Glu
    1310                1315                1320

Glu Asp  Gln Val Thr Thr Gly  Glu Ala Glu Ser Glu  Ala Pro Glu
    1325                1330                1335

Ile Leu  Val Pro Ala Gly Ile  Ser Asp Tyr Asp Val  Val Tyr Leu
    1340                1345                1350
```

-continued

```
Lys Pro  Leu Ala Gly Met Tyr  Lys Thr Ile Lys Lys  Gln Leu Glu
    1355                 1360                 1365

Asn His  Val Asn Ala Phe Asn  Thr Asn Ile Thr Asp  Met Leu Asp
    1370                 1375                 1380

Ser Arg  Leu Lys Lys Arg Asn  Tyr Phe Leu Glu Val  Leu Asn Ser
    1385                 1390                 1395

Asp Leu  Asn Pro Phe Lys Tyr  Ser Pro Ser Gly Glu  Tyr Ile Ile
    1400                 1405                 1410

Lys Asp  Pro Tyr Lys Leu Leu  Asp Leu Glu Lys Lys  Lys Lys Leu
    1415                 1420                 1425

Leu Gly  Ser Tyr Lys Tyr Ile  Gly Ala Ser Ile Asp  Lys Asp Leu
    1430                 1435                 1440

Ala Thr  Ala Asn Asp Gly Val  Thr Tyr Tyr Asn Lys  Met Gly Glu
    1445                 1450                 1455

Leu Tyr  Lys Thr His Leu Thr  Ala Val Asn Glu Glu  Val Lys Lys
    1460                 1465                 1470

Val Glu  Ala Asp Ile Lys Ala  Glu Asp Asp Lys Ile  Lys Lys Ile
    1475                 1480                 1485

Gly Ser  Asp Ser Thr Lys Thr  Thr Glu Lys Thr Gln  Ser Met Ala
    1490                 1495                 1500

Lys Lys  Ala Glu Leu Glu Lys  Tyr Leu Pro Phe Leu  Asn Ser Leu
    1505                 1510                 1515

Gln Lys  Glu Tyr Glu Ser Leu  Val Ser Lys Val Asn  Thr Tyr Thr
    1520                 1525                 1530

Asp Asn  Leu Lys Lys Val Ile  Asn Asn Cys Gln Leu  Glu Lys Lys
    1535                 1540                 1545

Glu Ala  Glu Ile Thr Val Lys  Lys Leu Gln Asp Tyr  Asn Lys Met
    1550                 1555                 1560

Asp Glu  Lys Leu Glu Glu Tyr  Lys Lys Ser Glu Lys  Lys Asn Glu
    1565                 1570                 1575

Val Lys  Ser Ser Gly Leu Leu  Glu Lys Leu Met Lys  Ser Lys Leu
    1580                 1585                 1590

Ile Lys  Glu Asn Glu Ser Lys  Glu Ile Leu Ser Gln  Leu Leu Asn
    1595                 1600                 1605

Val Gln  Thr Gln Leu Leu Thr  Met Ser Ser Glu His  Thr Cys Ile
    1610                 1615                 1620

Asp Thr  Asn Val Pro Asp Asn  Ala Ala Cys Tyr Arg  Tyr Leu Asp
    1625                 1630                 1635

Gly Met  Glu Glu Trp Arg Cys  Leu Leu Thr Phe Lys  Glu Glu Gly
    1640                 1645                 1650

Gly Lys  Cys Val Pro Gly Ser  Asn Val Thr Cys Lys  Asp Asn Asn
    1655                 1660                 1665

Gly Gly  Cys Ala Pro Glu Ala  Glu Cys Lys Met Thr  Asp Ser Asn
    1670                 1675                 1680

Lys Ile  Val Cys Lys Cys Thr  Lys Glu Gly Ser Glu  Pro Leu Phe
    1685                 1690                 1695

Glu Gly  Val Phe Cys Ser Ser  Ser Ser Phe Leu Ser  Leu Ser Phe
    1700                 1705                 1710

Leu Leu  Leu Met Leu Leu Phe  Leu Leu Cys Met Glu  Leu
    1715                 1720                 1725
```

<210> SEQ ID NO 6
<211> LENGTH: 387
<212> TYPE: DNA
<213> ORGANISM: Plasmodium malariae

<400> SEQUENCE: 6
tttttcgtta tcaattctca atgtgtaaca aatgaagatt atgaacaact cattcaaaag 60
ttgggaaaac tggaggaact agttgtagaa gggtataacc tatttcacaa aaaaaaattt 120
gccttaacag acattaataa ggatggtaat accagtacta ctgatgcaaa taataaagat 180
gatagtaagg tttcctccgt aacagcaaaa ataggaaatt ttgtcagcaa agttctaaac 240
ctgaatttgc caggttatgt tcagttaact ttttcaatta gggaattaat tacaaagtac 300
agtggtttga aaaatctaat tgaaggatat gaagaattca atgaattaat gtatggaatt 360
aactttcact atgatttatt aagggca 387

<210> SEQ ID NO 7
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 7
taacgaacga gatcttaa 18

<210> SEQ ID NO 8
<211> LENGTH: 18
<212> TYPE: DNA
<213> ORGANISM: Artificial Sequence
<220> FEATURE:
<223> OTHER INFORMATION: Description of Artificial Sequence: Synthetic
primer

<400> SEQUENCE: 8
gttcctctaa gaagcttt 18

<210> SEQ ID NO 9
<211> LENGTH: 29
<212> TYPE: DNA
<213> ORGANISM: Artificial Sequence
<220> FEATURE:
<223> OTHER INFORMATION: Description of Artificial Sequence: Synthetic
primer

<400> SEQUENCE: 9
tttttyrtta tcaawtgwca atgtgwaac 29

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
primer

<400> SEQUENCE: 10
gcyctyaaya aatcatartr raagtt 26

<210> SEQ ID NO 11
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 11

-continued aatgaagatt atgaacaact yattcaa 27

<210> SEQ ID NO 12
<211> LENGTH: 27
<212> TYPE: DNA
<213> ORGANISM: Artificial Sequence
<220> FEATURE:
<223> OTHER INFORMATION: Description of Artificial Sequence: Synthetic
primer

<400> SEQUENCE: 12
aattaattcc ctaattgaaa aagttaa 27

<210> SEQ ID NO 13
<211> LENGTH: 21
<212> TYPE: DNA
<213> ORGANISM: Artificial Sequence
<220> FEATURE:
<223> OTHER INFORMATION: Description of Artificial Sequence: Synthetic
primer

<400> SEQUENCE: 13
gaagctggar garctrcaga a 21

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 14
gaagaactrc agaaaaywcc mtc 23

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 15
aagttgggaa aactggagga ac 22

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 16
agggacctgg acatacgatg actg 24

<210> SEQ ID NO 17
<211> LENGTH: 12
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 17
gatccagtca tc 12

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 18
tcagaattac ttggtgtaga ctc 23

<210> SEQ ID NO 19
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 19
agaagggtat aacctatttc ac 22

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 20
ctagttcctc cagttttccc aac 23

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 21
gaaggctctt tatcttcaac ac 22

<210> SEQ ID NO 22
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 22
caacacatcc tccatcamct ag 22

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 23
cctggtgcta taaaggaacc ag 22

<210> SEQ ID NO 24

<211> LENGTH: 23
<212> TYPE: DNA
<213> ORGANISM: Artificial Sequence
<220> FEATURE:
<223> OTHER INFORMATION: Description of Artificial Sequence: Synthetic
primer

<400> SEQUENCE: 24
agatgtcgtg gaattacaag tac 23

<210> SEQ ID NO 25
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 25
ctctatatac tccagctaat gg 22

<210> SEQ ID NO 26
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 26
gaagttctcg tcgtatttgc tc 22

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
caagtggtta gcaagttaac ag 22

<210> SEQ ID NO 28
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
cggacataag attccttcta tc 22

<210> SEQ ID NO 29
<211> LENGTH: 22
<212> TYPE: DNA
<213> ORGANISM: Artificial Sequence
<220> FEATURE:
<223> OTHER INFORMATION: Description of Artificial Sequence: Synthetic
primer

<400> SEQUENCE: 29
ctgttaactt gctaaccact tg 22

<210> SEQ ID NO 30
<211> LENGTH: 24
<212> TYPE: DNA

```
<213> ORGANISM: Artificial Sequence
<220> FEATURE:
<223> OTHER INFORMATION: Description of Artificial Sequence: Synthetic
      primer

<400> SEQUENCE: 30

tgttgatgtt gctattagaa tcac                                            24


<210> SEQ ID NO 31
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

ccactgcaga ttgtgcagaa tctg                                            24


<210> SEQ ID NO 32
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

ttggtacaca tgtttctcca ac                                              22


<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

atctccattc ttctcgtcca tc                                              22


<210> SEQ ID NO 34
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

gttgttagat gtagattctg ctc                                             23


<210> SEQ ID NO 35
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

ttgaattgga ttactactta cgag                                            24


<210> SEQ ID NO 36
<211> LENGTH: 21
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 36
gatcaccttt acgtccctca g    21

<210> SEQ ID NO 37
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
gacaataaaa tgtgatcagt tag    23

<210> SEQ ID NO 38
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
agtaggttag atatgtcatt agatc    25

<210> SEQ ID NO 39
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
aggtacgtct tatacagagc ag    22

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
gaaacgagat tccaacatgt ttg    23

<210> SEQ ID NO 41
<211> LENGTH: 325
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
gaattccatg aacatcagcc agcaccagtg cgttaaaaag caatgtccgc agaactccgg    60
ttgcttccgt catctggacg aacgcgaaga gtgtaaatgc ctgctgaact acaaacaaga    120
aggcgataaa tgcgtggaaa atccgaaccc aacctgtaac gaaaacaatg gtggctgcga    180
cgcggatgct aaatgtaccg aggaagactc tggttccaac ggcaaaaaga tcacttgcga    240
atgtaccaag ccggacagct acccgctgtt cgacggtatt ttctgctctt ccagcaacca    300
tcatcaccat caccattgag gatcc 325

<210> SEQ ID NO 42
<211> LENGTH: 334
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 42
gaattccatg gttcagaccc agctgctgac tatgtcctct gaacacacct gtatcgacac 60
caacgtgccg gacaacgcgg cttgttaccg ttatctggac ggcaccgaag agtggcgctg 120
cctgctgact ttcaaagaag agggtggcaa gtgcgtaccg gcgagcaacg taacctgtaa 180
agataacaat ggcggttgcg caccagaagc tgaatgcaaa atgactgaca gcaacaagat 240
tgtgtgtaaa tgcaccaaag aaggctccga accgctgttt gaaggtgtgt tctgtagctc 300
ttccagccat catcaccatc accattgagg atcc 334

<210> SEQ ID NO 43
<211> LENGTH: 337
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 43
gaattccatg gttgattcta acgcgctgct gaatatctct gcaaaacacg cttgcaccga 60
aactaagtac ccggaaaacg ctggctgcta ccgctatgaa gatggtaaag aagtgtggcg 120
ctgtctgctg aactataaac tggttgacgg cggctgtgtt gaagatgaag aaccgtcttg 180
ccaggttaac aacggcggtt gcgcaccgga agctaactgc actaaaggtg atgataacaa 240
aattgtatgc gcgtgcaacg caccgtactc tgaaccgatc ttcgaaggcg tgttttgttc 300
ttcttcctct catcatcacc atcaccattg aggatcc 337

<210> SEQ ID NO 44
<211> LENGTH: 334
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 44
gaattccatg gtggattctg cacaactgct gtctatgggc tctaaacaca aatgtattga 60
tatcacgtat ccggacaacg caggctgcta ccgttttagc gatggccgtg aggagtggcg 120
ctgcctgctg aacttcaaaa aggttggtga gacctgcgtt ccgaacaaca acccgacctg 180
cgcggagaac aacggcggtt gcgacccgac tgccgactgt gcggaaagcg aaaacaataa 240
gattacctgc acgtgcaccg gtcagaacga gagctttttc gaaggtgtct tctgttcctc 300
ctcctctcat catcaccatc accattgagg atcc 334

<210> SEQ ID NO 45
<211> LENGTH: 103
<212> TYPE: PRT
<213> ORGANISM: Plasmodium falciparum

<400> SEQUENCE: 45

Met Asn Ile Ser Gln His Gln Cys Val Lys Lys Gln Cys Pro Gln Asn

-continued

```
1               5                   10                  15

Ser Gly Cys Phe Arg His Leu Asp Glu Arg Glu Glu Cys Lys Cys Leu
            20                  25                  30

Leu Asn Tyr Lys Gln Glu Gly Asp Lys Cys Val Glu Asn Pro Asn Pro
        35                  40                  45

Thr Cys Asn Glu Asn Asn Gly Gly Cys Asp Ala Asp Ala Lys Cys Thr
    50                  55                  60

Glu Glu Asp Ser Gly Ser Asn Gly Lys Lys Ile Thr Cys Glu Cys Thr
65                  70                  75                  80

Lys Pro Asp Ser Tyr Pro Leu Phe Asp Gly Ile Phe Cys Ser Ser Ser
                85                  90                  95

Asn His His His His His His
            100
```

<210> SEQ ID NO 46
<211> LENGTH: 106
<212> TYPE: PRT
<213> ORGANISM: Plasmodium vivax

<400> SEQUENCE: 46

```
Met Val Gln Thr Gln Leu Leu Thr Met Ser Ser Glu His Thr Cys Ile
1               5                   10                  15

Asp Thr Asn Val Pro Asp Asn Ala Ala Cys Tyr Arg Tyr Leu Asp Gly
            20                  25                  30

Thr Glu Glu Trp Arg Cys Leu Leu Thr Phe Lys Glu Glu Gly Gly Lys
        35                  40                  45

Cys Val Pro Ala Ser Asn Val Thr Cys Lys Asp Asn Asn Gly Gly Cys
    50                  55                  60

Ala Pro Glu Ala Glu Cys Lys Met Thr Asp Ser Asn Lys Ile Val Cys
65                  70                  75                  80

Lys Cys Thr Lys Glu Gly Ser Glu Pro Leu Phe Glu Gly Val Phe Cys
                85                  90                  95

Ser Ser Ser Ser His His His His His His
            100                 105
```

<210> SEQ ID NO 47
<211> LENGTH: 107
<212> TYPE: PRT
<213> ORGANISM: Plasmodium malariae

<400> SEQUENCE: 47

```
Met Val Asp Ser Asn Ala Leu Leu Asn Ile Ser Ala Lys His Ala Cys
1               5                   10                  15

Thr Glu Thr Lys Tyr Pro Glu Asn Ala Gly Cys Tyr Arg Tyr Glu Asp
            20                  25                  30

Gly Lys Glu Val Trp Arg Cys Leu Leu Asn Tyr Lys Leu Val Asp Gly
        35                  40                  45

Gly Cys Val Glu Asp Glu Glu Pro Ser Cys Gln Val Asn Asn Gly Gly
    50                  55                  60

Cys Ala Pro Glu Ala Asn Cys Thr Lys Gly Asp Asp Asn Lys Ile Val
65                  70                  75                  80

Cys Ala Cys Asn Ala Pro Tyr Ser Glu Pro Ile Phe Glu Gly Val Phe
                85                  90                  95

Cys Ser Ser Ser Ser His His His His His His
            100                 105
```

<210> SEQ ID NO 48

```
<211> LENGTH: 106
<212> TYPE: PRT
<213> ORGANISM: Plasmodium ovale

<400> SEQUENCE: 48

Met Val Asp Ser Ala Gln Leu Leu Ser Met Gly Ser Lys His Lys Cys
1               5                   10                  15

Ile Asp Ile Thr Tyr Pro Asp Asn Ala Gly Cys Tyr Arg Phe Ser Asp
            20                  25                  30

Gly Arg Glu Glu Trp Arg Cys Leu Leu Asn Phe Lys Lys Val Gly Glu
        35                  40                  45

Thr Cys Val Pro Asn Asn Asn Pro Thr Cys Ala Glu Asn Asn Gly Gly
    50                  55                  60

Cys Asp Pro Thr Ala Asp Cys Ala Glu Ser Glu Asn Asn Lys Ile Thr
65                  70                  75                  80

Cys Thr Cys Thr Gly Gln Asn Glu Ser Phe Phe Glu Gly Val Phe Cys
                85                  90                  95

Ser Ser Ser Ser His His His His His His
            100                 105


<210> SEQ ID NO 49
<211> LENGTH: 88
<212> TYPE: DNA
<213> ORGANISM: Plasmodium falciparum

<400> SEQUENCE: 49

atgaacatca gccagcacca gtgcgttaaa aagcaatgtc cgcagaactc cggttgcttc     60

cgtcatctgg acgaacgcga agagtgta                                        88


<210> SEQ ID NO 50
<211> LENGTH: 88
<212> TYPE: DNA
<213> ORGANISM: Plasmodium falciparum

<400> SEQUENCE: 50

ttcgttacag gttgggttcg gattttccac gcatttatcg ccttcttgtt tgtagttcag     60

caggcattta cactcttcgc gttcgtcc                                        88


<210> SEQ ID NO 51
<211> LENGTH: 88
<212> TYPE: DNA
<213> ORGANISM: Plasmodium falciparum

<400> SEQUENCE: 51

cgaacccaac ctgtaacgaa aacaatggtg gctgcgacgc ggatgctaaa tgtaccgagg     60

aagactctgg ttccaacggc aaaaagat                                        88


<210> SEQ ID NO 52
<211> LENGTH: 87
<212> TYPE: DNA
<213> ORGANISM: Plasmodium falciparum

<400> SEQUENCE: 52

gttgctggaa gagcagaaaa taccgtcgaa cagcgggtag ctgtccggct tggtacattc     60

gcaagtgatc tttttgccgt tggaacc                                         87


<210> SEQ ID NO 53
<211> LENGTH: 90
<212> TYPE: DNA
<213> ORGANISM: Plasmodium vivax
```

<400> SEQUENCE: 53
atggttcaga cccagctgct gactatgtcc tctgaacaca cctgtatcga caccaacgtg 60
ccggacaacg cggcttgtta ccgttatctg 90

<210> SEQ ID NO 54
<211> LENGTH: 90
<212> TYPE: DNA
<213> ORGANISM: Plasmodium vivax

<400> SEQUENCE: 54
tgctcgccgg tacgcacttg ccaccctctt ctttgaaagt cagcaggcag cgccactctt 60
cggtgccgtc cagataacgg taacaagccg 90

<210> SEQ ID NO 55
<211> LENGTH: 90
<212> TYPE: DNA
<213> ORGANISM: Plasmodium vivax

<400> SEQUENCE: 55
caagtgcgta ccggcgagca acgtaacctg taaagataac aatggcggtt gcgcaccaga 60
agctgaatgc aaaatgactg acagcaacaa 90

<210> SEQ ID NO 56
<211> LENGTH: 90
<212> TYPE: DNA
<213> ORGANISM: Plasmodium vivax

<400> SEQUENCE: 56
gctggaagag ctacagaaca caccttcaaa cagcggttcg gagccttctt tggtgcattt 60
acacacaatc ttgttgctgt cagtcatttt 90

<210> SEQ ID NO 57
<211> LENGTH: 33
<212> TYPE: DNA
<213> ORGANISM: Plasmodium falciparum

<400> SEQUENCE: 57
atcgaattcc atgaacatca gccagcacca gtg 33

<210> SEQ ID NO 58
<211> LENGTH: 38
<212> TYPE: DNA
<213> ORGANISM: Plasmodium falciparum

<400> SEQUENCE: 58
tggtgatggt gatgatggtt gctggaagag cagaaaat 38

<210> SEQ ID NO 59
<211> LENGTH: 29
<212> TYPE: DNA
<213> ORGANISM: Plasmodium vivax

<400> SEQUENCE: 59
atcgaattcc atggttcaga cccagctgc 29

<210> SEQ ID NO 60
<211> LENGTH: 38
<212> TYPE: DNA
<213> ORGANISM: Plasmodium vivax

<400> SEQUENCE: 60

-continued

```
tggtgatggt gatgatggct ggaagagcta cagaacac                                38


<210> SEQ ID NO 61
<211> LENGTH: 30
<212> TYPE: DNA
<213> ORGANISM: Plasmodium vivax

<400> SEQUENCE: 61

tatggatcct caatggtgat ggtgatgatg                                          30
```